(12) United States Patent
Salmans et al.

(10) Patent No.: US 12,247,985 B2
(45) Date of Patent: Mar. 11, 2025

(54) METHODS OF DETECTING TRANSTHYRETIN

(71) Applicant: Novo Nordisk A/S, Bagsvaerd (DK)

(72) Inventors: Joshua Reginald Salmans, South San Francisco, CA (US); Svetlana Alexander, Sunnyvale, CA (US); Robin Barbour, Walnut Creek, CA (US); Jianmin Li, Castro Valley, CA (US); Jeffrey N. Higaki, San Mateo, CA (US); Tarlochan S. Nijjar, Orinda, CA (US)

(73) Assignee: NOVO NORDISK A/S, Bagsvaerd (DK)

(*) Notice: Subject to any disclaimer, the term of this patent is extended or adjusted under 35 U.S.C. 154(b) by 1285 days.

(21) Appl. No.: 16/753,661

(22) PCT Filed: Oct. 5, 2018

(86) PCT No.: PCT/US2018/054723
§ 371 (c)(1),
(2) Date: Apr. 3, 2020

(87) PCT Pub. No.: WO2019/071206
PCT Pub. Date: Apr. 11, 2019

(65) Prior Publication Data
US 2020/0249244 A1    Aug. 6, 2020

Related U.S. Application Data

(60) Provisional application No. 62/569,438, filed on Oct. 6, 2017, provisional application No. 62/579,817, filed
(Continued)

(51) Int. Cl.
*G01N 33/68* (2006.01)
*A61K 39/395* (2006.01)
(Continued)

(52) U.S. Cl.
CPC ..... *G01N 33/6893* (2013.01); *A61K 39/3955* (2013.01); *A61K 49/0004* (2013.01);
(Continued)

(58) Field of Classification Search
CPC .... G01N 33/6893; G01N 21/66; G01N 21/76; G01N 33/54306; G01N 2458/30;
(Continued)

(56) References Cited

U.S. PATENT DOCUMENTS 5,530,101 A   6/1996  Queen et al.
8,871,447 B2 10/2014  Kayed et al.
(Continued)

FOREIGN PATENT DOCUMENTS

CA        2886254 A1   4/2014
CN      103492882 A    1/2014
(Continued)

OTHER PUBLICATIONS

Saha D, Huang L, Bussalleu E, Lefebvre DJ, Fort M, Van Doorsselaere J, Nauwynck HJ. Antigenic subtyping and epitopes' competition analysis of porcine circovirus type 2 using monoclonal antibodies. Vet Microbiol. May 25, 2012;157(1-2):13-22. (Year: 2012).*
(Continued)

*Primary Examiner* — Christopher L Chin
*Assistant Examiner* — Christina Lusi
(74) *Attorney, Agent, or Firm* — Alston & Bird LLP

(57) ABSTRACT

The invention provides methods of detecting transthyretin (TTR) using a capture antibody and a reporter antibody. The capture antibody binds preferentially to misfolded TTR over native tetrameric form of TTR. The capture antibody binds to an epitope within amino acid residues 89-97 or TTR or to an epitope within amino acid residues 101-109 of TTR. 9D5 and 18C5 are examples of suitable capture antibodies. The
(Continued)

methods can be used for diagnosing diseases or disorders associated with TTR accumulation or accumulation of TTR deposits (e.g., TTR amyloidosis) and for monitoring the efficacy of TTR therapies, among other applications.

26 Claims, 11 Drawing Sheets

Specification includes a Sequence Listing.

Related U.S. Application Data on Oct. 31, 2017, provisional application No. 62/647,582, filed on Mar. 23, 2018.

(51) Int. Cl.

| | | |
|---|---|---|
| A61K 49/00 | (2006.01) | |
| C07K 16/18 | (2006.01) | |
| G01N 21/66 | (2006.01) | |
| G01N 21/76 | (2006.01) | |
| G01N 33/543 | (2006.01) | |
| A61K 39/00 | (2006.01) | |

(52) U.S. Cl.
CPC .............. *C07K 16/18* (2013.01); *G01N 21/66* (2013.01); *G01N 21/76* (2013.01); *G01N 33/54306* (2013.01); *A61K 2039/505* (2013.01); *G01N 2458/30* (2013.01); *G01N 2800/28* (2013.01); *G01N 2800/325* (2013.01); *G01N 2800/52* (2013.01)

(58) Field of Classification Search
CPC ......... G01N 2800/28; G01N 2800/325; G01N 2800/52; G01N 2333/4728; G01N 33/74; G01N 33/566; G01N 33/54366; G01N 33/6896; A61K 39/3955; A61K 49/0004; A61K 2039/505; A61K 31/711; A61K 31/713; A61K 31/575; A61K 31/423; A61K 31/603; A61K 31/65; A61K 31/192; A61K 2300/00; C07K 16/18; C07K 2317/24; C07K 2317/34; C07K 2317/92
USPC ..................................... 436/512, 540; 424/91
See application file for complete search history.

(56) References Cited

U.S. PATENT DOCUMENTS

| | | |
|---|---|---|
| 9,534,048 B2 | 1/2017 | Chakrabartty et al. |
| 9,535,076 B2 | 1/2017 | Kayed et al. |
| 9,637,552 B2 | 5/2017 | Cashman et al. |
| 9,731,292 B2 | 8/2017 | Ermantraut et al. |
| 9,879,080 B2 | 1/2018 | Nijjar et al. |
| 10,253,100 B2 | 4/2019 | Igawa et al. |
| 10,464,999 B2 | 11/2019 | Liu et al. |
| 10,494,426 B2 | 12/2019 | Nijjar et al. |
| 10,618,965 B2 | 4/2020 | Igawa et al. |
| 10,633,433 B2 | 4/2020 | Nijjar et al. |
| 10,669,330 B2 | 6/2020 | Liu et al. |
| 10,906,967 B2 | 2/2021 | Nijjar et al. |
| 11,028,158 B2 | 6/2021 | Liu et al. |
| 11,912,759 B2 | 2/2024 | Liu et al. |
| 2002/0019335 A1 | 2/2002 | Solomon et al. |
| 2006/0280733 A1 | 12/2006 | Kayed et al. |
| 2007/0110750 A1 | 5/2007 | Glabe et al. |
| 2010/0233176 A1 | 9/2010 | Cashman et al. |
| 2011/0200609 A1 | 8/2011 | Glabe et al. |
| 2013/0344088 A1 | 12/2013 | Cosenza et al. |
| 2014/0056904 A1 | 2/2014 | Chakrabartty et al. |
| 2015/0353630 A1 | 12/2015 | Igawa et al. |
| 2016/0039916 A1 | 2/2016 | Jiang et al. |
| 2016/0251418 A1 | 9/2016 | Liu et al. |
| 2016/0257736 A1 | 9/2016 | Nijjar et al. |
| 2016/0257737 A1 | 9/2016 | Liu et al. |
| 2016/0340419 A1 | 11/2016 | Torikai et al. |
| 2016/0340420 A1 | 11/2016 | Zhang et al. |
| 2016/0347832 A1 | 12/2016 | Hosoi et al. |
| 2016/0355576 A1 | 12/2016 | Grimm et al. |
| 2017/0015737 A1 | 1/2017 | Nijjar et al. |
| 2017/0058023 A1 | 3/2017 | Liu et al. |
| 2017/0121398 A1 | 5/2017 | Nijjar et al. |
| 2018/0201670 A1 | 7/2018 | Nijar et al. |
| 2020/0055929 A1 | 2/2020 | Nijar et al. |
| 2020/0087386 A1 | 3/2020 | Liu et al. |
| 2020/0277361 A1 | 9/2020 | Nijar et al. |
| 2020/0331992 A1 | 10/2020 | Salmans et al. |
| 2020/0362023 A1 | 11/2020 | Hawe et al. |
| 2021/0188956 A1 | 6/2021 | Nijjar et al. |

FOREIGN PATENT DOCUMENTS

| | | |
|---|---|---|
| CN | 106255702 A | 12/2016 |
| EP | 1185296 B1 | 1/2011 |
| EP | 1578361 B1 | 4/2011 |
| EP | 2552955 B1 | 5/2017 |
| EP | 2679681 B1 | 8/2019 |
| EP | 2698431 B1 | 9/2020 |
| EP | 2857419 B1 | 1/2021 |
| JP | 2010-195710 A | 9/2010 |
| JP | 2014-510907 A | 5/2014 |
| JP | 2016-514091 A | 5/2016 |
| WO | WO 2003-080672 A1 | 10/2003 |
| WO | WO 2004/024090 A3 | 3/2004 |
| WO | WO 2005/025516 A2 | 3/2005 |
| WO | WO 2006/108234 A1 | 10/2006 |
| WO | WO 2008/005455 A3 | 1/2008 |
| WO | WO 2010/012004 A2 | 1/2010 |
| WO | WO 2010/030203 A1 | 3/2010 |
| WO | WO 2010/040209 A1 | 4/2010 |
| WO | WO 2010/099612 A1 | 9/2010 |
| WO | WO 2014/058924 A2 | 4/2014 |
| WO | WO 2014/124334 A2 | 8/2014 |
| WO | WO 2014/142334 A1 | 9/2014 |
| WO | WO 2015/010118 A2 | 1/2015 |
| WO | WO 2015/092077 A1 | 6/2015 |
| WO | WO 2015/115331 A1 | 8/2015 |
| WO | WO 2016/033326 A2 | 3/2016 |
| WO | WO 2016/120809 A1 | 8/2016 |
| WO | WO 2016/120810 A1 | 8/2016 |
| WO | WO 2016/120811 A1 | 8/2016 |
| WO | WO 2018/007922 A2 | 1/2018 |
| WO | WO 2018/007923 A2 | 1/2018 |
| WO | WO 2018/007924 A2 | 1/2018 |
| WO | WO 2019/071205 A1 | 4/2019 |
| WO | WO 2019/071206 A1 | 4/2019 |
| WO | WO 2019/108689 A1 | 6/2019 |
| WO | WO 2021/168156 A1 | 8/2021 |

OTHER PUBLICATIONS

Gioeva et al (Gioeva Z, Urban P, Meliss RR, Haag J, Axmann HD, Siebert F, Becker K, Radtke HG, Röcken C. Attr amyloid in the carpal tunnel ligament is frequently of wildtype transthyretin origin. Amyloid. Mar. 2013;20(1):1-6.) (Year: 2013).*

Goel et al. "Plasticity within the Antigen Combining Site May Manifest as Molecular Mimicry in the Humoral Immune Response," The Journal of Immunology (2004), 173(12):7358-7367 (Year: 2004).*

Lloyd et al. "Modelling the human immune response: performance of a 1011 human antibody repertoire against a broad panel of therapeutically relevant antigens," Protein Engineering, Design & Selection (2009), 22(3):159-168 (Year: 2009).*

Edwards et al. "The remarkable flexibility of the human antibody repertoire; isolation of over one thousand different antibodies to a single protein, BlyS," Journal of Molecular Biology (2003), 334:103-118 (Year: 2003).*

(56) References Cited

OTHER PUBLICATIONS

Harlow, E. and Lane, D., Antibodies: A Laboratory Manual (1988) Cold Spring Harbor Laboratory Press, Cold Spring Harbor, NY, pp. 23-26 (Year: 1988).*
Lederman et al. "A single amino acid substitution in a common African allele of the CD4 molecule ablates binding of the monoclonal antibody OKT4" Mol Immunol. Nov. 1991; 28(11):1171-81 (Year: 1991).*
Colman et al. Effects of amino-acid sequence changes on antibody-antigen interactions. Research in Immunology, 1994; 145(1):33-36 (Year: 1994).*
Coelho T, Maurer MS, Suhr Ob. Thaos—The Transthyretin Amyloidosis Outcomes Survey: initial report on clinical manifestations in patients with hereditary and wild-type transthyretin amyloidosis. Curr Med Res Opin. Jan. 2013;29(1):63-76. (Year: 2013).*
Bergström, et al., "Surface exposed epitopes and structural heterogeneity of in vivo formed transthyretin amyloid fibrils," Biophysical Research Communications, 348:532-539 (2006).
Goldsteins, et al., "Exposure of cryptic epitopes on transthyretin only in amyloid and in amyloidogenic mutants," Proc. Natl. Acad. Sci. USA, vol. 96, pp. 3108-3113 (Mar. 1999).
Gustavsson, et al., "Antigenic Mapping of Transthyretin Purified from Plasma and Amyloid Fibrils and within in Situ Tissue Localizations," American Journal of Pathology, vol. 144, No. 6, pp. 1301-1311 (Jun. 1994).
Redondo, et al., "Search for Intermediate Structures in Transthyretin Fibrillogenesis: Soluble Tetrameric Tyr78Phe TTR Expresses a Specific Epitope Present Only in Amyloid Fibrils," J. Mol. Biol., 304, 461-470 (2000).
Terazaki, et al., "Immunization in familial amyloidotic polyneuropathy: counteracting deposition by immunization with a Y78F TTR mutant," Laboratory Investigation, 86, 23-31 (2006).
Phay, et al., "Transthyretin Aggregate-Specific Antibodies Recognize Cryptic epitopes on Patient-Derived Amyloid Fibrils," Rejuvenation Research, vol. 17, No. 2, pp. 97-105 (2014).
PCT/IB2016/050415 International Search Report and Written Opinion mailed Mar. 24, 2016.
Leger, et al., "Humanization of Antibodies," Molecular Medicine and Medicinal Chemistry, pp. 1-23, (Jan. 1, 2011).
Almagro, et al., "Humanization of antibodies," Frontiers in Bioscience, 12:1619-1633, (Jan. 1, 2008).
PCT/IB2016/050414 International Search Report and Written Opinion mailed Apr. 25, 2016.
PCT/IB2016/050416 International Search Report and Written Opinion mailed May 18, 2016.
Hernandez, et al., "Identification of new pathogenic candidates for diabetic macular edema using fluorescence-based difference gel electrophoresis analysis", Diabetes Metab Res Rev, 29:499-506 (2013). [Retrieved from the Internet Mar. 8, 2017: https://www.researchgate.net/publication/236140050_Identification_of_new_pathogenic_candidates_for_diabetic_macular_edema_using_fluorescence-based_difference_gel_electrophoresis_analysis].
Dias-Santos, et al., "Macular and optic disc edema and retinal vascular leakage in familial amyloid polyneuropathy with a transthyretin Val30Met mutation: a case report", J Med Case Rep, 8:327 (Oct. 4, 2014).
U.S. Appl. No. 15/009,662 Restriction Requirement mailed Sep. 20, 2016.
U.S. Appl. No. 15/009,666 Restriction Requirement mailed Sep. 20, 2016.
Adekar, et al., "Inherent Anti-amyloidogenic Activity of Human Immunoglobulin γ Heavy Chains," J Biol Chem, 285(2):1066-74, (2010).
Cardoso, et al., "Transthyretin Fibrillogenesis Entails the Assembly of Monomers: A Molecular Model for in Vitro Assembled Transthyretin Amyloid-like Fibrils," J Mol Biol, 317:683-95, (2002).
Chen, et al., "Endoplasmic Reticulum Proteostasis Influences the Oligomeric State of an Amyloidogenic Protein Secreted from Mammalian Cells," Cell Chem Biol, 23:1282-1293, (2016).
Galant, et al., "Substoichiometric inhibition of transthyretin misfolding by immune-targeting sparsely populated misfolding intermediates: a potential diagnostic and therapeutic for TTR amyloidoses," Sci Rep, 6:1-11, srep 25080, Apr. 28, 2016. [Retrieved from the Internet Feb. 27, 2017: <www.nature.com/scientificreports>].
Higaki, et al., "Novel conformation-specific monoclonal antibodies against amyloidogenic forms of transthyretin," Amyloid, 23(2):86-97, (2016).
Jiang, et al., "An Engineered Transthyretin Monomer that Is Nonamyloidogenic, Unless It Is Partially Denatured," Biochemistry, 40(38):11442-11452, (2011).
Johnson, et al., "The Transthyretin Amyloidoses: From Delineating the Molecular Mechanism of Aggregation Linked to Pathology to a Regulatory-Agency-Approved Drug," J Mol Biol, 421:185-203, (2012).
Lai, et al., "The Acid-Mediated Denaturation Pathway of Transthyretin Yields a Conformational Intermediate That Can Self-Assemble into Amyloid," Biochemistry, 35(20):6470-6482, (1996).
Lashuel, et al., "Characterization of the Transthyretin Acid Denaturation Pathways by Analytical Ultracentrifugation: Implications for Wild-Type, V30M, and L55P Amyloid Fibril Formation," Biochemistry, 37(51):17851-17864, (1998).
Levites, et al., "A Human Monoclonal IgG That Binds Aβ Assemblies and Diverse Amyloids Exhibits Anti-Amyloid Activities in Vitro and in Vivo," J Neurosci, 35(16):6265-6276, (2015).
McCutchen, et al., "Comparison of Lethal and Nonlethal Transthyretin Variants and Their Relationship to Amyloid Disease," Biochemistry, 34(41):13527-13536, (1995).
Miroy, et al., "Inhibiting transthyretin amyloid fibril formation via protein stabilization," Proc Natl Acad Sci USA, 93:15051-15056, (1996).
O'Nuallain, et al., "Localization of a Conformational Epitope Common to Non-Native and Fibrillar Immunoglobulin Light Chains," Biochemistry, 46(5):1240-1247, (2007).
O'Nuallain, et al., "Conformational Abs recognizing a generic amyloid fibril epitope," Proc Natl Acad Sci USA, 99(3):1485-1490, (2002).
O'Nuallain, et al., "Anti-amyloidogenic Activity of IgGs Contained in Normal Plasma," J Clin Immunol, 30 Suppl 1:S37-S42, (2010).
Phay, et al., "IgG Conformer's Binding to Amyloidogenic Aggregates," PLoS One, 10(9):1-25, (2015).
Planque, et al., "Physiological IgM Class Catalytic Antibodies Selective for Transthyretin Amyloid," J Biol Chem, 289(19):13243-13258, (2014).
Planque, et al., "Specific Amyloid β Clearance by a Catalytic Antibody Construct," J Biol Chem, 290(16):10229-10241, (2015).
Quintas, et al., "Tetramer Dissociation and Monomer Partial Unfolding Precedes Protofibril Formation in Amyloidogenic Transthyretin Variants," J Biol Chem, 276(29):27207-27213, (2001).
Su, et al., "Antibody therapy for familial amyloidotic polyneuropathy," Amyloid, 19(51):45-46, (2012).
Hosoi, et al., "Novel Antibody for the Treatment of Transthyretin Amyloidosis," J Biol Chem, 291(48):25096-25105, (2016).
U.S. Appl. No. 15/009,667 Restriction Requirement mailed Dec. 30, 2016.
U.S. Appl. No. 15/009,662 Non-Final Office Action mailed Mar. 7, 2017.
Paul, "Fundamental Immunology" textbook under the heading "Fv Structure and Diversity in Three Dimensions," pp. 292-295, (1993).
Rudikoff, et al., "Single amino acid substitution altering antigen-binding specificity," Proc Natl Acad Sci USA, 79(6):1979-1983, (1982).
U.S. Appl. No. 15/009,662 Examiner Initiated Interview Summary mailed Mar. 7, 2017.
U.S. Appl. No. 15/009,666 Non-Final Office Action mailed Mar. 6, 2017.
U.S. Appl. No. 15/009,666 Examiner Initiated Interview Summary mailed Mar. 6, 2017.
U.S. Appl. No. 15/009,667 Non-Final Office Action mailed Mar. 29, 2017.
U.S. Appl. No. 15/201,423 Restriction Requirement mailed Jun. 5, 2017.

(56) References Cited

OTHER PUBLICATIONS

U.S. Appl. No. 15/201,416 Restriction Requirement mailed May 31, 2017.
U.S. Appl. No. 15/201,429 Restriction Requirement mailed Jul. 3, 2017.
PCT/IB2016/050416 International Preliminary Report on Patentability mailed Aug. 10, 2017.
PCT/IB2016/050415 International Preliminary Report on Patentability mailed Aug. 10, 2017.
PCT/IB2016/050414 International Preliminary Report on Patentability mailed Aug. 1, 2017.
U.S. Appl. No. 15/201,423 Non-Final Office Action mailed Oct. 19, 2017.
Sharma, et al., "Identification of Autoantibodies against Transthyretin for the Screening and Diagnosis of Rheumatoid Arthritis", PLoS One, vol. 9, Issue 4, (Apr. 2014).
PCT/IB2017/053991 Invitation to Pay Additional Fees mailed Nov. 2, 2017.
U.S. Appl. No. 15/201,429 Non-Final Office Action mailed Nov. 14, 2017.
PCT/IB2017/053991 International Search Report and Written Opinion mailed Jan. 17, 2018.
PCT/IB2017/053984 International Search Report and Written Opinion mailed Jan. 2, 2018.
PCT/IB2017/053987 International Search Report and Written Opinion mailed Jan. 31, 2018.
U.S. Appl. No. 15/201,429 Final Office Action mailed Jul. 9, 2018.
U.S. Appl. No. 15/201,423 Notice of Allowance and Examiner Initiated Interview Summary mailed Jun. 13, 2018.
U.S. Appl. No. 15/201,429 Advisory Action mailed Sep. 17, 2018.
U.S. Appl. No. 15/201,423 Notice of Allowance and Examiner Initiated Interview Summary mailed Oct. 12. 2018.
PCT/IB2017/053987 International Preliminary Report on Patentability mailed Jan. 8, 2019.
PCT/IB2017/053991 International Preliminary Report on Patentability mailed Jan. 8, 2019.
PCT/IB2017/053984 International Preliminary Report on Patentability mailed Jan. 8, 2019.
PCT/US2018/054723 International Search Report and Written Opinion mailed Jan. 3, 2018.
Ionis Pharmaceuticals Announces Phase 3 NEURO-TTR Study of Inotersen (IONIS-TTR$_{Rx}$) Meets Both Primary Endpoints, Press Release, Carlsbad California, May 15, 2017.
U.S. Appl. No. 15/201,423 Notice of Allowance and Examiner Initiated Interview Summary mailed Mar. 6, 2019.
PCT/US2018/062902 International Search Report and Written Opinion mailed Apr. 7, 2019.
PCT/US2018/054720 International Search Report and Written Opinion mailed Feb. 12, 2019.
Schonhoft, et al., "Peptide probes detect misfolded transthyretin oligomers in plasma of hereditary amyloidosis patients," Sci. Tranl. Med., 9, eaam 7621, (2017).
U.S. Appl. No. 15/201,429 Non-Final Office Action mailed Mar. 5, 2019.
U.S. Appl. No. 15/861,600 Notice of Allowance and Examiner Initiated Interview Summary mailed Mar. 18, 2019.
U.S. Appl. No. 15/201,423 Notice of Allowance mailed Jun. 12, 2019.
Damas, et al., "Review: TTR Amyloidosis—Structural Features Leading to Protein Aggregation and Their Implications on Therapeutic Strategies," Journal of Structural Biology, 120, 290-299, (2000).
U.S. Appl. No. 16/129,618 Non-Final Office Action and Interview Summary mailed Aug. 22, 2019.
Carvalho, et al., "Liver Transplantation in Transthyretin Amyloidosis: Issues and Challenges," Liver Transplantation, 21:282-292, (2015).
Murray, et al., "Physiological consequences of changes in the primary structure," Human Biochemistry, vol. 1, p. 34, right column, (1993).

U.S. Appl. No. 15/861,600 Notice of Allowance mailed Jul. 25, 2019.
U.S. Appl. No. 15/201,429 Notice of Allowance and Interview Summary mailed Sep. 25, 2019.
U.S. Appl. No. 15/201,429 Notice of Allowance mailed Jan. 23, 2020.
U.S. Appl. No. 16/129,618 Notice of Allowance and Interview Summary mailed Jan. 23, 2020.
Ando, et al., "Toransusairechin up-to-date," Rinshokagaku, vol. 37, pp. 375-382, (2008) English abstract.
EP 16702812.5 Third Party Observation submitted Jan. 31, 2020.
Prothena Corporation plc news release, "Prothena Discontinues Development of NEOD001 for AL Amyloidosis," Globe NewsWRE, Apr. 23, 2018.
PCT/US2018/054723 International Preliminary Report on Patentability mailed Apr. 16, 2020.
PCT/US2018/054720 International Preliminary Report on Patentability mailed Apr. 16, 2020.
PCT/US2018/062902 International Preliminary Report on Patentability mailed Jun. 2, 2020.
Chen, et al., Yearbook of Biotechnology Development, Military Medical Science Press, p. 115, published on Dec. 31, 2014, including a translation of the related Chinese Office Action mailed Aug. 4, 2020, in Chinese application No. 2016800158008 providing a brief statement of relevance.
Liu, et al., New Concept and Clinical Practice of Oncology, p. 291, China Medical Science Press, published on Dec. 31, 1994, including a translation of the related Chinese Office Action mailed Aug. 4, 2020, in Chinese application No. 2016800158008 providing a brief statement of relevance.
Wang, Antibody Technology, Military Medical Science Press, p. 129, published on Mar. 31, 2009, including a translation of the related Chinese Office Action mailed Aug. 4, 2020, in Chinese application No. 2016800158008 providing a brief statement of relevance.
Zhang, Essential Medical Immunology, Sichuan University Press, p. 340, published on May 31, 2007, including a translation of the related Chinese Office Action mailed Aug. 4, 2020, in Chinese application No. 2016800158008 providing a brief statement of relevance.
NCBI: CAA75032.1, published on Aug. 19, 1998; PIR: SS2059, published on Sep. 8, 2000.
U.S. Appl. No. 16/669,375 Notice of Allowance and Interview Summary mailed Sep. 18, 2020.
U.S. Appl. No. 16/789,319 Non-Final Office Action mailed Dec. 3, 2020.
U.S. Appl. No. 16/584,634 Notice of Allowance and Examiner Interview Summary mailed Feb. 5, 2021.
U.S. Appl. No. 16/753,307 Restriction Requirement mailed 04-26-202.
PCT/US2021/018632 International Search Report and Written Opinion mailed May 7, 2021.
Akasaki, et al., "Transthyretin Deposition in Articular Cartilage," Arthritis & Rheumatology, vol. 67, No. 8, pp. 2097-2107, (Aug. 2015).
Clement, et al., "Autoimmune response to transthyretin in juvenile idiopathic arthritis," JCI Insight, (2): e85633, (2016).
DeGregorio, et al., Left Atrial Morphology, Size and Function in Patients With Transthyretin Cardiac Amyloidosis and Primary Hypertrophic Cardiomyopathy,: Circulation Journal, 80: 1830-1837, (2016).
Gu, et al., Clinical and laboratory characteristics of patients having amyloidogenic transthyretin deposition in osteoarthritic knee joints, J. Zhejiang Unvi-Sci B (Biomed and Biotechnol), 15(1):92-99, (2014).
Mullins, et al., "Drusen associated with aging and age-related macular degeneration contain proteins common to extracellular deposits associated with atherosclerosis, elastosis, amyloidosis, and dense deposit disease," The FASEB Journal, vol. 14, pp. 836-846, (May 2000).
Sueyoski, et al., "Wild-type transthyretin-derived amyloidosis in various ligaments and tendons," Human Pathology, 42, 1259-1264, (2011).

(56) References Cited

OTHER PUBLICATIONS

Takanashi, et al., "Synovial deposition of wild-type transthyretin-derived amyloid in knee joint osteroarthritis patients," Amyloid, 20(3): 151-155, (2013).
Takinami, et al., "Identification of Potential Prognostic Markers for Knee Osteoarthritis by Serum Proeomic Analysis," Biomarker Insights, 8, 85-95, (2013).
Westermark, et al., "Transthyretin-derived amyloidosis: Probably a common cause of lumbar spinal stenosis," Upsala Journal of Medical Sciences, 119: 223228, (2014).
Yanagisawa, et al., "Amyloid deposits derived from transthyretin in the ligamentum flavum as related to lumbar spinal canal stenosis," Modern Pathology, 28, 201-207, (2015).
Ni, et al., "Transthyretin as a potential serological marker for the diagnosis of patients with early rheumatoid arthritis," Clin Exp Rheumatol, 31(3): 394-399, (2013).
"Synovial deposition of wild-type transthyretin-derived amyloid in knee joint osteoarthritis patients", Shinshu Medical Journal, vol. 62, No. 5, p. 329-330, (2014).
U.S. Appl. No. 16/753,307 Non-Final Office Action mailed Jul. 14, 2021.
Kussie, et al., "A Single Engineered Amino Acid Substitution Changes Antibody Fine Specificity," J Immunonol, 152(1): 146-152, (1994).
Sinai, "Rotator Cuff Injury," Accessed from cedars-sinai.org on Jul. 9, 2021, (2021).
Saelices, et al., "Uncovering the Mechanism of Aggregation of Human Transthyretin," Journal of Biological Chemistry, vol. 290, No. 48, pp. 28932-28943, (Nov. 27, 2015).
Chen, et al., "Enhancement and destruction of antibody function by somatic mutation: unequal occurrence is controlled by V gene combinatorial associations," EMBO Journal, vol. 14, No. 12, pp. 2784-2794, (1995).
Saldanha, Molecular Engineering I: Humanization, Handbook of Therapeutic Antibodies, edited by Stefan Dubel, Copyright 2007 Wiley-VCH Verlag Gmbh & Co. KGaA, Weinheim, excerpt, (2007).
EP 18864376.1 Supplemental European Search Report mailed Jun. 1, 2021.
EP 18882542.6 Supplemental European Search Report mailed Jul. 27, 2021.
Wang, et al., "Antibody Structure, Instability and Formulation," Journal of Pharmaceutical Sciences, vol. 96, No. 1, (Jan. 2007).
Daugherty, et al., "Formulation and Delivery Issues for Monoclonal Antibody Therapeutics," Advanced Drug Delivery Reviews, 58(5-6):686-42 (2006) with permission Elsevier.
U.S. Appl. No. 16/789,319 Notice of Allowance and Interview Summary mailed Oct. 27, 2021.
U.S. Appl. No. 16/789,319 Corrected Notice of Allowance mailed Nov. 19, 2021.
Liu et al., "The Proteomics Research of Sjogren's Syndrome," Journal of Kunming Medical University, 37(4) : 65-70, (2016).
PCT/US2021/018632 International Preliminary Report on Patentability mailed Aug. 23, 2022.
U.S. Appl. No. 17/127,719 Notice of Allowance and Interview Summary mailed Sep. 30, 2022.
Martinez-Naharro, et al., "Magnetic Resonance in Transthyretin Cardiac Amyloidosis," Journal of the American College of Cardiology, vol. 70, No. 4, (2017).
Gertz, et al., "Diagnosis, Prognosis, and Therapy of Transthyretin Amyloidosis," Journal of the American College of Cardiology, vol. 66, No. 21, (2015).
Ando, et al., "Transthyretin: its function and pathogenicity," Japan Pharmaceutical Society Journal, vol. 98, No. 8, pp. 2006-2012, (2009), English Abstract.
Sekijima, Pathogenesis and Therapeutic Strategy for Protein Misfolding Disease, the Shinshu Medical Journal, vol. 56, Issue 3, (2008). English Abstract.
U.S. Appl. No. 16/767,994 Restriction Requirement mailed Oct. 17, 2022.
U.S. Appl. No. 16/767,994 Non-Final Office Action mailed Jan. 18, 2023.
EP22195219 European Search Report mailed Jan. 5, 2023.
U.S. Appl. No. 17/307,968 Non-Final Office Action and Interview Summary mailed Mar. 9, 2023.
Package Insert for Herceptin, Roche, Jun. 25, 2014.
Package Insert for Xolair, Genentech USA, Inc. and Novaris Pharmaceuticals Corporation, revision date Sep. 2014 and initial date Jun. 2003.
U.S. Appl. No. 16/767,994 Final Office Action mailed May 22, 2023.
U.S. Appl. No. 16/767,994 Notice of Allowance and Interview Summary mailed Sep. 5, 2023.
U.S. Appl. No. 17/307,968 Notice of Allowance mailed Oct. 31, 2023.
U.S. Appl. No. 17/307,968 Notice of Allowance mailed Nov. 30, 2023.
Tamura et al., "Structural correlates of an anticarcinoma antibody: identification of specificity-determining residues (SDRs) and development of a minimally immunogenic antibody variant by retention of SDRs only," J Immunol, 1;164(3):1432-41, doi: 10.4049/jimmunol. 164.3.1432, (Feb. 2000).

* cited by examiner

SEQUENCE LISTING

<160> NUMBER OF SEQ ID NOS: 104

<210> SEQ ID NO 1
<211> LENGTH: 139
<212> TYPE: PRT
<213> ORGANISM: Artificial sequence
<220> FEATURE:
<223> OTHER INFORMATION: Synthesized

<400> SEQUENCE: 1

Met Asp Phe Gly Leu Ile Phe Phe Ile Val Ala Leu Leu Lys Gly Val
1               5                   10                  15

Gln Cys Glu Val Lys Leu Leu Glu Ser Gly Gly Gly Leu Val Gln Pro
            20                  25                  30

Gly Gly Ser Leu Asn Leu Ser Cys Val Ala Ser Gly Phe Asp Phe Ser
        35                  40                  45

Arg Phe Trp Met Ser Trp Ala Arg Gln Ala Pro Gly Arg Gly Gln Glu
    50                  55                  60

Trp Ile Gly Glu Ile Asn Pro Gly Ser Ser Thr Ile Asn Tyr Thr Pro
65                  70                  75                  80

Ser Leu Lys Asp Lys Phe Ile Ile Ser Arg Asp Asn Ala Lys Asn Thr
                85                  90                  95

Leu Phe Leu Gln Met Ser Lys Val Arg Ser Glu Asp Ser Ala Leu Tyr
            100                 105                 110

Tyr Cys Ala Arg Leu Gly Tyr Gly Asn Tyr Gly Trp Ala Leu Asp Tyr
        115                 120                 125

Trp Gly Gln Gly Thr Ser Val Thr Val Ser Ser
    130                 135

<210> SEQ ID NO 2
<211> LENGTH: 417
<212> TYPE: DNA
<213> ORGANISM: Artificial sequence
<220> FEATURE:
<223> OTHER INFORMATION: Synthesized

<400> SEQUENCE: 2
atggattttg ggctgatttt tttcattgtt gccctttta aagggtgtcca gtgtgaggta      60 aagcttctcg agtctggagg tggcctggtg cagcctggag gatccctgaa tctctcctgt    120
gtagcctcag gattcgattt tagtagattc tggatgagtt gggctcggca ggctccaggg    180
agaggacagg aatggattgg agagattaat ccaggaagca gtacgataaa ctatacgcca    240
tctctgaagg ataaaattca tcatctccaga gacaacgcca aaaatacgct gttcctgcaa    300
atgagcaaag tgagatctga ggactcagcc ctttattact gtgcaagact ggggtatggt    360
aactacggat gggctctgga ctactgggt caaggaacct cagtcaccgt ctcctca         417

<210> SEQ ID NO 3
<211> LENGTH: 131
<212> TYPE: PRT
<213> ORGANISM: Artificial sequence
<220> FEATURE:
<223> OTHER INFORMATION: Synthesized

<400> SEQUENCE: 3

Met Lys Leu Pro Val Arg Leu Leu Val Leu Met Phe Trp Ile Pro Ala
1               5                   10                  15

Ser Arg Ser Asp Val Leu Met Thr Gln Thr Pro Leu Ser Leu Pro Val
            20                  25                  30

Ser Leu Gly Asp Gln Ala Ser Ile Ser Cys Arg Ser Ser Gln Ser Ile
        35                  40                  45

Val Asp Ser Asn Gly Asn Thr Tyr Leu Glu Trp Tyr Leu Gln Lys Pro
    50                  55                  60

Gly Gln Ser Pro Lys Leu Leu Ile Tyr Lys Val Ser Asn Arg Phe Ser
65                  70                  75                  80

Gly Val Pro Asp Arg Phe Ser Gly Ser Gly Ser Gly Thr Asp Phe Thr
            85                  90                  95

Leu Lys Ile Ser Arg Val Glu Ala Glu Asp Leu Gly Ile Tyr Tyr Cys
            100                 105                 110

Phe Gln Gly Ser His Val Pro Leu Thr Phe Gly Ala Gly Thr Lys Leu
        115                 120                 125

Glu Leu Lys
    130

<210> SEQ ID NO 4
<211> LENGTH: 393
<212> TYPE: DNA
<213> ORGANISM: Artificial sequence
<220> FEATURE:
<223> OTHER INFORMATION: Synthesized

<400> SEQUENCE: 4
atgaagttgc ctgttaggct gttggtgctg atgttctgga ttcctgcttc cagaagtgat      60
gttttgatga cccaaactcc actctccctg cctgtcagtc ttggagatca agcctccatc     120
tcttgcagat ctagtcagag cattgtagat agtaatggaa acacctattt agaatggtac     180
ctgcagaaac caggccagtc tccaaagctc ctgatctaca agtttccaa ccgattttct      240 ggggtcccag acaggttcag tggcagtgga tcaggacag atttcacact caagatcagc     300
agagtggagg ctgaggatct gggaattat tactgctttc aaggttcaca tgttccgctc      360
acgttcggtg ctgggaccaa gttggagctg aaa                                 393

<210> SEQ ID NO 5
<211> LENGTH: 10
<212> TYPE: PRT
<213> ORGANISM: Artificial sequence
<220> FEATURE:
<223> OTHER INFORMATION: Synthesized

<400> SEQUENCE: 5

Gly Phe Asp Phe Ser Arg Phe Trp Met Ser
1               5                   10

<210> SEQ ID NO 6
<211> LENGTH: 30
<212> TYPE: DNA
<213> ORGANISM: Artificial sequence
<220> FEATURE:
<223> OTHER INFORMATION: Synthesized

<400> SEQUENCE: 6
ggattcgatt ttagtagatt ctggatgagt                                      30

<210> SEQ ID NO 7
<211> LENGTH: 17
<212> TYPE: PRT
<213> ORGANISM: Artificial sequence
<220> FEATURE:
<223> OTHER INFORMATION: Synthesized

<400> SEQUENCE: 7

Glu Ile Asn Pro Gly Ser Ser Thr Ile Asn Tyr Thr Pro Ser Leu Lys
1               5                   10                  15

Asp

<210> SEQ ID NO 8
<211> LENGTH: 51

<210> SEQ ID NO 8
<211> LENGTH: (not shown)
<212> TYPE: DNA
<213> ORGANISM: Artificial sequence
<220> FEATURE:
<223> OTHER INFORMATION: Synthesized

<400> SEQUENCE: 8
gagattaatc caggaagcag tacgataaac tatacgccat ctctgaagga t          51

<210> SEQ ID NO 9
<211> LENGTH: 12
<212> TYPE: PRT
<213> ORGANISM: Artificial sequence
<220> FEATURE:
<223> OTHER INFORMATION: Synthesized

<400> SEQUENCE: 9

Leu Gly Tyr Gly Asn Tyr Gly Trp Ala Leu Asp Tyr
1               5                   10

<210> SEQ ID NO 10
<211> LENGTH: 36
<212> TYPE: DNA
<213> ORGANISM: Artificial sequence
<220> FEATURE:
<223> OTHER INFORMATION: Synthesized

<400> SEQUENCE: 10
ctggggtatg gtaactacgg atgggctctg gactac                            36

<210> SEQ ID NO 11
<211> LENGTH: 16
<212> TYPE: PRT
<213> ORGANISM: Artificial sequence
<220> FEATURE:
<223> OTHER INFORMATION: Synthesized

<400> SEQUENCE: 11

Arg Ser Ser Gln Ser Ile Val Asp Ser Asn Gly Asn Thr Tyr Leu Glu
1               5                   10                  15

<210> SEQ ID NO 12
<211> LENGTH: 48
<212> TYPE: DNA
<213> ORGANISM: Artificial sequence
<220> FEATURE:
<223> OTHER INFORMATION: Synthesized

<400> SEQUENCE: 12
agatctagtc agagcattgt agatagtaat ggaaacacct atttagaa               48

<210> SEQ ID NO 13
<211> LENGTH: 7
<212> TYPE: PRT
<213> ORGANISM: Artificial sequence
<220> FEATURE:
<223> OTHER INFORMATION: Synthesized

<400> SEQUENCE: 13

Lys Val Ser Asn Arg Phe Ser
1               5

<210> SEQ ID NO 14
<211> LENGTH: 21
<212> TYPE: DNA
<213> ORGANISM: Artificial sequence
<220> FEATURE:
<223> OTHER INFORMATION: Synthesized

<400> SEQUENCE: 14
aaagtttcca accgattttc t                    21

<210> SEQ ID NO 15
<211> LENGTH: 9
<212> TYPE: PRT
<213> ORGANISM: Artificial sequence
<220> FEATURE:
<223> OTHER INFORMATION: Synthesized

<400> SEQUENCE: 15

Phe Gln Gly Ser His Val Pro Leu Thr
1               5

<210> SEQ ID NO 16
<211> LENGTH: 27
<212> TYPE: DNA
<213> ORGANISM: Artificial sequence
<220> FEATURE:
<223> OTHER INFORMATION: Synthesized

<400> SEQUENCE: 16
tttcaaggtt cacatgttcc gctcacg              27

<210> SEQ ID NO 17
<211> LENGTH: 330
<212> TYPE: PRT
<213> ORGANISM: Artificial sequence
<220> FEATURE:
<223> OTHER INFORMATION: Synthesized

<400> SEQUENCE: 17

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

```
Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 18
<211> LENGTH: 993
<212> TYPE: DNA
<213> ORGANISM: Artificial sequence
<220> FEATURE:
<223> OTHER INFORMATION: Synthesized

<400> SEQUENCE: 18
gcctccacca agggcccatc ggtcttcccc ctggcaccct cctccaagag cacctctggg      60
ggcacagcgg ccctgggctg cctggtcaag gactacttcc ccgaaccggt gacggtgtcg     120
tggaactcag gcgccctgac cagcggcgtg cacaccttcc cggctgtcct acagtcctca     180
ggactctact ccctcagcag cgtggtgacc gtgccctcca gcagcttggg cacccagacc     240
tacatctgca acgtgaatca caagcccagc aacaccaagg tggacaagag agttgagccc     300
aaatcttgtg acaaaactca cacatgccca ccgtgcccag cacctgaact cctgggggga     360
ccgtcagtct tcctcttccc cccaaaaccc aaggacaccc tcatgatctc ccggacccct     420
gaggtcacat gcgtggtggt ggacgtgagc cacgaagacc ctgaggtcaa gttcaactgg     480
tacgtggacg gcgtggaggt gcataatgcc aagacaaagc cgcgggagga gcagtacaac     540
agcacgtacc gtgtggtcag cgtcctcacc gtcctgcacc aggactggct gaatggcaag     600
gagtacaagt gcaaggtctc caacaaagcc ctcccagccc catcgagaa aaccatctcc      660 aaagccaaag ggcagccccg agaaccacag gtgtacacgc tgcccccatc ccgggaggag     720
atgaccaaga accaggtcag cctgacctgc ctggtcaaag gcttctatcc cagcgacatc     780
gccgtggagt gggagagcaa tgggcagccg gagaacaact acaagaccac gcctcccgtg     840
ctggactccg acggctcctt cttcctctat agcaagctca ccgtggacaa gagcaggtgg     900
cagcagggga acgtcttctc atgctccgtg atgcatgagg ctctgcacaa ccactacacg     960
cagaagagcc tctccctgtc cccgggtaaa tga                                  993

<210> SEQ ID NO 19
<211> LENGTH: 107
<212> TYPE: PRT
<213> ORGANISM: Artificial sequence
<220> FEATURE:
<223> OTHER INFORMATION: Synthesized

<400> SEQUENCE: 19

Arg Thr Val Ala Ala Pro Ser Val Phe Ile Phe Pro Pro Ser Asp Glu
```

```
1               5                   10                  15
Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
            35                  40                  45

Ser Gly Asn Ser Gln Glu Ser Val Thr Glu Gln Asp Ser Lys Asp Ser
            50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 20
<211> LENGTH: 327
<212> TYPE: DNA
<213> ORGANISM: Artificial sequence
<220> FEATURE:
<223> OTHER INFORMATION: Synthesized

<400> SEQUENCE: 20
cggggaactg tggctgcacc atctgtcttc atcttcccgc catctgatga gcagttgaaa    60
tctggaactg cctctgttgt gtgcctgctg aataacttct atcccagaga ggccaaagta   120
cagtggaagg tggataacgc cctccaatcg ggtaactccc aggagagtgt cacagagcag   180
gacagcaagg acagcaccta cagcctcagc agcaccctga cgctgagcaa agcagactac   240
gagaaacaca agtctacgc ctgcgaagtc acccatcagg gcctgagctc gcccgtcaca   300
aagagcttca cagggagga gtgttag                                        327

<210> SEQ ID NO 21
<211> LENGTH: 330
<212> TYPE: PRT
<213> ORGANISM: Artificial sequence
<220> FEATURE:
<223> OTHER INFORMATION: Synthesized

<400> SEQUENCE: 21

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
            50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
            130                 135                 140
```

```
Val Val Val Asp Val Ser His Glu Asp Pro Glu Val Lys Phe Asn Trp
145                 150                 155                 160

Tyr Val Asp Gly Val Glu Val His Asn Val Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
                260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
        290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 22
<211> LENGTH: 330
<212> TYPE: PRT
<213> ORGANISM: Artificial sequence
<220> FEATURE:
<223> OTHER INFORMATION: Synthesized

<400> SEQUENCE: 22

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175
```

```
Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 23
<211> LENGTH: 330
<212> TYPE: PRT
<213> ORGANISM: Artificial sequence
<220> FEATURE:
<223> OTHER INFORMATION: Synthesized

<400> SEQUENCE: 23

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Ala Ala Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205
```

```
Lys Ala Leu Pro Ala Pro Ile Glu Lys Thr Ile Ser Lys Ala Lys Gly
    210                 215                 220
Gln Pro Arg Glu Pro Gln Val Tyr Thr Leu Pro Pro Ser Arg Glu Glu
225                 230                 235                 240
Met Thr Lys Asn Gln Val Ser Leu Thr Cys Leu Val Lys Gly Phe Tyr
                245                 250                 255
Pro Ser Asp Ile Ala Val Glu Trp Glu Ser Asn Gly Gln Pro Glu Asn
            260                 265                 270
Asn Tyr Lys Thr Thr Pro Pro Val Leu Asp Ser Asp Gly Ser Phe Phe
        275                 280                 285
Leu Tyr Ser Lys Leu Thr Val Asp Lys Ser Arg Trp Gln Gln Gly Asn
    290                 295                 300
Val Phe Ser Cys Ser Val Met His Glu Ala Leu His Asn His Tyr Thr
305                 310                 315                 320
Gln Lys Ser Leu Ser Leu Ser Pro Gly Lys
                325                 330

<210> SEQ ID NO 24
<211> LENGTH: 107
<212> TYPE: PRT
<213> ORGANISM: Artificial sequence
<220> FEATURE:
<223> OTHER INFORMATION: Synthesized

<400> SEQUENCE: 24

Arg Thr Val Ala Ala Pro Ser Val Phe Ile Phe Pro Pro Ser Asp Glu
1               5                   10                  15
Gln Leu Lys Ser Gly Thr Ala Ser Val Val Cys Leu Leu Asn Asn Phe
            20                  25                  30
Tyr Pro Arg Glu Ala Lys Val Gln Trp Lys Val Asp Asn Ala Leu Gln
        35                  40                  45
Ser Gly Asn Ser Gln Glu Ser Val Thr Glu Gln Asp Ser Lys Asp Ser
    50                  55                  60
Thr Tyr Ser Leu Ser Ser Thr Leu Thr Leu Ser Lys Ala Asp Tyr Glu
65                  70                  75                  80
Lys His Lys Val Tyr Ala Cys Glu Val Thr His Gln Gly Leu Ser Ser
                85                  90                  95
Pro Val Thr Lys Ser Phe Asn Arg Gly Glu Cys
            100                 105

<210> SEQ ID NO 25
<211> LENGTH: 106
<212> TYPE: PRT
<213> ORGANISM: Artificial sequence
<220> FEATURE:
<223> OTHER INFORMATION: Synthesized

<400> SEQUENCE: 25

Thr Val Ala Ala Pro Ser Val Phe Ile Phe Pro Pro Ser Asp Glu Gln
1               5                   10                  15
Leu Lys Ser Gly Thr Ala Ser Val Val Cys Leu Leu Asn Asn Phe Tyr
            20                  25                  30
Pro Arg Glu Ala Lys Val Gln Trp Lys Val Asp Asn Ala Leu Gln Ser
        35                  40                  45
Gly Asn Ser Gln Glu Ser Val Thr Glu Gln Asp Ser Lys Asp Ser Thr
    50                  55                  60
Tyr Ser Leu Ser Ser Thr Leu Thr Leu Ser Lys Ala Asp Tyr Glu Lys
65                  70                  75                  80
```

-continued

```
His Lys Val Tyr Ala Cys Glu Val Thr His Gln Gly Leu Ser Ser Pro
                85                  90                  95

Val Thr Lys Ser Phe Asn Arg Gly Glu Cys
            100                 105

<210> SEQ ID NO 26
<211> LENGTH: 147
<212> TYPE: PRT
<213> ORGANISM: Homo sapiens

<400> SEQUENCE: 26

Met Ala Ser His Arg Leu Leu Leu Cys Leu Ala Gly Leu Val Phe
1               5                   10                  15

Val Ser Glu Ala Gly Pro Thr Gly Thr Gly Glu Ser Lys Cys Pro Leu
                20                  25                  30

Met Val Lys Val Leu Asp Ala Val Arg Gly Ser Pro Ala Ile Asn Val
                35                  40                  45

Ala Val His Val Phe Arg Lys Ala Ala Asp Asp Thr Trp Glu Pro Phe
        50                  55                  60

Ala Ser Gly Lys Thr Ser Glu Ser Gly Glu Leu His Gly Leu Thr Thr
65                  70                  75                  80

Glu Glu Glu Phe Val Glu Gly Ile Tyr Lys Val Glu Ile Asp Thr Lys
                85                  90                  95

Ser Tyr Trp Lys Ala Leu Gly Ile Ser Pro Phe His Glu His Ala Glu
                100                 105                 110

Val Val Phe Thr Ala Asn Asp Ser Gly Pro Arg Arg Tyr Thr Ile Ala
            115                 120                 125

Ala Leu Leu Ser Pro Tyr Ser Tyr Ser Thr Thr Ala Val Val Thr Asn
            130                 135                 140

Pro Lys Glu
145

<210> SEQ ID NO 27
<211> LENGTH: 127
<212> TYPE: PRT
<213> ORGANISM: Homo sapiens

<400> SEQUENCE: 27

Gly Pro Thr Gly Thr Gly Glu Ser Lys Cys Pro Leu Met Val Lys Val
1               5                   10                  15

Leu Asp Ala Val Arg Gly Ser Pro Ala Ile Asn Val Ala Val His Val
                20                  25                  30

Phe Arg Lys Ala Ala Asp Asp Thr Trp Glu Pro Phe Ala Ser Gly Lys
            35                  40                  45

Thr Ser Glu Ser Gly Glu Leu His Gly Leu Thr Thr Glu Glu Gln Phe
        50                  55                  60

Val Glu Gly Ile Tyr Lys Val Glu Ile Asp Thr Lys Ser Tyr Trp Lys
65                  70                  75                  80

Ala Leu Gly Ile Ser Pro Phe His Glu His Ala Glu Val Val Phe Thr
                85                  90                  95

Ala Asn Asp Ser Gly Pro Arg Arg Tyr Thr Ile Ala Ala Leu Leu Ser
                100                 105                 110

Pro Tyr Ser Tyr Ser Thr Thr Ala Val Val Thr Asn Pro Lys Glu
            115                 120                 125

<210> SEQ ID NO 28
```

```
<211> LENGTH: 127
<212> TYPE: PRT
<213> ORGANISM: Homo sapiens

<400> SEQUENCE: 28

Gly Pro Thr Gly Thr Gly Glu Ser Lys Cys Pro Leu Met Val Lys Val
1               5                   10                  15

Leu Asp Ala Val Arg Gly Ser Pro Ala Ile Asn Val Ala Val His Val
            20                  25                  30

Phe Arg Lys Ala Ala Asp Asp Thr Trp Glu Pro Phe Ala Ser Gly Lys
        35                  40                  45

Thr Ser Glu Ser Gly Glu Leu His Gly Leu Thr Thr Glu Glu Gln Phe
    50                  55                  60

Val Glu Gly Ile Tyr Lys Val Glu Ile Asp Thr Lys Ser Tyr Trp Lys
65                  70                  75                  80

Ala Leu Gly Ile Ser Pro Phe His Glu His Ala Glu Val Val Phe Thr
                85                  90                  95

Ala Asn Asp Ser Gly Pro Arg Arg Tyr Thr Ile Ala Ala Leu Leu Ser
            100                 105                 110

Pro Tyr Ser Tyr Ser Thr Thr Ala Val Val Thr Asn Pro Lys Glu
        115                 120                 125

<210> SEQ ID NO 29
<211> LENGTH: 138
<212> TYPE: PRT
<213> ORGANISM: Homo sapiens

<400> SEQUENCE: 29

Met Ala Ser His Arg Leu Leu Leu Leu Cys Leu Ala Gly Leu Val Phe
1               5                   10                  15

Val Ser Glu Ala Gly Pro Thr Gly Thr Gly Glu Ser Lys Cys Pro Leu
            20                  25                  30

Met Val Lys Val Leu Asp Ala Val Arg Gly Ser Pro Ala Ile Asn Val
        35                  40                  45

Ala Val His Val Phe Arg Lys Ala Ala Asp Asp Thr Trp Glu Pro Phe
    50                  55                  60

Ala Ser Gly Lys Thr Ser Glu Ser Gly Glu Leu His Gly Leu Thr Thr
65                  70                  75                  80

Glu Glu Gln Phe Val Glu Gly Ile Tyr Lys Val Glu Ile Asp Thr Lys
                85                  90                  95

Ser Tyr Trp Lys Ala Leu Gly Ile Ser Pro Phe His Glu His Ala Glu
            100                 105                 110

Val Val Phe Thr Ala Asn Asp Ser Gly Pro Arg Arg Tyr Thr Ile Ala
        115                 120                 125

Ala Leu Leu Ser Pro Tyr Ser Tyr Ser Thr Thr Ala Val Val Thr Asn Pro Lys Glu
    130                 135

<210> SEQ ID NO 30
<211> LENGTH: 9
<212> TYPE: PRT
<213> ORGANISM: Homo sapiens

<400> SEQUENCE: 30

Gly Pro Arg Arg Tyr Thr Ile Ala Ala
1               5

<210> SEQ ID NO 31
<211> LENGTH: 41
```

<212> TYPE: PRT
<213> ORGANISM: Homo sapiens

<400> SEQUENCE: 31

Phe His Glu His Ala Glu Val Val Phe Thr Ala Asn Asp Ser Gly Pro
1               5                   10                  15

Arg Arg Tyr Thr Ile Ala Ala Leu Leu Ser Pro Tyr Ser Tyr Ser Thr
            20                  25                  30

Thr Ala Val Val Thr Asn Pro Lys Glu
            35                  40

<210> SEQ ID NO 32
<211> LENGTH: 990
<212> TYPE: DNA
<213> ORGANISM: Artificial sequence
<220> FEATURE:
<223> OTHER INFORMATION: Synthesized

<400> SEQUENCE: 32
gcctccacca agggtccatc ggtcttcccc ctggcaccct cctccaagag cacctctggg      60
ggcacagcgg ccctgggctg cctggtcaag gactacttcc ccgaaccggt gacggtgtcg     120
tggaactcag gcgccctgac cagcggcgtg cacaccttcc cggctgtcct acagtcctca     180
ggactctact ccctcagcag cgtggtgacc gtgccctcca gcagcttggg cacccagacc     240
tacatctgca acgtgaatca caagcccagc aacaccaagg tggacaagag agttgagccc     300
aaatcttgtg acaaaactca cacatgccca ccgtgcccag cacctgaact cctgggggga     360
ccgtcagtct tcctcttccc cccaaaaccc aaggacaccc tcatgatctc ccggacccct     420
gaggtcacat gcgtggtggt ggacgtgagc cacgaagacc ctgaggtcaa gttcaactgg     480
tacgtggacg gcgtggaggt gcataatgcc aagacaaagc cgcggaggga gcagtacaac     540
agcacgtacc gtgtggtcag cgtcctcacc gtcctgcacc aggactggct gaatggcaag     600
gagtacaagt gcaaggtctc caacaaagcc ctcccagccc ccatcgagaa aaccatctcc     660
aaagccaaag ggcagccccg agaaccacag gtgtacaccc tgcccccatc ccgggaggag     720
atgaccaaga accaggtcag cctgacctgc ctggtcaaag gcttctatcc cagcgacatc     780
gccgtggagt gggagagcaa tgggcagccg gagaacaact acaagaccac gcctcccgtg     840
ctggactccg acggctcctt cttcctctat agcaagctca ccgtggacaa gagcaggtgg     900
cagcagggga acgtcttctc atgctccgtg atgcatgagg ctctgcacaa ccactacacg     960
cagaagagcc tctccctgtc cccgggtaaa                                     990

<210> SEQ ID NO 33
<211> LENGTH: 321
<212> TYPE: DNA
<213> ORGANISM: Artificial sequence
<220> FEATURE:
<223> OTHER INFORMATION: Synthesized

<400> SEQUENCE: 33
cgaactgtgg ctgcaccatc tgtcttcatc ttcccgccat ctgatgagca gttgaaatct      60
ggaactgcct ctgttgtgtg cctgctgaat aacttctatc ccagagaggc caaagtacag     120
tggaaggtgg ataacgccct ccaatcgggt aactcccagg agagtgtcac agagcaggac     180
agcaaggaca gcacctacag cctcagcagc accctgacgc tgagcaaagc agactacgag     240
aaacacaaag tctacgcctg cgaagtcacc catcagggcc tgagctcgcc cgtcacaaag     300
agcttcaaca ggggagagtg t                                              321

<210> SEQ ID NO 34
<211> LENGTH: 318
<212> TYPE: DNA
<213> ORGANISM: Artificial sequence
<220> FEATURE:
<223> OTHER INFORMATION: Synthesized

<400> SEQUENCE: 34

```
actgtggctg caccatctgt cttcatcttc ccgccatctg atgagcagtt gaaatctgga      60
actgcctctg ttgtgtgcct gctgaataac ttctatccca gagaggccaa agtacagtgg     120
aaggtggata cgccctcca atcgggtaac tcccaggaga gtgtcacaga gcaggacagc     180
aaggacagca cctacagcct cagcagcacc ctgacgctga gcaaagcaga ctacgagaaa     240
cacaaagtct acgcctgcga agtcacccat cagggcctga gctcgcccgt cacaaagagc     300
ttcaacaggg gagagtgt                                                   318
```

<210> SEQ ID NO 35
<211> LENGTH: 19
<212> TYPE: PRT
<213> ORGANISM: Artificial sequence
<220> FEATURE:
<223> OTHER INFORMATION: Synthesized

<400> SEQUENCE: 35

```
Met Asn Phe Gly Leu Ser Leu Ile Phe Leu Val Leu Val Leu Lys Gly
1               5                   10                  15

Val Gln Cys
```

<210> SEQ ID NO 36
<211> LENGTH: 57
<212> TYPE: DNA
<213> ORGANISM: Artificial sequence
<220> FEATURE:
<223> OTHER INFORMATION: Synthesized

<400> SEQUENCE: 36

```
atgaactttg ggctcagctt gattttcctt gtccttgttt taaaaggtgt ccagtgt        57
```

<210> SEQ ID NO 37
<211> LENGTH: 20
<212> TYPE: PRT
<213> ORGANISM: Artificial sequence
<220> FEATURE:
<223> OTHER INFORMATION: Synthesized

<400> SEQUENCE: 37

```
Met Glu Ser His Thr Gln Val Phe Val Phe Val Phe Leu Trp Leu Ser
1               5                   10                  15

Gly Val Asp Gly
            20
```

<210> SEQ ID NO 38
<211> LENGTH: 60
<212> TYPE: DNA
<213> ORGANISM: Artificial sequence
<220> FEATURE:
<223> OTHER INFORMATION: Synthesized

<400> SEQUENCE: 38

```
atggagtcac atactcaggt ctttgtattc gtgtttctct ggttgtctgg tgttgacgga     60
```

```
<210> SEQ ID NO 39
<211> LENGTH: 5
<212> TYPE: PRT
<213> ORGANISM: Artificial sequence
<220> FEATURE:
<223> OTHER INFORMATION: Synthesized

<400> SEQUENCE: 39

Ser Tyr Thr Met Ser
1               5

<210> SEQ ID NO 40
<211> LENGTH: 17
<212> TYPE: PRT
<213> ORGANISM: Artificial sequence
<220> FEATURE:
<223> OTHER INFORMATION: Synthesized

<400> SEQUENCE: 40

Glu Ile Asn Asn Ser Gly Asp Thr Thr Tyr Tyr Pro Asp Thr Val Lys
1               5                   10                  15

Gly

<210> SEQ ID NO 41
<211> LENGTH: 15
<212> TYPE: PRT
<213> ORGANISM: Artificial sequence
<220> FEATURE:
<223> OTHER INFORMATION: Synthesized

<400> SEQUENCE: 41

His Tyr Tyr Tyr Gly Gly Gly Tyr Gly Gly Trp Phe Phe Asp Val
1               5                   10                  15

<210> SEQ ID NO 42
<211> LENGTH: 16
<212> TYPE: PRT
<213> ORGANISM: Artificial sequence
<220> FEATURE:
<223> OTHER INFORMATION: Synthesized

<400> SEQUENCE: 42

Arg Ser Asn Lys Ser Leu Leu His Ser Asn Gly Asn Thr Tyr Leu Tyr
1               5                   10                  15

<210> SEQ ID NO 43
<211> LENGTH: 7
<212> TYPE: PRT
<213> ORGANISM: Artificial sequence
<220> FEATURE:
<223> OTHER INFORMATION: Synthesized

<400> SEQUENCE: 43

Arg Val Ser Asn Leu Ala Ser
1               5

<210> SEQ ID NO 44
<211> LENGTH: 9
<212> TYPE: PRT
<213> ORGANISM: Artificial sequence
<220> FEATURE:
<223> OTHER INFORMATION: Synthesized

<400> SEQUENCE: 44

Met Gln His Leu Glu Tyr Pro Leu Thr
1               5
```

<210> SEQ ID NO 45
<211> LENGTH: 9
<212> TYPE: PRT
<213> ORGANISM: Artificial sequence
<220> FEATURE:
<223> OTHER INFORMATION: Synthesized

<400> SEQUENCE: 45

Glu His Ala Glu Val Val Phe Thr Ala
1               5

<210> SEQ ID NO 46
<211> LENGTH: 5
<212> TYPE: PRT
<213> ORGANISM: Artificial sequence
<220> FEATURE:
<223> OTHER INFORMATION: Synthesized

<400> SEQUENCE: 46

Asn Tyr Ala Met Ser
1               5

<210> SEQ ID NO 47
<211> LENGTH: 16
<212> TYPE: PRT
<213> ORGANISM: Artificial sequence
<220> FEATURE:
<223> OTHER INFORMATION: Synthesized

<400> SEQUENCE: 47

Ser Ile Ser Ser Gly Gly Ser Thr Tyr Tyr Pro Asp Ser Val Lys Gly
1               5                   10                  15

<210> SEQ ID NO 48
<211> LENGTH: 9
<212> TYPE: PRT
<213> ORGANISM: Artificial sequence
<220> FEATURE:
<223> OTHER INFORMATION: Synthesized

<400> SEQUENCE: 48

Tyr Tyr Tyr Gly Gln Tyr Phe Asp Phe
1               5

<210> SEQ ID NO 49
<211> LENGTH: 11
<212> TYPE: PRT
<213> ORGANISM: Artificial sequence
<220> FEATURE:
<223> OTHER INFORMATION: Synthesized

<400> SEQUENCE: 49

Lys Ala Ser Gln Asp Val Ser Thr Thr Val Ala
1               5                   10

<210> SEQ ID NO 50
<211> LENGTH: 7
<212> TYPE: PRT
<213> ORGANISM: Artificial sequence
<220> FEATURE:
<223> OTHER INFORMATION: Synthesized

<400> SEQUENCE: 50

Ser Ala Ser Tyr Arg Cys Thr
1               5

```
<210> SEQ ID NO 51
<211> LENGTH: 9
<212> TYPE: PRT
<213> ORGANISM: Artificial sequence
<220> FEATURE:
<223> OTHER INFORMATION: Synthesized

<400> SEQUENCE: 51

Gln Gln His Tyr Ser Thr Pro Leu Thr
1               5

<210> SEQ ID NO 52
<211> LENGTH: 5
<212> TYPE: PRT
<213> ORGANISM: Artificial sequence
<220> FEATURE:
<223> OTHER INFORMATION: Synthesized

<400> SEQUENCE: 52

Asn Tyr Tyr Met Ser
1               5

<210> SEQ ID NO 53
<211> LENGTH: 17
<212> TYPE: PRT
<213> ORGANISM: Artificial sequence
<220> FEATURE:
<223> OTHER INFORMATION: Synthesized

<400> SEQUENCE: 53

Tyr Ile Ser Ile Asp Gly Asn Asn Ile Tyr His Pro Asp Ser Val Lys
1               5                   10                  15

Gly

<210> SEQ ID NO 54
<211> LENGTH: 9
<212> TYPE: PRT
<213> ORGANISM: Artificial sequence
<220> FEATURE:
<223> OTHER INFORMATION: Synthesized

<400> SEQUENCE: 54

Asp Ser Asp Tyr Gly Tyr Phe Asp Val
1               5

<210> SEQ ID NO 55
<211> LENGTH: 16
<212> TYPE: PRT
<213> ORGANISM: Artificial sequence
<220> FEATURE:
<223> OTHER INFORMATION: Synthesized

<400> SEQUENCE: 55

Arg Ser Ser Gln Ser Ile Val His Ser Asn Gly Asn Thr Tyr Leu Glu
1               5                   10                  15

<210> SEQ ID NO 56
<211> LENGTH: 7
<212> TYPE: PRT
<213> ORGANISM: Artificial sequence
<220> FEATURE:
<223> OTHER INFORMATION: Synthesized

<400> SEQUENCE: 56

Lys Val Ser Lys Arg Phe Ser
1               5
```

<210> SEQ ID NO 57
<211> LENGTH: 9
<212> TYPE: PRT
<213> ORGANISM: Artificial sequence
<220> FEATURE:
<223> OTHER INFORMATION: Synthesized

<400> SEQUENCE: 57

Phe Gln Gly Ser His Val Pro Leu Thr
1               5

<210> SEQ ID NO 58
<211> LENGTH: 455
<212> TYPE: PRT
<213> ORGANISM: Artificial sequence
<220> FEATURE:
<223> OTHER INFORMATION: Synthesized

<400> SEQUENCE: 58

Glu Val Gln Leu Val Glu Ser Gly Gly Asp Leu Val Lys Pro Gly Gly
1               5                   10                  15

Ser Leu Lys Leu Ser Cys Ala Ala Ser Gly Phe Thr Phe Ser Asn Tyr
            20                  25                  30

Gly Met Ser Trp Ile Arg Gln Thr Pro Asp Lys Arg Leu Glu Trp Val
        35                  40                  45

Ala Thr Ile Ser Ser Gly Gly Thr Tyr Thr Tyr Tyr Thr Glu Ser Val
    50                  55                  60

Lys Gly Arg Phe Thr Val Ser Arg Asp Asn Ala Lys Asn Thr Leu Ser
65                  70                  75                  80

Leu Gln Met Ser Asn Leu Lys Ser Asp Asp Thr Ala Met Tyr Tyr Cys
                85                  90                  95

Thr Arg Gln Ala Tyr Gly Arg Glu Tyr Phe Asp Val Trp Gly Thr Gly
            100                 105                 110

Thr Thr Val Thr Val Ser Ser Ala Lys Thr Thr Pro Pro Ser Val Tyr
        115                 120                 125

Pro Leu Ala Pro Gly Cys Gly Asp Thr Thr Gly Ser Ser Val Thr Leu
    130                 135                 140

Gly Cys Leu Val Lys Gly Tyr Phe Pro Glu Ser Val Thr Val Thr Trp
145                 150                 155                 160

Asn Ser Gly Ser Leu Ser Ser Ser Val His Thr Phe Pro Ala Leu Leu
                165                 170                 175

Gln Ser Gly Leu Tyr Thr Met Ser Ser Ser Val Thr Val Pro Ser Ser
            180                 185                 190

Thr Trp Pro Ser Gln Thr Val Thr Cys Ser Val Ala His Pro Ala Ser
        195                 200                 205

Ser Thr Thr Val Asp Lys Lys Leu Glu Pro Ser Gly Pro Ile Ser Thr
    210                 215                 220

Ile Asn Pro Cys Pro Pro Cys Lys Glu Cys His Lys Cys Pro Ala Pro
225                 230                 235                 240

Asn Leu Glu Gly Gly Pro Ser Val Phe Ile Phe Pro Pro Asn Ile Lys
                245                 250                 255

Asp Val Leu Met Ile Ser Leu Thr Pro Lys Val Thr Cys Val Val Val
            260                 265                 270

Asp Val Ser Glu Asp Asp Pro Asp Val Arg Ile Ser Trp Phe Val Asn
        275                 280                 285

Asn Val Glu Val His Thr Ala Gln Thr Gln Thr His Arg Glu Asp Tyr
    290                 295                 300

```
Asn Ser Thr Ile Arg Val Ser Ala Leu Pro Ile Gln His Gln Asp
305                 310                 315                 320

Trp Met Ser Gly Lys Glu Phe Lys Cys Lys Val Asn Asn Lys Asp Leu
            325                 330                 335

Pro Ser Pro Ile Glu Arg Thr Ile Ser Lys Ile Lys Gly Leu Val Arg
            340                 345                 350

Ala Pro Gln Val Tyr Ile Leu Pro Pro Ala Glu Gln Leu Ser Arg
            355                 360                 365

Lys Asp Val Ser Leu Thr Cys Leu Val Val Gly Phe Asn Pro Gly Asp
370                 375                 380

Ile Ser Val Glu Trp Thr Ser Asn Gly His Thr Glu Glu Asn Tyr Lys
385                 390                 395                 400

Asp Thr Ala Pro Val Leu Asp Ser Asp Gly Ser Tyr Phe Ile Tyr Ser
                405                 410                 415

Lys Leu Asp Ile Lys Thr Ser Thr Val Gly Glu Asn Arg Phe Leu Leu
            420                 425                 430

Met Gln Arg Glu Thr Arg Gly Ser Glu Lys Leu Leu Pro Glu Glu Asp
            435                 440                 445

His Leu Pro Ser Pro Gly Lys
    450                 455

<210> SEQ ID NO 59
<211> LENGTH: 219
<212> TYPE: PRT
<213> ORGANISM: Artificial sequence
<220> FEATURE:
<223> OTHER INFORMATION: Synthesized

<400> SEQUENCE: 59

Asp Ile Val Met Ser Gln Ser Pro Ser Ser Leu Ala Val Ser Ala Gly
1               5                   10                  15

Glu Lys Val Thr Met Ser Cys Lys Ser Ser Gln Ser Leu Phe Asp Ser
            20                  25                  30

Arg Thr Arg Lys Asn Tyr Leu Ala Trp Tyr Gln Gln Lys Pro Gly Gln
        35                  40                  45

Ser Pro Lys Leu Leu Ile Tyr Trp Ala Ser Asn Arg Glu Ser Gly Val
    50                  55                  60

Pro Asp Arg Phe Ile Gly Ser Gly Ser Gly Thr Asp Phe Thr Leu Thr
65                  70                  75                  80

Ile Ser Ser Val Gln Ala Glu Asp Leu Ala Val Tyr Phe Cys Lys Gln
                85                  90                  95

Ser Asn Tyr Leu Arg Thr Phe Gly Gly Gly Thr Arg Val Glu Ile Lys
            100                 105                 110

Arg Ala Asp Ala Ala Pro Thr Val Ser Ile Phe Pro Pro Ser Ser Glu
        115                 120                 125

Gln Leu Thr Ser Gly Gly Ala Ser Val Val Cys Phe Leu Asn Asn Phe
    130                 135                 140

Tyr Pro Lys Asp Ile Asn Val Lys Trp Lys Ile Asp Gly Ser Glu Arg
145                 150                 155                 160

Gln Asn Gly Val Leu Asn Ser Trp Thr Asp Gln Asp Ser Lys Asp Ser
                165                 170                 175

Thr Tyr Ser Met Ser Ser Thr Leu Thr Leu Thr Lys Asp Glu Tyr Glu
            180                 185                 190

Arg His Asn Ser Tyr Thr Cys Glu Ala Thr His Lys Thr Ser Thr Ser
        195                 200                 205
```

Pro Ile Val Lys Ser Phe Asn Arg Asn Glu Cys
    210                 215

<210> SEQ ID NO 60
<211> LENGTH: 5
<212> TYPE: PRT
<213> ORGANISM: Artificial sequence
<220> FEATURE:
<223> OTHER INFORMATION: Synthesized

<400> SEQUENCE: 60

Arg Tyr Trp Ile Thr
1               5

<210> SEQ ID NO 61
<211> LENGTH: 17
<212> TYPE: PRT
<213> ORGANISM: Artificial sequence
<220> FEATURE:
<223> OTHER INFORMATION: Synthesized

<400> SEQUENCE: 61

Asp Ile Tyr Pro Gly Ser Gly Arg Thr Asn Tyr Asn Glu Lys Phe Lys
1               5                   10                  15

Asn

<210> SEQ ID NO 62
<211> LENGTH: 9
<212> TYPE: PRT
<213> ORGANISM: Artificial sequence
<220> FEATURE:
<223> OTHER INFORMATION: Synthesized

<400> SEQUENCE: 62

Tyr Tyr Gly Ser Thr Tyr Phe Tyr Val
1               5

<210> SEQ ID NO 63
<211> LENGTH: 16
<212> TYPE: PRT
<213> ORGANISM: Artificial sequence
<220> FEATURE:
<223> OTHER INFORMATION: Synthesized

<400> SEQUENCE: 63

Arg Ser Ser Lys Ser Leu Leu Tyr Lys Asp Gly Lys Thr Tyr Leu Asn
1               5                   10                  15

<210> SEQ ID NO 64
<211> LENGTH: 7
<212> TYPE: PRT
<213> ORGANISM: Artificial sequence
<220> FEATURE:
<223> OTHER INFORMATION: Synthesized

<400> SEQUENCE: 64

Leu Met Ser Thr Arg Ala Ser
1               5

<210> SEQ ID NO 65
<211> LENGTH: 9
<212> TYPE: PRT
<213> ORGANISM: Artificial sequence
<220> FEATURE:
<223> OTHER INFORMATION: Synthesized

```
<400> SEQUENCE: 65

Gln Gln Leu Val Glu Tyr Pro Arg Thr
1               5

<210> SEQ ID NO 66
<211> LENGTH: 5
<212> TYPE: PRT
<213> ORGANISM: Artificial sequence
<220> FEATURE:
<223> OTHER INFORMATION: Synthesized

<400> SEQUENCE: 66

Ser Tyr Ala Met Ser
1               5

<210> SEQ ID NO 67
<211> LENGTH: 17
<212> TYPE: PRT
<213> ORGANISM: Artificial sequence
<220> FEATURE:
<223> OTHER INFORMATION: Synthesized

<400> SEQUENCE: 67

Ser Ile Ser Gly Ser Gly Asp Thr Thr Lys Tyr Thr Asp Ser Val Lys
1               5                   10                  15

Gly

<210> SEQ ID NO 68
<211> LENGTH: 11
<212> TYPE: PRT
<213> ORGANISM: Artificial sequence
<220> FEATURE:
<223> OTHER INFORMATION: Synthesized

<400> SEQUENCE: 68

Asp Gly Ser Gly Arg Ile Asp Pro Phe Ala Leu
1               5                   10

<210> SEQ ID NO 69
<211> LENGTH: 16
<212> TYPE: PRT
<213> ORGANISM: Artificial sequence
<220> FEATURE:
<223> OTHER INFORMATION: Synthesized

<400> SEQUENCE: 69

Arg Ser Ser Arg Ser Leu Val Tyr Ser Asp Gly Asn Ile Tyr Leu Asn
1               5                   10                  15

<210> SEQ ID NO 70
<211> LENGTH: 8
<212> TYPE: PRT
<213> ORGANISM: Artificial sequence
<220> FEATURE:
<223> OTHER INFORMATION: Synthesized

<400> SEQUENCE: 70

Lys Val Ser Asn Arg Asp Ser Gly
1               5

<210> SEQ ID NO 71
<211> LENGTH: 9
<212> TYPE: PRT
<213> ORGANISM: Artificial sequence
<220> FEATURE:
<223> OTHER INFORMATION: Synthesized
```

```
<400> SEQUENCE: 71

Met Gln Gly Thr His Trp Pro Arg Thr
1               5

<210> SEQ ID NO 72
<211> LENGTH: 13
<212> TYPE: PRT
<213> ORGANISM: Artificial sequence
<220> FEATURE:
<223> OTHER INFORMATION: Synthesized

<400> SEQUENCE: 72

Ala Asp Asp Thr Trp Glu Pro Phe Ala Ser Gly Lys Thr
1               5                   10

<210> SEQ ID NO 73
<211> LENGTH: 13
<212> TYPE: PRT
<213> ORGANISM: Artificial sequence
<220> FEATURE:
<223> OTHER INFORMATION: Synthesized

<400> SEQUENCE: 73

Thr Ser Glu Ser Gly Glu Leu His Gly Leu Thr Thr Glu
1               5                   10

<210> SEQ ID NO 74
<211> LENGTH: 13
<212> TYPE: PRT
<213> ORGANISM: Artificial sequence
<220> FEATURE:
<223> OTHER INFORMATION: Synthesized

<400> SEQUENCE: 74

Ala Leu Leu Ser Pro Tyr Ser Tyr Ser Thr Thr Ala Val
1               5                   10

<210> SEQ ID NO 75
<211> LENGTH: 5
<212> TYPE: PRT
<213> ORGANISM: Artificial sequence
<220> FEATURE:
<223> OTHER INFORMATION: Synthesized

<400> SEQUENCE: 75

Ser Tyr Thr Met Ser
1               5

<210> SEQ ID NO 76
<211> LENGTH: 17
<212> TYPE: PRT
<213> ORGANISM: Artificial sequence
<220> FEATURE:
<223> OTHER INFORMATION: Synthesized

<400> SEQUENCE: 76

Glu Ile Ser Asn Ser Gly Asp Thr Thr Tyr Tyr Pro Asp Thr Val Lys
1               5                   10                  15

Gly

<210> SEQ ID NO 77
<211> LENGTH: 15
<212> TYPE: PRT
<213> ORGANISM: Artificial sequence
<220> FEATURE:
```

```
<223> OTHER INFORMATION: Synthesized

<400> SEQUENCE: 77

His Tyr Tyr Tyr Gly Gly Tyr Gly Gly Trp Phe Phe Asp Val
1               5                   10                  15

<210> SEQ ID NO 78
<211> LENGTH: 16
<212> TYPE: PRT
<213> ORGANISM: Artificial sequence
<220> FEATURE:
<223> OTHER INFORMATION: Synthesized

<400> SEQUENCE: 78

Arg Ser Ser Lys Ser Leu Leu His Ser Asn Gly Asn Thr Tyr Leu Tyr
1               5                   10                  15

<210> SEQ ID NO 79
<211> LENGTH: 7
<212> TYPE: PRT
<213> ORGANISM: Artificial sequence
<220> FEATURE:
<223> OTHER INFORMATION: Synthesized

<400> SEQUENCE: 79

Arg Val Ser Asn Leu Ala Ser
1               5

<210> SEQ ID NO 80
<211> LENGTH: 9
<212> TYPE: PRT
<213> ORGANISM: Artificial sequence
<220> FEATURE:
<223> OTHER INFORMATION: Synthesized

<400> SEQUENCE: 80

Met Gln His Leu Glu Tyr Pro Leu Thr
1               5

<210> SEQ ID NO 81
<211> LENGTH: 121
<212> TYPE: PRT
<213> ORGANISM: Artificial sequence
<220> FEATURE:
<223> OTHER INFORMATION: Synthesized

<400> SEQUENCE: 81

Glu Val Lys Leu Leu Glu Ser Gly Gly Leu Val Gln Pro Gly Gly
1               5                   10                  15

Ser Leu Asn Leu Ser Cys Val Ala Ser Gly Phe Asp Phe Ser Arg Phe
                20                  25                  30

Trp Met Ser Trp Ala Arg Gln Ala Pro Gly Arg Gly Gln Glu Trp Ile
            35                  40                  45

Gly Glu Ile Asn Pro Gly Ser Ser Thr Ile Asn Tyr Thr Pro Ser Leu
        50                  55                  60

Lys Asp Lys Phe Ile Ile Ser Arg Asp Asn Ala Lys Asn Thr Leu Phe
65                  70                  75                  80

Leu Gln Met Ser Lys Val Arg Ser Glu Asp Ser Ala Leu Tyr Tyr Cys
                85                  90                  95

Ala Arg Leu Gly Tyr Gly Asn Tyr Gly Trp Ala Leu Asp Tyr Trp Gly
            100                 105                 110

Gln Gly Thr Ser Val Thr Val Ser Ser
            115                 120
```

```
<210> SEQ ID NO 82
<211> LENGTH: 122
<212> TYPE: PRT
<213> ORGANISM: Artificial sequence
<220> FEATURE:
<223> OTHER INFORMATION: Synthesized

<400> SEQUENCE: 82

Glu Val Lys Leu Val Glu Ser Gly Gly Gly Leu Val Gln Pro Gly Gly
1               5                   10                  15

Ser Arg Lys Leu Ser Cys Ala Ala Ser Gly Phe Thr Phe Ser Asp Tyr
            20                  25                  30

Gly Met Ala Trp Val Arg Gln Ala Pro Gly Lys Gly Pro Glu Trp Val
        35                  40                  45

Ala Phe Ile Ser Asn Leu Ala Tyr Ser Ile Tyr Tyr Ala Asp Thr Val
    50                  55                  60

Thr Gly Arg Phe Thr Ile Ser Arg Glu Asn Ala Lys Asn Thr Leu Tyr
65                  70                  75                  80

Leu Glu Met Ser Ser Leu Arg Ser Glu Asp Thr Ala Met Tyr Tyr Cys
                85                  90                  95

Ala Arg Tyr Asp Tyr Asp Asn Ile Leu Asp Tyr Val Met Asp Tyr Trp
            100                 105                 110

Gly Gln Gly Thr Ser Val Thr Val Ser Ser
        115                 120

<210> SEQ ID NO 83
<211> LENGTH: 112
<212> TYPE: PRT
<213> ORGANISM: Artificial sequence
<220> FEATURE:
<223> OTHER INFORMATION: Synthesized

<400> SEQUENCE: 83

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Gly Met Ser Trp Val Arg Gln Ala Pro Gly Lys Gly Leu Glu Leu Val
        35                  40                  45

Ala Ser Ile Asn Ser Asn Gly Gly Ser Thr Tyr Tyr Pro Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Ser Gly Asp Tyr Trp Gly Gln Gly Thr Thr Val Thr Val Ser Ser
            100                 105                 110

<210> SEQ ID NO 84
<211> LENGTH: 113
<212> TYPE: PRT
<213> ORGANISM: Homo sapiens

<400> SEQUENCE: 84

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30
```

Ser Met Asn Trp Val Arg Gln Ala Pro Gly Lys Gly Leu Glu Trp Val
            35                  40                  45

Ser Tyr Ile Ser Ser Ser Ser Thr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Tyr Phe Asp Tyr Trp Gly Gln Gly Thr Leu Val Thr Val Ser
            100                 105                 110

Ser

<210> SEQ ID NO 85
<211> LENGTH: 121
<212> TYPE: PRT
<213> ORGANISM: Artificial sequence
<220> FEATURE:
<223> OTHER INFORMATION: Synthesized

<400> SEQUENCE: 85

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asp Phe Ser Arg Phe
            20                  25                  30

Trp Met Ser Trp Val Arg Gln Ala Pro Gly Lys Gly Leu Glu Leu Val
            35                  40                  45

Ala Glu Ile Asn Pro Gly Ser Ser Thr Ile Asn Tyr Thr Pro Ser Leu
    50                  55                  60

Lys Asp Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Ser Leu Gly Tyr Gly Asn Tyr Gly Trp Ala Leu Asp Tyr Trp Gly
            100                 105                 110

Gln Gly Thr Thr Val Thr Val Ser Ser
            115                 120

<210> SEQ ID NO 86
<211> LENGTH: 121
<212> TYPE: PRT
<213> ORGANISM: Artificial sequence
<220> FEATURE:
<223> OTHER INFORMATION: Synthesized

<400> SEQUENCE: 86

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asp Phe Ser Arg Phe
            20                  25                  30

Trp Met Ser Trp Ala Arg Gln Ala Pro Gly Lys Gly Gln Glu Trp Ile
            35                  40                  45

Gly Glu Ile Asn Pro Gly Ser Ser Thr Ile Asn Tyr Thr Pro Ser Leu
    50                  55                  60

Lys Asp Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Leu Gly Tyr Gly Asn Tyr Gly Trp Ala Leu Asp Tyr Trp Gly
            100                 105                 110

Gln Gly Thr Thr Val Thr Val Ser Ser
        115                 120

<210> SEQ ID NO 87
<211> LENGTH: 112
<212> TYPE: PRT
<213> ORGANISM: Artificial sequence
<220> FEATURE:
<223> OTHER INFORMATION: Synthesized

<400> SEQUENCE: 87

Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Ser Ile Val Asp Ser
            20                  25                  30

Asn Gly Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Ile Tyr Tyr Cys Phe Gln Gly
                85                  90                  95

Ser His Val Pro Leu Thr Phe Gly Ala Gly Thr Lys Leu Glu Leu Lys
            100                 105                 110

<210> SEQ ID NO 88
<211> LENGTH: 112
<212> TYPE: PRT
<213> ORGANISM: Artificial sequence
<220> FEATURE:
<223> OTHER INFORMATION: Synthesized

<400> SEQUENCE: 88

Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Val His Ser
            20                  25                  30

Asp Gly Asn Thr Tyr Leu His Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Ser
                85                  90                  95

Thr His Val Pro Pro Thr Phe Gly Gly Gly Thr Lys Leu Glu Ile Lys
            100                 105                 110

<210> SEQ ID NO 89
<211> LENGTH: 112
<212> TYPE: PRT
<213> ORGANISM: Artificial sequence
<220> FEATURE:
<223> OTHER INFORMATION: Synthesized

<400> SEQUENCE: 89

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Val Tyr Ser
            20                  25                  30

Asn Gly Asp Thr Tyr Leu His Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Ser
                85                  90                  95

Thr His Val Pro Trp Thr Phe Gly Gln Gly Thr Lys Val Glu Ile Lys
            100                 105                 110

<210> SEQ ID NO 90
<211> LENGTH: 112
<212> TYPE: PRT
<213> ORGANISM: Homo sapiens

<400> SEQUENCE: 90

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Val His Ser
            20                  25                  30

Asp Gly Asn Thr Tyr Leu Asn Trp Phe Gln Gln Arg Pro Gly Gln Ser
        35                  40                  45

Pro Arg Arg Leu Ile Tyr Lys Val Ser Asn Arg Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Gly
                85                  90                  95

Thr His Trp Pro Trp Thr Phe Gly Gln Gly Thr Lys Val Glu Ile Lys
            100                 105                 110

<210> SEQ ID NO 91
<211> LENGTH: 112
<212> TYPE: PRT
<213> ORGANISM: Artificial sequence
<220> FEATURE:
<223> OTHER INFORMATION: Synthesized

<400> SEQUENCE: 91

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Ile Val Asp Ser
            20                  25                  30

Asn Gly Asn Thr Tyr Leu Glu Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
                85                  90                  95

Ser His Val Pro Leu Thr Phe Gly Gln Gly Thr Lys Val Glu Ile Lys

```
                    100                 105                 110

<210> SEQ ID NO 92
<211> LENGTH: 112
<212> TYPE: PRT
<213> ORGANISM: Artificial sequence
<220> FEATURE:
<223> OTHER INFORMATION: Synthesized

<400> SEQUENCE: 92

Asp Val Val Met Thr Gln Ser Pro Leu Ser Leu Pro Val Thr Pro Gly
1               5                   10                  15

Glu Pro Ala Ser Ile Ser Cys Arg Ser Ser Gln Ser Ile Val Asp Ser
            20                  25                  30

Asn Gly Asn Thr Tyr Leu Glu Trp Tyr Leu Gln Lys Pro Gly Gln Ser
        35                  40                  45

Pro Arg Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
                85                  90                  95

Ser His Val Pro Leu Thr Phe Gly Gln Gly Thr Lys Val Glu Ile Lys
            100                 105                 110

<210> SEQ ID NO 93
<211> LENGTH: 5
<212> TYPE: PRT
<213> ORGANISM: Artificial sequence
<220> FEATURE:
<223> OTHER INFORMATION: Synthesized

<400> SEQUENCE: 93

Arg Phe Trp Met Ser
1               5

<210> SEQ ID NO 94
<211> LENGTH: 7
<212> TYPE: PRT
<213> ORGANISM: Artificial sequence
<220> FEATURE:
<223> OTHER INFORMATION: Synthesized

<400> SEQUENCE: 94

Gly Phe Asp Phe Ser Arg Phe
1               5

<210> SEQ ID NO 95
<211> LENGTH: 6
<212> TYPE: PRT
<213> ORGANISM: Artificial sequence
<220> FEATURE:
<223> OTHER INFORMATION: Synthesized

<400> SEQUENCE: 95

Ser Arg Phe Trp Met Ser
1               5

<210> SEQ ID NO 96
<211> LENGTH: 6
<212> TYPE: PRT
<213> ORGANISM: Artificial sequence
<220> FEATURE:
<223> OTHER INFORMATION: Synthesized
```

```
<400> SEQUENCE: 96

Asn Pro Gly Ser Ser Thr
1               5

<210> SEQ ID NO 97
<211> LENGTH: 10
<212> TYPE: PRT
<213> ORGANISM: Artificial sequence
<220> FEATURE:
<223> OTHER INFORMATION: Synthesized

<400> SEQUENCE: 97

Glu Ile Asn Pro Gly Ser Ser Thr Ile Asn
1               5                   10

<210> SEQ ID NO 98
<211> LENGTH: 13
<212> TYPE: PRT
<213> ORGANISM: Artificial sequence
<220> FEATURE:
<223> OTHER INFORMATION: Synthesized

<400> SEQUENCE: 98

Trp Ile Gly Glu Ile Asn Pro Gly Ser Ser Thr Ile Asn
1               5                   10

<210> SEQ ID NO 99
<211> LENGTH: 13
<212> TYPE: PRT
<213> ORGANISM: Artificial sequence
<220> FEATURE:
<223> OTHER INFORMATION: Synthesized

<400> SEQUENCE: 99

Ala Arg Leu Gly Tyr Gly Asn Tyr Gly Trp Ala Leu Asp
1               5                   10

<210> SEQ ID NO 100
<211> LENGTH: 7
<212> TYPE: PRT
<213> ORGANISM: Artificial sequence
<220> FEATURE:
<223> OTHER INFORMATION: Synthesized

<400> SEQUENCE: 100

Asn Thr Tyr Leu Glu Trp Tyr
1               5

<210> SEQ ID NO 101
<211> LENGTH: 10
<212> TYPE: PRT
<213> ORGANISM: Artificial sequence
<220> FEATURE:
<223> OTHER INFORMATION: Synthesized

<400> SEQUENCE: 101

Leu Leu Ile Tyr Lys Val Ser Asn Arg Phe
1               5                   10

<210> SEQ ID NO 102
<211> LENGTH: 8
<212> TYPE: PRT
<213> ORGANISM: Artificial sequence
<220> FEATURE:
<223> OTHER INFORMATION: Synthesized
```

```
<400> SEQUENCE: 102

Phe Gln Gly Ser His Val Pro Leu
1               5

<210> SEQ ID NO 103
<211> LENGTH: 124
<212> TYPE: PRT
<213> ORGANISM: Artificial sequence
<220> FEATURE:
<223> OTHER INFORMATION: Synthesized

<400> SEQUENCE: 103

Glu Val Lys Leu Val Glu Ser Gly Gly Gly Leu Val Gln Pro Gly Gly
1               5                   10                  15

Ser Leu Lys Leu Ser Cys Ala Ala Ser Gly Phe Thr Phe Ser Ser Tyr
                20                  25                  30

Thr Met Ser Trp Val Arg Gln Thr Pro Glu Lys Arg Leu Glu Leu Val
            35                  40                  45

Ala Glu Ile Ser Asn Ser Gly Asp Thr Thr Tyr Tyr Pro Asp Thr Val
        50                  55                  60

Lys Gly Arg Phe Thr Phe Ser Arg Asp Asn Ala Lys Asn Thr Leu Tyr
65                  70                  75                  80

Leu Gln Met Ser Ser Leu Lys Ser Glu Asp Thr Ala Met Tyr Tyr Cys
                85                  90                  95

Ala Arg His Tyr Tyr Tyr Gly Gly Gly Tyr Gly Gly Trp Phe Phe Asp
            100                 105                 110

Val Trp Gly Thr Gly Thr Thr Val Thr Val Ser Ser
        115                 120

<210> SEQ ID NO 104
<211> LENGTH: 112
<212> TYPE: PRT
<213> ORGANISM: Artificial sequence
<220> FEATURE:
<223> OTHER INFORMATION: Synthesized

<400> SEQUENCE: 104

Asp Ile Val Met Thr Gln Ala Ala Pro Ser Val Pro Val Thr Pro Gly
1               5                   10                  15

Glu Ser Val Ser Ile Ser Cys Arg Ser Ser Lys Ser Leu Leu His Ser
                20                  25                  30

Asn Gly Asn Thr Tyr Leu Tyr Trp Phe Leu Gln Arg Pro Gly Gln Ser
            35                  40                  45

Pro Gln Leu Leu Ile Tyr Arg Val Ser Asn Leu Ala Ser Gly Val Pro
        50                  55                  60

Asp Arg Phe Ser Gly Ser Gly Ser Gly Thr Ala Phe Thr Leu Arg Ile
65                  70                  75                  80

Ser Arg Val Glu Ala Glu Asp Val Gly Val Tyr Tyr Cys Met Gln His
                85                  90                  95

Leu Glu Tyr Pro Leu Thr Phe Gly Ala Gly Thr Lys Leu Glu Leu Lys
            100                 105                 110
```

METHODS OF DETECTING TRANSTHYRETIN

CROSS REFERENCE TO RELATED APPLICATIONS

This application is a U.S. national stage entry of PCT/US2018/054723 filed Oct. 5, 2018, which claims the benefit under 35 USC 119(e) of U.S. Provisional Application No. 62/569,438, filed Oct. 6, 2017, of U.S. Provisional Application No. 62/579,817, filed Oct. 31, 2017, and of U.S. Provisional Application No. 62/647,582, filed Mar. 23, 2018, each of which is incorporated by reference in its entirety for all purposes.

REFERENCE TO A SEQUENCE LISTING

The Sequence Listing written in file 542797SEQL-ST.TXT is 63,402 bytes, was created on Apr. 3, 2020, and is hereby incorporated by reference.

BACKGROUND

Several diseases are thought to be caused by the abnormal folding and aggregation of disease-specific proteins. These proteins can accumulate into pathologically diagnostic accumulations, known as amyloids, which are visualized by certain histologic stains. Amyloids are thought to elicit inflammatory responses and have multiple negative consequences for the involved tissues. In addition, smaller aggregates of abnormally folded protein may exist and exert cytotoxic effects.

Transthyretin (TTR) is one of the many proteins that are known to misfold and aggregate (e.g., undergo amyloidogenesis). Transthyretin-mediated amyloidosis (ATTR) encompasses two forms of disease: familial disease arising from misfolding of a mutated or variant TTR, and a sporadic, non-genetic disease caused by misfolding and aggregation of wild-type TTR. The process of TTR amyloidogenesis can cause pathology in the nervous system and/or heart, as well as in other tissues.

SUMMARY OF THE CLAIMED INVENTION

In one aspect, the invention provides a method of detecting misfolded transthyretin (TTR) in a biological sample, the method comprising: (a) contacting a biological sample with a capture antibody that specifically binds to an epitope within residues 89-97 of TTR and a reporter antibody that specifically binds to a different epitope of TTR; wherein if misfolded TTR is present in the sample, the capture antibody and reporter antibody bind to the misfolded TTR forming a sandwich complex; and (b) detecting the reporter antibody that forms a sandwich complex in step (a), if any, to indicate presence or absence of the misfolded TTR.

In some such methods, the biological sample is from a hereditary ATTR patient. In some such methods, the biological sample is from a hereditary ATTR patient carrying a mutation selected from the group consisting of V30M, Y114C, G47R, S50I, T49S, F33V, A45T, E89K, E89Q, and V122I. In some such methods, the mutation is selected from the group consisting of V30M, Y114C, and S50I. In some such methods, the mutation is V30M. In some such methods, the mutation is Y114C. In some such methods, the mutation is S50I. In some such methods, the mutation is E89K. In some such methods, the mutation is E89Q.

In some such methods, the capture antibody is 9D5. In some such methods, the capture antibody is 9D5 and the reporter antibody is a polyclonal anti-TTR antibody. In some such methods, the reporter antibody is 18C5, 8C3, 7G7, AD7F6, RT24, NI-301.35G11, MFD101, MDF102, MFD103, MFD105, MFD107, MFD108, MFD109, MFD111, MFD114, or a chimeric version or humanized version thereof, or a polyclonal anti-TTR antibody.

In some such methods, the capture antibody is 9D5 and the reporter antibody is 18C5, or a chimeric version or humanized version thereof. In some such methods, the capture antibody is 9D5 and the reporter antibody is 8C3, or a chimeric version or humanized version thereof. In some such methods, the capture antibody is 9D5 and the reporter antibody is 7G7, or a chimeric version or humanized version thereof.

In some such methods, the capture antibody is 9D5 and the reporter antibody is AD7F6, or a chimeric version or humanized version thereof. In some such methods, the capture antibody is 9D5 and the reporter antibody is RT24, or a chimeric version or humanized version thereof. In some such methods, the capture antibody is 9D5 and the reporter antibody is NI-301.35G11, or a chimeric version or humanized version thereof.

In some such methods, the capture antibody is 9D5 and the reporter antibody is MFD101, or a chimeric version or humanized version thereof. In some such methods, the capture antibody is 9D5 and the reporter antibody is MDF102, or a chimeric version or humanized version thereof. In some such methods, the capture antibody is 9D5 and the reporter antibody is MFD103, In some such methods, the capture antibody is 9D5 and the reporter antibody is MFD105, or a chimeric version or humanized version thereof. In some such methods, the capture antibody is 9D5 and the reporter antibody is MFD107, or a chimeric version or humanized version thereof. In some such methods, the capture antibody is 9D5 and the reporter antibody is MFD108, or a chimeric version or humanized version thereof. In some such methods, the capture antibody is 9D5 and the reporter antibody is MFD109, or a chimeric version or humanized version thereof. In some such methods, the capture antibody is 9D5 and the reporter antibody is MFD111, or a chimeric version or humanized version thereof. In some such methods, the capture antibody is 9D5 and the reporter antibody is MFD114, or a chimeric version or humanized version thereof.

In some such methods, the reporter antibody is an antibody that binds within residues 101-109, 118-122, 115-124, 53-63, 54-61, 36-49, 49-61, 109-121, 30-66, 70-127, 80-127, 90-127, 100-127, 110-127, or 115-127 of TTR.

Some such methods detect misfolded TTR including an E89K substitution. Some such methods detect misfolded TTR including an E89Q substitution.

In some such methods, the biological sample is a first aliquot of a collected sample and the method further comprises repeating step (a) and (b) on a second aliquot of the collected sample further comprising a test antibody that competes with the capture antibody for binding to TTR, wherein reduced reporter antibody forming the sandwich complex on repeating the steps provides an indication of the test antibody's ability to bind to misfolded TTR.

In some such methods, the test antibody is 14G8 or a chimeric or humanized form thereof, the capture antibody is 9D5, and the reporter antibody is a polyclonal anti-TTR antibody. In some such methods, the test antibody is a humanized form of 14G8.

In another aspect, the invention provides a method of determining in vivo target engagement of a test antibody administered to a subject, which target is an epitope within residues 89-97 of misfolded transthyretin (mis-TTR) by detecting the mis-TTR remaining in a biological sample from the subject treated with the test antibody, the method comprising: (a) contacting the biological sample with a capture antibody that specifically binds to an epitope within residues 89-97 and a reporter antibody that specifically binds to a different epitope within TTR from that of the capture antibody; wherein if misfolded TTR is present in the sample, the capture antibody and reporter antibody bind to the misfolded TTR forming a sandwich complex; and (b) detecting the reporter antibody forming a sandwich complex in step (a), if any, to indicate presence or absence of the misfolded TTR.

In some such methods, the biological sample is from a hereditary ATTR patient. In some such methods, the biological sample is from a hereditary ATTR patient carrying a mutation selected from the group consisting of V30M, Y114C, G47R, S50I, T49S, F33V, A45T, E89K, E89Q, and V122I. In some such methods, the mutation is selected from the group consisting of V30M, Y114C, and S50I. In some such methods, the mutation is V30M. In some such methods, the mutation is Y114C. In some such methods, the mutation is S50I. In some such methods, the mutation is E89K. In some such methods, the mutation is E89Q.

In some such methods, a reduction of detection of misfolded TTR in the treated subject relative to the detection of misfolded TTR in a biological sample from an untreated subject correlates with positive target engagement and treating the subject with the same or a lesser amount of the test antibody. In some such methods, the treated subject and the untreated subject are the same individual.

In some such methods, the capture antibody is 9D5 and the reporter antibody is 9D5, wherein the capture antibody and the reporter antibody have different labels. In some such methods, the capture antibody is 9D5 and the reporter antibody is 14G8. In some such methods, the capture antibody is 9D5 and the reporter antibody is 5A1. In some such methods, the capture antibody is 9D5 and the reporter antibody is 6C1. In some such methods, the reporter antibody competes for binding with the capture antibody for binding multimeric misfolded transthyretin.

In some embodiments, the reporter antibody has an electrochemiluminescent label and is detected by electrochemiluminescence. In some methods of the invention, the capture antibody has a biotin label.

In an embodiment, the methods are performed qualitatively. In an embodiment, the methods are performed quantitatively to indicate an absolute or relative amount of the misfolded TTR.

In some such methods, the capture antibody is bound to a solid phase before the contacting step. In some such methods, the capture antibody is attached to the solid phase via a linker. In some such methods, the solid phase comprises at least one electrode.

Some such methods further comprise comparing a signal from the reporter antibody with a signal from the reporter antibody in a control sample containing a known amount of misfolded TTR to determine the amount of misfolded TTR in the sample.

Some such methods further comprise comparing a signal from the reporter antibody from a calibration curve of signal versus amount of misfolded TTR to determine the amount of misfolded TTR in the sample. In some such methods, a signal from the reporter antibody is proportional to the amount of misfolded TTR in the sample.

In some such methods, the sample is a sample from a human. In some such methods, the sample is a body fluid. In some such methods, the sample is plasma of a human.

In an embodiment, the presence of misfolded TTR is used to diagnose a subject from whom the sample was obtained with a transthyretin-mediated amyloidosis. In an embodiment, the transthyretin-mediated amyloidosis is a familial transthyretin amyloidosis or a sporadic wild-type transthyretin amyloidosis. In an embodiment, the subject has been identified as at risk of a familial transthyretin amyloidosis based on genetic testing.

In an embodiment, the subject does not show symptoms of a familial transthyretin amyloidosis. In an embodiment, the subject does not have polyneuropathy or cardiomyopathy.

In an embodiment, the familial transthyretin amyloidosis is familial amyloid cardiomyopathy (FAC), familial amyloid polyneuropathy (FAP), or central nervous system selective amyloidosis (CNSA).

In an embodiment, the biological sample is from a patient receiving treatment for a transthyretin-mediated amyloidosis.

In another aspect, the invention provides a method of adjusting treatment of a subject with a transthyretin-mediated amyloidosis, comprising comparing the amount of misfolded TTR detected in the subject previously treated for transthyretin mediated amyloidosis with the amount of misfolded TTR detected in the subject prior to treatment or during an earlier stage of treatment; and (a) increasing the dose or frequency of administration of the prior treatment if the amount of misfolded TTR is the same or greater than that previously detected; or (b) decreasing the dose or frequency of administration of the prior treatment or discontinuing the prior treatment if the amount of misfolded TTR is less than that previously detected. In an embodiment, the misfolded TTR is detected by a method comprising contacting a biological sample with a capture antibody that specifically binds to an epitope within residues 89-97 of TTR and a reporter antibody that specifically binds to a different epitope of TTR; wherein if misfolded TTR is present in the sample, the capture antibody and reporter antibody bind to the misfolded TTR forming a sandwich complex; and detecting the reporter antibody that binds to the misfolded TTR in step (a), if any, to indicate presence or absence of the misfolded TTR.

In some such methods, the prior treatment is by intravenous administration of an anti-TTR antibody and if the amount of misfolded TTR is less than that previously detected, the prior treatment is discontinued and replaced with treatment with a TTR stabilizer, antisense oligonucleotide based therapy, RNA interference therapy or combination therapy with doxycycline and tauroursodeoxycholic acid. In some such methods, the subject no longer receives treatment with the anti-TTR antibody. In some such methods, the TTR tetramer stabilizer is tafamidis or diflunisal. In some such methods, the TTR tetramer stabilizer is diflunisal. In some such methods, the antisense oligonucleotide based therapeutic is inotersen. In some such methods, the RNAi based therapeutic is patisiran or revusiran.

In some such methods, the anti-TTR antibody is 14G8. In some such methods, the subject no longer receives treatment with the anti-TTR antibody. In some such methods, the TTR tetramer stabilizer is tafamidis or diflunisal. In some such methods, the TTR tetramer stabilizer is diflunisal. In some such methods, the antisense oligonucleotide based therapeutic is inotersen. In some such methods, the RNAi based therapeutic is patisiran or revusiran.

In another aspect, the invention provides a method of adjusting treatment of a subject with a transthyretin-mediated amyloidosis, comprising (a) comparing the amount of reporter antibody binding in a sample from a subject before initiating treatment for transthyretin mediated amyloidosis with the amount of reporter antibody binding detected in the subject after initiating treatment; and (b) increasing the dose or frequency of administration of the treatment if the amount of reporter antibody binding is the same or greater than that previously detected; or (c) decreasing the dose or frequency of administration of the treatment or discontinuing the treatment if the amount of reporter antibody binding is less than that previously detected. In an embodiment, the reporter antibody binding is detected by a method comprising contacting a biological sample with a capture antibody that specifically binds to an epitope within residues 89-97 of TTR and a reporter antibody that specifically binds to a different epitope of TTR; wherein if misfolded TTR is present in the sample, the capture antibody and reporter antibody bind to the misfolded TTR forming a sandwich complex; and detecting the reporter antibody that binds to the misfolded TTR in step (a), if any, to indicate presence or absence of the misfolded TTR.

In some methods, a transthyretin-mediated amyloidosis is distinguished from amyloid light-chain (AL) amyloidosis. In some methods, the sample is from a transgenic mouse with a transgene expressing human TTR.

In another aspect, the invention provides a method of determining a ratio of the level of total multimeric misfolded transthyretin (TTR) to the level of total misfolded TTR in a biological sample; the method comprising:
  (a) dividing a biological sample into two portions;
  (b) detecting total misfolded TTR in a first portion of the biological sample by
    (i) contacting the first portion of the biological sample with a capture antibody that specifically binds to an epitope within residues 89-97 of TTR and a reporter antibody that specifically binds to a different epitope of TTR; wherein if misfolded TTR is present in the sample, the capture antibody and reporter antibody bind to the misfolded TTR forming a sandwich complex; and
    (ii) detecting the reporter antibody forming a sandwich complex in step (b)(i), if any, to indicate presence or absence of the misfolded TTR;
  (c) detecting total multimeric misfolded TTR in a second portion of the biological sample by
    (i) contacting the second portion of the biological sample with a capture antibody that specifically binds to an epitope within residues 89-97 and a reporter antibody that specifically binds to an epitope within residues 89-97 of TTR; wherein if multimeric misfolded TTR is present in the sample, the capture antibody and reporter antibody bind to the multimeric misfolded TTR forming a sandwich complex; and
    (ii) detecting the reporter antibody forming a sandwich complex in step (c)(i), if any, to indicate presence or absence of the multimeric misfolded TTR.
  (d) calculating a ratio of the level of total multimeric misfolded TTR of (c) to the level of total misfolded TTR of (b).

In one aspect, the invention provides a method of detecting misfolded transthyretin (TTR) in a biological sample, the method comprising contacting a biological sample with a capture antibody that specifically binds to an epitope within residues 101-109 of TTR and a reporter antibody that specifically binds to a different epitope of TTR; wherein if misfolded TTR is present in the sample, the capture antibody and reporter antibody bind to the misfolded TTR forming a sandwich complex; and detecting the reporter antibody that binds to the misfolded TTR in step (a), if any, to indicate presence or absence of the misfolded TTR.

In some such methods, the capture antibody is 18C5. In some such methods, the capture antibody is 18C5 and the reporter antibody is a polyclonal anti-TTR antibody. In some such methods, the reporter antibody is 9D5, 14G8, 5A1, 6C1, 8C3, 7G7, AD7F6, RT24, NI-301.35G11, MFD101, MDF102, MFD103, MFD105, MFD107, MFD108, MFD109, MFD111, MFD114, or a chimeric version or humanized version thereof.

In some such methods, the capture antibody is 18C5 and the reporter antibody is 9D5, or a chimeric version or humanized version thereof. In some such methods, the capture antibody is 18C5 and the reporter antibody is 14G8, or a chimeric version or humanized version thereof. In some such methods, the capture antibody is 18C5 and the reporter antibody is 5A1, or a chimeric version or humanized version thereof. In some such methods, the capture antibody is 18C5 and the reporter antibody is 6C1, or a chimeric version or humanized version thereof. In some such methods, the capture antibody is 18C5 and the reporter antibody is 8C3, or a chimeric version or humanized version thereof. In some such methods, the capture antibody is 18C5 and the reporter antibody is 7G7, or a chimeric version or humanized version thereof.

In some such methods, the capture antibody is 18C5 and the reporter antibody is AD7F6, or a chimeric version or humanized version thereof. In some such methods, the capture antibody is 18C5 and the reporter antibody is RT24, or a chimeric version or humanized version thereof. In some such methods, the capture antibody is 18C5 and the reporter antibody is NI-301.35G11, or a chimeric version or humanized version thereof.

In some such methods, the capture antibody is 18C5 and the reporter antibody is MFD101, or a chimeric version or humanized version thereof. In some such methods, the capture antibody is 18C5 and the reporter antibody is MDF102, or a chimeric version or humanized version thereof. In some such methods, the capture antibody is 18C5 and the reporter antibody is MFD103, or a chimeric version or humanized version thereof. In some such methods, the capture antibody is 18C5 and the reporter antibody is MFD105, or a chimeric version or humanized version thereof. In some such methods, the capture antibody is 18C5 and the reporter antibody is MFD107, or a chimeric version or humanized version thereof. In some such methods, the capture antibody is 18C5 and the reporter antibody is MFD108, or a chimeric version or humanized version thereof. In some such methods, the capture antibody is 18C5 and the reporter antibody is MFD109, or a chimeric version or humanized version thereof. In some such methods, the capture antibody is 18C5 and the reporter antibody is MFD111, or a chimeric version or humanized version thereof. In some such methods, the capture antibody is 18C5 and the reporter antibody is MFD114, or a chimeric version or humanized version thereof.

In some such methods, the reporter antibody is an antibody that binds within residues 89-97, 118-122, 115-124, 53-63, 54-61, 36-49, 49-61, 109-121, 30-66, 70-127, 80-127, 90-127, 100-127, 110-127, or 115-127 of TTR.

In another aspect, the invention provides a method of detecting multimeric misfolded transthyretin (TTR) in a biological sample, the method comprising contacting a biological sample with a capture antibody that specifically binds to an epitope within residues 101-109 and a reporter antibody that specifically binds to an epitope within residues 101-109 of TTR; wherein if multimeric misfolded TTR is present in the sample, the capture antibody and reporter antibody bind to the multimeric misfolded TTR forming a sandwich complex; and detecting the reporter antibody that binds to the multimeric misfolded TTR in step (a), if any, to indicate presence or absence of the multimeric misfolded TTR.

In some such methods, the capture antibody is 18C5 and the reporter antibody is 18C5, wherein the capture antibody and the reporter antibody have different labels. In some such methods, the reporter antibody competes for binding with the capture antibody for binding multimeric misfolded transthyretin.

In some embodiments, the reporter antibody has an electrochemiluminescent label and is detected by electrochemiluminescence. In some methods of the invention, the capture antibody has a biotin label.

In an embodiment, the methods are performed qualitatively. In an embodiment, the methods are performed quantitatively to indicate an absolute or relative amount of the misfolded TTR.

In some such methods, the capture antibody is bound to a solid phase before the contacting step. In some such methods, the capture antibody is attached to the solid phase via a linker. In some such methods, the solid phase comprises at least one electrode.

Some such methods further comprise comparing a signal from the reporter antibody with a signal from the reporter antibody in a control sample containing a known amount of misfolded TTR to determine the amount of misfolded TTR in the sample.

Some such methods further comprise comparing a signal from the reporter antibody from a calibration curve of signal versus amount of misfolded TTR to determine the amount of misfolded TTR in the sample. In some such methods, a signal from the reporter antibody is proportional to the amount of misfolded TTR in the sample.

In some such methods, the sample is from a human. In some such methods, the sample is a body fluid. In some such methods, the sample is plasma of a human.

In an embodiment, the presence of misfolded TTR is used to diagnose a subject from whom the sample was obtained with a transthyretin-mediated amyloidosis. In an embodiment, the transthyretin-mediated amyloidosis is a familial transthyretin amyloidosis or a sporadic wild-type transthyretin amyloidosis. In an embodiment, the subject has been identified as at risk of a familial transthyretin amyloidosis based on genetic testing.

In an embodiment, the subject does not show symptoms of a familial transthyretin amyloidosis. In an embodiment, the subject does not have polyneuropathy or cardiomyopathy.

In an embodiment, the familial transthyretin amyloidosis is familial amyloid cardiomyopathy (FAC), familial amyloid polyneuropathy (FAP), or central nervous system selective amyloidosis (CNSA).

In an embodiment, the biological sample is from a patient receiving treatment for a transthyretin-mediated amyloidosis.

In another aspect, the invention provides a method of adjusting treatment of a subject with a transthyretin-mediated amyloidosis, comprising comparing the amount of misfolded TTR in a sample from a subject previously treated for transthyretin mediated amyloidosis with the amount of misfolded TTR detected in the subject prior to treatment or during an earlier stage of treatment; and increasing the dose or frequency of administration of the prior treatment if the amount of misfolded TTR is the same or greater than that previously detected; or decreasing the dose or frequency of administration of the prior treatment or discontinuing the prior treatment if the amount of misfolded TTR is less than that previously detected. In an embodiment, the misfolded TTR is detected by a method comprising contacting a biological sample with a capture antibody that specifically binds to an epitope within residues 101-109 of TTR and a reporter antibody that specifically binds to a different epitope of TTR; wherein if misfolded TTR is present in the sample, the capture antibody and reporter antibody bind to the misfolded TTR forming a sandwich complex; and detecting the reporter antibody that binds to the misfolded TTR in step (a), if any, to indicate presence or absence of the misfolded TTR.

In some such methods, the prior treatment is by intravenous administration of an anti-TTR antibody and if the amount of misfolded TTR is less than that previously detected, the prior treatment is discontinued and replaced with treatment with a TTR stabilizer, antisense oligonucleotide based therapy, RNA interference therapy or combination therapy with doxycycline and tauroursodeoxycholic acid. In some such methods, the subject no longer receives treatment with the anti-TTR antibody. In some such methods, the TTR tetramer stabilizer is tafamidis or diflunisal. In some such methods, the TTR tetramer stabilizer is diflunisal. In some such methods, the antisense oligonucleotide based therapeutic is inotersen. In some such methods, the RNAi based therapeutic is patisiran or revusiran.

In some such methods, the anti-TTR antibody is 14G8. In some such methods, the subject no longer receives treatment with the anti-TTR antibody. In some such methods, the TTR tetramer stabilizer is tafamidis or diflunisal. In some such methods, the TTR tetramer stabilizer is diflunisal. In some such methods, the antisense oligonucleotide based therapeutic is inotersen. In some such methods, the RNAi based therapeutic is patisiran or revusiran.

In another aspect, the invention provides a method of adjusting treatment of a subject with a transthyretin-mediated amyloidosis, comprising (a) comparing the amount of reporter antibody binding in a sample from a subject before initiating treatment for transthyretin mediated amyloidosis with the amount of reporter antibody binding detected in the subject after initiating treatment; and (b) increasing the dose or frequency of administration of the treatment if the amount of reporter antibody binding is the same or greater than that previously detected; or (c) decreasing the dose or frequency of administration of the treatment or discontinuing the treatment if the amount of reporter antibody binding is less than that previously detected. In an embodiment, the reporter antibody binding is detected by a method comprising contacting a biological sample with a capture antibody that specifically binds to an epitope within residues 101-109 of TTR and a reporter antibody that specifically binds to a different epitope of TTR; wherein if misfolded TTR is present in the sample, the capture antibody and reporter antibody bind to the misfolded TTR forming a sandwich complex; and detecting the reporter antibody that binds to the misfolded TTR in step (a), if any, to indicate presence or absence of the misfolded TTR.

In some methods, a transthyretin-mediated amyloidosis is distinguished from amyloid light-chain (AL) amyloidosis. In some methods, the sample is from a transgenic mouse with a transgene expressing human TTR.

In another aspect, the invention provides a method of determining a ratio of the level of total multimeric misfolded transthyretin (TTR) to the level of total misfolded TTR in a biological sample; the method comprising:
  (a) dividing a biological sample into two portions;
  (b) detecting total misfolded TTR in a first portion of the biological sample by
    (i) contacting the first portion of the biological sample with a capture antibody that specifically binds to an epitope within residues 101-109 of TTR and a reporter antibody that specifically binds to a different epitope of TTR; wherein if misfolded TTR is present in the sample, the capture antibody and reporter antibody bind to the misfolded TTR forming a sandwich complex; and
    (ii) detecting the reporter antibody bound to the misfolded TTR in step (i), if any, to indicate presence or absence of the misfolded TTR;
  (c) detecting total multimeric misfolded TTR in a second portion of the biological sample by
    (i) contacting the second portion of the biological sample with a capture antibody that specifically binds to an epitope within residues 101-109 and a reporter antibody that specifically binds to an epitope within residues 101-109 of TTR; wherein if multimeric misfolded TTR is present in the sample, the capture antibody and reporter antibody bind to the multimeric misfolded TTR forming a sandwich complex; and
    (ii) detecting the reporter antibody bound to the multimeric misfolded TTR in step (a), if any, to indicate presence or absence of the multimeric misfolded TTR.
  (d) calculating a ratio of the level of total multimeric misfolded TTR of (c) to the level of total misfolded TTR of (b).

In one aspect, the invention provides a method of detecting misfolded transthyretin (TTR) in a biological sample, the method comprising contacting a biological sample with a capture antibody that specifically binds to an epitope within residues 101-109 of TTR and a reporter antibody that specifically binds to a different epitope of TTR; wherein if misfolded TTR is present in the sample, the capture antibody and reporter antibody bind to the misfolded TTR forming a sandwich complex; and detecting the reporter antibody that binds to the misfolded TTR in step (a), if any, to indicate presence or absence of the misfolded TTR.

In some such methods, the biological sample is from a hereditary ATTR patient. In some such methods, the biological sample is from a hereditary ATTR patient carrying a mutation selected from the group consisting of V30M, Y114C, and S50I. In some such methods, the mutation is V30M. In some such methods, the mutation is Y114C. In some such methods, the mutation is S50I.

In some such methods, the capture antibody is 18C5. In some such methods, the capture antibody is 18C5 and the reporter antibody is a polyclonal anti-TTR antibody. In some such methods, the reporter antibody is 9D5, 14G8, 5A1, 6C1, 8C3, 7G7, AD7F6, RT24, NI-301.35G11, MFD101, MDF102, MFD103, MFD105, MFD107, MFD108, MFD109, MFD111, MFD114, or a chimeric version or humanized version thereof.

In some such methods, the capture antibody is 18C5 and the reporter antibody is 9D5, or a chimeric version or humanized version thereof. In some such methods, the capture antibody is 18C5 and the reporter antibody is 14G8, or a chimeric version or humanized version thereof. In some such methods, the capture antibody is 18C5 and the reporter antibody is 5A1, or a chimeric version or humanized version thereof. In some such methods, the capture antibody is 18C5 and the reporter antibody is 6C1, or a chimeric version or humanized version thereof. In some such methods, the capture antibody is 18C5 and the reporter antibody is 8C3, or a chimeric version or humanized version thereof. In some such methods, the capture antibody is 18C5 and the reporter antibody is 7G7, or a chimeric version or humanized version thereof.

In some such methods, the capture antibody is 18C5 and the reporter antibody is AD7F6, or a chimeric version or humanized version thereof. In some such methods, the capture antibody is 18C5 and the reporter antibody is RT24, or a chimeric version or humanized version thereof. In some such methods, the capture antibody is 18C5 and the reporter antibody is NI-301.35G11, or a chimeric version or humanized version thereof.

In some such methods, the capture antibody is 18C5 and the reporter antibody is MFD101, or a chimeric version or humanized version thereof. In some such methods, the capture antibody is 18C5 and the reporter antibody is MDF102, or a chimeric version or humanized version thereof. In some such methods, the capture antibody is 18C5 and the reporter antibody is MFD103, or a chimeric version or humanized version thereof. In some such methods, the capture antibody is 18C5 and the reporter antibody is MFD105, or a chimeric version or humanized version thereof. In some such methods, the capture antibody is 18C5 and the reporter antibody is MFD107, or a chimeric version or humanized version thereof. In some such methods, the capture antibody is 18C5 and the reporter antibody is MFD108, or a chimeric version or humanized version thereof. In some such methods, the capture antibody is 18C5 and the reporter antibody is MFD109, or a chimeric version or humanized version thereof. In some such methods, the capture antibody is 18C5 and the reporter antibody is MFD111, or a chimeric version or humanized version thereof. In some such methods, the capture antibody is 18C5 and the reporter antibody is MFD114, or a chimeric version or humanized version thereof.

In some such methods, the reporter antibody is an antibody that binds within residues 89-97, 118-122, 115-124, 53-63, 54-61, 36-49, 49-61, 109-121, 30-66, 70-127, 80-127, 90-127, 100-127, 110-127, or 115-127 of TTR.

In one aspect, the invention provides a method of determining in vivo target engagement of a test antibody administered to a subject, which target is an epitope within residues 101-109 of misfolded transthyretin (mis-TTR) by detecting the mis-TTR remaining in a biological sample from the subject treated with the test antibody, the method comprising: (a) contacting the biological sample with a capture antibody that specifically binds to an epitope within residues 101-109 and a reporter antibody that specifically binds to a different epitope within TTR from that of the capture antibody; wherein if misfolded TTR is present in the sample, the capture antibody and reporter antibody bind to the misfolded TTR forming a sandwich complex; and (b) detecting the reporter antibody forming a sandwich complex in step (a), if any, to indicate presence or absence of the misfolded TTR.

In some such methods, the biological sample is from a hereditary ATTR patient. In some such methods, the biological sample is from a hereditary ATTR patient carrying a mutation selected from the group consisting of V30M, Y114C, and S50I. In some such methods, the mutation is V30M. In some such methods, the mutation is Y114C. In some such methods, the mutation is S50I.

In some such methods, the capture antibody is 18C5, wherein the capture antibody and the reporter antibody have different labels. In some such methods, the reporter antibody competes for binding with the capture antibody for binding multimeric misfolded transthyretin.

In some embodiments, the reporter antibody has an electrochemiluminescent label and is detected by electrochemiluminescence. In some methods of the invention, the capture antibody has a biotin label.

In an embodiment, the methods are performed qualitatively. In an embodiment, the methods are performed quantitatively to indicate an absolute or relative amount of the misfolded TTR.

In some such methods, the capture antibody is bound to a solid phase before the contacting step. In some such methods, the capture antibody is attached to the solid phase via a linker. In some such methods, the solid phase comprises at least one electrode.

Some such methods further comprise comparing a signal from the reporter antibody with a signal from the reporter antibody in a control sample containing a known amount of misfolded TTR to determine the amount of misfolded TTR in the sample.

Some such methods further comprise comparing a signal from the reporter antibody from a calibration curve of signal versus amount of misfolded TTR to determine the amount of misfolded TTR in the sample. In some such methods, a signal from the reporter antibody is proportional to the amount of misfolded TTR in the sample.

In some such methods, the sample is from a human. In some such methods, the sample is a body fluid. In some such methods, the sample is plasma of a human.

In an embodiment, the presence of misfolded TTR is used to diagnose a subject from whom the sample was obtained with a transthyretin-mediated amyloidosis. In an embodiment, the transthyretin-mediated amyloidosis is a familial transthyretin amyloidosis or a sporadic wild-type transthyretin amyloidosis. In an embodiment, the subject has been identified as at risk of a familial transthyretin amyloidosis based on genetic testing.

In an embodiment, the subject does not show symptoms of a familial transthyretin amyloidosis. In an embodiment, the subject does not have polyneuropathy or cardiomyopathy.

In an embodiment, the familial transthyretin amyloidosis is familial amyloid cardiomyopathy (FAC), familial amyloid polyneuropathy (FAP), or central nervous system selective amyloidosis (CNSA).

In an embodiment, the biological sample is from a patient receiving treatment for a transthyretin-mediated amyloidosis.

In another aspect, the invention provides a method of adjusting treatment of a subject with a transthyretin-mediated amyloidosis, comprising comparing the amount of misfolded TTR in a sample from a subject previously treated for transthyretin mediated amyloidosis with the amount of misfolded TTR detected in the subject prior to treatment or during an earlier stage of treatment; and increasing the dose or frequency of administration of the prior treatment if the amount of misfolded TTR is the same or greater than that previously detected; or decreasing the dose or frequency of administration of the prior treatment or discontinuing the prior treatment if the amount of misfolded TTR is less than that previously detected. In an embodiment, the misfolded TTR is detected by a method comprising contacting a biological sample with a capture antibody that specifically binds to an epitope within residues 101-109 of TTR and a reporter antibody that specifically binds to a different epitope of TTR; wherein if misfolded TTR is present in the sample, the capture antibody and reporter antibody bind to the misfolded TTR forming a sandwich complex; and detecting the reporter antibody that binds to the misfolded TTR in step (a), if any, to indicate presence or absence of the misfolded TTR.

In some such methods, the prior treatment is by intravenous administration of an anti-TTR antibody and if the amount of misfolded TTR is less than that previously detected, the prior treatment is discontinued and replaced with treatment with a TTR stabilizer, antisense oligonucleotide based therapy, RNA interference therapy or combination therapy with doxycycline and tauroursodeoxycholic acid. In some such methods, the subject no longer receives treatment with the anti-TTR antibody. In some such methods, the TTR tetramer stabilizer is tafamidis or diflunisal. In some such methods, the TTR tetramer stabilizer is diflunisal. In some such methods, the antisense oligonucleotide based therapeutic is inotersen. In some such methods, the RNAi based therapeutic is patisiran or revusiran.

In some such methods, the anti-TTR antibody is 14G8. In some such methods, the subject no longer receives treatment with the anti-TTR antibody. In some such methods, the TTR tetramer stabilizer is tafamidis or diflunisal. In some such methods, the TTR tetramer stabilizer is diflunisal. In some such methods, the antisense oligonucleotide based therapeutic is inotersen. In some such methods, the RNAi based therapeutic is patisiran or revusiran.

In another aspect, the invention provides a method of adjusting treatment of a subject with a transthyretin-mediated amyloidosis, comprising comparing the amount of reporter antibody binding detected by the methods herein in a sample from a subject before initiating treatment for transthyretin mediated amyloidosis with the amount of reporter antibody binding detected in the subject after initiating treatment; and increasing the dose or frequency of administration of the treatment if the amount of reporter antibody binding is the same or greater than that previously detected; or decreasing the dose or frequency of administration of the treatment or discontinuing the treatment if the amount of reporter antibody binding is less than that previously detected. In an embodiment, the misfolded TTR is detected by a method comprising contacting a biological sample with a capture antibody that specifically binds to an epitope within residues 101-109 of TTR and a reporter antibody that specifically binds to a different epitope of TTR; wherein if misfolded TTR is present in the sample, the capture antibody and reporter antibody bind to the misfolded TTR forming a sandwich complex; and detecting the reporter antibody that binds to the misfolded TTR in step (a), if any, to indicate presence or absence of the misfolded TTR.

In some methods, a transthyretin-mediated amyloidosis is distinguished from amyloid light-chain (AL) amyloidosis. In some methods, the sample is from a transgenic mouse with a transgene expressing human TTR.

In another aspect, the invention provides a method of determining a ratio of the level of total multimeric misfolded transthyretin (TTR) to the level of total misfolded TTR in a biological sample; the method comprising:

(a) dividing a biological sample into two portions;
(b) detecting total misfolded TTR in a first portion of the biological sample by
  (i) contacting the first portion of the biological sample with a capture antibody that specifically binds to an epitope within residues 101-109 of TTR and a reporter antibody that specifically binds to a different epitope of TTR; wherein if misfolded TTR is present in the sample, the capture antibody and reporter antibody bind to the misfolded TTR forming a sandwich complex; and
  (ii) detecting the reporter antibody bound to the misfolded TTR in step (i), if any, to indicate presence or absence of the misfolded TTR;
(d) detecting total multimeric misfolded TTR in a second portion of the biological sample by
  (i) contacting the second portion of the biological sample with a capture antibody that specifically binds to an epitope within residues 101-109 and a reporter antibody that specifically binds to an epitope within residues 101-109 of TTR; wherein if multimeric misfolded TTR is present in the sample, the capture antibody and reporter antibody bind to the multimeric misfolded TTR forming a sandwich complex; and
  (ii) detecting the reporter antibody bound to the multimeric misfolded TTR in step (a), if any, to indicate presence or absence of the multimeric misfolded TTR.
(e) calculating a ratio of the level of total multimeric misfolded TTR of (c) to the level of total misfolded TTR of (b).

BRIEF DESCRIPTION OF THE SEQUENCES

Figure 1:
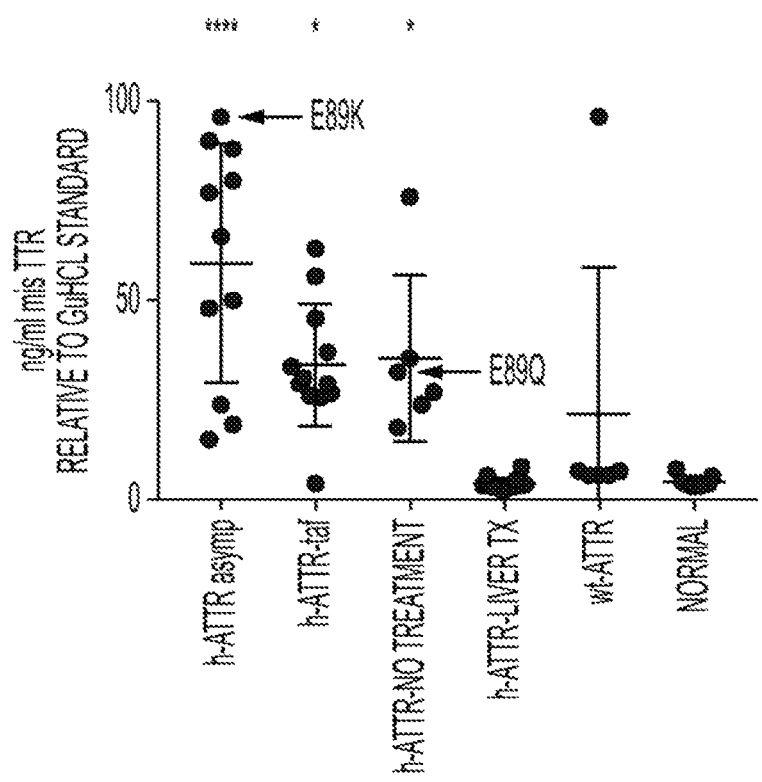
FIG. 1 depicts the results of a sandwich immunoassay employing the Meso Scale Discovery (MSD) electrochemiluminescence platform showing that 9D5 detects elevated misfolded TTR in plasma samples from transthyretin-mediated amyloidosis (ATTR) patients that had not undergone a liver transplant, in an assay using a polyclonal anti-TTR reporter antibody.

SEQ ID NO:1 sets forth the amino acid sequence of a heavy chain variable region of the mouse 18C5 antibody with signal peptide.

SEQ ID NO:2 sets forth a nucleic acid sequence encoding a heavy chain variable region of the mouse 18C5 antibody with signal peptide.

SEQ ID NO:3 sets forth the amino acid sequence of a light chain variable region of the mouse 18C5 antibody with signal peptide.

SEQ ID NO:4 sets forth a nucleic acid sequence encoding a light chain variable region of the mouse 18C5 antibody with signal peptide.

SEQ ID NO:5 sets forth the amino acid sequence of a Kabat/Chothia Composite CDR-H1 of the mouse 18C5 antibody.

SEQ ID NO:6 sets forth a nucleic acid sequence encoding a Kabat/Chothia Composite composite CDR-H1 of the mouse 18C5 antibody.

SEQ ID NO:7 sets forth the amino acid sequence of a Kabat/Chothia Composite CDR-H2 of the mouse 18C5 antibody.

SEQ ID NO:8 sets forth a nucleic acid sequence encoding a Kabat/Chothia Composite CDR-H2 of the mouse 18C5 antibody.

SEQ ID NO:9 sets forth the amino acid sequence of a Kabat/Chothia Composite CDR-H3 of the mouse 18C5 antibody.

SEQ ID NO:10 sets forth a nucleic acid sequence encoding a Kabat/Chothia Composite CDR-H3 of the mouse 18C5 antibody.

SEQ ID NO:11 sets forth the amino acid sequence of a Kabat/Chothia Composite CDR-L1 of the mouse 18C5 antibody.

SEQ ID NO:12 sets forth a nucleic acid sequence encoding a Kabat/Chothia Composite CDR-L1 of the mouse 18C5 antibody.

SEQ ID NO:13 sets forth the amino acid sequence of a Kabat/Chothia Composite CDR-L2 of the mouse 18C5 antibody.

SEQ ID NO:14 sets forth a nucleic acid sequence encoding a Kabat/Chothia Composite CDR-L2 of the mouse 18C5 antibody.

SEQ ID NO:15 sets forth the amino acid sequence of a Kabat/Chothia Composite CDR-L3 of the mouse 18C5 antibody.

SEQ ID NO:16 sets forth a nucleic acid sequence encoding the a Kabat/Chothia Composite CDR-L3 of the mouse 18C5 antibody.

SEQ ID NO:17 sets forth the amino acid sequence of a chimeric 18C5 heavy chain constant region (human IgG1).

SEQ ID NO:18 sets forth a nucleic acid sequence encoding the amino acid sequence of a chimeric 18C5 heavy chain constant region (human IgG1).

SEQ ID NO:19 sets forth the amino acid sequence of a chimeric 18C5 light chain constant region (human kappa).

SEQ ID NO:20 sets forth a nucleic acid sequence encoding the amino acid sequence of a chimeric 18C5 light chain constant region (human kappa).

SEQ ID NO:21 sets forth the amino acid sequence of an exemplary IgG1 heavy chain constant region.

SEQ ID NO:22 sets forth the amino acid sequence of an exemplary IgG1 G1m3 heavy chain constant region.

SEQ ID NO:23 sets forth the amino acid sequence of an exemplary IgG1 G1m3 heavy chain constant region.

SEQ ID NO:24 sets forth the amino acid sequence of an exemplary light chain constant region with N-terminal Arginine.

SEQ ID NO:25 sets forth the amino acid sequence of an exemplary light chain constant region without N-terminal Arginine.

SEQ ID NO:26 sets forth the amino acid sequence of human transthyretin set forth in accession number P02766.1 (UniProt).

SEQ ID NO:27 sets forth the amino acid sequence of human transthyretin set forth in accession number AAB35639.1 (GenBank).

SEQ ID NO:28 sets forth the amino acid sequence of human transthyretin set forth in accession number AAB35640.1 (GenBank).

SEQ ID NO:29 sets forth the amino acid sequence of human transthyretin set forth in accession number and ABI63351.1 (GenBank).

SEQ ID NO:30 sets forth the amino acid sequence of residues 101-109 of human transthyretin.

SEQ ID NO:31 sets forth the amino acid sequence of residues 87-127 of human transthyretin.

SEQ ID NO:32 sets forth a nucleic acid sequence encoding an exemplary IgG1 G1m3 heavy chain constant region.

SEQ ID NO:33 sets forth a nucleic acid sequence encoding an exemplary light chain constant region with C-terminal Arginine.

SEQ ID NO:34 sets forth a nucleic acid sequence encoding an exemplary light chain constant region without C-terminal Arginine.

SEQ ID NO:35 sets forth the amino acid sequence of a heavy chain constant region signal peptide.

SEQ ID NO:36 sets forth a nucleic acid sequence encoding a heavy chain constant region signal peptide.

SEQ ID NO:37 sets forth the amino acid sequence of a light chain constant region signal peptide.

SEQ ID NO:38 sets forth a nucleic acid sequence encoding a light chain constant region signal peptide.

SEQ ID NO: 39 sets forth the amino acid sequence of a Kabat CDR-H1 of antibody 14G8.

SEQ ID NO: 40 sets forth the amino acid sequence of a Kabat CDR-H2 of antibody 14G8.

SEQ ID NO: 41 sets forth the amino acid sequence of a Kabat CDR-H3 of antibody 14G8.

SEQ ID NO: 42 sets forth the amino acid sequence of a Kabat CDR-L1 of antibody 14G8.

SEQ ID NO: 43 sets forth the amino acid sequence of a Kabat CDR-L2 of antibody 14G8.

SEQ ID NO: 44 sets forth the amino acid sequence of a Kabat CDR-L3 of antibody 14G8.

SEQ ID NO: 45 sets forth the amino acid sequence of an epitope of antibody 5A1.

SEQ ID NO: 46 sets forth the amino acid sequence of a Kabat CDR-H1 of antibody 5A1.

SEQ ID NO: 47 sets forth the amino acid sequence of a Kabat CDR-H2 of antibody 5A1.

SEQ ID NO: 48 sets forth the amino acid sequence of a Kabat CDR-H3 of antibody 5A1.

SEQ ID NO: 49 sets forth the amino acid sequence of a Kabat CDR-L1 of antibody 5A1.

SEQ ID NO: 50 sets forth the amino acid sequence of a Kabat CDR-L2 of antibody 5A1.

SEQ ID NO: 51 sets forth the amino acid sequence of a Kabat CDR-L3 of antibody 5A1.

SEQ ID NO: 52 sets forth the amino acid sequence of a Kabat CDR-H1 of antibody 6C1.

SEQ ID NO: 53 sets forth the amino acid sequence of a Kabat CDR-H2 of antibody 6C1.

SEQ ID NO: 54 sets forth the amino acid sequence of a Kabat CDR-H3 of antibody 6C1.

SEQ ID NO: 55 sets forth the amino acid sequence of a Kabat CDR-L1 of antibody 6C1.

SEQ ID NO: 56 sets forth the amino acid sequence of a Kabat CDR-L2 of antibody 6C1.

SEQ ID NO: 57 sets forth the amino acid sequence of a Kabat CDR-L3 of antibody 6C1.

SEQ ID NO: 58 sets forth the amino acid sequence of a VH region of antibody AD7F6.

SEQ ID NO: 59 sets forth the amino acid sequence of a VL region of antibody AD7F6.

SEQ ID NO: 60 sets forth the amino acid sequence of a CDR-H1 of antibody RT24.

SEQ ID NO: 61 sets forth the amino acid sequence of a CDR-H2 of antibody RT24.

SEQ ID NO: 62 sets forth the amino acid sequence of a CDR-H3 of antibody RT24.

SEQ ID NO:63 sets forth the amino acid sequence of a CDR-L1 of antibody RT24.

SEQ ID NO: 64 sets forth the amino acid sequence of a CDR-L2 of antibody RT24.

SEQ ID NO: 65 sets forth the amino acid sequence of a CDR-L3 of antibody RT24.

SEQ ID NO: 66 sets forth the amino acid sequence of a CDR-H1 of antibody NI-301.35G11.

SEQ ID NO:67 sets forth the amino acid sequence of a CDR-H2 of antibody NI-301.35G11.

SEQ ID NO: 68 sets forth the amino acid sequence of a CDR-H3 of antibody NI-301.35G11.

SEQ ID NO: 69 sets forth the amino acid sequence of a CDR-L1 of antibody NI-301.35G11.

SEQ ID NO: 70 sets forth the amino acid sequence of a CDR-L2 of antibody NI-301.35G11.

SEQ ID NO: 71 sets forth the amino acid sequence of a CDR-L3 of antibody NI-301.35G11.

SEQ ID NO: 72 sets forth the amino acid sequence of an epitope of antibodies MFD101, MDF102, MFD103, MFD105.

SEQ ID NO: 73 sets forth the amino acid sequence of an epitope of antibodies MFD107, MFD108, MFD109, MFD111.

SEQ ID NO: 74 sets forth the amino acid sequence of an epitope of antibody MFD114.

SEQ ID NO: 75 sets forth the amino acid sequence of a Kabat CDR-H1 of antibody 9D5.

SEQ ID NO: 76 sets forth the amino acid sequence of a Kabat CDR-H2 of antibody 9D5.

SEQ ID NO: 77 sets forth the amino acid sequence of a Kabat CDR-H3 of antibody 9D5.

SEQ ID NO: 78 sets forth the amino acid sequence of a Kabat CDR-L1 of antibody 9D5.

SEQ ID NO: 79 sets forth the amino acid sequence of a Kabat CDR-L2 of antibody 9D5.

SEQ ID NO: 80 sets forth the amino acid sequence of a Kabat CDR-L3 of antibody 9D5.

SEQ ID NO:81 sets forth the amino acid sequence of a mature heavy chain variable region of the mouse 18C5 antibody.

SEQ ID NO: 82 sets forth the amino acid sequence of a heavy chain variable region of the murine anti-pyroglutamate-Abeta antibody Fab c #17, GenBank Acc. No. 1212215935.

SEQ ID NO: 83 sets forth the amino acid sequence of a heavy chain variable region of humanized Crenezumab Fab (CreneFab) PDB: 5VZY, GenBank Acc. No. 1229749875.

SEQ ID NO: 84 sets forth the amino acid sequence of a heavy chain variable region of the human germline sequence IGHV3-48*01, GenBank Acc. No. 1FN550289.1.

SEQ ID NO: 85 sets forth the amino acid sequence of a heavy chain variable region of the humanized 18C5 antibody hu18C5-VH_1.

SEQ ID NO: 86 sets forth the amino acid sequence of a heavy chain variable region of the humanized 18C5 antibody hu18C5-VH_2.

SEQ ID NO:87 sets forth the amino acid sequence of a mature light chain variable region of the mouse 18C5 antibody.

SEQ ID NO: 88 sets forth the amino acid sequence of a light chain variable region of the murine anti-pyroglutamate-Abeta antibody Fab c #17, GenBank Acc. No. 1212215934.

SEQ ID NO: 89 sets forth the amino acid sequence of a light chain variable region of humanized Crenezumab Fab (CreneFab) PDB: 5VZY, GenBank Acc. No. 1229749876.

SEQ ID NO: 90 sets forth the amino acid sequence of a light chain variable region of the human germline sequence IGKV2-30*2, GenBank Acc. No. CAA77315.

SEQ ID NO: 91 sets forth the amino acid sequence of a light chain variable region of the humanized 18C5 antibody hu18C5-VL_1.

SEQ ID NO: 92 sets forth the amino acid sequence of a light chain variable region of the humanized 18C5 antibody hu18C5-VL_2.

SEQ ID NO: 93 sets forth the amino acid sequence of Kabat CDR-H1 of the mouse 18C5 antibody.

SEQ ID NO: 94 sets forth the amino acid sequence of Chothia CDR-H1 of the mouse 18C5 antibody.

SEQ ID NO: 95 sets forth the amino acid sequence of Contact CDR-H1 of the mouse 18C5 antibody.

SEQ ID NO: 96 sets forth the amino acid sequence of Chothia CDR-H2 of the mouse 18C5 antibody.

SEQ ID NO: 97 sets forth the amino acid sequence of AbM CDR-H2 of the mouse 18C5 antibody.

SEQ ID NO: 98 sets forth the amino acid sequence of Contact CDR-H2 of the mouse 18C5 antibody.

SEQ ID NO: 99 sets forth the amino acid sequence of Contact CDR-H3 of the mouse 18C5 antibody.

SEQ ID NO: 100 sets forth the amino acid sequence of Contact CDR-L1 of the mouse 18C5 antibody.

SEQ ID NO: 101 sets forth the amino acid sequence of Contact CDR-L2 of the mouse 18C5 antibody.

SEQ ID NO: 102 sets forth the amino acid sequence of Contact CDR-L3 of the mouse 18C5 antibody.

SEQ ID NO: 103 sets forth the amino acid sequence of a heavy chain variable region of the mouse 9D5 antibody.

SEQ ID NO: 104 sets forth the amino acid sequence of a light chain variable region of the mouse 9D5 antibody.

DEFINITIONS

Monoclonal antibodies or other biological entities are typically provided in isolated form. This means that an antibody or other biologically entity is typically at least 50% w/w pure of interfering proteins and other contaminants arising from its production or purification but does not exclude the possibility that the monoclonal antibody is combined with an excess of pharmaceutically acceptable carrier(s) or other vehicle intended to facilitate its use. Sometimes monoclonal antibodies are at least 60%, 70%, 80%, 90%, 95% or 99% w/w pure of interfering proteins and contaminants from production or purification. Often an isolated monoclonal antibody or other biological entity is the predominant macromolecular species remaining after its purification.

Specific binding of an antibody to its target antigen means an affinity of at least $10^6$, $10^7$, $10^8$, $10^9$, or $10^{10}$ $M^{-1}$. Specific binding is detectably higher in magnitude and distinguishable from non-specific binding occurring to at least one unrelated target. Specific binding can be the result of formation of bonds between particular functional groups or particular spatial fit (e.g., lock and key type) whereas nonspecific binding is usually the result of van der Waals forces. Specific binding does not however necessarily imply that an antibody binds one and only one target.

The basic antibody structural unit is a tetramer of subunits. Each tetramer includes two identical pairs of polypeptide chains, each pair having one "light" (about 25 kDa) and one "heavy" chain (about 50-70 kDa). The amino-terminal portion of each chain includes a variable region of about 100 to 110 or more amino acids primarily responsible for antigen recognition. This variable region is initially expressed linked to a cleavable signal peptide. The variable region without the signal peptide is sometimes referred to as a mature variable region. Thus, for example, a light chain mature variable region means a light chain variable region without the light chain signal peptide. The carboxy-terminal portion of each chain defines a constant region primarily responsible for effector function.

Light chains are classified as either kappa or lambda. Heavy chains are classified as gamma, mu, alpha, delta, or epsilon, and define the antibody's isotype as IgG, IgM, IgA, IgD and IgE, respectively. Within light and heavy chains, the variable and constant regions are joined by a "J" region of about 12 or more amino acids, with the heavy chain also including a "D" region of about 10 or more amino acids. See generally, *Fundamental Immunology*, Paul, W., ed., 2nd ed. Raven Press, N.Y., 1989, Ch. 7 (incorporated by reference in its entirety for all purposes).

An immunoglobulin light or heavy chain variable region (also referred to herein as a "light chain variable domain" ("VL domain") or "heavy chain variable domain" ("VH domain"), respectively) consists of a "framework" region interrupted by three "complementarity determining regions" or "CDRs." The framework regions serve to align the CDRs for specific binding to an epitope of an antigen. The CDRs include the amino acid residues of an antibody that are primarily responsible for antigen binding. From amino-terminus to carboxyl-terminus, both VL and VH domains comprise the following framework (FR) and CDR regions: FR1, CDR1, FR2, CDR2, FR3, CDR3, and FR4. CDRs 1, 2, and 3 of a VL domain are also referred to herein, respectively, as CDR-L1, CDR-L2, and CDR-L3; CDRs 1, 2, and 3 of a VH domain are also referred to herein, respectively, as CDR-H1, CDR-H2, and CDR-H3.

The assignment of amino acids to each VL and VH domain is in accordance with any conventional definition of CDRs. Conventional definitions include, the Kabat definition (Kabat, *Sequences of Proteins of Immunological Interest* (National Institutes of Health, Bethesda, MD, 1987 and 1991), The Chothia definition (Chothia & Lesk, *J. Mol. Biol.* 196:901-917, 1987; Chothia et al., Nature 342:878-883, 1989); a composite of Chothia Kabat CDR in which CDR-H1 is a composite of Chothia and Kabat CDRs; the AbM definition used by Oxford Molecular's antibody modelling software; and, the contact definition of Martin et al (bioinfo.org.uk/abs) (see Table 1). Kabat provides a widely used numbering convention (Kabat numbering) in which corresponding residues between different heavy chains or between different light chains are assigned the same number. When an antibody is said to comprise CDRs by a certain definition of CDRs (e.g., Kabat) that definition specifies the minimum number of CDR residues present in the antibody (i.e., the Kabat CDRs). It does not exclude that other residues falling within another conventional CDR definition but outside the specified definition are also present. For example, an antibody comprising CDRs defined by Kabat includes among other possibilities, an antibody in which the CDRs contain Kabat CDR residues and no other CDR residues, and an antibody in which CDR H1 is a composite Chothia-Kabat CDR H1 and other CDRs contain Kabat CDR residues and no additional CDR residues based on other definitions.

TABLE 1

Conventional Definitions of CDRs Using Kabat Numbering

| Loop | Kabat | Chothia | Composite of Chothia & Kabat | AbM | Contact |
|---|---|---|---|---|---|
| L1 | L24--L34 | L24--L34 | L24--L34 | L24--L34 | L30--L36 |
| L2 | L50--L56 | L50--L56 | L50--L56 | L50--L56 | L46--L55 |
| L3 | L89--L97 | L89--L97 | L89--L97 | L89--L97 | L89--L96 |
| H1 | H31--H35B | H26--H32 ... H34* | H26--H35B* | H26--H35B | H30--H35B |
| H2 | H50--H65 | H52--H56 | H50--H65 | H50--H58 | H47--H58 |
| H3 | H95--H102 | H95--H102 | H95--H102 | H95--H102 | H93--H101 |

*CDR-H1 by Chothia can end at H32, H33, or H34 (depending on the length of the loop). This is because the Kabat numbering scheme places insertions of extra residues at 35A and 35B, whereas Chothia numbering places them at 31A and 31B. If neither H35A nor H35B (Kabat numbering) is present, the Chothia CDR-H1 loop ends at H32. If only H35A is present, it ends at H33. If both H35A and H35B are present, it ends at H34.

The term "antibody" includes intact antibodies and binding fragments thereof. Typically, fragments compete with the intact antibody from which they were derived for specific binding to the target including separate heavy chains, light chains Fab, Fab', F(ab')$_2$, F(ab)c, Dabs, nanobodies, and Fv. Fragments can be produced by recombinant DNA techniques, or by enzymatic or chemical separation of intact immunoglobulins. The term "antibody" also includes a bispecific antibody and/or a humanized antibody. A bispecific or bifunctional antibody is an artificial hybrid antibody having two different heavy/light chain pairs and two different binding sites (see, e.g., Songsivilai and Lachmann, *Clin. Exp. Immunol.*, 79:315-321 (1990); Kostelny et al., *J. Immunol.*, 148:1547-53 (1992)). In some bispecific antibodies, the two different heavy/light chain pairs include a humanized 9D5 heavy chain/light chain pair and a heavy chain/light chain pair specific for a different epitope on transthyretin than that bound by 9D5. In some bispecific antibodies, the two different heavy/light chain pairs include a humanized 18C5 heavy chain/light chain pair and a heavy chain/light chain pair specific for a different epitope on transthyretin than that bound by 18C5.

In some bispecific antibodies, one heavy chain/light chain pair is a humanized 9D5 antibody or a humanized 18C5 antibody as further disclosed below and the other heavy chain/light chain pair is from an antibody that binds to a receptor expressed on the blood brain barrier, such as an insulin receptor, an insulin-like growth factor (IGF) receptor, a leptin receptor, or a lipoprotein receptor, or a transferrin receptor (Friden et al., *Proc. Natl. Acad. Sci. USA* 88:4771-4775, 1991; Friden et al., *Science* 259:373-377, 1993). Such a bispecific antibody can be transferred cross the blood brain barrier by receptor-mediated transcytosis. Brain uptake of the bispecific antibody can be further enhanced by engineering the bispecific antibody to reduce its affinity to the blood brain barrier receptor. Reduced affinity for the receptor resulted in a broader distribution in the brain (see, e.g., Atwal et al., *Sci. Trans. Med.* 3, 84ra43, 2011; Yu et al., *Sci. Trans. Med.* 3, 84ra44, 2011).

Exemplary bispecific antibodies can also be: (1) a dual-variable-domain antibody (DVD-Ig), where each light chain and heavy chain contains two variable domains in tandem through a short peptide linkage (Wu et al., Generation and Characterization of a Dual Variable Domain Immunoglobulin (DVD-Ig™) Molecule, In: *Antibody Engineering*, Springer Berlin Heidelberg (2010)); (2) a Tandab, which is a fusion of two single chain diabodies resulting in a tetravalent bispecific antibody that has two binding sites for each of the target antigens; (3) a flexibody, which is a combination of scFvs with a diabody resulting in a multivalent molecule; (4) a so-called "dock and lock" molecule, based on the "dimerization and docking domain" in Protein Kinase A, which, when applied to Fabs, can yield a trivalent bispecific binding protein consisting of two identical Fab fragments linked to a different Fab fragment; or (5) a so-called Scorpion molecule, comprising, e.g., two scFvs fused to both termini of a human Fc-region. Examples of platforms useful for preparing bispecific antibodies include BiTE (Micromet), DART (MacroGenics), Fcab and Mab2 (F-star), Fc-engineered IgG1 (Xencor) or DuoBody (based on Fab arm exchange, Genmab).

The term "epitope" refers to a site on an antigen to which an antibody binds. An epitope can be formed from contiguous amino acids or noncontiguous amino acids juxtaposed by tertiary folding of one or more proteins. Epitopes formed from contiguous amino acids (also known as linear epitopes) are typically retained on exposure to denaturing solvents whereas epitopes formed by tertiary folding (also known as conformational epitopes) are typically lost on treatment with denaturing solvents. An epitope typically includes at least 3, and more usually, at least 5 or 8-10 amino acids in a unique spatial conformation. Methods of determining spatial conformation of epitopes include, for example, x-ray crystallography and 2-dimensional nuclear magnetic resonance. See, e.g., Epitope Mapping Protocols, in Methods in Molecular Biology, Vol. 66, Glenn E. Morris, Ed. (1996). The epitope can be linear, such as an epitope of, for example, 2-5, 3-5, 3-9, or 5-9 contiguous amino acids from SEQ ID NO:26, including for example, two or more contiguous amino acids within residues 89-97 of the mature region of SEQ ID NO:26. The epitope can also be a conformational epitope including, for example, two or more non-contiguous segments of amino acids within residues 89-97 of the mature region of SEQ ID NO:26. If an antibody is said to bind to an epitope within amino acid residues 89-97 of transthyretin (TTR) (the mature region of SEQ ID NO:26), for example, what is meant is that the epitope is within the recited range of amino acids including those defining the outer-limits of the range. It does not necessarily mean that every amino acid within the range constitutes part of the epitope. Thus, for example, an epitope within amino acid residues 89-97 of TTR may consist of amino acids 89-97, 89-96, 90-97, 89-95, 90-96, 91-97, 89-94, 90-95, 91-96, 92-97, 89-93, 90-94, 91-95, 92-96, 93-97, 89-92, 90-93, 91-94, 92-95, 93-96, 94-97, 89-91, 90-92, 91-93, 92-94, 93-95, 94-96, 95-97 of SEQ ID NO:26, among other linear segments of SEQ ID NO:45, or in the case of conformational epitopes, non-contiguous segments of amino acids of SEQ ID NO:45. Epitopes can include E89K and E89Q substitutions, E being the wildtype residue).

The epitope can be linear, such as an epitope of, for example, 2-5, 3-5, 3-9, or 5-9 contiguous amino acids from SEQ ID NO:26, including for example, two or more contiguous amino acids within residues 101-109 of the mature region of SEQ ID NO:26. The epitope can also be a conformational epitope including, for example, two or more non-contiguous segments of amino acids within residues 101-109 of the mature region of SEQ ID NO:26. If an antibody is said to bind to an epitope within amino acid residues 101-109 of transthyretin (TTR) (the mature region of SEQ ID NO:26), for example, what is meant is that the epitope is within the recited range of amino acids including those defining the outer-limits of the range. It does not necessarily mean that every amino acid within the range constitutes part of the epitope. Thus, for example, an epitope within amino acid residues 101-109 of TTR may consist of amino acids 101-109, 101-108, 102-109, 101-107, 102-108, 103-109, 101-106, 102-107, 103-108, 104-109, 101-105, 102-106, 103-107, 104-108, 105-109, 101-104, 102-105, 103-106, 104-107, 105-108, 106-109, 101-103, 102-104, 103-105, 104-106, 105-107, 106-108, 107-109, 101-102, 102-103, 103-104, 104-105, 105-106, 106-107, 107-108, or 108-109 of SEQ ID NO:26, among other linear segments of SEQ ID NO:30, or in the case of conformational epitopes, non-contiguous segments of amino acids of SEQ ID NO:30.

Antibodies that recognize the same or overlapping epitopes can be identified in a simple immunoassay showing the ability of one antibody to compete with the binding of another antibody to a target antigen. The epitope of an antibody can also be defined by X-ray crystallography of the antibody bound to its antigen to identify contact residues. Alternatively, two antibodies have the same epitope if all amino acid mutations in the antigen that reduce or eliminate binding of one antibody reduce or eliminate binding of the other. Two antibodies have overlapping epitopes if some amino acid mutations that reduce or eliminate binding of one antibody reduce or eliminate binding of the other.

Competition between antibodies is determined by an assay in which an antibody under test inhibits specific binding of a reference antibody to a common antigen (see, e.g., Junghans et al., *Cancer Res.* 50:1495, 1990). A test antibody competes with a reference antibody if an excess of a test antibody (e.g., at least 2×, 5×, 10×, 20× or 100×) inhibits binding of the reference antibody by at least 50% as measured in a competitive binding assay. Some test antibodies inhibit binding of the references antibody by at least 75%, 90% or 99%. Antibodies identified by competition assay (competing antibodies) include antibodies binding to the same epitope as the reference antibody and antibodies binding to an adjacent epitope sufficiently proximal to the epitope bound by the reference antibody for steric hindrance to occur.

The term "native" with respect to the structure transthyretin (TTR) refers to the normal folded structure of TTR in its properly functioning state (i.e., a TTR tetramer). As TTR is a tetramer in its natively folded form, non-native forms of TTR include, for example, misfolded TTR tetramers, TTR monomers, aggregated forms of TTR, and fibril forms of TTR. Non-native forms of TTR can include molecules comprising wild-type TTR amino acid sequences or mutations.

The term "misfolded" with respect to TTR refers to the secondary and tertiary structure of a TTR polypeptide monomer or multimer, and indicates that the polypeptide has adopted a conformation that is not normal for that protein in its properly functioning state. Although TTR misfolding can be caused by mutations in the protein (e.g., deletion, substitution, or addition), wild-type TTR proteins can also be misfolded in diseases, exposing specific epitopes.

The term "pharmaceutically acceptable" means that the carrier, diluent, excipient, or auxiliary is compatible with the other ingredients of the formulation and not substantially deleterious to the recipient thereof.

The term "patient" includes human and other mammalian subjects that receive either prophylactic or therapeutic treatment.

An individual is at increased risk of a disease if the subject has at least one known risk-factor (e.g., genetic, biochemical, family history, and situational exposure) placing individuals with that risk factor at a statistically significant greater risk of developing the disease than individuals without the risk factor.

The term "biological sample" refers to a sample of biological material within or obtainable from a biological source, for example a human or mammalian subject. Such samples can be organs, organelles, tissues, sections of tissues, bodily fluids, peripheral blood, blood plasma, blood serum, cells, molecules such as proteins and peptides, and any parts or combinations derived therefrom. The term biological sample can also encompass any material derived by processing the sample. Derived material can include cells or their progeny. Processing of the biological sample may involve one or more of filtration, distillation, extraction, concentration, fixation, inactivation of interfering components, and the like.

The term "control sample" refers to a biological sample not known or suspected to include monomeric, misfolded, aggregated, or fibril forms of transthyretin (TTR), such as in TTR amyloid deposits. Control samples can be obtained from individuals not afflicted with a TTR amyloidosis or a specifically chosen type of TTR amyloidosis. Alternatively, control samples can be obtained from patients afflicted with TTR amyloidosis or a specifically chosen type of TTR amyloidosis. Such samples can be obtained at the same time as a biological sample thought to comprise the TTR amyloidosis or on a different occasion. A biological sample and a control sample can both be obtained from the same tissue (e.g., a tissue section containing both TTR amyloid deposits and surrounding normal tissue). Preferably, control samples consist essentially or entirely of tissue free of TTR amyloid deposits and can be used in comparison to a biological sample thought to comprise TTR amyloid deposits. Preferably, the tissue in the control sample is the same type as the tissue in the biological sample (e.g., cardiomyocytes in the heart).

The term "disease" refers to any abnormal condition that impairs physiological function. The term is used broadly to encompass any disorder, illness, abnormality, pathology, sickness, condition, or syndrome in which physiological function is impaired, irrespective of the nature of the etiology.

The term "symptom" refers to a subjective evidence of a disease, such as altered gait, as perceivable by a subject. A "sign" refers to objective evidence of a disease as observable by a physician.

For purposes of classifying amino acids substitutions as conservative or nonconservative, amino acids are grouped as follows: Group I (hydrophobic side chains): met, ala, val, leu, ile; Group II (neutral hydrophilic side chains): asn, gln, cys, ser, thr; Group III (acidic side chains): asp, glu; Group IV (basic side chains): his, lys, arg; Group V (residues influencing chain orientation): gly, pro; and Group VI (aromatic side chains): trp, tyr, phe. Conservative substitutions involve substitutions between amino acids in the same class. Non-conservative substitutions constitute exchanging a member of one of these classes for a member of another.

Percentage sequence identities are determined with antibody sequences maximally aligned by the Kabat numbering convention. After alignment, if a subject antibody region (e.g., the entire mature variable region of a heavy or light chain) is being compared with the same region of a reference antibody, the percentage sequence identity between the subject and reference antibody regions is the number of positions occupied by the same amino acid in both the subject and reference antibody region divided by the total number of aligned positions of the two regions, with gaps not counted, multiplied by 100 to convert to percentage.

Compositions or methods "comprising" or "including" one or more recited elements may include other elements not specifically recited. For example, a composition that "comprises" or "includes" an antibody may contain the antibody alone or in combination with other ingredients.

Designation of a range of values includes all integers within or defining the range, and all subranges defined by integers within the range.

Unless otherwise apparent from the context, the term "about" encompasses values within a standard margin of error of measurement (e.g., SEM) of a stated value.

Statistical significance means $p \leq 0.05$.

Antibodies of the invention can be administered concomitant with another treatment for the same indication as the antibody, meaning that the other treatment is administered at least once during the period in which the antibody is administered, such period beginning one month before the first dosing and ending one month after the last dosing of the antibody. The other treatment can be administered at recurring intervals during this period, which may or may not be the same as the intervals at which the antibody is administered. The other treatment may be a symptomatic treatment.

A treatment is symptomatic if it only affects one or more symptoms of a disease, not its cause, i.e., its etiology.

The singular forms of the articles "a," "an," and "the" include plural references unless the context clearly dictates otherwise. For example, the term "a compound" or "at least one compound" can include a plurality of compounds, including mixtures thereof.

DETAILED DESCRIPTION

I. General

The invention provides antibodies that specifically bind to residues 89-97 or to residues 101-109 of transthyretin (TTR). Some antibodies bind any or all of monomeric, misfolded, aggregated, or fibril forms of TTR preferentially relative to native tetrameric form of TTR. Some antibodies bind either or both of monomeric or misfolded forms of TTR preferentially relative to native tetrameric form of TTR. The antibodies can be used for treating or effecting prophylaxis of diseases or disorders associated with TTR accumulation or accumulation of TTR deposits (e.g., TTR amyloidosis). The antibodies can also be used for diagnosing TTR amyloidosis and inhibiting or reducing aggregation of TTR. The antibodies can also be used to demonstrate pharmacodynamics effects of a transthyretin-mediated amyloidosis therapy, among other applications. Preferential binding means an association constant at least five times higher for any or all of monomeric, misfolded, aggregated, or fibril forms of TTR than for native tetrameric form of TTR. Optionally, the association constant is at least ten times higher for any or all of monomeric, misfolded, aggregated, or fibril forms of TTR than for native tetrameric form of TTR. Optionally, the antibody, such as 9D5 or 18C5, for example, lacks specific binding to native tetrameric form of TTR.

II. Target Molecules

Transthyretin (TTR) is a 127-amino acid, 55 kDa serum and cerebrospinal fluid transport protein primarily synthesized by the liver. It has also been referred to as prealbumin, thyroxine binding prealbumin, ATTR, and TBPA. In its native state, TTR exists as a tetramer. In homozygotes, the tetramers comprise identical 127-amino-acid beta-sheet-rich subunits. In heterozygotes, the TTR tetramers are made up of variant and/or wild-type subunits, typically combined in a statistical fashion.

The established function of TTR in the blood is to transport holo-retinol binding protein. Although TTR is the major carrier of thyroxine (T4) in the blood of rodents, utilizing binding sites that are orthogonal to those used for holo-retinol binding protein, the T4 binding sites are effectively unoccupied in humans.

TTR is one of at least thirty different human proteins whose extracellular misfolding and/or misassembly (amyloidogenesis) into a spectrum of aggregate structures is thought to cause degenerative diseases referred to as amyloid diseases. TTR undergoes conformational changes in order to become amyloidogenic. Dissociation of the TTR tetramer and partial unfolding exposes stretches of largely uncharged hydrophobic residues in an extended conformation that efficiently misassemble into largely unstructured spherical aggregates that ultimately undergo conformation conversion into cross-beta sheet amyloid structures.

Unless otherwise apparent from context, reference to transthyretin (TTR) or its fragments or domains includes the natural human amino acid sequences including isoforms, mutants (e.g., E89K and E89Q), and allelic variants thereof. Exemplary TTR polypeptide sequences are designated by Accession Numbers P02766.1 (UniProt) (SEQ ID NO:26), AAB35639.1 (GenBank) (SEQ ID NO:27), AAB35640.1 (GenBank) (SEQ ID NO:28), and ABI63351.1 (GenBank) (SEQ ID NO:29). Residues are numbered according to Swiss Prot P02766.1, with the first amino acid of the mature protein (i.e., not including the 20 amino acid signal sequence) designated residue 1. In any other TTR protein, residues are numbered according to the corresponding residues in P02766.1 on maximum alignment.

III. Transthyretin Amyloidosis

Transthyretin (TTR) amyloidosis is a systemic disorder characterized by pathogenic, misfolded TTR and the extracellular deposition of amyloid fibrils composed of TTR. TTR amyloidosis is generally caused by destabilization of the native TTR tetramer form (due to environmental or genetic conditions), leading to dissociation, misfolding, and aggregation of TTR into amyloid fibrils that accumulate in various organs and tissues, causing progressive dysfunction. See, e.g., Almeida and Saraiva, *FEBS Letters* 586:2891-2896 (2012); Ando et al., *Orphanet Journal of Rare Diseases* 8:31 (2013).

In humans, both wild-type TTR tetramers and mixed tetramers comprised of mutant and wild-type subunits can dissociate, misfold, and aggregate, with the process of amyloidogenesis leading to the degeneration of affected tissue. Thus, TTR amyloidoses encompass diseases caused by pathogenic misfolded TTR resulting from mutations in TTR or resulting from non-mutated, misfolded TTR.

For example, wild-type ATTR amyloidosis (also called senile systemic amyloidosis or SSA) and senile cardiac amyloidosis (SCA) are age-related types of amyloidosis that result from the deposition of wild-type TTR amyloid outside and within the cardiomyocytes of the heart. TTR amyloidosis is also the most common form of hereditary (familial) amyloidosis, which is caused by mutations that destabilize the TTR protein. The TTR amyloidoses associated with point mutations in the TTR gene include familial amyloid polyneuropathy (FAP), familial amyloid cardiomyopathy (FAC), and the rare central nervous system selective amyloidosis (CNSA). Patients with hereditary (familial) TTR amyloidosis are almost always heterozygotes, meaning that the TTR tetramers are composed of mutant and/or wild-type TTR subunits, generally statistically distributed. Hereditary (familial) versions of TTR amyloidosis are generally autosomal dominant and are typically earlier onset than the sporadic diseases (SSA and SCA).

There are over 100 mutations in the gene encoding TTR that have been implicated in the autosomal dominant disorders FAP and FAC. See, e.g., US 2014/0056904; Saraiva, *Hum. Mutat.* 17(6):493-503 (2001); *Damas and Saraiva, J. Struct. Biol.* 130:290-299; Dwulet and Benson, *Biochem. Biophys. Res. Commun.* 114:657-662 (1983). These amyloid-causing mutations are distributed throughout the entire molecule of TTR. Generally, the more destabilizing the mutant subunits are to the TTR tetramer structure, the earlier the onset of amyloid disease. The pathogenic potential of a TTR variant is generally determined by a combination of its instability and its cellular secretion efficiency. The initial pathology caused by some TTR variants comes from their selective destruction of cardiac tissue, whereas that from other TTR variants comes from compromising the peripheral and autonomic nervous system. The tissue damage caused by TTR amyloidogenesis appear to stem largely from the toxicity of small, diffusible TTR aggregates, although accumulation of extracellular amyloid may contribute and almost certainly compromises organ structure in the late stages of the TTR amyloidosis. Exemplary TTR mutations include V30M, Y114C, G47R, S50I, E61L, T49S, F33V, A45T, E89K, E89Q, and V122I.

TTR amyloidosis presents in many different forms, with considerable phenotypic variation across individuals and geographic locations. For example, TTR amyloidosis can present as a progressive, axonal sensory autonomic and motor neuropathy. TTR amyloidosis can also present as an infiltrative cardiomyopathy.

The age at onset of disease-related symptoms varies between the second and ninth decades of life, with great variations across different populations. The multisystem involvement of TTR amyloidosis is a clue to its diagnosis. For example, TTR amyloidosis diagnosis is considered when one or several of the following are present: (1) family history of neuropathic disease, especially associated with heart failure; (2) neuropathic pain or progressive sensory disturbances of unknown etiology; (3) carpal tunnel syndrome without obvious cause, particularly if it is bilateral and requires surgical release; (4) gastrointestinal motility disturbances or autonomic nerve dysfunction of unknown etiology (e.g., erectile dysfunction, orthostatic hypotension, neurogenic bladder); (5) cardiac disease characterized by thickened ventricular walls in the absence of hypertension; (6) advanced atrio-ventricular block of unknown origin, particularly when accompanied by a thickened heart; and (6) vitreous body inclusions of the cotton-wool type. See Ando et al., *Orphanet Journal of Rare Diseases* 8:31 (2013). Other symptoms can include, for example, polyneuropathy, sensory loss, pain, weakness in lower limbs, dyshidrosis, diarrhea, constipation, weight loss, and urinary incontinence/retention.

Diagnosis of TTR amyloidosis typically relies on target organ biopsies, followed by histological staining of the excised tissue with the amyloid-specific dye, Congo red. If a positive test for amyloid is observed, immunohistochemical staining and mass spectroscopic identification of TTR is subsequently performed to ensure that the precursor protein responsible for amyloid formation is indeed TTR. Antibodies disclosed herein are useful in distinguishing TTR amyloidosis from a non-TTR amyloidosis e.g. amyloid light-chain (AL) amyloidosis, also known as primary systemic amyloidosis. For familial forms of the diseases, demonstration of a mutation in the gene encoding TTR is then needed before diagnosis can be made. This can be accomplished, for example, through isoelectric focusing electrophoresis, polymerase chain reaction, or laser dissection/liquid chromatography-tandem mass spectrometry. See, e.g., US 2014/0056904; Ruberg and Berk, *Circulation* 126:1286-1300 (2012); Ando et al., *Orphanet Journal of Rare Diseases* 8:31 (2013).

IV. Antibodies

A. Binding Specificity and Functional Properties

The invention provides monoclonal antibodies binding to transthyretin (TTR) protein, more specifically, to epitopes within amino acid residues 89-97 (SEQ ID NO:45) or to epitopes within amino acid residues 101-109 (SEQ ID NO:30) of TTR. Such epitopes are buried in the native TTR tetramer and exposed in monomeric, misfolded, aggregated, or fibril forms of TTR.

Such antibodies include 9D5, 18C5, and their chimeric, veneered and humanized forms. 9D5 specifically binds within amino acid residues 89-97 (SEQ ID NO:45) of TTR. 18C5 specifically binds within amino acid residues 101-109 (SEQ ID NO: 30) of TTR. These antibodies are further characterized by their ability to bind to monomeric, misfolded, aggregated, or fibril forms of TTR but not to native tetrameric form of TTR. Ability to bind to specific proteins or fragments thereof may be demonstrated using exemplary assay formats provided in the examples. Unless otherwise apparent from the context, reference to 9D5 or 18C5 should be understood as referring to any of the mouse, chimeric, veneered or humanized forms. A hybridoma cell line that produces monoclonal antibody 9D5 was deposited with the Patent Depository of the American Type Culture Collection (ATCC), Manassas, Virginia, 20110-2209 on Apr. 4, 2017 and assigned Patent Deposit No. PTA-124078. A hybridoma cell line that produces monoclonal antibody 18C5 was deposited with the Patent Depository of the American Type Culture Collection (ATCC), Manassas, Virginia, 20110-2209 on _____ Oct. 31, 2017 _____ and assigned Patent Deposit No. PTA-124570 _____.

Some antibodies bind to the same or overlapping epitope as an antibody designated 9D5. The sequences of the heavy and light chain mature variable regions of 9D5 are designated SEQ ID NOs: 81 and 82, respectively. Other antibodies having such a binding specificity can be produced by immunizing mice with TTR, or a portion thereof including the desired epitope (e.g., SEQ ID NO:45), and screening resulting antibodies for binding to monomeric TTR or a peptide comprising SEQ ID NO:45, optionally in competition with an antibody having the variable regions of mouse 18C5 (IgG1,kappa). Fragments of TTR including the desired epitope can be linked to a carrier that helps elicit an antibody response to the fragment and/or be combined with an adjuvant that helps elicit such a response. Such antibodies can be screened for differential binding to wild-type, monomeric versions of TTR or a fragment thereof (e.g., SEQ ID NO:26) compared with mutants of specified residues.

Some antibodies bind to the same or overlapping epitope as an antibody designated 18C5. The sequences of the heavy and light chain mature variable regions of 18C5 are designated SEQ ID NOs: 1 and 3, respectively. Other antibodies having such a binding specificity can be produced by immunizing mice with TTR, or a portion thereof including the desired epitope (e.g., SEQ ID NO:30), and screening resulting antibodies for binding to monomeric TTR or a peptide comprising SEQ ID NO:30, optionally in competition with an antibody having the variable regions of mouse 18C5 (IgG1, kappa). Fragments of TTR including the desired epitope can be linked to a carrier that helps elicit an antibody response to the fragment and/or be combined with an adjuvant that helps elicit such a response. Such antibodies can be screened for differential binding to wild-type, monomeric versions of TTR or a fragment thereof (e.g., SEQ ID NO:26) compared with mutants of specified residues.

Screening against such mutants more precisely defines the binding specificity to allow identification of antibodies whose binding is inhibited by mutagenesis of particular residues and which are likely to share the functional properties of other exemplified antibodies. The mutations can be systematic replacement substitution with alanine (or serine or glycine if an alanine is present already) one residue at a time, or more broadly spaced intervals, throughout the target or throughout a section thereof in which an epitope is known to reside. If the same set of mutations significantly reduces the binding of two antibodies, the two antibodies bind the same epitope.

Antibodies having the binding specificity of a selected murine antibody (e.g., 9D5 or 18C5) can also be produced using a variant of the phage display method. See Winter, WO 92/20791. This method is particularly suitable for producing human antibodies. In this method, either the heavy or light chain variable region of the selected murine antibody is used as a starting material. If, for example, a light chain variable region is selected as the starting material, a phage library is constructed in which members display the same light chain variable region (i.e., the murine starting material) and a different heavy chain variable region. The heavy chain variable regions can for example be obtained from a library of rearranged human heavy chain variable regions. A phage showing strong specific binding (e.g., at least $10^8$ and preferably at least $10^9 M^{-1}$) for monomeric TTR or a fragment thereof (e.g., amino acid residues 89-97 or amino acid residues 101-109) is selected. The heavy chain variable region from this phage then serves as a starting material for constructing a further phage library. In this library, each phage displays the same heavy chain variable region (i.e., the region identified from the first display library) and a different light chain variable region. The light chain variable regions can be obtained for example from a library of rearranged human variable light chain regions. Again, phage showing strong specific binding for monomeric TTR or a fragment thereof (e.g., amino acid residues 89-97 or amino acid residues 101-109) are selected. The resulting antibodies usually have the same or similar epitope specificity as the murine starting material.

Other antibodies can be obtained by mutagenesis of cDNA encoding the heavy and light chains of an exemplary antibody, such as 9D5 or 18C5. Monoclonal antibodies that are at least 70%, 80%, 90%, 95%, 96%, 97%, 98%, or 99% identical to 9D5 or 18C5 in amino acid sequence of the mature heavy and/or light chain variable regions and maintain its functional properties, and/or which differ from the respective antibody by a small number of functionally inconsequential amino acid substitutions (e.g., conservative substitutions), deletions, or insertions are also included in the invention. Monoclonal antibodies having at least one or all six CDR(s) as defined by conventional definition, but preferably Kabat, that are 90%, 95%, 99% or 100% identical to corresponding CDRs of 9D5 or 18C5 are also included.

The invention also provides antibodies having some or all (e.g., 3, 4, 5, and 6) CDRs entirely or substantially from 9D5 or 18C5. Such antibodies can include a heavy chain variable region that has at least two, and usually all three, CDRs entirely or substantially from the heavy chain variable region of 9D5 or 18C5 and/or a light chain variable region having at least two, and usually all three, CDRs entirely or substantially from the light chain variable region of 9D5 or 18C5. The antibodies can include both heavy and light chains. A CDR is substantially from a corresponding 9D5 or 18C5 CDR when it contains no more than 4, 3, 2, or 1 substitutions, insertions, or deletions, except that CDR-H2 (when defined by Kabat) can have no more than 6, 5, 4, 3, 2, or 1 substitutions, insertions, or deletions. Such antibodies can have at least 70%, 80%, 90%, 95%, 96%, 97%, 98%, or 99% identity to 9D5 or 18C5 in the amino acid sequence of the mature heavy and/or light chain variable regions and maintain their functional properties, and/or differ from 9D5 or 18C5 by a small number of functionally inconsequential amino acid substitutions (e.g., conservative substitutions), deletions, or insertions.

Kabat CDRs (CDR-H1, CDR-H2, CDR-H3) of the heavy chain of 9D5 are designated SEQ ID NOs: 75, 76, and 77, respectively, and Kabat CDRs (CDR-L1, CDR-L2, CDR-L3) of the light chain of 9D5 are designated SEQ ID NOs: 78, 79, and 80, respectively.

Kabat/Chothia Composite CDRs (CDR-H1, CDR-H2, CDR-H3) of the heavy chain of 18C5 are designated SEQ ID NOs: 5, 7, and 9, respectively, and Kabat/Chothia Composite CDRs (CDR-L1, CDR-L2, CDR-L3) of the light chain of 18C5 are designated SEQ ID NOs: 11, 13, and 15, respectively.

Table 2 indicates the 18C5 CDRs as defined by Kabat, Chothia, Composite of Chothia and Kabat (also referred to herein as "Kabat/Chothia Composite"), AbM, and Contact.

TABLE 2

18C5 CDRs as defined by Kabat, Chothia, Composite of Chothia and Kabat, AbM, and Contact, Using Kabat Numbering

| Loop | Kabat | Chothia | Composite of Chothia & Kabat | AbM | Contact |
|---|---|---|---|---|---|
| L1 | L24--L34 | L24--L34 | L24--L34 | L24--L34 | L30--L36 |
|  | SEQ ID NO: 11 | SEQ ID NO: 11 | SEQ ID NO: 11 | SEQ ID NO: 11 | SEQ ID NO: 100 |
| L2 | L50--L56 | L50--L56 | L50--L56 | L50--L56 | L46--L55 |
|  | SEQ ID NO: 13 | SEQ ID NO: 13 | SEQ ID NO: 13 | SEQ ID NO: 13 | SEQ ID NO: 101 |
| L3 | L89--L97 | L89--L97 | L89--L97 | L89--L97 | L89--L96 |
|  | SEQ ID NO: 15 | SEQ ID NO: 15 | SEQ ID NO: 15 | SEQ ID NO: 15 | SEQ ID NO: 102 |
| H1 | H31--H35B | H26--H32 | H26--H35B | H26--H35B | H30--H35B |
|  | SEQ ID NO: 93 | SEQ ID NO: 94 | SEQ ID NO: 5 | SEQ ID NO: 5 | SEQ ID NO: 95 |
| H2 | H50--H65 | H52--H56 | H50--H65 | H50--H58 | H47--H58 |
|  | SEQ ID NO: 7 | SEQ ID NO: 96 | SEQ ID NO: 7 | SEQ ID NO: 97 | SEQ ID NO: 98 |
| H3 | H95--H102 | H95--H102 | H95--H102 | H95--H102 | H93-H101 |
|  | SEQ ID NO: 9 | SEQ ID NO: 9 | SEQ ID NO: 9 | SEQ ID NO: 9 | SEQ ID NO: 99 |

Some antibodies identified by such assays can bind to monomeric, misfolded, aggregated, or fibril forms of TTR but not to native tetrameric form of TTR, as described in the examples or otherwise. Likewise, some antibodies are immunoreactive on TTR-mediated amyloidosis tissue but not on healthy tissue.

Some antibodies can inhibit or reduce aggregation of TTR, inhibit or reduce TTR fibril formation, reduce or clear TTR deposits or aggregated TTR, or stabilize non-toxic conformations of TTR in an animal model or clinical trial. Some antibodies can treat, effect prophylaxis of, or delay the onset of a TTR amyloidosis as shown in an animal model or clinical trial. Exemplary animal models for testing activity against a TTR amyloidosis include those described in Kohno et al., *Am. J Path.* 150(4):1497-1508 (1997); Teng et al., *Laboratory Investigations* 81:385-396 (2001); Wakasugi et al., *Proc. Japan Acad.* 63B:344-347 (1987); Shimada et al., *Mol. Biol. Med.* 6:333-343 (1989); Nagata et al., *J. Biochem.* 117:169-175 (1995); Sousa et al., *Am. J. Path.* 161:1935-1948 (2002); and Santos et al., *Neurobiology of Aging* 31:280-289 (2010).

Anti-TTR antibodies including chimeric and humanized versions thereof, are useful in combination therapies, in bispecific antibodies, in methods of diagnosis and/or treatment of TTR associated disorders, and in methods of detecting TTR. Such anti-TTR antibodies, may include antibodies as in Table 3 below.

TABLE 3

Anti-TTR antibodies.

| Name | Epitope on TTR as reported | VH/VL or CDRs as reported | Reference |
|---|---|---|---|
| 9D5 | EHAEVVFTA (89-97) (SEQ ID NO: 45) | Kabat CDRs: CDR-H1 SEQ ID NO: 75 CDR-H2 SEQ ID NO: 76 CDR-H3 SEQ ID NO: 77 CDR-L1 SEQ ID NO: 78 CDR-L2 SEQ ID NO: 79 CDR-L3 SEQ ID NO: 80 | WO 2016/120810 A1 ATCC Deposit No. PTA-124078 Date: Apr. 4, 2017 |
| 14G8 | EHAEVVFTA (89-97) (SEQ ID NO: 45) | Kabat CDRs CDR-H1 SEQ ID NO: 39 CDR-H2 SEQ ID NO: 40 CDR-H3 SEQ ID NO: 41 CDR-L1 SEQ ID NO: 42 CDR-L2 SEQ ID NO: 43 CDR-L3 SEQ ID NO: 44 | WO 2016/120810 A1 ATCC Deposit No. PTA-124079 Date: Apr. 4, 2017 |
| 5A1 | EHAEVVFTA (89-97) (SEQ ID NO: 45) | Kabat CDRs CDR-H1 SEQ ID NO: 46 CDR-H2 SEQ ID NO: 47 CDR-H3 SEQ ID NO: 48 CDR-L1 SEQ ID NO 49 CDR-L2 SEQ ID NO: 50 CDR-L3 SEQ ID NO: 51 | WO 2016/120811 ATCC Deposit No. PTA-124080 Date: Apr. 4, 2017 |
| 6C1 | EHAEVVFTA (89-97) (SEQ ID NO: 45) | Kabat CDRs CDR-H1 SEQ ID NO: 52 CDR-H2 SEQ ID NO: 53 CDR-H3 SEQ ID NO: 54 CDR-L1 SEQ ID NO: 55 CDR-L2 SEQ ID NO: 56 CDR-L3 SEQ ID NO: 57 | WO 2016/120809 ATCC Deposit No. PTA-124077 Date: Apr. 4, 2017 |
| 18C5 | GPRRYTIAA (101-109) (SEQ ID NO: 30) | Kabat/Chothia Composite CDRs: CDR-H1 SEQ ID NO: 5 CDR-H2 SEQ ID NO: 7 CDR-H3 SEQ ID NO: 9 CDR-L1 SEQ ID NO: 11 CDR-L2 SEQ ID NO: 13 CDR-L3 SEQ ID NO: 15 | US Provisional Appl. 62/596,438, filed Oct. 6, 2017 |
| AD7F6 | | VH SEQ ID NO: 58 VL SEQ ID NO: 59 | WO 2010/030203 A1 |
| RT24 | 118-122, 115-124 | CDR-H1 SEQ ID NO: 60 CDR-H2 SEQ ID NO: 61 CDR-H3 SEQ ID NO: 62 CDR-L1 SEQ ID NO: 63 CDR-L2 SEQ ID NO: 64 CDR-L3 SEQ ID NO: 65 | WO 2015/115331 |
| NI-301.35G11 | 53-63, 54-61 | CDR-H1 SEQ ID NO: 66 CDR-H2 SEQ ID NO: 67 CDR-H3 SEQ ID NO: 68 CDR-L1 SEQ ID NO: 69 CDR-L2 SEQ ID NO: 70 CDR-L3 SEQ ID NO: 71 | US 2016/0355576 A1 ( |

TABLE 3-continued

Anti-TTR antibodies.

| Name | Epitope on TTR as reported | VH/VL or CDRs as reported | Reference |
|---|---|---|---|
| MFD101, MDF102, MFD103, MFD105 | ADDTWEPFASGKT (residues 36-49) (SEQ ID NO: 72) | | US 2016/0039916 A1 |
| MFD107, MFD108, MFD109, MFD111 | TSESGELHGLTTE (residues 49-61) (SEQ ID NO: 73) | | US 2016/0039916 A1 |
| MFD114 | ALLSPYSYSTTAV (residues 109-121) (SEQ ID NO: 74) | | US 2016/0039916 A1 |
| | 30-66 | | US 2016/0039916 A1 |
| | 70-127 | | US 2016/0039916 A1 |
| | 80-127 | | US 2016/0039916 A1 |
| | 90-127 | | US 2016/0039916 A1 |
| | 100-127 | | US 2016/0039916 A1 |
| | 110-127 | | US 2016/0039916 A1 |
| | 115-127 | | US 2016/0039916 A1 |

B. Non-Human Antibodies

The production of other non-human antibodies, e.g., murine, guinea pig, primate, rabbit or rat, against monomeric TTR or a fragment thereof (e.g., amino acid residues 89-97 or amino acid residues 101-109) can be accomplished by, for example, immunizing the animal with TTR or a fragment thereof. See Harlow & Lane, Antibodies, *A Laboratory Manual* (CSHP NY, 1988) (incorporated by reference for all purposes). Such an immunogen can be obtained from a natural source, by peptide synthesis, or by recombinant expression. Optionally, the immunogen can be administered fused or otherwise complexed with a carrier protein. Optionally, the immunogen can be administered with an adjuvant. Several types of adjuvant can be used as described below. Complete Freund's adjuvant followed by incomplete adjuvant is preferred for immunization of laboratory animals. Rabbits or guinea pigs are typically used for making polyclonal antibodies. Mice are typically used for making monoclonal antibodies. Antibodies are screened for specific binding to monomeric TTR or an epitope within TTR (e.g., an epitope comprising one or more of amino acid residues 89-97 or of amino acid residues 101-109). Such screening can be accomplished by determining binding of an antibody to a collection of monomeric TTR variants, such as TTR variants containing amino acid residues 89-97 amino acid residues 101-109 or mutations within these residues, and determining which TTR variants bind to the antibody. Binding can be assessed, for example, by Western blot, FACS or ELISA.

C. Humanized Antibodies

A humanized antibody is a genetically engineered antibody in which CDRs from a non-human "donor" antibody are grafted into human "acceptor" antibody sequences (see, e.g., Queen, U.S. Pat. Nos. 5,530,101 and 5,585,089; Winter, U.S. Pat. No. 5,225,539; Carter, U.S. Pat. No. 6,407,213; Adair, U.S. Pat. No. 5,859,205; and Foote, U.S. Pat. No. 6,881,557). The acceptor antibody sequences can be, for example, a mature human antibody sequence, a composite of such sequences, a consensus sequence of human antibody sequences, or a germline region sequence. Thus, a humanized antibody is an antibody having at least three, four, five or all CDRs entirely or substantially from a donor antibody and variable region framework sequences and constant regions, if present, entirely or substantially from human antibody sequences. Similarly a humanized heavy chain has at least one, two and usually all three CDRs entirely or substantially from a donor antibody heavy chain, and a heavy chain variable region framework sequence and heavy chain constant region, if present, substantially from human heavy chain variable region framework and constant region sequences. Similarly a humanized light chain has at least one, two and usually all three CDRs entirely or substantially from a donor antibody light chain, and a light chain variable region framework sequence and light chain constant region, if present, substantially from human light chain variable region framework and constant region sequences. Other than nanobodies and dAbs, a humanized antibody comprises a humanized heavy chain and a humanized light chain. A CDR in a humanized antibody is substantially from a corresponding CDR in a non-human antibody when at least 85%, 90%, 95% or 100% of corresponding residues (as defined by any conventional definition but preferably defined by Kabat) are identical between the respective CDRs. The variable region framework sequences of an antibody chain or the constant region of an antibody chain are substantially from a human variable region framework sequence or human constant region respectively when at least 85%, 90%, 95% or 100% of corresponding residues defined by any conventional definition but preferably defined by Kabat are identical. To be classified as humanized under the 2014 World Health Organization (WHO) International non-proprietary names (INN) definition of humanized antibodies, an antibody must have at least 85% identity in the mature variable regions to human germline antibody sequences (i.e., prior to somatic hypermutation). Mixed antibodies are antibodies for which one antibody chain (e.g., heavy chain) meets the threshold but the other chain (e.g., light chain) does not meet the threshold. An antibody is classified as chimeric if neither chain meets the threshold, even though the variable framework regions for both chains were substantially human with some murine backmutations. See, Jones et al. (2016) The INNs and outs of antibody nonproprietary names, mAbs 8:1, 1-9, DOI: 10.1080/19420862.2015.1114320. See also "WHO-INN: International nonproprietary names (INN) for biological and biotechnological substances (a review)" (Internet) 2014. Available from: http://www.who.int/medicines/services/inn/BioRev2014.pdf), incorporated herein by reference. For the avoidance of doubt, the term "humanized" as used herein is not intended to be limited to the 2014 WHO INN definition of humanized antibodies. Some of the humanized antibodies provided herein have at least 85% sequence identity to human germline sequences in either or both mature variable regions and some of the humanized antibodies provided herein have less than 85% sequence identity to human germline sequences in either or both mature variable regions. Some of the mature heavy chain variable regions of the humanized antibodies provided herein have from about 60% to 100% sequence identity to human germ line sequences, such as, for example, in the range of about 60% to 69%, 70% to 79%, 80% to 84%, or 85% to 89%. Some of the mature heavy chain variable regionsheavy chains fall below the 2014 WHO INN definition and have, for example, about 64%, 65%, 66%, 67%, 68%, 69%, 70%, 71%, 72%, 73%, 74%, 75%, 76%, 77%, 78%, 79%, 80%, 81%, or 82%, 83%, or 84% sequence identity to human germ line sequences, while other mature heavy chain variable regions meet the 2014 WHO INN definition and have about 85%, 86%, 87%, 88%, 89% or greater sequence identity to human germ line sequences. Some of the mature light chain variable regions of the humanized antibodies provided herein have from about 60% to 100% sequence identity to human germ line sequences, such as, for example, in the range of about 80% to 84% or 85% to 89%. Some of the mature light chain variable regions fall below the 2014 WHO INN definition and have, for example, about 81%, 82%, 83% or 84% sequence identity to human germ line sequences, while other mature light chain variable regions meet the 2014 WHO INN definition and have about 85%, 86%, 87%, 88%, 89% or greater sequence identity to human germ line sequences. Some humanized antibodies provided herein that are "chimeric" under the 2014 WHO INN definition have mature heavy chain variable regions with less than 85% identity to human germ line sequences paired with mature light chain variable regions having less than 85% identity to human germ line sequences. Some humanized antibodies provided herein are "mixed" under the 2014 WHO INN definition, for example, having a mature heavy chain variable region with at least 85% sequence identity to human germ line sequences paired with a mature light chain variable region having less than 85% sequence identity to human germ line sequences, or vice versa. Some humanized antibodies provided herein meet the 2014 WHO INN definition of "humanized" and have a mature heavy chain variable region with at least 85% sequence identity to human germ line sequences paired with a mature light chain variable region having at least 85% sequence identity to human germ line sequences. Exemplary 18C5 antibodies that meet the 2014 WHO INN definition of "humanized" include antibodies having a mature heavy chain variable region with an amino acid sequence of SEQ ID NO:85 or SEQ ID NO: 86 paired with a mature light chain variable region having an amino acid sequence of SEQ ID NO:91 or SEQ ID NO:92.

Although humanized antibodies often incorporate all six CDRs (preferably as defined by Kabat) from a mouse antibody, they can also be made with less than all CDRs (e.g., at least 3, 4, or 5 CDRs) from a mouse antibody (e.g., Pascalis et al., *J. Immunol.* 169:3076, 2002; Vajdos et al., *J. of Mot. Biol.,* 320: 415-428, 2002; Iwahashi et al., *Mol. Immunol.* 36:1079-1091, 1999; Tamura et al, *J. Immunol.,* 164:1432-1441, 2000).

In some antibodies only part of the CDRs, namely the subset of CDR residues required for binding, termed the SDRs, are needed to retain binding in a humanized antibody. CDR residues not contacting antigen and not in the SDRs can be identified based on previous studies (for example residues H60-H65 in CDR H2 are often not required), from regions of Kabat CDRs lying outside Chothia hypervariable loops (Chothia, *J. Mol. Biol.* 196:901, 1987), by molecular modeling and/or empirically, or as described in Gonzales et al., *Mol. Immunol.* 41: 863, 2004. In such humanized antibodies at positions in which one or more donor CDR residues is absent or in which an entire donor CDR is omitted, the amino acid occupying the position can be an amino acid occupying the corresponding position (by Kabat numbering) in the acceptor antibody sequence. The number of such substitutions of acceptor for donor amino acids in the CDRs to include reflects a balance of competing considerations. Such substitutions are potentially advantageous in decreasing the number of mouse amino acids in a humanized antibody and consequently decreasing potential immunogenicity. However, substitutions can also cause changes of affinity, and significant reductions in affinity are preferably avoided. Positions for substitution within CDRs and amino acids to substitute can also be selected empirically.

The human acceptor antibody sequences can optionally be selected from among the many known human antibody sequences to provide a high degree of sequence identity (e.g., 65-85% identity) between a human acceptor sequence variable region frameworks and corresponding variable region frameworks of a donor antibody chain.

An example of an acceptor sequence for the 18C5 heavy chain is the humanized Crenezumab Fab (CreneFab) VH, with PDB accession code 5VZY (SEQ ID NO:83). An example of an acceptor sequence for the 18C5 light chain is the humanized Crenezumab Fab (CreneFab) VL, with PDB accession code 5VZY (SEQ ID NO:89). Another example of an acceptor sequence for the 18C5 light chain is the human germline gene IGKV2-30*02 (SEQ ID NO:90).

If more than one human acceptor antibody sequence is selected for a chain (either light or heavy), a composite or hybrid of those acceptors can be used for that chain, and the amino acids used at different can be taken from any of the human acceptor antibody sequences used.

Certain amino acids from the human variable region framework residues can be selected for substitution based on their possible influence on CDR conformation and/or binding to antigen. Investigation of such possible influences is by modeling, examination of the characteristics of the amino acids at particular locations, or empirical observation of the effects of substitution or mutagenesis of particular amino acids.

For example, when an amino acid differs between a murine variable region framework residue and a selected human variable region framework residue, the human framework amino acid can be substituted by the equivalent framework amino acid from the mouse antibody when it is reasonably expected that the amino acid:

(1) noncovalently binds antigen directly;
(2) is adjacent to a CDR region or within a CDR as defined by Chothia but not Kabat;
(3) otherwise interacts with a CDR region (e.g., is within about 6 Å of a CDR region), (e.g., identified by modeling the light or heavy chain on the solved structure of a homologous known immunoglobulin chain); or
(4) is a residue participating in the VL-VH interface.

The invention provides humanized forms of the murine 18C5 antibody including 2 exemplified humanized heavy chain mature variable regions (hu18C5-VH_v1 (SEQ ID NO:85), and hu18C5-VH_v2 (SEQ ID NO:86)), and 2 exemplified humanized light chain mature variable regions (hu18C5-VL_v1 (SEQ ID NO:91) and hu18C5-VL_v2 (SEQ ID NO:92)).

In an embodiment, humanized sequences are generated using a two-stage PCR protocol that allows introduction of multiple mutations, deletions, and insertions using QuikChange site-directed mutagenesis [Wang, W. and Malcolm, B. A. (1999) *BioTechniques* 26:680-682)].

Framework residues from classes (1) through (3) as defined by Queen, U.S. Pat. No. 5,530,101, are sometimes alternately referred to as canonical and vernier residues. Framework residues that help define the conformation of a CDR loop are sometimes referred to as canonical residues (Chothia & Lesk, *J. Mol. Biol.* 196:901-917 (1987); Thornton & Martin, *J. Mol. Biol.* 263:800-815 (1996)). Framework residues that support antigen-binding loop conformations and play a role in fine-tuning the fit of an antibody to antigen are sometimes referred to as vernier residues (Foote & Winter, *J. Mol. Biol* 224:487-499 (1992)).

Other framework residues that are candidates for substitution are residues creating a potential glycosylation site. Still other candidates for substitution are acceptor human framework amino acids that are unusual for a human immunoglobulin at that position. These amino acids can be substituted with amino acids from the equivalent position of the mouse donor antibody or from the equivalent positions of more typical human immunoglobulins.

Other framework residues that are candidates for substitution are N-terminal glutamic acid residues (E) that may be replaced with glutamine (Q).

Exemplary humanized antibodies are humanized forms of the mouse 18C5, designated Hu18C5.

Figure 11:
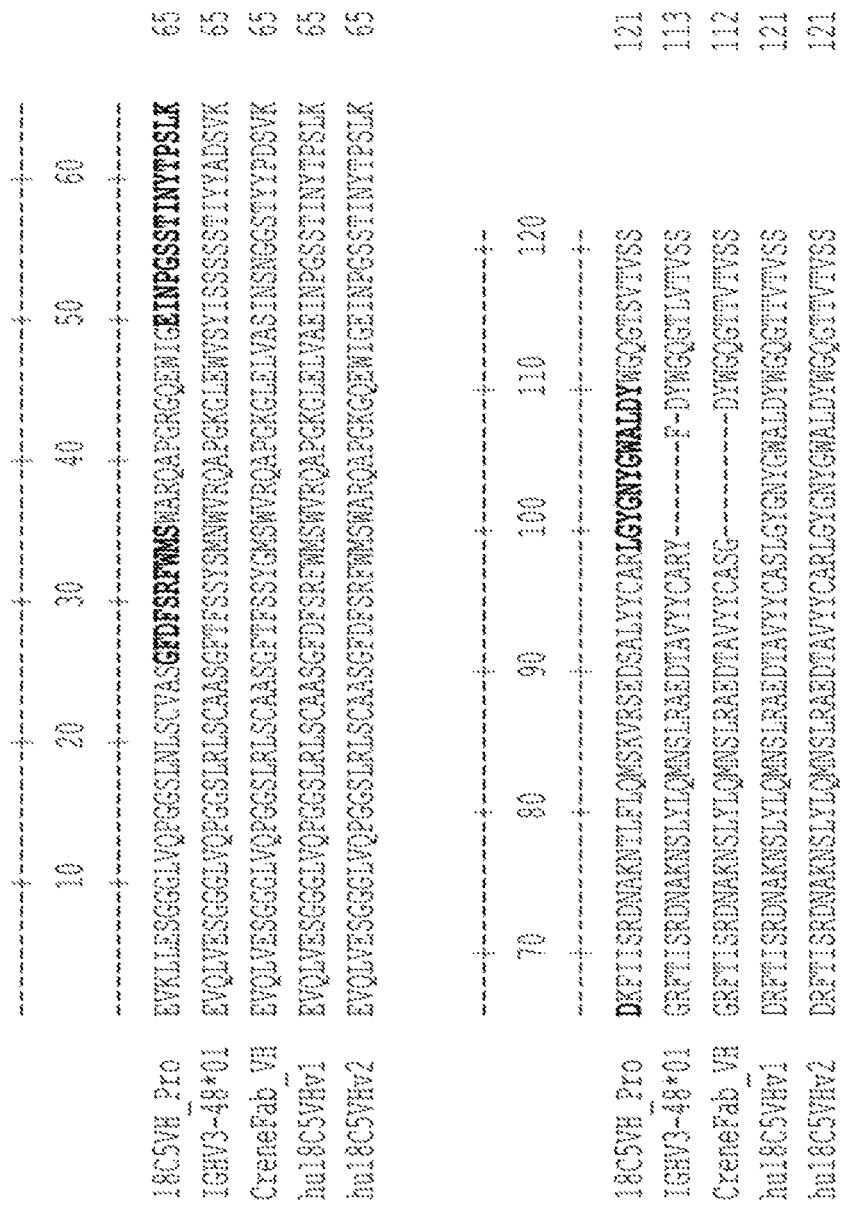
FIG. 11 depicts an alignment of heavy chain variable regions of the mouse 18C5 antibody (SEQ ID NO: 81), human germline sequence IGHV3-48*01 (SEQ ID NO:84), human acceptor 5VZY-VH_huFrwk (Crenefab-VH) (SEQ ID NO:83), and humanized versions of the 18C5 antibody (hu18C5 VH-v1 and hu18C5 VH-v2, SEQ ID NOs: 84 and 85, respectively). CDRs defined according to Kabat/Chothia Composite are bolded in the mouse 18C5 heavy chain variable region sequence.
Figure 12:
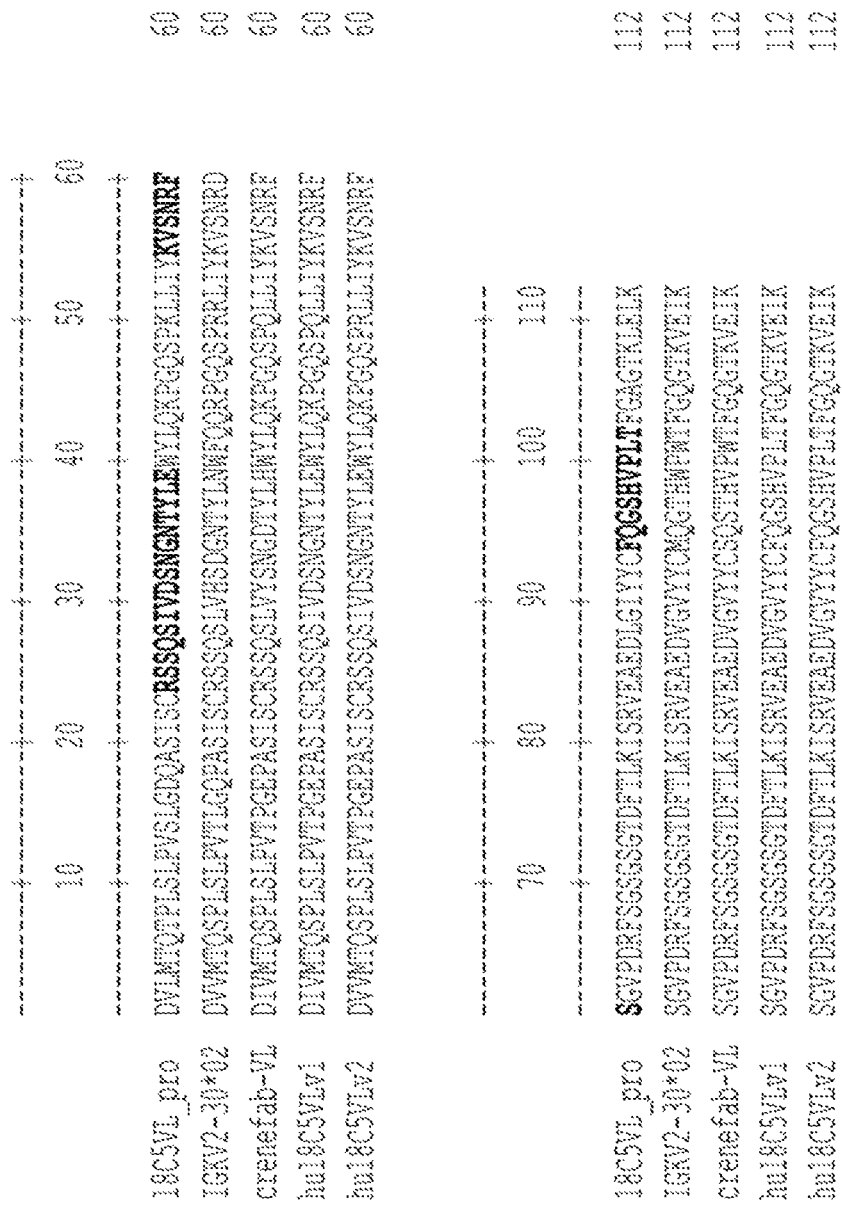
FIG. 12 depicts an alignment of light chain variable regions of the mouse 18C5 antibody (SEQ ID NO:87), human germline sequence IGKV2-30*02 (SEQ ID NO:90), human acceptor 5VZY-VL_huFrwk (Crenefab-VL) (SEQ ID NO:89), and humanized versions of the 18C5 antibody (hu18C5-VL-v1 and hu18C5-VL-v2, SEQ ID NOs: 91 and 92, respectively). CDRs defined according to Kabat/Chothia Composite are bolded in the mouse 18C5 light chain variable region sequence.

The mouse antibody 18C5 comprises mature heavy and light chain variable regions having amino acid sequences comprising SEQ ID NO: 81 and SEQ ID NO:87, respectively. The invention provides 2 exemplified humanized mature heavy chain variable regions: hu18C5-VH_v1 and hu18C5-VH_v2. The invention further provides 2 exemplified human mature light chain variable regions: hu18C5-VL_v1 and hu18C5-VL_v2. Alignments of the murine 18C5 and various humanized antibodies are shown for the light chain variable regions (Table 8 and FIG. 12), and heavy chain variable regions (Table 9 and FIG. 11).

For reasons such as possible influence on CDR conformation and/or binding to antigen, mediating interaction between heavy and light chains, interaction with the constant region, being a site for desired or undesired post-translational modification, being an unusual residue for its position in a human variable region sequence and therefore potentially immunogenic, getting aggregation potential, and other reasons, the following 8 variable region framework positions of 18C5 were considered as candidates for substitutions in the 2 exemplified human mature light chain variable regions and the 2 exemplified human mature heavy chain variable regions, as further specified in Example 7: L2 (I2V), L45 (Q45R), H37 (V37A), H45 (L45Q), H47 (L47W), H48 (V48I), H49 (A49G), and H94 (S94R).

Here, as elsewhere, the first-mentioned residue is the residue of a humanized antibody formed by grafting Kabat CDRs or a composite Chothia Kabat CDR in the case of CDR-H1 into a human acceptor framework, and the second-mentioned residue is a residue being considered for replacing such residue. Thus, within variable region frameworks, the first mentioned residue is human, and within CDRs, the first mentioned residue is mouse.

Exemplified antibodies include any permutations or combinations of the exemplified mature heavy and light chain variable regions of 18C5 e.g., hu18C5VH_v1/hu18C5VL_v1, hu18C5VH_v1/hu18C5VL_v2, hu18C5VH_v2/hu18C5VL_v1, or hu18C5VH_v2/hu18C5VL_v2.

The invention provides variants of the 18C5 humanized antibody in which the humanized mature heavy chain variable region shows at least 90%, 95%, 96%, 97%, 98%, or 99% identity to any one of hu18C5-VH_v1, and hu18C5-VH_v2. (SEQ ID NOs: 85-86) and the humanized mature light chain variable region shows at least 90%, 95%, 96%, 97%, 98%, or 99% identity to any one of hu18C5-VL_v1, and hu18C5-VL_v2, (SEQ ID NOs: 91-92). In some such antibodies at least 1, 2, 3, 4, 5, 6, 7, or all 8, of the backmutations or other mutations found in SEQ ID NO:86 and SEQ ID NO:92 are retained.

In some humanized 18C5 antibodies, at least one of the following positions is occupied by the amino acid as specified: H37 is occupied by V or A, H45 is occupied by L or Q, H47 is occupied by L or W, H48 is occupied by L or I, H49 is occupied by A or G, and H94 is occupied by S or R.

In some humanized 18C5 antibodies, positions H37, H45, H47, H48, H49, and H94 in the VH region are occupied by A, Q, W, I, G, and R, respectively, as in hu18C5-VH_v2.

In some humanized 18C5 antibodies, at least one of the following positions is occupied by the amino acid as specified: L2 is occupied by I or V and L45 is occupied by Q or R.

In some humanized 18C5 antibodies, positions L2 and L45 in the VL region are occupied by V and R, respectively, as in hu18C5-VL_v2.

In some humanized 18C5 antibodies, the variable heavy chain has ≥85% identity to human sequence. In some humanized 18C5 antibodies, the variable light chain has ≥85% identity to human sequence. In some humanized 18C5 antibodies, each of the variable heavy chain and variable light chain has ≥85% identity to human germline sequence.

The CDR regions of such humanized antibodies can be identical or substantially identical to the CDR regions of the 9D5 or 18C5 mouse donor antibody. The CDR regions can be defined by any conventional definition, such as those in Table 1, but are preferably as defined by Kabat or Kabat+Chothia composite.

Variable regions framework positions are in accordance with Kabat numbering unless otherwise stated. Other such variants typically differ from the sequences of the exemplified Hu18C5 heavy and light chains by a small number (e.g., typically no more than 1, 2, 3, 5, 10, or 15) of replacements, deletions or insertions.

A possibility for additional variation in humanized 9D5 or 18C5 variants is additional backmutations in the variable region frameworks. Many of the framework residues not in contact with the CDRs in the humanized mAb can accommodate substitutions of amino acids from the corresponding positions of the donor mouse mAb or other mouse or human antibodies, and even many potential CDR-contact residues are also amenable to substitution. Even amino acids within the CDRs may be altered, for example, with residues found at the corresponding position of the human acceptor sequence used to supply variable region frameworks. In addition, alternate human acceptor sequences can be used, for example, for the heavy and/or light chain. If different acceptor sequences are used, one or more of the backmutations recommended above may not be performed because the corresponding donor and acceptor residues are already the same without backmutations.

Some replacements or backmutations in Hu9D5 or Hu18C5 variants (whether or not conservative) have no substantial effect on the binding affinity or potency of the humanized mAb, that is, its ability to bind to monomeric TTR (e.g., the potency in some or all of the assays described in the present examples of the variant humanized 9D5 or 18C5 antibody is essentially the same, i.e., within experimental error, as that of murine 9D5 or murine 18C5). Exemplary humanized 9D5 variants are described in WO 2016/120810.

D. Chimeric and Veneered Antibodies

The invention further provides chimeric and veneered forms of non-human antibodies, particularly the 9D5 or 18C5 antibodies of the examples.

A chimeric antibody is an antibody in which the mature variable regions of light and heavy chains of a non-human antibody (e.g., a mouse) are combined with human light and heavy chain constant regions. Such antibodies substantially or entirely retain the binding specificity of the mouse antibody, and are about two-thirds human sequence. In an embodiment, a chimeric 18C5 antibody has a mature heavy chain variable region amino acid sequence of SEQ ID NO:81, a mature light chain variable region amino acid sequence of SEQ ID NO:87, a human heavy chain constant region amino acid sequence of SEQ ID NO: 17, and a human light chain constant region amino acid sequence of SEQ ID NO: 19. An exemplary chimeric 9D5 antibody is described in WO 2016/120810.

A veneered antibody is a type of humanized antibody that retains some and usually all of the CDRs and some of the non-human variable region framework residues of a non-human antibody but replaces other variable region framework residues that may contribute to B- or T-cell epitopes, for example exposed residues (Padlan, *Mol. Immunol.* 28:489, 1991) with residues from the corresponding positions of a human antibody sequence. The result is an antibody in which the CDRs are entirely or substantially from a non-human antibody and the variable region frameworks of the non-human antibody are made more human-like by the substitutions. Veneered forms of the 9D5 or 18C5 antibody are included in the invention.

E. Human Antibodies

Human antibodies against monomeric TTR or a fragment thereof (e.g., amino acid residues 89-97 (SEQ ID NO:45) of TTR, or amino acid residues 101-109 (SEQ ID NO:30) of TTR) are provided by a variety of techniques described below. Some human antibodies are selected by competitive binding experiments, by the phage display method of Winter, above, or otherwise, to have the same epitope specificity as a particular mouse antibody, such as one of the mouse monoclonal antibodies described in the examples. Human antibodies can also be screened for particular epitope specificity by using only a fragment of TTR, such as a TTR variant containing only amino acid residues 89-97 or amino acid residues 101-109 of TTR, as the target antigen, and/or by screening antibodies against a collection of TTR variants, such as TTR variants containing various mutations within amino acid residues 89-97 or amino acid residues 101-109 of TTR.

Methods for producing human antibodies include the trioma method of Oestberg et al., *Hybridoma* 2:361-367 (1983); Oestberg, U.S. Pat. No. 4,634,664; and Engleman et al., U.S. Pat. No. 4,634,666, use of transgenic mice including human immunoglobulin genes (see, e.g., Lonberg et al., WO93/12227 (1993); U.S. Pat. Nos. 5,877,397; 5,874,299; 5,814,318; 5,789,650; 5,770,429; 5,661,016; 5,633,425; 5,625,126; 5,569,825; 5,545,806; Neuberger, *Nat. Biotechnol.* 14:826 (1996); and Kucherlapati, WO 91/10741 (1991)) and phage display methods (see, e.g., Dower et al., WO 91/17271; McCafferty et al., WO 92/01047; U.S. Pat. Nos. 5,877,218; 5,871,907; 5,858,657; 5,837,242; 5,733,743; and 5,565,332).

F. Selection of Constant Region

The heavy and light chain variable regions of chimeric, veneered or humanized antibodies can be linked to at least a portion of a human constant region. The choice of constant region depends, in part, whether antibody-dependent cell-mediated cytotoxicity, antibody dependent cellular phagocytosis and/or complement dependent cytotoxicity are desired. For example, human isotypes IgG1 and IgG3 have complement-dependent cytotoxicity and human isotypes IgG2 and IgG4 do not. Human IgG1 and IgG3 also induce stronger cell mediated effector functions than human IgG2 and IgG4. Light chain constant regions can be lambda or kappa. Numbering conventions for constant regions include EU numbering (Edelman, G. M. et al., *Proc. Natl. Acad. USA,* 63, 78-85 (1969)), Kabat numbering (Kabat, *Sequences of Proteins of Immunological Interest* (National Institutes of Health, Bethesda, MD, 1991, IMGT unique numbering (Lefranc M.-P. et al., IMGT unique numbering for immunoglobulin and T cell receptor constant domains and Ig superfamily C-like domains, Dev. Comp. Immunol., 29, 185-203 (2005), and IMGT exon numbering (Lefranc, supra).

One or several amino acids at the amino or carboxy terminus of the light and/or heavy chain, such as the C-terminal lysine of the heavy chain, may be missing or derivatized in a proportion or all of the molecules. Substitutions can be made in the constant regions to reduce or increase effector function such as complement-mediated cytotoxicity or ADCC (see, e.g., Winter et al., U.S. Pat. No. 5,624,821; Tso et al., U.S. Pat. No. 5,834,597; and Lazar et al., *Proc. Natl. Acad. Sci. USA* 103:4005, 2006), or to prolong half-life in humans (see, e.g., Hinton et al., *J. Biol. Chem.* 279:6213, 2004). Exemplary substitutions include a Gln at position 250 and/or a Leu at position 428 (EU numbering is used in this paragraph for the constant region) for increasing the half-life of an antibody. Substitution at any or all of positions 234, 235, 236 and/or 237 reduce affinity for Fcγ receptors, particularly FcγRI receptor (see, e.g., U.S. Pat. No. 6,624,821). An alanine substitution at positions 234, 235, and 237 of human IgG1 can be used for reducing effector functions. Some antibodies have alanine substitution at positions 234, 235 and 237 of human IgG1 for reducing effector functions. Optionally, positions 234, 236 and/or 237 in human IgG2 are substituted with alanine and position 235 with glutamine (see, e.g., U.S. Pat. No. 5,624, 821). In some antibodies, a mutation at one or more of positions 241, 264, 265, 270, 296, 297, 322, 329, and 331 by EU numbering of human IgG1 is used. In some antibodies, a mutation at one or more of positions 318, 320, and 322 by EU numbering of human IgG1 is used. In some antibodies, positions 234 and/or 235 are substituted with alanine and/or position 329 is substituted with glycine. In some antibodies, positions 234 and 235 are substituted with alanine, such as in SEQ ID NO:23. In some antibodies, the isotype is human IgG2 or IgG4.

An exemplary human light chain kappa constant region has the amino acid sequence of SEQ ID NO:24. The N-terminal arginine of SEQ ID NO:24 can be omitted, in which case light chain kappa constant region has the amino acid sequence of SEQ ID NO:25. An exemplary human IgG1 heavy chain constant region has the amino acid sequence of SEQ ID NO:21 (with or without the C-terminal lysine). Antibodies can be expressed as tetramers containing two light and two heavy chains, as separate heavy chains, light chains, as Fab, Fab', F(ab')2, and Fv, or as single chain antibodies in which heavy and light chain mature variable domains are linked through a spacer.

Human constant regions show allotypic variation and isoallotypic variation between different individuals, that is, the constant regions can differ in different individuals at one or more polymorphic positions. Isoallotypes differ from allotypes in that sera recognizing an isoallotype bind to a non-polymorphic region of a one or more other isotypes. Thus, for example, another heavy chain constant region is of IgG1 G1m3 allotype and has the amino acid sequence of SEQ ID NO:22. Another heavy chain constant region of the IgG1 G1m3 allotype has the amino acid sequence of SEQ ID NO:23 (with or without the C-terminal lysine). Reference to a human constant region includes a constant region with any natural allotype or any permutation of residues occupying positions in natural allotypes.

G. Expression of Recombinant Antibodies

A number of methods are known for producing chimeric and humanized antibodies using an antibody-expressing cell line (e.g., hybridoma). For example, the immunoglobulin variable regions of antibodies can be cloned and sequenced using well known methods. In one method, the heavy chain variable VH region is cloned by RT-PCR using mRNA prepared from hybridoma cells. Consensus primers are employed to the VH region leader peptide encompassing the translation initiation codon as the 5' primer and a g2b constant regions specific 3' primer. Exemplary primers are described in U.S. patent publication US 2005/0009150 by Schenk et al. (hereinafter "Schenk"). The sequences from multiple, independently derived clones can be compared to ensure no changes are introduced during amplification. The sequence of the VH region can also be determined or confirmed by sequencing a VH fragment obtained by 5' RACE RT-PCR methodology and the 3' g2b specific primer.

The light chain variable VL region can be cloned in an analogous manner. In one approach, a consensus primer set is designed for amplification of VL regions using a 5' primer designed to hybridize to the VL region encompassing the translation initiation codon and a 3' primer specific for the Ck region downstream of the V-J joining region. In a second approach, 5'RACE RT-PCR methodology is employed to clone a VL encoding cDNA. Exemplary primers are described in Schenk, supra. The cloned sequences are then combined with sequences encoding human (or other non-human species) constant regions. Exemplary sequences encoding human constant regions include SEQ ID NO:32, which encodes a human IgG1 constant region, and SEQ ID NOs:33 and 34, which encode a human kappa light chain constant region.

In one approach, the heavy and light chain variable regions are re-engineered to encode splice donor sequences downstream of the respective VDJ or VJ junctions and are cloned into a mammalian expression vector, such as pCMV-hγ1 for the heavy chain and pCMV-Mcl for the light chain. These vectors encode human γ1 and Ck constant regions as exonic fragments downstream of the inserted variable region cassette. Following sequence verification, the heavy chain and light chain expression vectors can be co-transfected into CHO cells to produce chimeric antibodies. Conditioned media is collected 48 hours post-transfection and assayed by western blot analysis for antibody production or ELISA for antigen binding. The chimeric antibodies are humanized as described above.

Chimeric, veneered, humanized, and human antibodies are typically produced by recombinant expression. Recombinant polynucleotide constructs typically include an expression control sequence operably linked to the coding sequences of antibody chains, including naturally associated or heterologous expression control elements, such as a promoter. The expression control sequences can be promoter systems in vectors capable of transforming or transfecting eukaryotic or prokaryotic host cells. Once the vector has been incorporated into the appropriate host, the host is maintained under conditions suitable for high level expression of the nucleotide sequences and the collection and purification of the crossreacting antibodies.

These expression vectors are typically replicable in the host organisms either as episomes or as an integral part of the host chromosomal DNA. Commonly, expression vectors contain selection markers, e.g., ampicillin resistance or hygromycin resistance, to permit detection of those cells transformed with the desired DNA sequences.

*E. coli* is one prokaryotic host useful for expressing antibodies, particularly antibody fragments. Microbes, such as yeast, are also useful for expression. *Saccharomyces* is a yeast host with suitable vectors having expression control sequences, an origin of replication, termination sequences, and the like as desired. Typical promoters include 3-phosphoglycerate kinase and other glycolytic enzymes. Inducible yeast promoters include, among others, promoters from alcohol dehydrogenase, isocytochrome C, and enzymes responsible for maltose and galactose utilization.

Mammalian cells can be used for expressing nucleotide segments encoding immunoglobulins or fragments thereof. See Winnacker, From Genes to Clones, (VCH Publishers, N Y, 1987). A number of suitable host cell lines capable of secreting intact heterologous proteins have been developed, and include CHO cell lines, various COS cell lines, HeLa cells, HEK293 cells, L cells, and non-antibody-producing myelomas including Sp2/0 and NS0. The cells can be nonhuman. Expression vectors for these cells can include expression control sequences, such as an origin of replication, a promoter, an enhancer (Queen et al., *Immunol. Rev.* 89:49 (1986)), and necessary processing information sites, such as ribosome binding sites, RNA splice sites, polyadenylation sites, and transcriptional terminator sequences. Expression control sequences can include promoters derived from endogenous genes, cytomegalovirus, SV40, adenovirus, bovine papillomavirus, and the like. See Co et al., *J. Immunol.* 148:1149 (1992).

Alternatively, antibody coding sequences can be incorporated in transgenes for introduction into the genome of a transgenic animal and subsequent expression in the milk of the transgenic animal (see, e.g., U.S. Pat. Nos. 5,741,957; 5,304,489; and 5,849,992). Suitable transgenes include coding sequences for light and/or heavy chains operably linked with a promoter and enhancer from a mammary gland specific gene, such as casein or beta lactoglobulin.

The vectors containing the DNA segments of interest can be transferred into the host cell by methods depending on the type of cellular host. For example, calcium chloride transfection is commonly utilized for prokaryotic cells, whereas calcium phosphate treatment, electroporation, lipofection, biolistics, or viral-based transfection can be used for other cellular hosts. Other methods used to transform mammalian cells include the use of polybrene, protoplast fusion, liposomes, electroporation, and microinjection. For production of transgenic animals, transgenes can be microinjected into fertilized oocytes or can be incorporated into the genome of embryonic stem cells, and the nuclei of such cells transferred into enucleated oocytes.

Having introduced vector(s) encoding antibody heavy and light chains into cell culture, cell pools can be screened for growth productivity and product quality in serum-free media. Top-producing cell pools can then be subjected of FACS-based single-cell cloning to generate monoclonal lines. Specific productivities above 50 pg or 100 pg per cell per day, which correspond to product titers of greater than 7.5 g/L culture, can be used. Antibodies produced by single cell clones can also be tested for turbidity, filtration properties, PAGE, IEF, UV scan, HP-SEC, carbohydrate-oligosaccharide mapping, mass spectrometry, and binding assay, such as ELISA or Biacore. A selected clone can then be banked in multiple vials and stored frozen for subsequent use.

Once expressed, antibodies can be purified according to standard procedures of the art, including protein A capture, HPLC purification, column chromatography, gel electrophoresis and the like (see generally, Scopes, *Protein Purification* (Springer-Verlag, NY, 1982)).

Methodology for commercial production of antibodies can be employed, including codon optimization, selection of promoters, selection of transcription elements, selection of terminators, serum-free single cell cloning, cell banking, use of selection markers for amplification of copy number, CHO terminator, or improvement of protein titers (see, e.g., U.S. Pat. Nos. 5,786,464; 6,114,148; 6,063,598; 7,569,339; WO2004/050884; WO2008/012142; WO2008/012142; WO2005/019442; WO2008/107388; WO2009/027471; and U.S. Pat. No. 5,888,809).

H. Antibody Screening Assays

Antibodies can be subject to several screens including binding assays, functional screens, screens in animal models of diseases associated with TTR deposits, and clinical trials. Binding assays test for specific binding and, optionally, affinity and epitope specificity to monomeric TTR or a fragment thereof. For example, binding assays can screen for antibodies that bind to amino acid residues 89-97 (SEQ ID NO:45) or amino acid residues 101-109 (SEQ ID NO:30) of TTR, which are epitopes that are buried in the native TTR tetramer and exposed in monomeric, misfolded, aggregated, or fibril forms of TTR. Antibodies can also be screened for the ability to bind pre-fibrillar, non-native conformations of TTR and TTR amyloid fibrils but not native TTR conformations. For example, antibodies can be screened for the ability to bind to monomeric forms of TTR created by dissociation or disaggregation of native tetrameric TTR, and can be counter-screened against native tetrameric TTR, as described in the examples or otherwise. Likewise, antibodies can also be screened for their immunoreactivity on TTR-mediated amyloidosis tissue but not on healthy tissue. Such screens are sometimes performed in competition with an exemplary antibody, such as an antibody having the variable regions of 9D5 or of 18C5 or IgG1 kappa isotype. Optionally, either the antibody or TTR target is immobilized in such assay.

Functional assays can be performed in cellular models including cells naturally expressing TTR or transfected with DNA encoding TTR or a fragment thereof. Suitable cells include cells derived from cardiac tissue or other tissues affected by TTR amyloidogenesis. Cells can be screened for reduced levels of monomeric, misfolded, aggregated, or fibril forms of TTR (e.g., by Western blotting or immunoprecipitation of cell extracts or supernatants) or reduced toxicity attributable to monomeric, misfolded, aggregated, or fibril forms of TTR. For example, antibodies can be tested for the ability to inhibit or reduce aggregation of TTR, inhibit or reduce TTR fibril formation, reduce TTR deposits, clear aggregated TTR, or stabilize non-toxic conformations of TTR.

Other functional assays can be performed in solution, such as testing whether an antibody is capable of disrupting or reducing TTR fibril formation when monomeric TTR or misfolded TTR intermediates in solution are contacted with the antibody. The extent of fibril formation can be probed by turbidity measurements, for example, at 400 nm on a UV-visible spectrometer equipped with a temperature control unit. Thioflavin-T can also be used to assess the extent of amyloid fibril formation. For example, a five-fold molar excess of Thioflavin-T can be added to TTR samples and left at room temperature for 30 minutes before measurements are taken. Thioflavin-T fluorescence can be monitored using a spectrofluorimeter. See US 2014/0056904.

Animal model screens test the ability of the antibody to therapeutically or prophylactically treat signs or symptoms in an animal model simulating a human disease associated with accumulation of TTR or TTR deposits. Such diseases include types of TTR amyloidosis, such as wild-type ATTR amyloidosis (also called senile systemic amyloidosis SSA), senile cardiac amyloidosis (SCA), familial amyloid polyneuropathy (FAP), familial amyloid cardiomyopathy (FAC), and central nervous system selective amyloidosis (CNSA). Suitable signs or symptoms that can be monitored include the presence and extent of amyloid deposits in various tissues, such as the gastrointestinal tract or heart. The extent of reduction of amyloid deposits can be determined by comparison with an appropriate control, such the level of TTR amyloid deposits in control animals that have received a control antibody (e.g., an isotype matched control antibody), a placebo, or no treatment at all. An exemplary animal model for testing activity against a TTR amyloidosis is a mouse model carrying a null mutation at the endogenous mouse Ttr locus and the human mutant TTR gene comprising a V30M mutation that is associated with familial amyloidotic polyneuropathy. See, e.g., Kohno et al., *Am. J. Path.* 150(4):1497-1508 (1997); Cardoso and Saraiva, *FASEB J* 20(2):234-239 (2006). Similar models also exist, including other models for familial versions of TTR amyloidosis and models for sporadic versions of TTR amyloidosis. See, e.g., Teng et al., *Lab. Invest.* 81(3): 385-396 (2001); Ito and Maeda, Mouse Models of Transthyretin Amyloidosis, in Recent Advances in Transthyretin Evolution, Structure, and Biological Functions, pp. 261-280 (2009) (Springer Berlin Heidelberg). Transgenic animals can include a human TTR transgene, such as a TTR transgene with a mutation associated with TTR amyloidosis or a wild-type TTR transgene. To facilitate testing in animal models, chimeric antibodies having a constant region appropriate for the animal model can be used (e.g., mouse-rat chimeras could be used for testing antibodies in rats). It can be concluded that a humanized version of an antibody will be effective if the corresponding mouse antibody or chimeric antibody is effective in an appropriate animal model and the humanized antibody has similar binding affinity (e.g., within experimental error, such as by a factor of 1.5, 2, or 3).

Clinical trials test for safety and efficacy in a human having a disease associated with TTR amyloidosis.

I. Nucleic Acids

The invention further provides nucleic acids encoding any of the heavy and light chains described above (e.g., SEQ ID NOs: 2, 4, 18, and 20). Optionally, such nucleic acids further encode a signal peptide and can be expressed with the signal peptide linked to the constant region (e.g., signal peptides having amino acid sequences of SEQ ID NOs:35 (heavy chain) and 37 (light chain) that can be encoded by SEQ ID NOs:36 (heavy chain) and 38 (light chain), respectively. Coding sequences of nucleic acids can be operably linked with regulatory sequences to ensure expression of the coding sequences, such as a promoter, enhancer, ribosome binding site, transcription termination signal, and the like. The nucleic acids encoding heavy and light chains can occur in isolated form or can be cloned into one or more vectors. The nucleic acids can be synthesized by, for example, solid state synthesis or PCR of overlapping oligonucleotides. Nucleic acids encoding heavy and light chains can be joined as one contiguous nucleic acid, e.g., within an expression vector, or can be separate, e.g., each cloned into its own expression vector.

J. Conjugated Antibodies

Conjugated antibodies that specifically bind to antigens exposed in pathogenic forms of TTR but not in native tetrameric form of TTR, such as amino acid residues 89-97 (SEQ ID NO:45) or amino acid residues 101-109 (SEQ ID NO:30) of TTR, are useful in detecting the presence of monomeric, misfolded, aggregated, or fibril forms of TTR; monitoring and evaluating the efficacy of therapeutic agents being used to treat patients diagnosed with a TTR amyloidosis; inhibiting or reducing aggregation of TTR; inhibiting or reducing TTR fibril formation; reducing or clearing TTR deposits; stabilizing non-toxic conformations of TTR; or treating or effecting prophylaxis of a TTR amyloidosis in a patient. For example, such antibodies can be conjugated with other therapeutic moieties, other proteins, other antibodies, and/or detectable labels. See WO 03/057838; U.S. Pat. No. 8,455,622.

Conjugated therapeutic moieties can be any agent that can be used to treat, combat, ameliorate, prevent, or improve an unwanted condition or disease in a patient, such as a TTR amyloidosis. Therapeutic moieties can include, for example, immunomodulators or any biologically active agents that facilitate or enhance the activity of the antibody. An immunomodulator can be any agent that stimulates or inhibits the development or maintenance of an immunologic response. If such therapeutic moieties are coupled to an antibody specific for monomeric, misfolded, aggregated, or fibril forms of TTR, such as the antibodies described herein, the coupled therapeutic moieties will have a specific affinity for non-native, pathogenic forms of TTR over native tetrameric form of TTR. Consequently, administration of the conjugated antibodies directly targets tissues comprising pathogenic forms of TTR with minimal damage to surrounding normal, healthy tissue. This can be particularly useful for therapeutic moieties that are too toxic to be administered on their own. In addition, smaller quantities of the therapeutic moieties can be used.

Examples of suitable therapeutic moieties include drugs that reduce levels of TTR, stabilize the native tetrameric structure of TTR, inhibit aggregation of TTR, disrupt TTR fibril or amyloid formation, or counteract cellular toxicity. See, e.g., Almeida and Saraiva, *FEBS Letters* 586:2891-2896 (2012); Saraiva, *FEBS Letters* 498:201-203 (2001); Ando et al., *Orphanet Journal of Rare Diseases* 8:31 (2013); Ruberg and Berk, *Circulation* 126:1286-1300 (2012); Johnson et al., *J. Mol. Biol.* 421(2-3):185-203 (2012, Ueda and Ando, Translational Neurodegeneration 3:19 (2014), and Hawkins et al. Annals of Medicine 47:625-638 (2015)). For example, antibodies can be conjugated to tafamidis, diflunisal, AG10, ALN-TTR01, ALNTTR02, antisense oligonucleotides such as IONIS TTRRx (inotersen), siRNAs such as patisiran or revusiran, doxycycline (doxy), tauroursodeoxycholic acid (TUDCA), Doxy-TUDCA, cyclodextrin (CyD), 4'-iodo-4'-deoxydoxorubicin (IDOX), epigallocatechin gallate (EGCG), curcumin, resveratrol (3,5,4'-trihydroxystilbene), or antibodies to serum amyloid P component (SAP). Other representative therapeutic moieties include other agents known to be useful for treatment, management, or amelioration of a TTR amyloidosis or symptoms of a TTR amyloidosis. See, e.g., Ando et al., *Orphanet Journal of Rare Diseases* 8:31 (2013) for common clinical symptoms of TTR amyloidosis and typical agents used to treat those symptoms.

Antibodies can also be coupled with other proteins. For example, antibodies can be coupled with Fynomers. Fynomers are small binding proteins (e.g., 7 kDa) derived from the human Fyn SH3 domain. They can be stable and soluble, and they can lack cysteine residues and disulfide bonds. Fynomers can be engineered to bind to target molecules with the same affinity and specificity as antibodies. They are suitable for creating multi-specific fusion proteins based on antibodies. For example, Fynomers can be fused to N-terminal and/or C-terminal ends of antibodies to create bi- and tri-specific FynomAbs with different architectures. Fynomers can be selected using Fynomer libraries through screening technologies using FACS, Biacore, and cell-based assays that allow efficient selection of Fynomers with optimal properties. Examples of Fynomers are disclosed in Grabulovski et al., *J. Biol. Chem.* 282:3196-3204 (2007); Bertschinger et al., *Protein Eng. Des. Sel.* 20:57-68 (2007); Schlatter et al., *MAbs.* 4:497-508 (2011); Banner et al., *Acta. Crystallogr. D. Biol. Crystallo* 69(Pt6):1124-1137 (2013); and Brack et al., *Mol. Cancer Ther.* 13:2030-2039 (2014).

The antibodies disclosed herein can also be coupled or conjugated to one or more other antibodies (e.g., to form antibody heteroconjugates). Such other antibodies can bind to different epitopes within TTR or a portion thereof or can bind to a different target antigen. Such anti-TTR antibodies binding to TTR epitopes different from that of 9D5 or 18C5, may include antibodies as in Table 3.

Antibodies can also be coupled with a detectable label. Such antibodies can be used, for example, for diagnosing a TTR amyloidosis, for monitoring progression of a TTR amyloidosis, and/or for assessing efficacy of treatment. Such antibodies are particularly useful for performing such determinations in subjects having or being susceptible to a TTR amyloidosis, or in appropriate biological samples obtained from such subjects. Representative detectable labels that may be coupled or linked to an antibody disclosed herein include various enzymes, such as horseradish peroxidase, alkaline phosphatase, beta-galactosidase, or acetylcholinesterase; prosthetic groups, such streptavidin, avidin or biotin; fluorescent materials, such as umbelliferone, DyLight fluors, fluorescein, fluorescein isothiocyanate, rhodamine, dichlorotriazinylamine fluorescein, dansyl chloride or phycoerythrin; luminescent materials, such as luminol; bioluminescent materials, such as luciferase, luciferin, and aequorin; radioactive materials, such as yttrium$^{90}$ (90Y), radiosilver-111, radiosilver-199, Bismuth$^{213}$, iodine ($^{131}$I, $^{125}$I, $^{123}$I, $^{121}$I), carbon ($^{14}$C), sulfur ($^{5}$S), tritium ($^{3}$H), indium ($^{115}$In, $^{113}$In, $^{112}$In, $^{111}$In), technetium ($^{99}$Tc), thallium ($^{201}$Ti), gallium ($^{68}$Ga, $^{67}$Ga), palladium ($^{103}$Pd), molybdenum ($^{99}$Mo), xenon ($^{133}$Xe), fluorine ($^{18}$F), $^{153}$Sm, $^{177}$Lu, $^{159}$Gd, $^{149}$Pm, $^{140}$La, $^{175}$Yb, $^{166}$Ho, $^{90}$Y, $^{47}$Sc, $^{186}$Re, $^{188}$Re, $^{142}$Pr, $^{105}$Rh, $^{97}$Ru, $^{68}$Ge, $^{57}$Co, $^{65}$Zn, $^{85}$Sr, $^{32}$P, $^{153}$Gd, $^{169}$Yb, $^{51}$Cr, $^{54}$Mn, $^{75}$Se, $^{133}$Sn, and $^{117}$Tin; positron emitting metals using various positron emission tomographies; nonradioactive paramagnetic metal ions; and molecules that are radiolabelled or conjugated to specific radioisotopes. Representative detectable labels that may be coupled or linked to an antibody disclosed herein include electrochemiluminescent labels, for example MSD GOLD SULFO-TAG NETS-Ester (SULFO-TAG) (Meso Scale Diagnostics, Rockville, MD).

Linkage of radioisotopes to antibodies may be performed with conventional bifunction chelates. For radiosilver-111 and radiosilver-199 linkage, sulfur-based linkers may be used. See Hazra et al., *Cell Biophys.* 24-25:1-7 (1994). Linkage of silver radioisotopes may involve reducing the immunoglobulin with ascorbic acid. For radioisotopes such as 111In and 90Y, ibritumomab tiuxetan can be used and will react with such isotopes to form 111In-ibritumomab tiuxetan and 90Y-ibritumomab tiuxetan, respectively. See Witzig, *Cancer Chemother. Pharmacol.*, 48 Suppl 1:S91-S95 (2001).

Therapeutic moieties, other proteins, other antibodies, and/or detectable labels may be coupled or conjugated, directly or indirectly through an intermediate (e.g., a linker), to a murine, chimeric, veneered, or humanized 9D5 or 18C5 antibody using techniques known in the art. See e.g., Arnon et al., "Monoclonal Antibodies For Immunotargeting Of Drugs In Cancer Therapy," in Monoclonal Antibodies And Cancer Therapy, Reisfeld et al. (eds.), pp. 243-56 (Alan R. Liss, Inc. 1985); Hellstrom et al., "Antibodies For Drug Delivery," in Controlled Drug Delivery (2nd Ed.), Robinson et al. (eds.), pp. 623-53 (Marcel Dekker, Inc. 1987); Thorpe, "Antibody Carriers Of Cytotoxic Agents In Cancer Therapy: A Review," in Monoclonal Antibodies 84: Biological And Clinical Applications, Pinchera et al. (eds.), pp. 475-506 (1985); "Analysis, Results, And Future Prospective Of The Therapeutic Use Of Radiolabeled Antibody In Cancer Therapy," in Monoclonal Antibodies For Cancer Detection And Therapy, Baldwin et al. (eds.), pp. 303-16 (Academic Press 1985); and Thorpe et al., *Immunol. Rev.*, 62:119-58 (1982). Suitable linkers include, for example, cleavable and non-cleavable linkers. Different linkers that release the coupled therapeutic moieties, proteins, antibodies, and/or detectable labels under acidic or reducing conditions, on exposure to specific proteases, or under other defined conditions can be employed.

V. Therapeutic Applications

The above antibodies can be used for treating or effecting prophylaxis of a disease in a patient having or at risk for the disease mediated at least in part by transthyretin (TTR), and particularly by monomeric, misfolded, aggregated, or fibril forms of TTR. Although an understanding of mechanism is not required for practice, it is believed that any or all of the following mechanisms may contribute to treatment of TTR amyloidosis using the above antibodies: antibody-mediated inhibition of TTR aggregation and fibril formation, antibody-mediated stabilization of non-toxic conformations of TTR (e.g., tetrameric forms), or antibody-mediated clearance of aggregated TTR, oligomeric TTR, or monomeric TTR. Antibody-drug conjugates can have additional mechanisms of action determined by the conjugated moiety.

Antibodies are administered in an effective regime meaning a dosage, route of administration and frequency of administration that delays the onset, reduces the severity, inhibits further deterioration, and/or ameliorates at least one sign or symptom of a disorder being treated. If a patient is already suffering from a disorder, the regime can be referred to as a therapeutically effective regime. If the patient is at elevated risk of the disorder relative to the general population but is not yet experiencing symptoms, the regime can be referred to as a prophylactically effective regime. In some instances, therapeutic or prophylactic efficacy can be observed in an individual patient relative to historical controls or past experience in the same patient. In other instances, therapeutic or prophylactic efficacy can be demonstrated in a preclinical or clinical trial in a population of treated patients relative to a control population of untreated patients.

The frequency of administration depends on the half-life of the antibody in the circulation, the condition of the patient and the route of administration among other factors. The frequency can be daily, weekly, monthly, quarterly, or at irregular intervals in response to changes in the patient's condition or progression of the disorder being treated. An exemplary frequency for intravenous administration is between weekly and quarterly over a continuous cause of treatment, although more or less frequent dosing is also possible. For subcutaneous administration, an exemplary dosing frequency is daily to monthly, although more or less frequent dosing is also possible.

The number of dosages administered depends on whether the disorder is acute or chronic and the response of the disorder to the treatment. For acute disorders or acute exacerbations of a chronic disorder, between 1 and 10 doses are often sufficient. Sometimes a single bolus dose, optionally in divided form, is sufficient for an acute disorder or acute exacerbation of a chronic disorder. Treatment can be repeated for recurrence of an acute disorder or acute exacerbation. For chronic disorders, an antibody can be administered at regular intervals, e.g., weekly, fortnightly, monthly, quarterly, every six months for at least 1, 5 or 10 years, or the life of the patient.

VI. Pharmaceutical Compositions and Methods of Use

Provided herein are several methods of diagnosing, monitoring, treating or effecting prophylaxis of diseases or conditions mediated at least in part by transthyretin (TTR), and particularly by monomeric, misfolded, aggregated, or fibril forms of TTR (e.g., TTR amyloidosis). Examples of such diseases include familial TTR amyloidoses, such as familial amyloid cardiomyopathy (FAC), familial amyloid polyneuropathy (FAP), or central nervous system selective amyloidosis (CNSA), and sporadic TTR amyloidoses, such as senile systemic amyloidosis (SSA) or senile cardiac amyloidosis (SCA). Antibodies described above can be incorporated into a pharmaceutical composition for use in such methods. In general, an antibody or pharmaceutical composition containing an antibody is administered to a subject in need thereof. Patients amenable to treatment include individuals at risk of TTR amyloidosis but not showing symptoms, as well as patients presently showing symptoms. Some patients can be treated during the prodromal stage of TTR amyloidosis.

The pharmaceutical compositions can be administered prophylactically to individuals who have a known genetic risk of TTR amyloidosis. Such individuals include those having relatives who have experienced such a disease, and those whose risk is determined by analysis of genetic or biochemical markers (e.g., mutations in TTR associated with TTR amyloidosis), including using the diagnostic methods provided herein. For example, there are over 100 mutations in the gene encoding TTR that have been implicated in TTR amyloidosis. See, e.g., US 2014/0056904; Saraiva, *Hum. Mutat.* 17(6):493-503 (2001); Damas and Saraiva, *J. Struct. Biol.* 130:290-299; Dwulet and Benson, *Biochem. Biophys. Res. Commun.* 114:657-662 (1983).

Individuals suffering from TTR amyloidosis can sometimes be recognized from the clinical manifestations of TTR amyloidosis, including one or more of the following: (1) family history of neuropathic disease, especially associated with heart failure; (2) neuropathic pain or progressive sensory disturbances of unknown etiology; (3) carpal tunnel syndrome without obvious cause, particularly if it is bilateral and requires surgical release; (4) gastrointestinal motility disturbances or autonomic nerve dysfunction of unknown etiology (e.g., erectile dysfunction, orthostatic hypotension, neurogenic bladder); (5) cardiac disease characterized by thickened ventricular walls in the absence of hypertension; (6) advanced atrio-ventricular block of unknown origin, particularly when accompanied by a thickened heart; and (6) vitreous body inclusions of the cotton-wool type. See Ando et al., *Orphanet Journal of Rare Diseases* 8:31 (2013). Definitive diagnosis of TTR amyloidosis, however, typically relies on target organ biopsies, followed by histological staining of the excised tissue with the amyloid-specific dye, Congo red. If a positive test for amyloid is observed, immunohistochemical staining and mass spectroscopic identification of TTR are subsequently performed to ensure that the precursor protein responsible for amyloid formation is indeed TTR. For familial forms of the diseases, demonstration of a mutation in the gene encoding TTR is then needed before a definitive diagnosis can be made.

The identification of the subject can occur in a clinical setting, or elsewhere, such as in the subject's home, for example, through the subject's own use of a self-testing kit. For example, the subject can be identified based on various symptoms such as peripheral neuropathy (sensory and motor), autonomic neuropathy, gastrointestinal impairment, cardiomyopathy, nephropathy, or ocular deposition. See Ando et al., *Orphanet Journal of Rare Diseases* 8:31 (2013). The subject can also be identified by increased levels of non-native forms of TTR in plasma samples from the subject compared to control samples, as disclosed in the examples.

As warranted by family history, genetic testing, or medical screening for TTR amyloidosis, treatment can begin at any age (e.g., 20, 30, 40, 50, 60, or 70 years of age). Treatment typically entails multiple dosages over a period of time and can be monitored by assaying antibody or activated T-cell or B-cell responses to a therapeutic agent (e.g., a truncated form of TTR comprising amino acid residues 89-97 or comprising amino acid residues 101-109) over time. If the response falls, a booster dosage is indicated.

In prophylactic applications, an antibody or a pharmaceutical composition of the same is administered to a subject susceptible to, or otherwise at risk of a disease (e.g., TTR amyloidosis) in a regime (dose, frequency and route of administration) effective to reduce the risk, lessen the severity, or delay the onset of at least one sign or symptom of the disease. In therapeutic applications, an antibody or immunogen to induce an antibody is administered to a subject suspected of, or already suffering from a disease (e.g., TTR amyloidosis) in a regime (dose, frequency and route of administration) effective to ameliorate or at least inhibit further deterioration of at least one sign or symptom of the disease.

A regime is considered therapeutically or prophylactically effective if an individual treated subject achieves an outcome more favorable than the mean outcome in a control population of comparable subjects not treated by methods disclosed herein, or if a more favorable outcome is demonstrated for a regime in treated subjects versus control subjects in a controlled clinical trial (e.g., a phase II, phase II/III, or phase III trial) or an animal model at the $p < 0.05$ or 0.01 or even 0.001 level.

An effective regime of an antibody can be used for, e.g., inhibiting or reducing aggregation of TTR in a subject having or at risk of a condition associated with TTR accumulation; inhibiting or reducing TTR fibril formation in a subject having or at risk of a condition associated with TTR accumulation; reducing or clearing TTR deposits or aggregated TTR in a subject having or at risk of a condition associated with TTR accumulation; stabilizing non-toxic conformations of TTR in a subject having or at risk of a condition associated with TTR accumulation; inhibiting toxic effects of TTR aggregates, fibrils or deposits in a subject having or at risk of a condition associated with TTR accumulation; diagnosing the presence or absence of TTR amyloid accumulation in a tissue suspected of comprising the amyloid accumulation; determining a level of TTR deposits in a subject by detecting the presence of bound antibody in the subject following administration of the antibody; detecting the presence of monomeric, misfolded, aggregated, or fibril forms of TTR in a subject; monitoring and evaluating the efficacy of therapeutic agents being used to treat patients diagnosed with a TTR amyloidosis; inducing an immune response comprising antibodies to TTR in a subject; delaying the onset of a condition associated with TTR amyloid accumulation in a subject; or treating or effecting prophylaxis of a TTR amyloidosis in a patient.

Effective doses vary depending on many different factors, such as means of administration, target site, physiological state of the subject, whether the subject is human or an animal, other medications administered, and whether treatment is prophylactic or therapeutic.

An exemplary dose range for antibodies can be from about 0.1-20, or 0.5-5 mg/kg body weight (e.g., 0.5, 1, 2, 3, 4 or 5 mg/kg) or 10-1500 mg as a fixed dosage. The dosage depends on the condition of the patient and response to prior treatment, if any, whether the treatment is prophylactic or therapeutic and whether the disorder is acute or chronic, among other factors.

Antibody can be administered in such doses daily, on alternative days, weekly, fortnightly, monthly, quarterly, or according to any other schedule determined by empirical analysis. An exemplary treatment entails administration in multiple doses over a prolonged period, for example, of at least six months. Additional exemplary treatment regimes entail administration once per every two weeks or once a month or once every 3 to 6 months.

Antibodies can be administered via a peripheral route. Routes of administration include topical, intravenous, oral, subcutaneous, intraarterial, intracranial, intrathecal, intraperitoneal, intranasal or intramuscular. Routes for administration of antibodies can be intravenous or subcutaneous. Intravenous administration can be, for example, by infusion over a period such as 30-90 min. This type of injection is most typically performed in the arm or leg muscles. In some methods, agents are injected directly into a particular tissue where deposits have accumulated, for example intracranial injection.

Pharmaceutical compositions for parenteral administration can be sterile and substantially isotonic (250-350 mOsm/kg water) and manufactured under GMP conditions. Pharmaceutical compositions can be provided in unit dose form (i.e., the dose for a single administration). Pharmaceutical compositions can be formulated using one or more physiologically acceptable carriers, diluents, excipients or auxiliaries. The formulation depends on the route of administration chosen. For injection, antibodies can be formulated in aqueous solutions, e.g., in physiologically compatible buffers such as Hank's solution, Ringer's solution, or physiological saline or acetate buffer (to reduce discomfort at the site of injection). The solution can contain formulatory agents such as suspending, stabilizing and/or dispersing agents. Alternatively antibodies can be in lyophilized form for constitution with a suitable vehicle, e.g., sterile pyrogen-free water, before use.

The regimes can be administered in combination with, concomitantly with, or sequentially with another agent effective in treatment or prophylaxis of the disease being treated. Such agents can include siRNA to inhibit expression of TTR or Vyndaqel, a stabilizer of TTR in tetramer formation. Such agents can include TTR tetramer stabilizers such as tafamidis or diflunisal (see, .e.g., WO2011116123, U.S. Pat. No. 9,150,489), gene therapies to suppress TTR expression such as antisense oligonucleotides such as IONIS-TTRRx (inotersen) (see, e.g., U.S. Pat. Nos. 8,101,743, 8,697,860, 9,061,044, and 9,399,774; Japanese Patent No. JP5896175) or siRNAs such as patisiran or revusiran (see, e.g., WO2016033326), amyloid degrader compounds such as doxycycline (doxy), tauroursodeoxycholic acid (TUDCA), Doxy-TUDCA, cyclodextrin (CyD), 4'-iodo-4'-deoxydoxorubicin (IDOX), or antibodies to serum amyloid P component (SAP).

Another agent effective in treatment or prophylaxis of the disease being treated may be administered to a subject who has previously been treated with an antibody disclosed herein. The subject treated with another agent effective in treatment or prophylaxis of the disease being treated may no longer be receiving treatment with an antibody disclosed herein.

Treatment with antibodies disclosed herein can be combined with other treatments effective against the disorder being treated. Combination treatments can be formulated together or administered separately. Some examples of treatments useful for combination therapies include a second anti-TTR antibody that binds an epitope different from that of 9D5 or 18C5, for example an antibody as disclosed in Table 3.

After treatment, the subject's condition can be evaluated to determine the progress or efficacy of such treatment. Such methods preferably test for changes in TTR amyloid levels or levels of non-native forms of TTR. For example, TTR amyloid levels may be evaluated to determine improvement relative to the subject's TTR amyloid levels under comparable circumstances prior to treatment. The subject's TTR amyloid levels can also be compared with control populations under comparable circumstances. The control populations can be similarly afflicted, untreated subjects or normal untreated subjects (among other control subjects). Improvement relative to similarly afflicted, untreated subjects or levels approaching or reaching the levels in untreated normal subjects indicates a positive response to treatment.

TTR amyloid levels can be measured by a number of methods, including imaging techniques. Examples of suitable imaging techniques include PET scanning with radio-labeled TTR of fragments thereof, TTR antibodies or fragments thereof, Congo-red-based amyloid imaging agents, such as, e.g., PIB (US 2011/0008255), amyloid-imaging peptide p31 (Biodistribution of amyloid-imaging peptide, p31, correlates with amyloid quantitation based on Congo red tissue staining, Wall et al., Abstract No. 1573, 2011 ISNM Annual Meeting), and other PET labels. Levels of non-native forms of TTR can be measured, for example, by performing SDS-PAGE/Western blot or Meso Scale Discovery plate assays with the antibodies disclosed herein on plasma samples or biopsy samples from a subject and comparing to control samples, as described in the examples.

A. Diagnostics and Monitoring Methods

Also provided are methods of detecting an immune response against TTR in a patient suffering from or susceptible to diseases associated with TTR deposition or pathogenic forms of TTR (e.g., monomeric, misfolded, aggregated, or fibril forms of TTR). The methods can be used to monitor a course of therapeutic and prophylactic treatment with the agents provided herein. The antibody profile following passive immunization typically shows an immediate peak in antibody concentration followed by an exponential decay. Without a further dose, the decay approaches pretreatment levels within a period of days to months depending on the half-life of the antibody administered. For example, the half-life of some human antibodies is of the order of 20 days.

In some methods, a baseline measurement of antibody to TTR in the subject is made before administration, a second measurement is made soon thereafter to determine the peak antibody level, and one or more further measurements are made at intervals to monitor decay of antibody levels. When the level of antibody has declined to baseline or a predetermined percentage of the peak less baseline (e.g., 50%, 25% or 10%), administration of a further dose of antibody is administered. In some methods, peak or subsequent measured levels less background are compared with reference levels previously determined to constitute a beneficial prophylactic or therapeutic treatment regime in other subjects. If the measured antibody level is significantly less than a reference level (e.g., less than the mean minus one or, preferably, two standard deviations of the reference value in a population of subjects benefiting from treatment) administration of an additional dose of antibody is indicated.

Also provided are methods of detecting monomeric, misfolded, aggregated, or fibril forms of TTR in a subject, for example, by measuring TTR amyloid or pathogenic forms of TTR (e.g., monomeric, misfolded, aggregated, or fibril forms of TTR) in a sample from a subject or by in vivo imaging of TTR in a subject. Such methods are useful to diagnose or confirm diagnosis of diseases associated with such pathogenic forms of TTR (e.g., TTR amyloidosis), or susceptibility thereto. The methods can also be used on asymptomatic subjects. The presence of monomeric, misfolded, aggregated, or fibril forms of TTR indicates susceptibility to future symptomatic disease. The methods are also useful for monitoring disease progression and/or response to treatment in subjects who have been previously diagnosed with a TTR amyloidosis.

Biological samples obtained from a subject having, suspected of having, or at risk of having a TTR amyloidosis can be contacted with the antibodies disclosed herein to assess the presence of monomeric, misfolded, aggregated, or fibril forms of TTR. For example, levels of monomeric, misfolded, aggregated, or fibril forms of TTR in such subjects may be compared to those present in healthy subjects. Alternatively, levels of TTR amyloid or pathogenic forms of TTR (e.g., monomeric, misfolded, aggregated, or fibril forms of TTR) in such subjects receiving treatment for the disease may be compared to those of subjects who have not been treated for a TTR amyloidosis. Some such tests involve a biopsy of tissue obtained from such subjects. ELISA assays can also be used, for example, for assessing levels of monomeric, misfolded, aggregated, or fibril forms of TTR in fluid samples. Some such ELISA assays involve anti-TTR antibodies that preferentially bind monomeric, misfolded, aggregated, or fibril forms of TTR relative to native tetrameric form of TTR.

Some such tests are sandwich immunoassays. Some such immunoassays employ the Meso Scale Discovery (MSD) electrochemiluminescence platform (Meso Scale Diagnostics, Rockville, MD.) Some such immunoassays use electrochemiluminescent labels on reporter antibodies, e.g., MSD Assays (Meso Scale Diagnostics, Rockville, MD.) For example, the reporter antibody can be labeled with a SULFO-TAG label ((Meso Scale Diagnostics, Rockville, MD). Plates useful in electrochemiluminescent assays may incorporate electrodes (e.g., MSD plates (Meso Scale Diagnostics, Rockville, MD). Plates useful in electrochemiluminescent assays may incorporate electrodes in the bottom of each well (e.g., MSD plates, (Meso Scale Diagnostics, Rockville, MD). Some assays employ a labeled capture antibody. For example, the labeled capture antibody can be 9D5 or 18C5 or a humanized, chimeric, or veneered variant thereof. Some assays employ a labeled reporter antibody. For example, the labeled reporter antibody can be 9D5 or 18C5 or a humanized, chimeric, or veneered variant thereof. The labeled reporter antibody can also be an antibody of Table 3, or a humanized, chimeric, or veneered variant thereof. The labeled reporter antibody can be an antibody that binds TTR with no conformational specificity. In an embodiment, the antibody that binds TTR with no conformational specificity can be 8C3 or 7G7 or a humanized, chimeric, or veneered variant thereof (See, e.g., WO 2016/120811). In an embodiment, the antibody that binds TTR with no conformational specificity can be a polyclonal antibody. In an embodiment, the polyclonal antibody is a polyclonal rabbit ami-human prealbumin (Cat. No. A000202-2, Dako, Agilent Technologies, Inc, Santa Clara, CA). In an embodiment, the polyclonal rabbit anti-TTR antibody is Sigma, Catalog No. HPA002550 (Sigma-Aldrich, St. Louis, MO).

Some assays detect all misfolded TTR in a sample (i.e., all misfolded forms of TTR including monomers and multimers). Other assays specifically detect monomeric misfolded TTR or multimeric misfolded TTR. Other assays detect all forms of TTR (misfolded forms and native tetrameric form). Some such assays employ a capture antibody that specifically binds to an epitope within residues 89-97 of TTR or an epitope within residues 101-109 of TTR and a reporter antibody that specifically binds to a different epitope of TTR; wherein if misfolded TTR is present in the sample, the capture antibody and reporter antibody bind to the misfolded TTR forming a sandwich complex; and wherein detection of the reporter antibody that binds to the misfolded TTR, if any, indicates presence or absence of all the misfolded forms of TTR present in the sample. Such reporter antibodies can include 18C5, 9D5, 14G8, 5A1, 6C1, AD7F6, RT24, NI-301.35G11, MFD101, MDF102, MFD103, MFD105, MFD107, MFD108, MFD109, MFD111, MFD114, or a chimeric version or humanized version thereof. Such reporter antibodies can include an antibody which binds within residues 89-97, 101-109, 118-122, 115-124, 53-63, 54-61, 36-49, 49-61, 109-121, 30-66, 70-127, 80-127, 90-127, 100-127, 110-127, or 115-127 of TTR. Such reporter antibodies can include 8C3 or 7G7 (see, e.g., WO 2016/120811). Such reporter antibodies can include a polyclonal rabbit anti-human prealbumin (Cat. No. A000202-2, Dako, Agilent Technologies, Inc, Santa Clara, CA) or a polyclonal rabbit anti-TTR antibody (Sigma, Catalog No. HPA002550, Sigma-Aldrich, St. Louis, MO). Some such assays detect misfolded forms of TTR in a biological sample from hereditary TTR amyloidosis patients carrying a mutation at position 89 within the 9D5 epitope of TTR. Exemplary mutations are E89K TTR and E89Q TTR. Some such assays employ a 9D5 capture antibody and a polyclonal anti-TTR reporter antibody or an 18C5 reporter antibody.

Some assays detect multimeric forms of misfolded TTR in a sample. Such assays can be configured to detect multimeric misfolded TTR preferentially or exclusively over monomeric misfolded TTR. Some such assays employ a capture antibody that specifically binds to an epitope within residues 89-97 or 101-109 of TTR and a reporter antibody that specifically binds to an epitope within residues 89-97 or 101-109 of TTR. Such a combination of capture and reporter antibodies can bind preferentially or exclusively to multimeric TTR over monomeric because the multiple copies of TTR provide multiple epitopes for antibody binding. Detection of reporter antibody binding to multimeric misfolded TTR, if any, indicates presence or absence of the multimeric misfolded TTR. In some such assays, the reporter antibody competes for binding TTR with the capture antibody and/or the reporter and capture antibody bind to the same or overlapping epitope of TTR. In some such assays the capture antibody binds a first misfolded TTR molecule in the multimeric misfolded TTR, and the reporter antibody binds a second misfolded TTR molecule in the multimeric misfolded TTR. Competition for binding between the capture and the reporter antibodies precludes or at least reduces (depending on whether competition is the result of overlapping epitopes or steric hindrance) simultaneous binding and detection of monomeric misfolded TTR. In some such assays, detection of the reporter antibody binding that binds to the second misfolded TTR molecule in the multimeric misfolded TTR indicates presence or absence of multimeric misfolded TTR.

The antibodies disclosed herein can be used in a method of determining a ratio of the level of total multimeric misfolded transthyretin (TTR) to the level of total misfolded TTR in a biological sample. A first portion of a biological sample can be assayed for all misfolded TTR in a sample (i.e., all misfolded forms of TTR including monomers and multimers) in a first assay wherein monomeric misfolded and multimeric misfolded TTR are detected. The first assay can employ a capture antibody that specifically binds to an epitope within residues 89-97 or 101-109 of TTR and a reporter antibody that specifically binds to a different epitope of TTR. If misfolded TTR is present in the sample, the capture antibody and reporter antibody bind to the misfolded TTR forming a sandwich complex. Detection of the reporter antibody that binds to the misfolded TTR, if any, indicates presence or absence of the misfolded TTR in the sample. A second portion of a biological sample can be assayed for multimeric forms of misfolded TTR a biological sample in a second assay that detects multimeric misfolded TTR preferentially over monomeric misfolded TTR. The second assay can employ a capture antibody that specifically binds to an epitope within residues 89-97 or 101-109 of TTR and a reporter antibody that specifically binds to an epitope within residues 89-97 or 101-109 of TTR. If multimeric misfolded TTR is present in the sample, the capture antibody and reporter antibody bind to the multimeric misfolded TTR forming a sandwich complex. The capture and the reporter antibody can bind simultaneously preferentially or exclusively to the multimeric misfolded TTR, if any, to indicate presence or absence of the multimeric misfolded TTR. In some such assays, the reporter antibody competes for binding TTR with the capture antibody or binds to the same or overlapping epitope as the capture antibody. In some such assays the capture antibody binds a first misfolded TTR molecule in the multimeric misfolded TTR, and the reporter antibody binds a second misfolded TTR molecule in the multimeric misfolded TTR. Competition for binding between the capture and the reporter antibodies precludes or at least reduces (depending on whether competition is the result of overlapping epitopes or steric hindrance) simultaneous binding and detection of monomeric misfolded TTR. In some such assays, detection of the reporter antibody binding that binds to the second misfolded TTR molecule in the multimeric TTR indicates presence or absence of multimeric misfolded TTR. In some assays, a ratio of multimeric misfolded TTR to all misfolded TTR is calculated.

The antibodies disclosed herein can also be used in a method of determining a ratio of the level of all misfolded TTR to total TTR (misfolded forms and native tetrameric form) in a biological sample. A first portion of a biological sample can be assayed for all misfolded TTR in a sample (i.e., all misfolded forms of TTR including monomers and multimers), in a first assay wherein monomeric misfolded and multimeric misfolded TTR are detected. The first assay can employ a capture antibody that specifically binds to an epitope within residues 89-97 or 101-109 of TTR and a reporter antibody that specifically binds to a different epitope of TTR. If misfolded TTR is present in the sample, the capture antibody and reporter antibody bind to the misfolded TTR forming a sandwich complex. Detection of the reporter antibody binding to the misfolded TTR, if any, indicates presence or absence of the misfolded TTR in the sample. A second portion of a biological sample can be assayed for total TTR (misfolded forms and native tetrameric form) in a second assay wherein total TTR is detected. The second assay can employ a capture antibody that binds TTR with no conformational specificity and a reporter antibody that binds TTR with no conformational specificity. If TTR is present in the sample, the capture antibody and reporter antibody bind to the TTR forming a sandwich complex. Detection of the reporter antibody binding to the TTR, if any, indicates presence or absence of TTR present in the sample. A ratio of all misfolded TTR to total TTR (misfolded forms and native tetrameric form) can be calculated.

The in vivo imaging methods can work by administering a reagent, such as antibody that binds to monomeric, misfolded, aggregated, or fibril forms of TTR in the subject, and then detecting the reagent after it has bound. Such antibodies typically bind to an epitope within residues 89-97 or 101-109 of TTR. If desired, the clearing response can be avoided by using antibody fragments lacking a full length constant region, such as Fabs. In some methods, the same antibody can serve as both a treatment and diagnostic reagent.

Diagnostic reagents can be administered by intravenous injection into the body of the subject, or via other routes deemed reasonable. The dose of reagent should be within the same ranges as for treatment methods. Typically, the reagent is labeled, although in some methods, the primary reagent with affinity for monomeric, misfolded, aggregated, or fibril forms of TTR is unlabeled and a secondary labeling agent is used to bind to the primary reagent. The choice of label depends on the means of detection. For example, a fluorescent label is suitable for optical detection. Use of paramagnetic labels is suitable for tomographic detection without surgical intervention. Radioactive labels can also be detected using PET or SPECT.

Diagnosis is performed by comparing the number, size, and/or intensity of labeled loci to corresponding base line values. The base line values can represent the mean levels in a population of undiseased individuals. Base line values can also represent previous levels determined in the same subject. For example, base line values can be determined in a subject before beginning treatment, and measured values thereafter compared with the base line values. A decrease in values relative to base line generally signals a positive response to treatment.

Monitoring of changes in amount of misfolded TTR, multimeric misfolded TTR, transthyretin deposits, anti-TTR antibody binding or the like allows adjustment of a treatment regime in response to the treatment. Then a determination can be made whether to adjust treatment and if desired treatment can be adjusted in response to the monitoring. A significant change means that comparison of the value of a parameter after treatment relative to basement provides some evidence that treatment has or has not resulted in a beneficial effect. In some instances, a change of values of a parameter in a patient itself provides evidence that treatment has or has not resulted in a beneficial effect. In other instances, the change of values, if any, in a patient, is compared with the change of values, if any, in a representative control population of patients not undergoing treatment. A difference in response in a particular patient from the normal response in the control patient (e.g., mean plus variance of a standard deviation) can also provide evidence that a treatment regime is or is not achieving a beneficial effect in a patient. Changes in the above TTR parameters can also be combined with other change(s) in signs or symptoms such as side effects in determining whether and how to adjust treatment.

In some patients, monitoring indicates that the amount of misfolded TTR, multimeric misfolded TTR, transthyretin deposits, or anti-TTR antibody binding is the same or greater than previously detected. In such patients, if there are no unacceptable side effects, the treatment regime can be continued as is or even increased in frequency of administration and/or dose if not already at the maximum recommended dose.

In some patients, monitoring indicates a detectable decline in amount of misfolded TTR, misfolded multimeric TTR, transthyretin deposits, anti-TTR antibody binding or the like but that amount of misfolded TTR, multimeric misfolded TTR, transthyretin deposits, or anti-TTR antibody binding remains above normal. In such patients, if there are no unacceptable side effects, the treatment regime can be continued as is or even increased in frequency of administration and/or dose if not already at the maximum recommended dose. Alternatively, in some such patients, the treatment regime can be discontinued and replaced with treatment with other agents, such as a TTR tetramer stabilizer, an antisense oligonucleotide based therapeutic, an RNA interference (RNAi) based therapeutic or doxycycline plus tauroursodeoxycholic acid.

If the monitoring indicates an amount of misfolded TTR, multimeric misfolded TTR, transthyretin deposits, anti-TTR antibody binding or the like in a patient has already been reduced to at or near a normal level of amount of misfolded TTR, multimeric misfolded TTR, transthyretin deposits, or amount of anti-TTR antibody binding, the treatment regime can be adjusted from one of induction (i.e., that reduces the level of amount of misfolded TTR, multimeric misfolded TTR, transthyretin deposits, or anti-TTR antibody binding) to one of maintenance (i.e., that maintains amount of misfolded TTR, multimeric misfolded TTR, transthyretin deposits, or anti-TTR antibody binding at an approximately constant level). Such a regime can be effected by reducing the dose and or frequency of administering the treatment. Alternatively, in some such patients, the treatment regime can be discontinued and replaced with treatment with other agents, such as a TTR tetramer stabilizer, an antisense oligonucleotide based therapeutic, an RNA interference (RNAi) based therapeutic or doxycycline plus tauroursodeoxycholic acid.

In other patients, monitoring can indicate that the treatment regime is having some beneficial effect but a suboptimal effect. An optimal effect can be defined as a percentage reduction in amount of misfolded TTR, multimeric misfolded TTR, transthyretin deposits, or anti-TTR antibody binding within the top half or quartile of the change in amount of misfolded TTR, multimeric misfolded TTR, transthyretin deposits, or amount of anti-TTR antibody binding) experienced by a representative sample of patients undergoing the treatment regime at a given time point after commencing therapy. A patient experiencing a smaller decline or a patient whose amount of misfolded TTR, multimeric misfolded TTR, transthyretin deposits, or anti-TTR antibody binding remains constant or even increases but to a lesser extent than expected in the absence the treatment regime (e.g., as inferred from a control group of patients not administered the treatment regime) can be classified as experiencing a positive but suboptimal response. Such patients can optionally be subject to an adjustment of regime in which the dose and or frequency of administration of an agent is increased. Alternatively, or additionally if upward adjustment does not result in an improved response, in some such patients, the treatment regime can be discontinued and replaced with treatment with other agents, such as a TTR tetramer stabilizer, an antisense oligonucleotide based therapeutic, an RNA interference (RNAi) based therapeutic or doxycycline plus tauroursodeoxycholic acid.

In some patients, amount of misfolded TTR, multimeric misfolded TTR, transthyretin deposits, or anti-TTR antibody binding may increase in similar or greater fashion to misfolded TTR, multimeric misfolded TTR, transthyretin deposits, or anti-TTR antibody binding in patients not receiving treatment. If such increases persist over a period of time, treatment can if desired be discontinued in favor of treatment with one or more other agents.

Diagnostic methods with antibodies disclosed herein can be performed in combination with a second anti-TTR antibody that binds an epitope different from that of 9D5 or 18C5, for example an antibody as disclosed in Table 3.

The assays disclosed herein can also be used to assess target engagement (pharmacodynamics effects) of unbound (free) misfolded-TTR in a biological sample from a subject by an antibody being used or tested for use in treatment. Such an antibody is referred to in the present assay as being a test antibody because it is being tested for its target engagement. In the present assay, the biological sample can be an aliquot of a larger sample, referred to as a collected sample, such that the assay can be run in a parallel manner of multiple aliquots of the collected sample. The test antibody competes with the capture antibody (or alternatively the reporter antibody) for binding to TTR. The test antibody can bind to the same epitope as the capture antibody (or the reporter antibody). The sandwich assay described above can be run in parallel for first and second aliquots of a collected sample, which are usually of the same volume. One aliquot is supplemented with the test antibody and both aliquots are supplemented with capture and reporter antibodies. In the aliquot without the test antibody, detection of the reporter antibody as part of a sandwich provides an indication of presence and amount of misfolded TTR in a sample. In the aliquot with the test antibody, detection of a reduced amount of reporter antibody as part of a sandwich relative to the aliquot without the test antibody provides an indication the test antibody is binding to misfolded TTR and thereby competing with either the capture or reporter antibody and reducing formation of a sandwich between the capture antibody, misfolded TTR and the reporter antibody. Such an assay can be performed on additional aliquots containing increasing amounts of the test antibody (as well as capture antibody) further to characterize binding of the test antibody to misfolded TTR. The sample can be from a subject with a TTR amyloidosis. The sample can be from a subject with a hereditary TTR amyloidosis. The subject with a hereditary TTR amyloidosis may carry a mutation selected from the group consisting of V30M, Y114C, G47R, S50I, E61L, T49S, F33V, A45T, E89K, E89Q, and V122I. In some such assays, the biological sample is a plasma sample. In some such assays, the assay is performed with a 9D5 or 18C5 capture antibody and a polyclonal anti-TTR reporter antibody. Such an assay can be used to inform on target engagement in clinical trials of an antibody intended for therapeutic use as disclosed herein. In some such assays, the test antibody is 14G8, and the assay is performed with a 9D5 or 18C5 capture antibody and a polyclonal anti-TTR reporter antibody.

The assays disclosed herein can be used to measure pharmocodynamic effects of therapies targeting misfolded forms of TTR. In some such assays, target engagement of unbound (free) mis-TTR in a biological sample is measured after ex-vivo treatment (spiking) of a biological sample with a test antibody. The assays disclosed herein can also be used to measure efficacy of a test antibody in a patient. Biological samples are collected from a patient before and after treatment with a test antibody. In some such assays, target engagement of unbound (free) mis-TTR in a biological sample is measured before and after in vivo treatment of a patient with a test antibody. In some assays the target of the test antibody is an epitope within residues 89-97 of TTR. In some assays the target of the test antibody is an epitope within residues 101-109 of TTR.

The present methods also allow distinction of a transthyretin-mediated amyloidosis from a non-TTR amyloidosis, e.g. amyloid light-chain (AL) amyloidosis, also known as primary systemic amyloidosis.

IX. Kits

The invention further provides kits (e.g., containers) comprising the 9D5 or 18C5 antibodies disclosed herein and related materials, such as instructions for use (e.g., package insert). The instructions for use may contain, for example, instructions for administration of the antibodies and optionally one or more additional agents. The containers of antibodies may be unit doses, bulk packages (e.g., multi-dose packages), or sub-unit doses.

Package insert refers to instructions customarily included in commercial packages of therapeutic products that contain information about the indications, usage, dosage, administration, contraindications and/or warnings concerning the use of such therapeutic products Kits can also include a second container comprising a pharmaceutically-acceptable buffer, such as bacteriostatic water for injection (BWFI), phosphate-buffered saline, Ringer's solution and dextrose solution. It can also include other materials desirable from a commercial and user standpoint, including other buffers, diluents, filters, needles, and syringes.

X. Other Applications

The antibodies can be used for detecting monomeric, misfolded, aggregated, or fibril forms of transthyretin (TTR), or fragments thereof, in the context of clinical diagnosis or treatment or in research. For example, the antibodies can be used to detect the presence of monomeric, misfolded, aggregated, or fibril forms of TTR in a biological sample as an indication that the biological sample comprises TTR amyloid deposits. Binding of the antibodies to the biological sample can be compared to binding of the antibodies to a control sample. The control sample and the biological sample can comprise cells of the same tissue origin. Control samples and biological samples can be obtained from the same individual or different individuals and on the same occasion or on different occasions. If desired, multiple biological samples and multiple control samples are evaluated on multiple occasions to protect against random variation independent of the differences between the samples. A direct comparison can then be made between the biological sample(s) and the control sample(s) to determine whether antibody binding (i.e., the presence of monomeric, misfolded, aggregated, or fibril forms of TTR) to the biological sample(s) is increased, decreased, or the same relative to antibody binding to the control sample(s). Increased binding of the antibody to the biological sample(s) relative to the control sample(s) indicates the presence of monomeric, misfolded, aggregated, or fibril forms of TTR in the biological sample(s). In some instances, the increased antibody binding is statistically significant. Optionally, antibody binding to the biological sample is at least 1.5-fold, 2-fold, 3-fold, 4-fold, 5-fold, 10-fold, 20-fold, or 100-fold higher than antibody binding to the control sample.

In addition, the antibodies can be used to detect the presence of monomeric, misfolded, aggregated, or fibril forms of TTR in a biological sample to monitor and evaluate the efficacy of a therapeutic agent being used to treat a patient diagnosed with a TTR amyloidosis. A biological sample from a patient diagnosed with a TTR amyloidosis is evaluated to establish a baseline for the binding of the antibodies to the sample (i.e., a baseline for the presence of the monomeric, misfolded, aggregated, or fibril forms of TTR in the sample) before commencing therapy with the therapeutic agent. In some instances, multiple biological samples from the patient are evaluated on multiple occasions to establish both a baseline and measure of random variation independent of treatment. A therapeutic agent is then administered in a regime. The regime may include multiple administrations of the agent over a period of time. Optionally, binding of the antibodies (i.e., presence of monomeric, misfolded, aggregated, or fibril forms of TTR) is evaluated on multiple occasions in multiple biological samples from the patient, both to establish a measure of random variation and to show a trend in response to immunotherapy. The various assessments of antibody binding to the biological samples are then compared. If only two assessments are made, a direct comparison can be made between the two assessments to determine whether antibody binding (i.e., presence of monomeric, misfolded, aggregated, or fibril forms of TTR) has increased, decreased, or remained the same between the two assessments. If more than two measurements are made, the measurements can be analyzed as a time course starting before treatment with the therapeutic agent and proceeding through the course of therapy. In patients for whom antibody binding to biological samples has decreased (i.e., the presence of monomeric, misfolded, aggregated, or fibril forms of TTR), it can be concluded that the therapeutic agent was effective in treating the TTR amyloidosis in the patient. The decrease in antibody binding can be statistically significant. Optionally, binding decreases by at least 1%, 2%, 3%, 4%, 5%, 10%, 15%, 20%, 30%, 40%, 50%, 60%, 70%, 80%, 90%, or 100%. Assessment of antibody binding can be made in conjunction with assessing other signs and symptoms of TTR amyloidosis.

The antibodies can also be used as research reagents for laboratory research in detecting monomeric, misfolded, aggregated, or fibril forms of TTR, or fragments thereof. In such uses, antibodies can be labeled with fluorescent molecules, spin-labeled molecules, enzymes, or radioisotopes, and can be provided in the form of kit with all the necessary reagents to perform the detection assay. The antibodies can also be used to purify monomeric, misfolded, aggregated, or fibril forms of TTR, or binding partners of monomeric, misfolded, aggregated, or fibril forms of TTR, e.g., by affinity chromatography.

The antibodies can also be used for inhibiting or reducing aggregation of TTR, inhibiting or reducing TTR fibril formation, reducing or clearing TTR deposits or TTR aggregates, or stabilizing non-toxic conformations of TTR in a biological sample. The biological sample can comprise, for example, blood, serum, plasma, or tissue (e.g., tissue from the heart, peripheral nervous system, autonomic nervous system, kidneys, eyes, abdominal fat, or gastrointestinal tract). In some instances, TTR aggregation, TTR fibril formation, or TTR deposits are inhibited or reduced by at least 10%, 20%, 25%, 30%, 40%, 50%, or 75%, (e.g., 10%-75% or 30%-70%). Assays for detecting fibril formation are described elsewhere herein. See also US 2014/0056904.

All patent filings, websites, other publications, accession numbers and the like cited above or below are incorporated by reference in their entirety for all purposes to the same extent as if each individual item were specifically and individually indicated to be so incorporated by reference. If different versions of a sequence are associated with an accession number at different times, the version associated with the accession number at the effective filing date of this application is meant. The effective filing date means the earlier of the actual filing date or filing date of a priority application referring to the accession number if applicable. Likewise if different versions of a publication, website or the like are published at different times, the version most recently published at the effective filing date of the application is meant unless otherwise indicated. Any feature, step, element, embodiment, or aspect of the invention can be used in combination with any other unless specifically indicated otherwise. Although the present invention has been described in some detail by way of illustration and example for purposes of clarity and understanding, it will be apparent that certain changes and modifications may be practiced within the scope of the appended claims.

EXAMPLES

Example 1. Materials and Reagent Preparation

TABLE 4

Materials and assay reagents

| Identity | Description | Lot/Batch/Cat No. | Supplier |
|---|---|---|---|
| Mouse 14G8 | 2.95 mg/mL in 1 × PBS | PB-0334 | Prothena |
| Goat anti-mouse IgG | IRDye 800CW conjugated, reconstituted with 0.5 mL H$_2$O | Cat. 925-32210 | LI-COR |
| h14G8 | 49.4 mg/mL in formulation buffer (25 mM Histidine, 230 mM Trehalose, 0.02% Polysorbate 20, pH 6.5) | PNA PRX004 MSR01 DS02 | Rentschler |
| Neutravidin | 10 mg vial reconstituted in water then diluted to 1 mg/mL in PBS | Cat. 31000 | ThermoFisher Scientific |
| Guanidine mis-TTR Standard | 1 mg/mL wild-type TTR in 6M Guanidine HCl 1 × PBS | PB-0216 | Prothena |
| 9D5 anti-misfolded-TTR-biotin mAb | 1 mg/mL | PS021017D | Prothena |
| Rabbit anti-Hu TTR-SULFO-TAG polyclonal Ab (Dako) | 1 mg/mL | PS022317A | Prothena |
| Human PreAlbumin (TTR) ELISA kit | Measures Total human TTR | Cat. AB 108895 | Abcam |
| SULFO-TAG-mouse-anti-misfolded TTR, Clone 18C5 | | PB-0386, Conjugate lot#01302017ST-JML | Prothena |

Cat = catalog;; Hu = human; mAb = monoclonal antibody; MSD = Meso Scale Discovery; TTR = transthyretin; mis-TTR = misfolded TTR; ST SULFO-TAG; PBS Phosphate Buffered Saline pH 7.4.

Reagent Preparation

Biotinylation of 9D5: 1 mg/mL 9D5 in PBS was biotinylated following manufacturer's instructions with the exception of a 10M excess of NHS-biotin (Thermo-Fisher Cat. 21329) to antibody which was used instead of a 20M excess.

SULFO-TAG of Rabbit anti-TTR pAb: Antibody (Cat. No. A000202-2, Dako, Agilent Technologies, Inc, Santa Clara, CA) was diluted to 1 mg/mL in PBS then desalted using a Zeba spin column (ThermoFisher Scientific). 50 µL of cold H$_2$O was added to SULFO-TAG to reconstitute and then the material was vortexed. 2.2 µL of reconstituted SULFO-TAG was added to 50 µL of diluted antibody, vortexed, incubated 2 hours at RT, and stored in the dark at 4C.

Preparation of the Guanidine HCl misfolded-TTR Standard: Denatured human TTR was prepared by incubating 1 mg/mL purified recombinant human wild-type TTR in 1×PBS containing 6M guanidine hydrochloride for 24 hours at 4° C., then aliquoted and frozen at −70° C.

Example 2. ECL Method for Determination of Free Misfolded-TTR in Plasma

Free (unbound) misfolded-TTR, including monomer, was detected in human plasma using a quantitative ECL (Meso Scale Discovery; MSD) assay research method. A 96-well MSD plate was coated with 30 µL per well of 4 µg/mL neutravidin in PBS, incubated overnight at 4° C., and washed three times in TBS containing 0.05% Tween 20. Plates had non-specific binding sites blocked with 3% MSD Blocker A (MSD #: R93BA-4) in PBS for 1 hour at room temperature with shaking, then washed three times. 30 µL of 1 µg/mL biotinylated 9D5 in Assay Buffer (1% MSD Blocker A/PBS+0.05% Tween-20) was added to each well and incubated 1 hour at room temperature with shaking. The standard curve was prepared from a fresh aliquot of TTR in 6M guanidine HCl diluted into Diluent 2 (MSD #: R51BB-3). Standard Curve consisted of seven 4-fold dilutions starting at 200 ng/mL ending at 49 pg/mL. Patient or control plasma was diluted 1:5 in MSD Diluent 2. Standard or diluted plasma (30 µL) were added to the plates in duplicate, incubated at room temperature with shaking for 2 hours then washed. 30 µL of the polyclonal anti-TTR SULFO-TAG label ((Cat. No. A000202-2, Dako, Agilent Technologies, Inc, Santa Clara, CA) at 1 µg/mL in assay buffer was added to each well, incubated 1 hour with shaking then washed. 150 µL/well of 1×MSD Read Buffer T (MSD #: R92TC-1) was added to each well and read within 10 min on a MSD Sector Imager S600. The top and the bottom standard were anchor points and the curve had a quantitative range in neat plasma of 1 to 500 ng/mL equivalents based on the guanidine-HCl TTR standard.

Example 3. Bioanalysis of Free Misfolded-TTR in TTR Amyloidosis Patient PLASMA Individual and mean free misfolded-TTR levels (ng-eq/mL) in TTR Amyloidosis patient and normal plasma combined from two assay occasions are shown in FIG. 1.

Results are shown in FIG. 1. The first column (labeled h-ATTR asympto") depicts results for asymptomatic patients with hereditary TTR amyloidosis. The second column (labeled h-ATTR-taf") depicts results for patients with hereditary TTR amyloidosis treated with tafamidis. The third column (labeled h-ATTR-no treatment") depicts results for untreated patients with hereditary TTR amyloidosis. The fourth column (labeled "h-ATTR liver TX") depicts results for patients with hereditary TTR amyloidosis with a liver transplant. The fifth column (labeled "WT-ATTR") depicts results for patients with wild-type ATTR amyloidosis. The sixth column (labeled "Normal") depicts results for healthy volunteers. Points are individual data and bars are mean and SD. *0.01-0.05, 0.0005-0.0099, *0.0001-0.005, and ****<0.0001 compared to Normal control (non-parametric Kruskal-Wallis test with Dunn's multiplicity adjustment).

Abbreviations used in FIG. 1:
asympt=asymptomatic; ATTR=amyloid transthyretin; eq=equivalents; GuHCL=guanidine hydrochloride; h=hereditary; mis=misfolded; std=standard; Tx=transplant; wt=wild type Among hereditary TTR amyloidosis patients, there were significantly higher mean levels of misfolded-TTR in untreated patients, including showing asymptomatic carriers show misfolded-TTR before disease symptoms, and tafamidis-treated patients still show circulating misfolded- TTR, however in liver transplant patients levels were similar to normal controls with little or no detectable misfolded-TTR. Mean misfolded-TTR concentrations in the hereditary TTR amyloidosis patient samples with elevated levels ranged from 32 to 59 ng-eq/mL compared to 4 ng-eq/mL in normal controls. Hereditary TTR amyloidosis liver transplant patients produce normally folded TTR resulting in misfolded-TTR levels that were similar to normal, healthy subjects. The wild-type ATTR amyloidosis patient samples, with the exception of a single outlier, also had little or no detectable misfolded-TTR similar to normal plasma, suggesting that misfolding of TTR may occur locally within the affected tissue and misfolded-TTR does not readily circulate in this wild-type ATTR amyloidosis patient subset.

Among the noted outliers in the tafamidis-treated (1 low misfolded-TTR), and wild-type ATTR amyloidosis (1 high misfolded-TTR) patient samples, it is not clear if divergent values represent normal patient variation or were due to procedural error (i.e. inadvertent mis-labeling of samples). As a result, all reported values were included in data evaluations.

Additionally, the assay is able to detect misfolded-TTR in plasma from hereditary TTR amyloidosis patients carrying mutations at position 89 within the 9D5 epitope of TTR. Two mutations (E89K and E89Q) that fall within the 9D5 epitope (amino acid residues 89-97) did not affect 9D5 binding in the assay. While alanine mapping of the epitope showed this residue to be less important for antibody binding, it was unknown if substitutions that were not conserved for example acidic to basic amino acid (E89K) or charged to non-charged (E89Q) would impact antibody binding. The arrows in FIG. 1 indicate these substitutions and the suitability of the assay for mutations at this amino acid. Table 5 shows all samples tested and the results in the 9D5-Dako polyclonal assay.

TABLE 5 samples tested and the results in the 9D5-Dako assay

| Pro ID | Collaborator ID | Age | Sex | TTR Mutation | Treatment | misfolded-TTR (ng-eq/mL) |
|---|---|---|---|---|---|---|
| 1 | 8120326 | 37 | M | V30M | Liver TX | 4 |
| 2 | 16091078 | 67 | F | V30M | Untreated | 24 |
| 4 | 3098983 | 44 | M | V30M | Liver TX | 4 |
| 5 | 98084122 | 44 | F | Y114C | Tafamidis | 26 |
| 6 | 1051830 | 45 | F | V30M | Liver TX | 3 |
| 7 | 12004496 | 44 | M | V30M | Liver TX | 3 |
| 8 | 16032804 | 74 | M | V30M | Untreated | 27 |
| 10 | 13097486 | 39 | M | V30M | Tafamidis | 26 |
| 11 | 11017266 | 30 | F | V30M | Liver TX | 3 |
| 12 | 14094510 | 72 | M | V30M | Tafamidis | 27 |
| 13 | 14053483 | 66 | M | V30M | Tafamidis | 29 |
| 14 | 96038112 | 53 | F | V30M | Liver TX | 2 |
| 15 | 11019596 | 48 | M | V30M | Tafamidis | 33 |
| 16 | 8099635 | 44 | F | V30M | Liver TX | 4 |
| 17 | 8110529 | 41 | F | V30M | Tafamidis | 45 |
| 18 | 16015447 | 52 | M | G47R | Liver TX | 4 |
| 19 | 95023663 | 54 | F | V30M | Liver TX | 3 |
| 20 | 4080271 | 38 | M | Y114C | Tafamidis | 29 |
| 21 | 16012192 | 34 | M | S50I | Asymptom | 19 |
| 22 | 84041739 | 54 | F | V30M | Liver TX | 3 |
| 23 | 98063581 | 38 | F | S50I | Asymptom | 24 |
| 24 | 16123223 | 24 | M | V30M | Untreated | 35 |
| 25 | 15085485 | 35 | F | V30M | Tafamidis | 30 |
| 26 | 5069417 | 37 | F | V30M | Liver TX | 6 |
| 27 | 8095365 | 48 | F | V30M | Liver TX | 4 |
| 28 | 8099602 | 70 | F | V30M | Tafamidis | 37 |
| 29 | 16050297 | 27 | F | G47R | Asymptom | 48 |
| 30 | 16013388 | 68 | F | V30M | Tafamidis | 63 |
| 31 | 94045408 | 63 | F | V30M | Liver TX | 5 |
| 32 | 9105775 | 48 | M | V30M | Liver TX | 8 |
| 33 | 8127510 | 42 | F | V30M | Asymptom | 66 |
| 34 | 16129566 | 62 | M | E61L | Tafamidis | 4 |
| 35 | 9007376 | 34 | F | V30M | Asymptom | 88 |
| 36 | 98029314 | 41 | F | V30M | Asymptom | 77 |
| 37 | 15030924 | 26 | M | V30M | Asymptom | 80 |
| 38 | 15030913 | 27 | F | V30M | Asymptom | 90 |
| 39 | 17032391 | 39 | M | T49S | Asymptom | 15 |
| 40 | 12120567 | 64 | M | V30M | Tafamidis | 56 |
| 42 | 13063964 | 41 | F | Y114C | | |
| 44 | 17057097 | 62 | M | V30M | | |
| 45 | 17090197 | 72 | M | V30M | | |
| 46 | 14044203 | 27 | F | Y114C | Asymptom | |
| 47 | 15048606 | 38 | M | F33V | | |
| SSA-1 | 15090038 | 81 | M | wt-ATTR | Untreated | 6 |
| SSA-2 | 85017908 | 84 | F | wt-ATTR | Untreated | 6 |
| SSA-3 | 16023646 | 78 | M | wt-ATTR | Untreated | 6 |
| N1 | n/a | 38 | M | Normal | n/a | 7 |
| N2 | n/a | 22 | F | Normal | n/a | 3 |
| N3 | n/a | 24 | F | Normal | n/a | 4 |
| N4 | n/a | 42 | M | Normal | n/a | 4 |
| N5 | n/a | 29 | F | Normal | n/a | 3 |
| N6 | n/a | 34 | F | Normal | n/a | 3 |

TABLE 5-continued samples tested and the results in the 9D5-Dako assay

| Pro ID | Collaborator ID | Age | Sex | TTR Mutation | Treatment | misfolded-TTR (ng-eq/mL) |
|---|---|---|---|---|---|---|
| N7 | n/a | 51 | M | Normal | n/a | 3 |
| N8 | n/a | 30 | M | Normal | n/a | 4 |
| N9 | n/a | 28 | M | Normal | n/a | 6 |
| 1 | 03PA17002004001 | n/a | M | A45T | Asymptom | 50 |
| 2 | 557722 | n/a | M | E89K | Asymptom | 96 |
| 3 | 913320 | n/a | F | E89Q | Untreated | 32 |
| 4 | 03PA17000804 | n/a | F | V122I | Untreated | 18 |
| 5 | 03PA17002702 | n/a | M | V30M | Untreated | 76 |
| 6 | 03PA17001104 | n/a | M | wt-ATTR | Untreated | 96 |
| 7 | 03PA17001904 | n/a | M | wt-ATTR | Untreated | 7 |
| 8 | 03PA17000704 | n/a | M | wt-ATTR | Untreated | 7 |

Asymptom = asymptomatic;
ATTR = amyloid transthyretin;
eq = equivalents;
mis = misfolded;
n/a = not applicable;
wt = wild type

Figure 9:
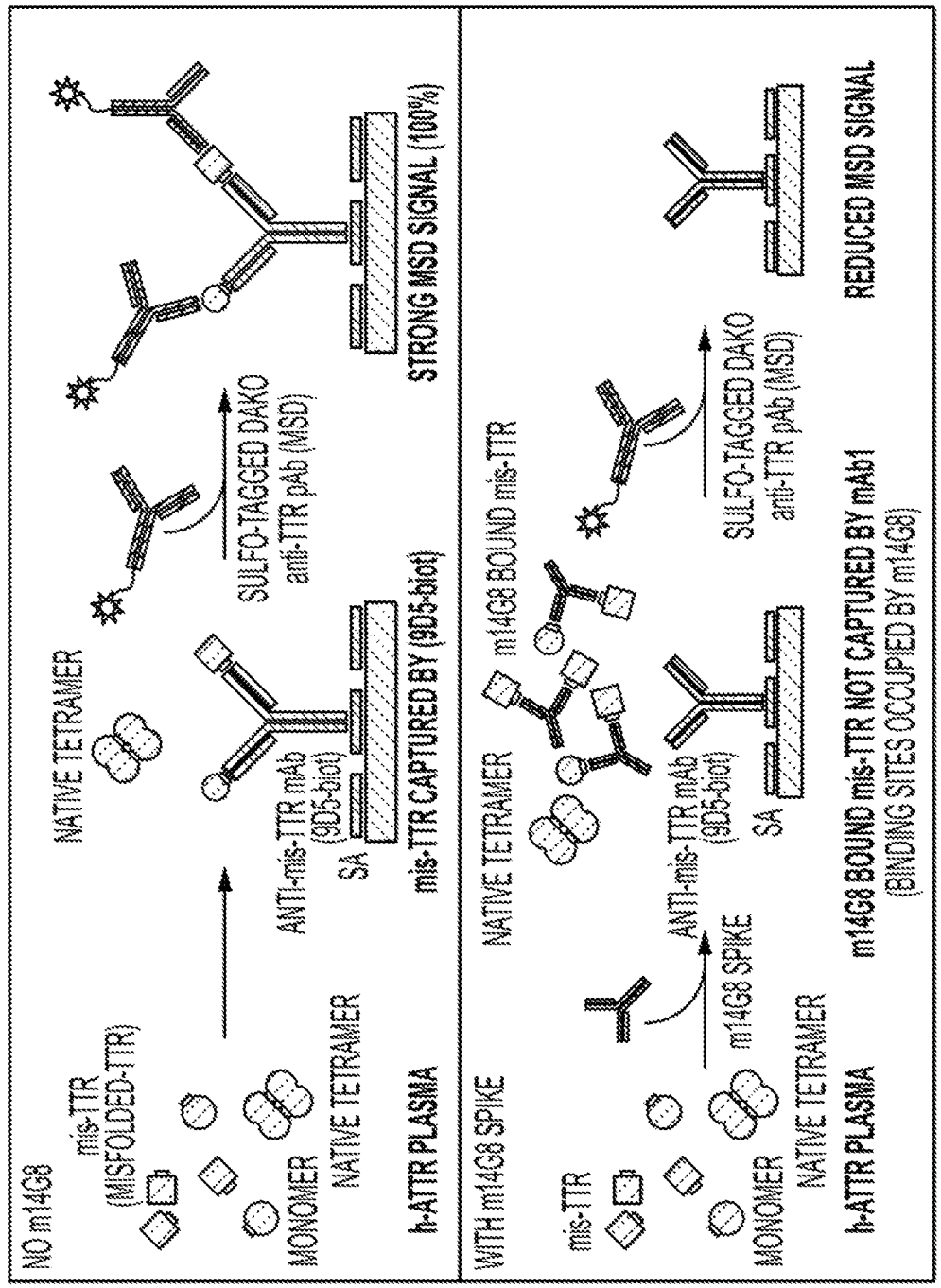
FIG. 9 depicts a diagram of a pharmacodynamic assay to measure binding of a mis-TTR mAb (m14G8) to plasma mis-TTR (target engagement).

Example 4. Ex Vivo Target Engagement Assay in Selected TTR Amyloidosis Patient Samples with Elevated Misfolded-TTR Levels To measure the ability of a potential mis-TTR therapeutic antibody (m14G8, mouse 14G8) to bind to plasma mis-TTR (target engagement), ATTR plasma (V30M) with high levels of mis-TTR were treated ex-vivo with increasing amount of m14G8. Binding of m14G8 to plasma mis-TTR (target) should decrease the amount of remaining unbound (free) mis-TTR since binding sites become occupied with m14G8, resulting in a concentration-dependent decrease in the MSD signal and evidence of target engagement by this mis-TTR mAb. FIG. 9 depicts a diagram of such a target engagement assay.

Plasma samples from 12 patients with elevated levels of misfolded-TTR as measured in the free misfolded-TTR assay were selected for analysis in a target engagement experiment to show m14G8 (mouse 14G8) reduces levels of free misfolded-TTR when spiked into patient plasma. Since 9D5 (MSD plate ligand) and m14G8 bind to the same epitope and compete for free misfolded-TTR, the assay effectively quantitates free misfolded-TTR unbound to m14G8 (i.e. bound to 9D5), resulting in a reduction in ECL signal detection when competed off by m14G8 bound to misfolded-TTR. Neat TTR amyloidosis patient plasma was spiked with a range of m14G8 concentrations (0, 12, 40, 120, 400 or 1200 µg/mL) and incubated for 30 minutes at room temperature. Samples were diluted 1:5 and the assay and standard curves were run as described in Example 2.

Figure 2:
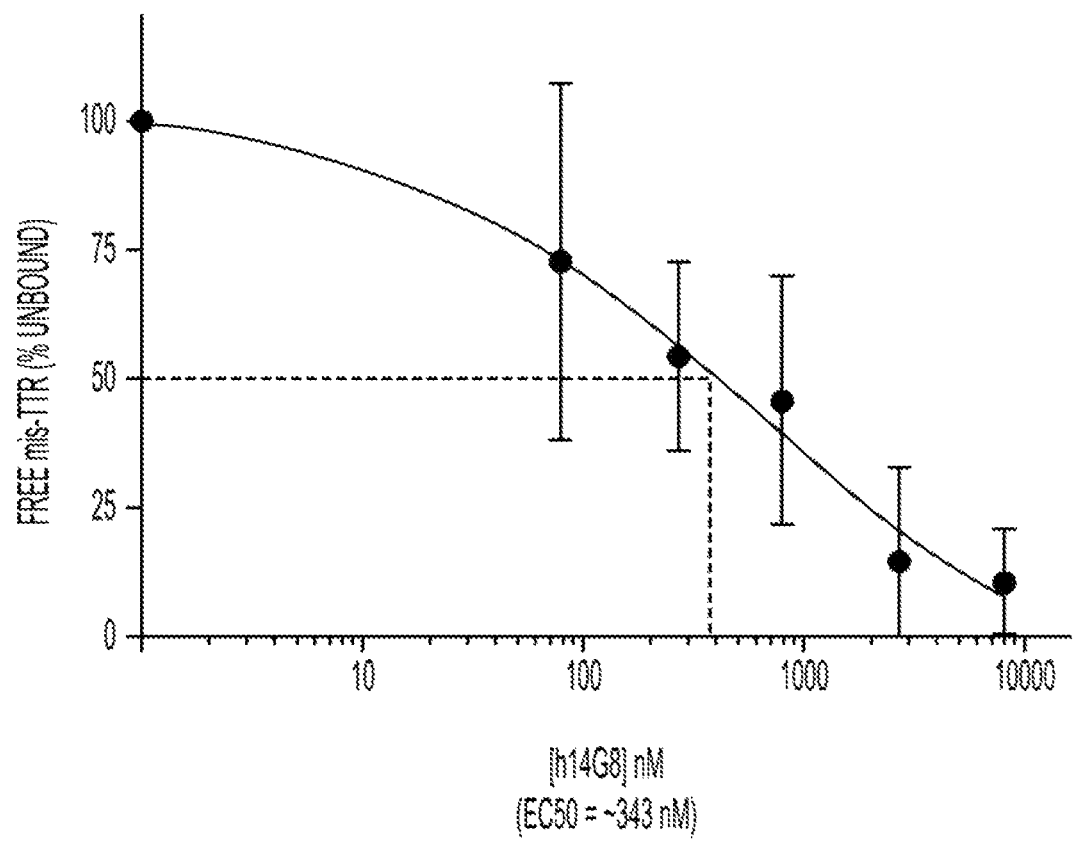
FIG. 2 depicts results of an ex vivo target engagement assay, using a 9D5 capture antibody and a polyclonal anti-TTR reporter antibody, showing that m14G8 reduces levels of free misfolded TTR when spiked into patient plasma.

FIG. 2 shows the antibody competition curve for exemplary TTR amyloidosis patient plasma samples with elevated misfolded-TTR levels indicating free misfolded-TTR (%) levels in the presence of increasing concentrations of m14G8.

Abbreviations used in FIG. 2:
EC50=effective concentration 50% (free/unbound to m14G8); mis=misfolded Mean (point) and SD (bar) of 12 individual h-ATTR plasma samples (each spiked sample value normalized to its pre-spike ECL signal at 0 nM m14G8 in plasma, i.e. 100% unbound misfolded-TTR). Line represents asymmetric sigmoidal nonlinear curve fit of data.

High background was compensated for by subtracting background signal at maximal competition. Since the bioassay only detects misfolded-TTR not bound to m14G8 (free misfolded-TTR), binding of misfolded-TTR by m14G8 results in decreased ECL signal with increased m14G8 in plasma. Accordingly, a m14G8 concentration-dependent reduction in free misfolded-TTR levels (%) was observed confirming m14G8 was able to target (bind) misfolded-TTR (including monomer) in h-ATTR patient plasma at an estimated EC50 of 343 nM (~50 µg/mL). This assay is used to inform on target engagement in 14G8 trials.

Example 5: ECL Method for Determination of Free Misfolded-TTR in Plasma (9D5/18C5)

Method: Free (unbound) misfolded-TTR, including monomer, was detected in human plasma using a quantitative ECL (Meso Scale Discovery; MSD) assay research method. A 96-well MSD plate was coated with 30 µL per well of 4 µg/mL neutravidin in PBS, incubated overnight at 4° C., and washed three times in TBS containing 0.05% Tween 20. Plates had non-specific binding sites blocked with 3% MSD Blocker A in PBS for 1 hour at room temperature with shaking, then washed three times. 30 µL of 1 µg/mL 9D5-biotin in Assay Buffer (1% MSD Blocker A/PBS+0.05% Tween-20) was added to each well and incubated 1 hour at room temperature with shaking. The standard curve was prepared from a fresh aliquot of TTR in 6M guanidine HCl diluted into Assay Buffer. Standard Curve consisted of seven 5-fold dilutions starting at 1000 ng/mL ending at 64 pg/mL. Patient or control plasma was diluted 1:5 in Assay Buffer. Standard or diluted plasma (30 µL) were added to the plates in duplicate, incubated at room temperature with shaking for 1 hour then washed. 30 µL of the SULFO-TAG labeled 18C5 at 1 µg/mL in assay buffer was added to each well, incubated 1 hour with shaking then washed. 150 µL/well of 1×MSD Read Buffer T was added to each well and read within 10 minutes on a MSD Sector Imager S600. The top and the bottom standard were anchor points and the curve had a quantitative range in neat plasma of 1.6 to 1000 ng/mL equivalents based on the guanidine-HCl TTR standard.

Figure 3:
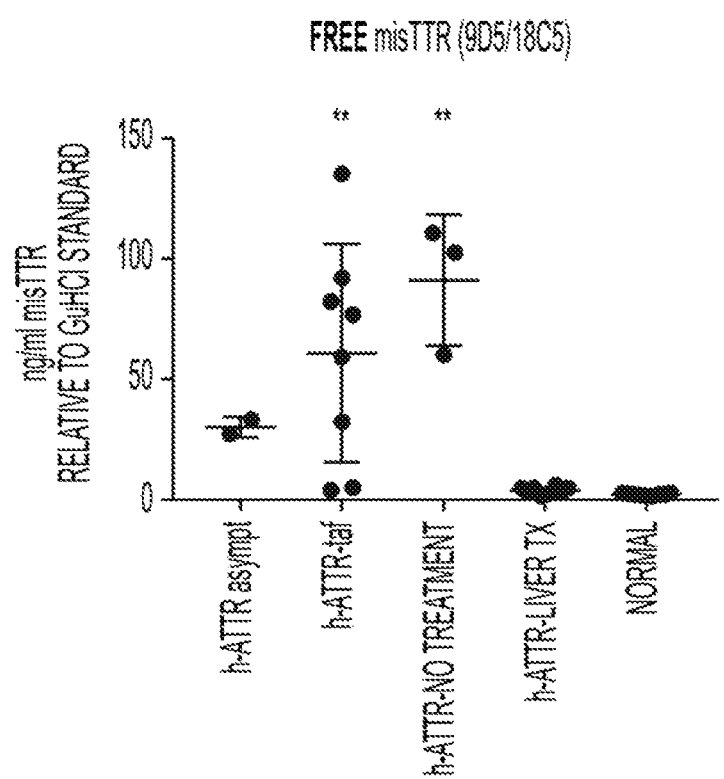
FIG. 3 depicts the results of a sandwich immunoassay employing the Meso Scale Discovery (MSD) electrochemiluminescence platform showing that 9D5 detects elevated misfolded TTR in plasma samples from transthyretin-mediated amyloidosis (ATTR) patients that had not undergone a liver transplant, in an assay using an 18C5 reporter antibody.

Results are shown in FIG. 3. The first column (labeled "h-ATTR asympto") depicts results for asymptomatic patients with hereditary TTR amyloidosis. The second column (labeled "h-ATTR-taf") depicts results for patients with hereditary TTR amyloidosis treated with tafamidis. The third column (labeled "h-ATTR-no treatment") depicts results for untreated patients with hereditary TTR amyloidosis. The fourth column (labeled "h-ATTR liver TX") depicts results for patients with hereditary TTR amyloidosis with a liver transplant. The fifth column (labeled "Normal") depicts results for normal patients.

Points are individual data and bars are mean and SD. *0.01-0.05, 0.0005-0.0099, *0.0001-0.005, ****<0.0001, compared to Normal control (non-parametric Kruskal-Wallis test with Dunn's multiplicity adjustment).

Abbreviations used in FIG. 3:

asym=asymptomatic; ATTR=amyloid transthyretin; eq=equivalents; GuHCl=guanidine hydrochloride; h=hereditary; mis=misfolded; std=standard; Tx=transplant; wt=wild type

Example 6. Preparation of the Immunogen and Immunization or Mice for 18C5

Both BALB/c and C57BL/6 female mice were injected with transthyretin engineered with a mutation at F87M and L110M referred to as transthyretin-double mutant (TTR-DM). Intraperitoneal injection of 50 µg/mouse for three injections followed by 25 µg/mouse for 3 injections and followed by 10 µg/mouse for 4 injections of TTR-DM emulsified in RIBI adjuvant were injected weekly using 5 BALB/c, additionally 5 C57BL/6 mice were injected for 3 injections at 50 µg/mouse, 3 injections at 25 µg/mouse and 4 injections at 10 µg/mouse emulsified in RIBI adjuvant. Mice were titered against the TTR-DM, Native tetrameric TTR, and his-MCAM. Mice with the highest titers to TTR-DM and lowest titers to Native tetrameric TTR and his-MCAM (BALB/c #1 and 5 and C57BL/6 #4 and 5) were fused by a modification of Kohler and Milstein. Resultant hybridomas were screened against TTR-DM, native tetrameric TTR and his-MCAM. Hybridomas showing specificity to TTR-DM were cloned and further characterized. 18C5 was identified.

Example 7. Characterization of 18C5 by BIAcore

Analysis was performed using a Biacore T200 to compare the binding affinity of murine antibodies to recombinant human TTR denatured in 6M Guanidine Hydrochloride (Gu-hTTR), Cynomolgus TTR denatured in 6 M Guanidine Hydrochloride (Gu-cTTR) and native tetrameric human TTR. Anti-Mouse antibody was immobilized on sensor chip CM3 (GE Healthcare Life Sciences) via amine coupling, and murine antibodies (ligand) were captured to a level to ensure a maximum binding of analyte of 50 RU (approximately 250RU of ligand binding). Various concentrations of Gu-TTR (ranging from 0.4 nM to 100 nM) were passed over the captured ligand at 50 µL/min in running buffer (HBS+0.05% P-20, 1 mg/mL BSA, 50 mM Gu-HCl) for 300 s association time and 900 s dissociation time. Regeneration of the chip surface was accomplished by 2 short injections of 10 mM Glycine-HCl at pH 1.7. Concentrations of Gu-cTTR used ranged from 1-1000 nM, while concentrations of Human TTR tetramer ranged from 10 nM to 10,000 nM. Data was blank subtracted to both a sensor not containing ligand and 0 nM analyte concentration. Analysis was performed using a global 1:1 fit with Biacore Evaluation software (v3.0) with bulk refractive index set to zero RU. Binding data are shown in Table 6.

TABLE 6

Binding data of 18C5 toward human misfolded TTR and Cynomolgus misfolded TTR, and human TTR tetramer.

| TTR | ka 1/Ms | kd 1/s | $K_D$ nM |
|---|---|---|---|
| Human misfolded TTR | $1.1 \times 10^5$ | $6.2 \times 10^{-4}$ | 5.9 nM |
| Cynomolgus misfolded TTR | $1.0 \times 10^5$ | $9.2 \times 10^{-4}$ | Minimal binding at highest concentration, hard to estimate KD |
| Human TTR tetramer | $2.2 \times 10^3$ | $2.2 \times 10^{-4}$ | Minimal binding at highest concentration, hard to estimate KD |

Example 8. Characterization of Chimeric 18C5 by BIAcore

Analysis was performed using a Biacore T200 to compare the binding affinity of murine and chimeric antibodies to recombinant human TTR denatured in 6M Guanidine Hydrochloride (Gu-hTTR). Anti-Human antibody was immobilized on flow cells 1 and 2, Anti-Mouse antibody was immobilized on flow cells 3 and 4 on sensor chip CM3 (GE Healthcare Life Sciences) via amine coupling, chimeric and murine 18C5 antibodies (ligand) were captured to a level to ensure a maximum binding of analyte of 50 RU (approximately 250RU of ligand binding). Various concentrations of Gu-TTR (ranging from 0.4 nM to 100 nM) were passed over the captured ligand at 50 µL/min in running buffer (HBS+0.05% P-20, 1 mg/mL BSA, 50 mM Gu-HCl) for 300 s association time and 900 s dissociation time. Regeneration of the chip surface was accomplished by 2 short injections of 3M Magnesium Chloride or 2 short injections of 10 mM Glycine-HCl at pH 1.7. Data was blank subtracted to both a sensor not containing ligand and 0 nM analyte concentration. Analysis was performed using a global 1:1 fit with Biacore Evaluation software (v3.0) with bulk refractive index set to zero RU. Binding data are shown in Table 7.

A mature heavy chain variable region amino acid sequence of a chimeric 18C5 antibody is provided as SEQ ID NO:81, a mature light chain variable region amino acid sequence of a chimeric 18C5 antibody is provided as SEQ ID NO:87, a human heavy chain constant region amino acid sequence of SEQ ID NO: 17, and a human light chain constant region amino acid sequence of SEQ ID NO: 19.

TABLE 7

Binding data for murine and chimeric antibodies to recombinant human TTR denatured in 6M Guanidine Hydrochloride (Gu-hTTR).

| TTR | ka 1/Ms | kd 1/s | $K_D$ nM |
|---|---|---|---|
| Chimeric 18C5 | $1.3 \times 10^5$ | $1.6 \times 10^{-4}$ | 1.8 nM |
| Murine 18C5 | $9.9 \times 10^4$ | $2.1 \times 10^{-4}$ | 2.2 nM |

Example 9. Epitope Mapping of 18C5

Initial mapping showed the epitope for 18C5 lies within 87-127 of SEQ ID NO: 26. Further mapping showed the epitope to lie between 101-109 of SEQ ID NO:26. The much lower affinity to misfolded Cynomolgus TTR suggest that amino acid 104 is important as this is the only amino acid substitution between human and Cynomolgus TTR.

Example 10. Sequence of 18C5

18C5 hybridoma clone LA89 18C5. A1.A1 frozen cell pellet was used for mRNA extraction and purification.

mRNA isolation & purification was performed using Oligotex direct mRNA mini kit (Qiagen, cat#72022) protocol. Briefly, 9×10$^6$ hybridoma clone cells were lysed and homogenized in the presence of highly denaturing guanidine-isothiocyanate buffer, which inactivates RNases. Oligotex suspension was added to the lysis mix, hybridization was allowed to take place between the oligo dT30 of the oligotex particles and the poly-A tail of the mRNA. Contaminations were then washed and poly-A+ RNA was eluted. mRNA was reverse transcribed to cDNA using Marathon cDNA amplification kit (Clontech, cat#634913). An adaptor was ligated to the 5' terminus of the cDNA. 5' RACE method was used to amplify V regions. 5' V region consensus primers and constant region specific anchor primers were used for PCR. Amplified V regions were cloned into pTOPO cloning vector and transformed into Top10 E. coli. 15-20 individual colonies were grown up and purified plasmid was sequenced. A clone sequence was considered a genuine V region sequence if it met following criteria No stop codon between Met and C region
The sequence contains key features of antibody V regions
The sequence contains definable CDRs.
Minimum three independent clones with matching ORF
Variable region sequences determined were cloned into expression vectors and transfected into CHOs cells. Purified chimeric antibody was characterized for binding using murine 18C5 as control antibody.

The mature heavy chain variable amino acid sequence of 18C5 is provided as SEQ ID NO:81, and the mature light chain variable amino acid sequence of 18C5 is provided as SEQ ID NO:87. The Kabat/Chothia Composite heavy chain CDR-H1, CDR-H2, and CDR-H3 amino acid sequences are provided as SEQ ID NOs 5, 7, and 9, respectively. The Kabat/Chothia Composite light chain CDR-L1, CDR-L2, and CDR-L3 amino acid sequences are provided as SEQ ID NOs 11, 13, and 15, respectively.

Example 11. Specificity of 18C5 Demonstrated by Western Blot Analysis

Figure 4:
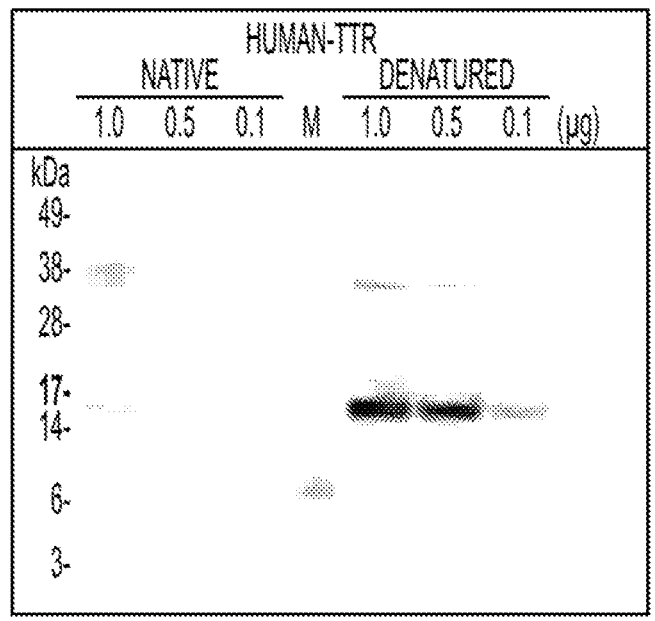
FIG. 4 depicts results of a Western blot experiment showing that 18C5 has strong reactivity toward denatured TTR monomer, minor reactivity toward denatured dimer, and very weak reactivity toward native TTR species.

To demonstrate the conformational specificity of 18C5 toward non-native (denatured) TTR, a Western blot analysis was performed as follows:
Procedure:
SDS-Polyacrylamide Gels
Native TTR: A 1.0, 0.5, and 0.1 µg sample of recombinant human TTR in LDS sample buffer (Life Technologies) was run on a 10% NuPAGE bis-tris gel (MES buffer; 90 V, 105 min) and transferred to nitrocellulose membranes for Western blot analysis.
Denatured TTR: Recombinant human TTR was prepared as described above for native TTR except the LDS sample buffer contained reducing agent and the samples were denatured by boiling prior to SDS-PAGE.
Western Blot Analysis
SDS-PAGE gels were blotted onto nitrocellulose membranes (iBlot, Life Technologies), treated with blocking buffer (LI-COR, Lincoln, NE) and incubated in 1.0-µg/mL primary antibody, washed with 1×TBS and placed in 1:20,000 dilution of IRDye 800CW-conjugated goat-anti-mouse or anti-rabbit secondary antibody (LI-COR, Lincoln, NE), then imaged on an Odyssey CLx infrared imager (LI-COR, Lincoln, NE).
Results and Conclusions:
Western blot of native vs denatured recombinant TTR (FIG. 4) showed that 18C5 had very weak reactivity toward native TTR species (Lanes 1-3), but very strong reactivity toward denatured TTR monomer (~15 kDa) with minor reactivity toward denatured dimer (~30 kDa) (Lanes 5-7). Lane 4 shows molecular weight markers.

Figure 5:
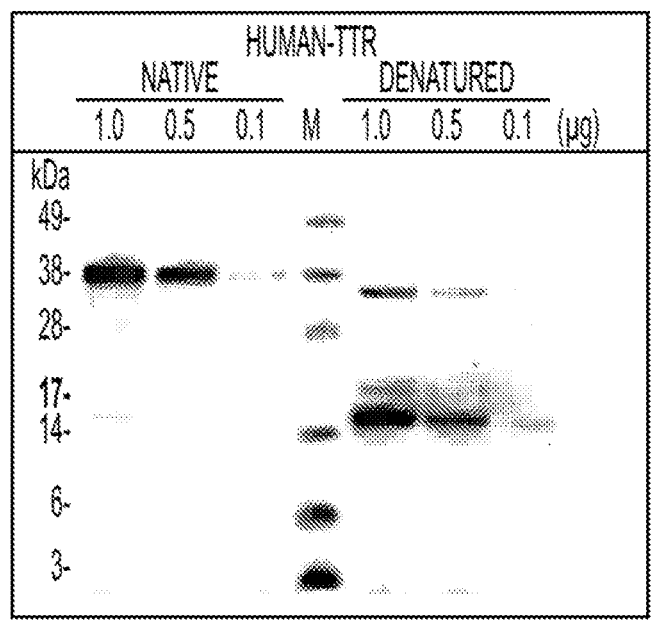
FIG. 5 depicts results of a Western blot experiment showing that a commercial TTR antibody could not distinguish between native versus denatured TTR and showed very strong reactivity toward monomeric as well as dimeric native and denatured TTR

In contrast, a commercial TTR antibody (Sigma, Catalog No. HPA002550) that is not conformationally specific did not distinguish between native versus denatured TTR and showed very strong reactivity toward monomeric as well as dimeric native and denatured TTR (FIG. 5). Lanes 1-3 show results for Native TTR; Lane 4 shows molecular weight markers, and Lanes 5-7 show results for Denatured TTR.

Example 12 18C5 Use in a Potential Diagnostic for TTR Amyloidosis

A sandwich immunoassay employing the Meso Scale Discovery (MSD) electrochemiluminescence platform was used to detect total misfolded TTR (Total misTTR) in patient plasma samples. Samples were from normal patients and patients with transthyretrin-mediated amyloidosis (ATTR). Patients with transthyretrin-mediated amyloidosis (ATTR) had the following TTR mutations and treatments: ATTR (V30M familial amyloid polyneuropathy (FAP)) with Liver Transplant, ATTR (V30M familial amyloid polyneuropathy (FAP)) No Treatment, ATTR (V30M familial amyloid polyneuropathy (FAP)) with Tafamidis, ATTR (Y114C familial amyloid polyneuropathy (FAP)) with Tafamidis, and ATTR (S50I) No Treatment.

Briefly, 96-well MSD standard plate was first coated with NeutrAvidin Protein (Thermo Fisher Scientific, Waltham, MA), followed by blocking with 3% Blocker A in PBS (MSD, Rockville, MD). Biotinylated 18C5 was then added to each well at 0.5 µg/mL to capture misfolded TTR. Plasma samples were diluted 5-fold in 1% Blocker A/PBS before transferred to the MSD plate, along with guanidine denatured TTR as reference standard. After 1-hour incubation, misfolded TTR bound to the wells was detected with SULFO-TAG™-labeled Polyclonal Rabbit Anti-Human TTR (Agilent Technologies, Santa Clara, CA). Chemiluminescence signals proportional to the amount of misfolded TTR were generated by addition of 1×MSD Read Buffer and captured on a MESO SECTOR S 600 plate reader.

Figure 6:
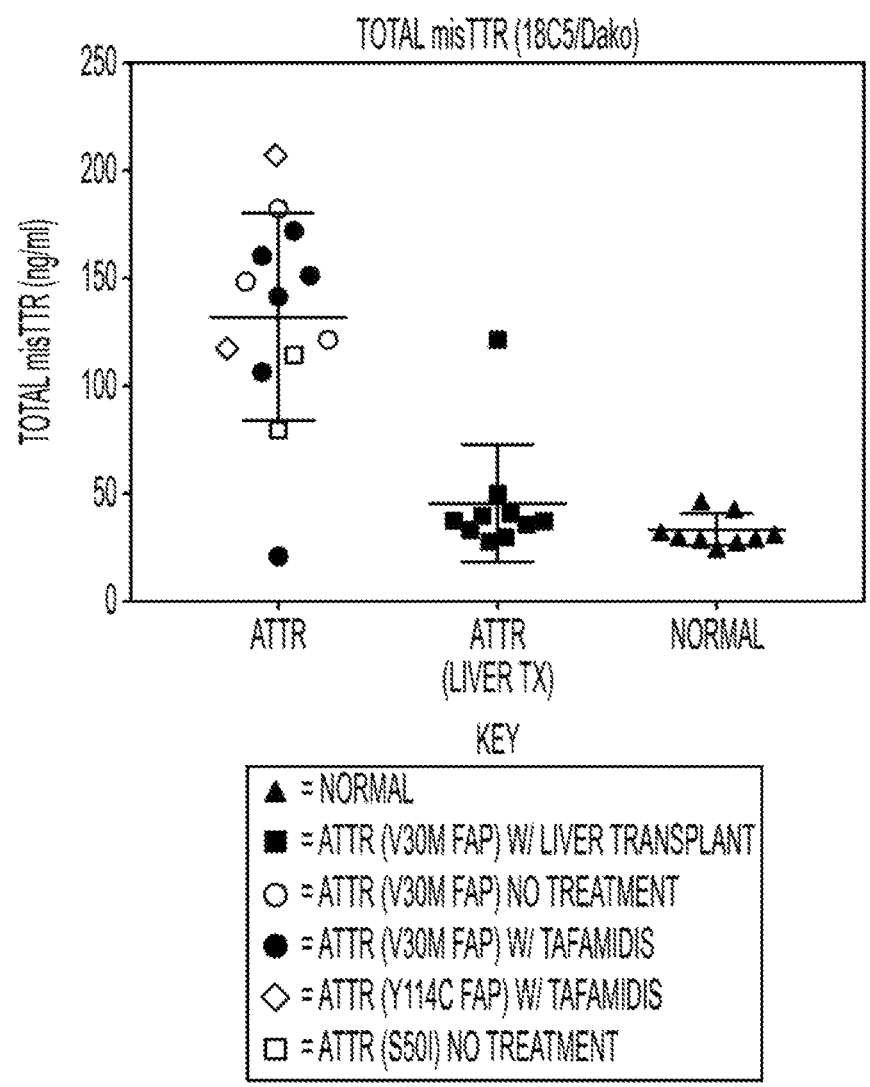
FIG. 6 depicts the results of a sandwich immunoassay employing the Meso Scale Discovery (MSD) electrochemiluminescence platform showing that 18C5 detects elevated misfolded TTR in plasma samples from transthyretin-mediated amyloidosis (ATTR) patients that had not undergone a liver transplant.

Results are shown in FIG. 6. The first column (labeled "ATTR") depicts results for patients with transthyretrin-mediated amyloidosis (ATTR) with either no treatment or with tafamidis. The second column (labeled "ATTR (Liver TX)" depicts results for patients with transthyretrin-mediated amyloidosis (ATTR) with a liver transplant. The third column (labeled "Normal") depicts results for normal patients. 18C5 detected elevated misfolded TTR in all but one of the transthyretrin-mediated amyloidosis (ATTR) patients that had not undergone a liver transplant. Transthyretrin-mediated amyloidosis (ATTR) patients undergoing a liver transplant and normal patients showed low levels of misfolded TTR with one exception in the Liver transplant group. It should be noted that the levels are ng/ml equivalents based off a guanidine denatured TTR standard curve. The two patients with results that were anomalous were collected on the same day and is possible the samples were switched when aliquoted.

Example 13. 18C5-18C5 for Determination of Multimeric Misfolded TTR

A sandwich immunoassay employing the Meso Scale Discovery (MSD) electrochemiluminescence platform was used to detect total multimeric misfolded TTR (Total Multimeric misTTR) in patient plasma samples. Samples were from normal patients and patients with transthyretrin-mediated amyloidosis (ATTR). Patients with transthyretrin-mediated amyloidosis (ATTR) had the following TTR mutations and treatments: ATTR (V30M familial amyloid polyneuropathy (FAP)) with Liver Transplant, ATTR (V30M familial amyloid polyneuropathy (FAP)) No Treatment, ATTR (V30M familial amyloid polyneuropathy (FAP)) with Tafamidis, ATTR (Y114C familial amyloid polyneuropathy (FAP)) with Tafamidis, and ATTR (S50I) No Treatment.

MSD plates were coated overnight with 4 µg/mL NeutrAvidin. Plates were blocked for 1 hour with 3% MSD Blocker A, then washed 3× with Tris Buffered Saline with 0.1% Tween-20 (TBS-T). 1 µg/mL biotinylated 18C5 was added for 1 hour, followed by 3× wash with TBS-T. Samples were diluted 5-fold in sample diluent (PBS+0.1% BSA+0.05% Triton X-100) and then were added to the plate in duplicate. A standard curve of TTR-DM was used ranging in concentration from 64 µg/mL to 1 µg/mL, with a 0 µg/mL blank. Plates were washed 3× with TBS-T, followed by an addition of 1 µg/mL 18C5 labeled with MSD Sulfo-tag, in sample diluent, and incubated for 1 hour. Finally, plates were washed 3× with TBS-T, and 150 uL of MSD Read Buffer T was added, and plates were read on the MESO SECTOR S 600 plate reader. Samples were analyzed using MSD Discovery Workbench 4.0.

Figure 7:
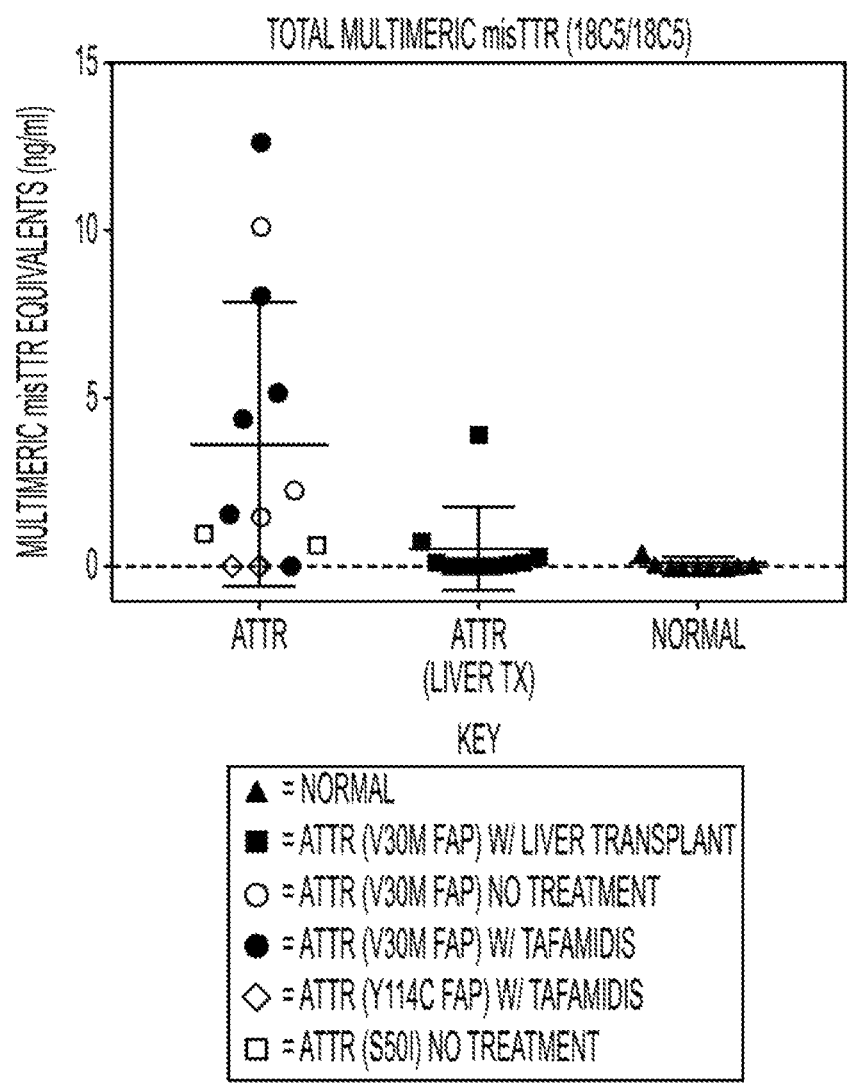
FIG. 7 depicts the results of a sandwich immunoassay employing the Meso Scale Discovery (MSD) electrochemiluminescence platform showing that 18C5 detects elevated multimeric misfolded TTR in plasma samples from transthyretin-mediated amyloidosis (ATTR) patients that had not undergone a liver transplant.

Results are shown in FIG. 7. The first column (labeled "ATTR") depicts results for patients with transthyretrin-mediated amyloidosis (ATTR) with either no treatment or with tafamidis. The second column (labeled "ATTR (Liver TX)" depicts results for patients with transthyretrin-mediated amyloidosis (ATTR) with a liver transplant. The third column (labeled "Normal") depicts results for normal patients. While not as many of the samples were positive for multimeric TTR, all positives were in the TTR patient samples, there was a statistical difference using a Kruskal Wallis test with Dunn correction of P=0.04 with patient samples to patients with liver transplant and P=0.004 between patients and normal controls. There was no significance between normal controls and patients treated with liver transplant.

Example 14. 9D5 Detects Elevated Levels of Mis-TTR (Misfolded TTR Monomers and Oligomers) in Plasma from Hereditary ATTR Patients Collection of ATTR and normal plasma
Blood from ATTR patients with a positive diagnosis of hereditary (h-ATTR) and wildtype ATTR (WT-ATTR) were collected in 7ml Vacutainer K2-EDTA tubes and centrifuged to remove cellular debris. The plasma fractions were aliquoted into 1.5ml LoBind Eppendorf tubes and immediately frozen. Plasma samples from healthy normal volunteers were collected in the same fashion. All samples were used immediately after thawing and not refrozen. Samples are as described in Table 5.

Analysis of ATTR plasma by Western blot
Plasma samples were diluted 10-fold into lithium dodecyl sulfate sample buffer (Life Technologies), loaded (12 µL) on a 10% NuPAGE bis-tris gel, electrophoresed at 90V for 105 min., transferred to a nitrocellulose membrane and probed with 1.0 µg/mL mis-TTR 9D5 followed by 1:20,000 dilution of IRDye 800CW-conjugated goat-anti-mouse secondary antibody (LICOR). The blot was then rinsed and imaged on an Odyssey CLx infrared imager (LI-COR). Results are shown in FIG. 8.

Figure 8:
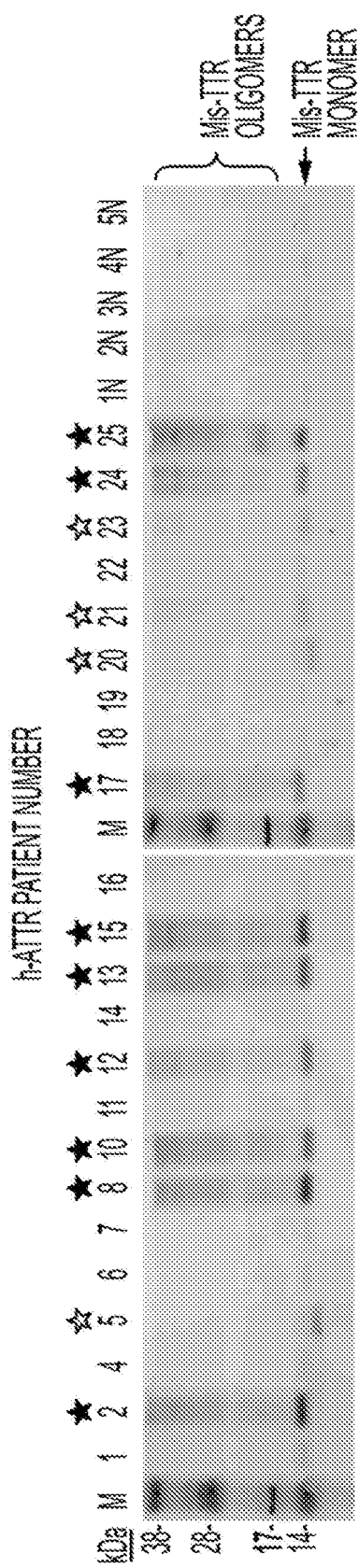
FIG. 8 depicts the results of a Western blot experiment showing that 9D5 detects elevated levels of mis-TTR (misfolded TTR monomers and oligomers) in plasma from hereditary ATTR patients.

Legend of FIG. 8:
Primary mAb: 1 µg/ml 9D5; M, molecular weight markers (BioRad); solid black star, non-liver transplanted TTR-V30M patients; hatched star, (Patients 5, 20) TTR-T114C; open star, (Patients 21, 23) TTR-550I; no star, liver transplantation; 1N-5N, normal (correspond to Pro IDs N1-N5 in Table 5).

The conformation-specific mis-TTR antibody 9D5 detects elevated levels of mis-TTR species (monomers and oligomers) in plasma derived from hereditary ATTR patients. In contrast, plasma from hereditary ATTR patients that had undergone liver transplantation therapy had barely detectable levels of mis-TTR similar to those in plasma from normal individuals.

Example 15. Elevated Levels of Mis-TTR in Plasma from Hereditary ATTR Patients

Collection of ATTR and Normal Plasma
Blood from ATTR patients with a positive diagnosis of hereditary (h-ATTR) and wildtype ATTR (WT-ATTR) were collected in 7ml Vacutainer K2-EDTA tubes and centrifuged to remove cellular debris. The plasma fractions were aliquoted into 1.5ml LoBind Eppendorf tubes and immediately frozen. Plasma samples from healthy normal volunteers were collected in the same fashion. All samples were used immediately after thawing and not refrozen. Samples are as described in Table 5.

Total mis-TTR in human plasma was detected using a Meso Scale Discovery (MSD) qualitative electrochemiluminescence assay. MSD plates were coated overnight with 4 µg/mL NeutrAvidin followed by 1 µg/mL biotinylated mis-TTR 9D5. Plasma samples were diluted 5-fold in sample diluent (PBS+0.1% BSA+0.05% Tween-20) prior to adding to the plate. Plates were washed with TBS-T, followed by the addition of 1 µg/mL anti-TTR polyclonal antibody (Dako) labeled with MSD Sulfo-tag. Plates were washed with TB S-T and read on an MSD Sector S 600 after addition of 150 µL/well of diluted MSD Read Buffer T. Samples were analyzed using MSD Discovery Workbench 4.0.

Figure 10:
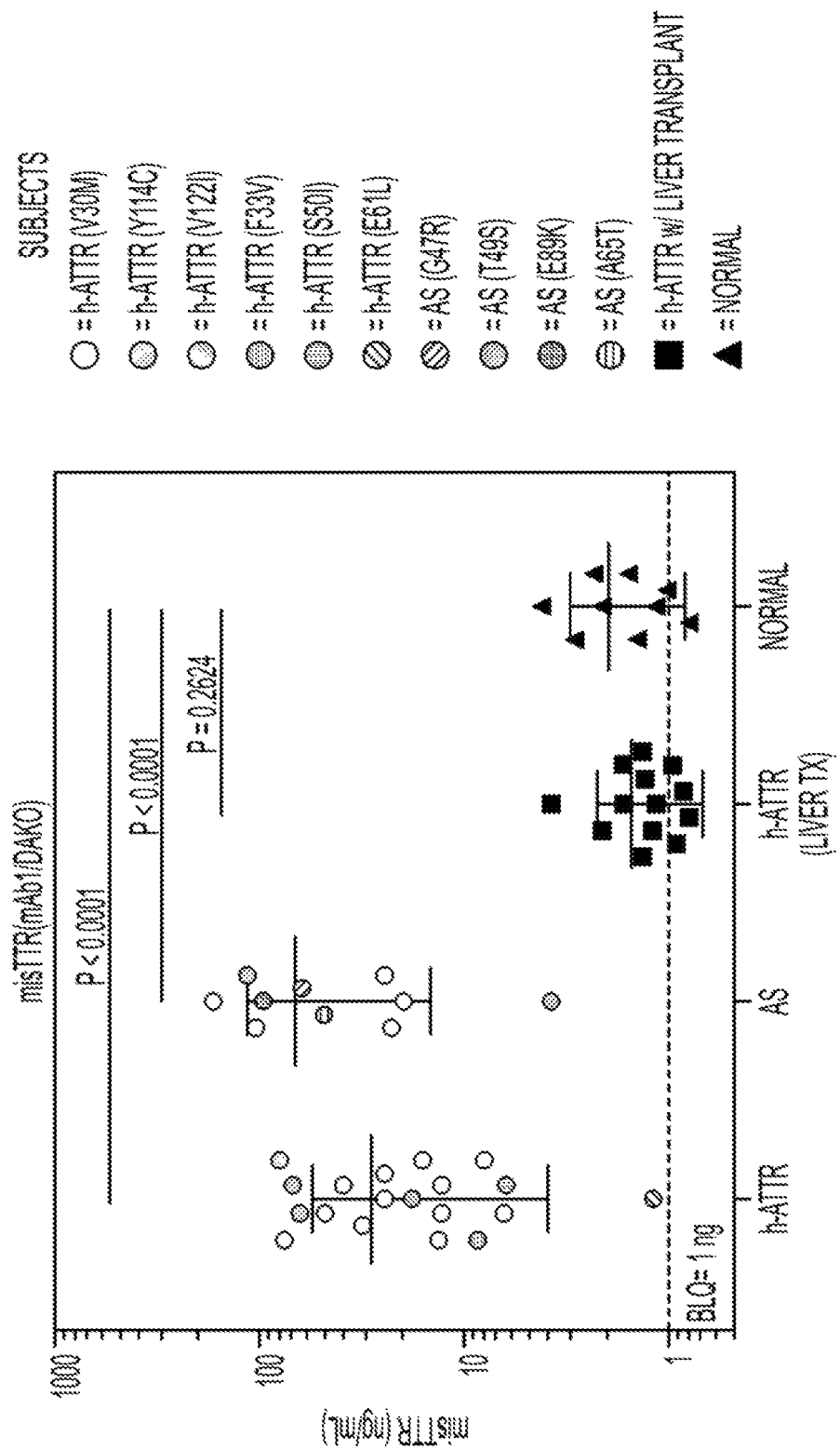
FIG. 10 depicts the results of a sandwich immunoassay employing the Meso Scale Discovery (MSD) electrochemiluminescence platform showing that 9D5 detects elevated misfolded TTR in plasma samples from transthyretin-mediated amyloidosis (ATTR) patients that had not undergone a liver transplant, in an assay using a polyclonal anti-TTR reporter antibody.

Results are shown in FIG. 10.
Legend of FIG. 10:
h-ATTR, hereditary ATTR; Liver TX, liver transplant. Limits of quantification (BLQ) of 1.0 ng/ml; Bars represent group means and SD; p values, Mann-Whitney test.

mis-TTR levels in plasma from hereditary ATTR patients are significantly elevated relative to normal controls. Elevated levels of mis-TTR were also observed in asymptomatic individuals positively genotyped for TTR mutations. Normal, low (<10 ng/ml to BLQ) levels of mis-TTR were observed in plasma from hereditary ATTR patients that had undergone liver transplantation treatment.

Example 7. Design of Humanized 18C5 Antibodies

The starting point or donor antibody for humanization was the mouse antibody 18C5. The heavy chain variable amino acid sequence of mature m18C5 is provided as SEQ ID NO: 81. The light chain variable amino acid sequence of mature m18C5 is provided as SEQ ID NO:87. The heavy chain Kabat/Chothia Composite CDR1, CDR2, and CDR3 amino acid sequences are provided as SEQ ID NOs:5, 7, and 9, respectively. The light chain Kabat CDR1, CDR2, and CDR3 amino acid sequences are provided as SEQ ID NOs:11, 13, and 15 respectively. Kabat numbering is used throughout.

Alignment of the variable region sequences of 18C5 with the consensus sequences of antibody variable regions from Kabat, et al. indicates that the heavy chain variable region (VH) of 18C5 belongs to mouse VH subgroup 3b, which corresponds to human VH subgroup 3. The kappa light chain variable region (VL) of 18C5 belongs to mouse Vk subgroup 2, which corresponds to human Vk subgroup 2. [Kabat E. A., et al, (1991) Sequences of Proteins of Immunological Interest, Fifth Edition. NIH Publication No. 91-3242.].

The residues at the interface between the Vk and Vh domains are the ones commonly found, except that Ala is at position 37 in heavy chain, whereas typically Val or Ile is at this position. Leu at position 95 in Vh is typically Asp, Gly or Ser. These positions are candidates for back mutations. For the Vk chain Glu 34 is typically Ala, His, Asn or Ser, and these positions are candidates for back mutations.

The CDRs of 18C5 VH and VL were identified using Martin's sequence-based CDR-identification rules. The CDRs were then assigned to the Chothia canonical classes using the summary of key residues presented in Table 3.5 of Martin (Martin ACR. (2010). In: Kontermann R and Dithel S (eds). *Antibody Engineering*. Heidelberg, Germany: Springer International Publishing AG.):

CDR-H1 consists of 10 amino acids and is similar to Chothia canonical class 1.
CDR-H2 consists of 17 amino acids and is similar to Chothia canonical class 3.
CDR-H3 consists of 4 amino acids; there are no classes for CDR-H3.
CDR-L1 consists of 16 amino acids and is similar to Chothia canonical class 4.
CDR-L2 consists of 7 amino acids and is of Chothia canonical class 1.
CDR-L3 consists of 9 amino acids and is similar to Chothia canonical class 1.

A search was made over the protein sequences in the PDB database [Deshpande et al, 2005, Nucleic Acids Research 33:D233-D237] to find structures, which would provide a rough structural model of 18C5. The crystal structure of murine anti-pyroglutamate-Abeta antibody Fab c #17 (PDB code 5MYK) [Piechotta, A. et al. ((2017) J. Biol. Chem. 292: 12713-12724) was used for both Vh and Vk structure since it had good resolution (1.6 A°) and overall sequence similarity to 18C5 Vh and Vk, retaining the same canonical structures for the loops. Bioluminate software was used to model a rough structure of 18C5. This software is licensed from Schrodinger Inc.

The frameworks of 18C5 VH and VL share a high degree of sequence similarity with the corresponding regions of humanized Crenezumab Fab (CreneFab) PDB: 5VZY, designed by Ultsch M, et al. ((2016) Sci Rep. 6:39374) The variable domains of 18C5 and CreneFab also share identical lengths for the CDR-H1, H2, L1, L2, and L3 loops. The framework regions of CreneFab VH (5VZY-VH) and VL (5VZY-VL) were chosen as the acceptor sequences for the CDRs of 18C5. Bioluminate software was used to model the structure. This software is licensed from Schrodinger Inc.

Heavy and light chain variant sequences resulting from antibody humanization process were further aligned to human germ line sequences using IMGT Domain GapAlign tool to assess the humanness of the heavy and light chain as outlined by WHO INN committee guidelines. (WHO-INN: International nonproprietary names (INN) for biological and biotechnological substances (a review) (Internet) 2014. Available from: http://www. who.int/medicines/services/inn/BioRev2014.pdf) Residues were changed to align with corresponding human germ line sequence, where possible, to enhance humanness. For humanized VL_v2 variant, a Q45R mutation was introduced to render the sequence more similar to human germline gene IGKV2-30*02 (GenBank acc. No. CAA77315; SEQ ID NO:90). The amino acid sequences consisting of CreneFab frameworks and 18C5 CDRs are designated hu18C5-VH_v1 and hu18C5-VL_v1.

Additional versions of hu18C5-VH and hu18C5-VL were designed to enable assessment of various framework residues for their contributions to antigen binding and immunogenicity. The positions considered for mutation include those that:

define the canonical CDR conformations (summarized in Martin 2010), are within the Vernier zone (Foote J and Winter G. (1992). *J Mot Biol.* 224(2):487-99), localize to the VH/VL domain interface (summarized in Leger OJP and Saldanha J. (2000) Preparation of recombinant antibodies from immune rodent spleens and the design of their humanization by CDR grafting. In: Shepherd P and Dean C (eds). *Monoclonal Antibodies: a Practical Approach*. Oxford, UK: Oxford University Press), are susceptible to post-translational modifications, such as glycosylation or pyroglutamination, are occupied by residues that are predicted to clash with CDRs, according to the model of 18C5 CDRs grafted onto Crenezumab Fab frameworks, or are occupied by residues that are rare among sequenced human antibodies, where either the parental mouse 18C5 residue or some other residue is much more prevalent.

2 humanized heavy chain variable region variants and 2 humanized light chain variable region variants were constructed containing different permutations of substitutions: hu18C5-VH_v1 and hu18C5-VH_v2, (SEQ ID NOs: 85-86, respectively) and hu18C5-VL_v1 and hu18C5-VL_v2 v6 (SEQ ID NOs: 91-92, respectively). (Tables 8 and 9). The exemplary humanized Vk and Vh designs, with backmutations and other mutations based on selected human frameworks, are shown in Tables 8 and 9, respectively. The bolded areas in Tables 8 and 9 indicate the CDRs as defined by Kabat/Chothia Composite. A "-" indicates no amino acid at the indicated position. SEQ ID NOs: 86 and 92 contain backmutations and other mutations as shown in Table 10. The amino acids at positions in hu18C5-VH_v1 and hu18C5-VH_v2 are listed in Table 11. The amino acids at positions in hu18C5-VL_v1 and hu18C5-VL_v2 are listed in Table 12. The percentage humanness for humanized VH chains hu18C5-VH_v1 and hu18C5-VH_v2 (SEQ ID NOs: 85-86, respectively) with respect to the most similar human germline gene IGHV3-48*01, and for humanized VL chains hu18C5-VL_v1 and hu18C5-VL_v2 (SEQ ID NOs:91-92, respectively) with respect to the most similar human germline gene IGKV2-30*02, is shown in Table 13.

TABLE 8

Humanized 18C5 VL Regions

| Linear residue # | Kabat residue # | FR or CDR | Murine 18C5 VL (SEQ ID NO: 87) | Acceptor 5VZY-VL_huFrwk (CreneFab) Acc. # 5VZY (SEQ ID NO: 89) | hu18C5-VL_v1 (SEQ ID NO: 91) | hu18C5-VL_v2 (SEQ ID NO: 92) |
|---|---|---|---|---|---|---|
| 1 | 1 | Fr1 | D | D | D | D |
| 2 | 2 | Fr1 | V | I | I | V |
| 3 | 3 | Fr1 | L | V | V | V |
| 4 | 4 | Fr1 | M | M | M | M |
| 5 | 5 | Fr1 | T | T | T | T |
| 6 | 6 | Fr1 | Q | Q | Q | Q |
| 7 | 7 | Fr1 | T | S | S | S |
| 8 | 8 | Fr1 | P | P | P | P |
| 9 | 9 | Fr1 | L | L | L | L |
| 10 | 10 | Fr1 | S | S | S | S |
| 11 | 11 | Fr1 | L | L | L | L |
| 12 | 12 | Fr1 | P | P | P | P |
| 13 | 13 | Fr1 | V | V | V | V |
| 14 | 14 | Fr1 | S | T | T | T |
| 15 | 15 | Fr1 | L | P | P | P |
| 16 | 16 | Fr1 | G | G | G | G |
| 17 | 17 | Fr1 | D | E | E | E |
| 18 | 18 | Fr1 | Q | P | P | P |
| 19 | 19 | Fr1 | A | A | A | A |
| 20 | 20 | Fr1 | S | S | S | S |
| 21 | 21 | Fr1 | I | I | I | I |
| 22 | 22 | Fr1 | S | S | S | S |
| 23 | 23 | Fr1 | C | C | C | C |
| 24 | 24 | CDR-L1 | R | R | R | R |
| 25 | 25 | CDR-L1 | S | S | S | S |
| 26 | 26 | CDR-L1 | S | S | S | S |
| 27 | 27 | CDR-L1 | Q | Q | Q | Q |
| 28 | 27A | CDR-L1 | S | S | S | S |
| 29 | 27B | CDR-L1 | I | L | I | I |
| 30 | 27C | CDR-L1 | V | V | V | V |
| 31 | 27D | CDR-L1 | D | Y | D | D |
| 32 | 27E | CDR-L1 | S | S | S | S |
| 33 | 27F | CDR-L1 |   | — | — | — |
| 34 | 28 | CDR-L1 | N | N | N | N |
| 35 | 29 | CDR-L1 | G | G | G | G |
| 36 | 30 | CDR-L1 | N | D | N | N |
| 37 | 31 | CDR-L1 | T | T | T | T |
| 38 | 32 | CDR-L1 | Y | Y | Y | Y |
| 39 | 33 | CDR-L1 | L | L | L | L |
| 40 | 34 | CDR-L1 | E | H | E | E |
| 41 | 35 | Fr2 | W | W | W | W |
| 42 | 36 | Fr2 | Y | Y | Y | Y |
| 43 | 37 | Fr2 | L | L | L | L |
| 44 | 38 | Fr2 | Q | Q | Q | Q |
| 45 | 39 | Fr2 | K | K | K | K |
| 46 | 40 | Fr2 | P | P | P | P |
| 47 | 41 | Fr2 | G | G | G | G |
| 48 | 42 | Fr2 | Q | Q | Q | Q |
| 49 | 43 | Fr2 | S | S | S | S |
| 50 | 44 | Fr2 | P | P | P | P |
| 51 | 45 | Fr2 | K | Q | Q | R |
| 52 | 46 | Fr2 | L | L | L | L |
| 53 | 47 | Fr2 | L | L | L | L |
| 54 | 48 | Fr2 | I | I | I | I |
| 55 | 49 | Fr2 | Y | Y | Y | Y |
| 56 | 50 | CDR-L2 | K | K | K | K |
| 57 | 51 | CDR-L2 | V | V | V | V |
| 58 | 52 | CDR-L2 | S | S | S | S |
| 59 | 53 | CDR-L2 | N | N | N | N |
| 60 | 54 | CDR-L2 | R | R | R | R |
| 61 | 55 | CDR-L2 | F | F | F | F |
| 62 | 56 | CDR-L2 | S | S | S | S |
| 63 | 57 | Fr3 | G | G | G | G |
| 64 | 58 | Fr3 | V | V | V | V |
| 65 | 59 | Fr3 | P | P | P | P |
| 66 | 60 | Fr3 | D | D | D | D |
| 67 | 61 | Fr3 | R | R | R | R |
| 68 | 62 | Fr3 | F | F | F | F |
| 69 | 63 | Fr3 | S | S | S | S |
| 70 | 64 | Fr3 | G | G | G | G |
| 71 | 65 | Fr3 | S | S | S | S |
| 72 | 66 | Fr3 | G | G | G | G |
| 73 | 67 | Fr3 | S | S | S | S |
| 74 | 68 | Fr3 | G | G | G | G |

TABLE 8-continued

Humanized 18C5 VL Regions

| Linear residue # | Kabat residue # | FR or CDR | Murine 18C5 VL (SEQ ID NO: 87) | Acceptor 5VZY-VL_huFrwk (CreneFab) Acc. # 5VZY (SEQ ID NO: 89) | hu18C5-VL_v1 (SEQ ID NO: 91) | hu18C5-VL_v2 (SEQ ID NO: 92) |
|---|---|---|---|---|---|---|
| 75 | 69 | Fr3 | T | T | T | T |
| 76 | 70 | Fr3 | D | D | D | D |
| 77 | 71 | Fr3 | F | F | F | F |
| 78 | 72 | Fr3 | T | T | T | T |
| 79 | 73 | Fr3 | L | L | L | L |
| 80 | 74 | Fr3 | K | K | K | K |
| 81 | 75 | Fr3 | I | I | I | I |
| 82 | 76 | Fr3 | S | S | S | S |
| 83 | 77 | Fr3 | R | R | R | R |
| 84 | 78 | Fr3 | V | V | V | V |
| 85 | 79 | Fr3 | E | E | E | E |
| 86 | 80 | Fr3 | A | A | A | A |
| 87 | 81 | Fr3 | E | E | E | E |
| 88 | 82 | Fr3 | D | D | D | D |
| 89 | 83 | Fr3 | L | V | V | V |
| 90 | 84 | Fr3 | G | G | G | G |
| 91 | 85 | Fr3 | I | V | V | V |
| 92 | 86 | Fr3 | Y | Y | Y | Y |
| 93 | 87 | Fr3 | Y | Y | Y | Y |
| 94 | 88 | Fr3 | C | C | C | C |
| 95 | 89 | CDR-L3 | F | S | F | F |
| 96 | 90 | CDR-L3 | Q | Q | Q | Q |
| 97 | 91 | CDR-L3 | G | S | G | G |
| 98 | 92 | CDR-L3 | S | T | S | S |
| 99 | 93 | CDR-L3 | H | H | H | H |
| 100 | 94 | CDR-L3 | V | V | V | V |
| 101 | 95 | CDR-L3 | P | P | P | P |
| 102 | 95A | CDR-L3 | — | — | — | — |
| 103 | 95B | CDR-L3 | — | — | — | — |
| 104 | 95C | CDR-L3 | — | — | — | — |
| 105 | 95D | CDR-L3 | — | — | — | — |
| 106 | 95E | CDR-L3 | — | — | — | — |
| 107 | 95F | CDR-L3 | — | — | — | — |
| 108 | 96 | CDR-L3 | L | W | L | L |
| 109 | 97 | CDR-L3 | T | T | T | T |
| 110 | 98 | Fr4 | F | F | F | F |
| 111 | 99 | Fr4 | G | G | G | G |
| 112 | 100 | Fr4 | A | Q | Q | Q |
| 113 | 101 | Fr4 | G | G | G | G |
| 114 | 102 | Fr4 | T | T | T | T |
| 115 | 103 | Fr4 | K | K | K | K |
| 116 | 104 | Fr4 | L | V | V | V |
| 117 | 105 | Fr4 | E | E | E | E |
| 118 | 106 | Fr4 | L | I | I | I |
| 119 | 106A | Fr4 | — | — | — | — |
| 120 | 107 | Fr4 | K | K | K | K |

TABLE 9

Humanized 18C5 VH Regions

| Linear residue # | Kabat residue # | FR or CDR | Murine 18C5 VH (SEQ ID NO: 81) | Acceptor 5VZY-VH_huFrwk (CreneFab) Acc. # 5VZY (SEQ ID NO: 83) | hu18C5-VH_v1 (SEQ ID NO: 85) | hu18C5-VH_v2 (SEQ ID NO: 86) |
|---|---|---|---|---|---|---|
| 1 | 1 | Fr1 | E | E | E | E |
| 2 | 2 | Fr1 | V | V | V | V |
| 3 | 3 | Fr1 | K | Q | Q | Q |
| 4 | 4 | Fr1 | L | L | L | L |
| 5 | 5 | Fr1 | L | V | V | V |
| 6 | 6 | Fr1 | E | E | E | E |
| 7 | 7 | Fr1 | S | S | S | S |
| 8 | 8 | Fr1 | G | G | G | G |
| 9 | 9 | Fr1 | G | G | G | G |
| 10 | 10 | Fr1 | G | G | G | G |
| 11 | 11 | Fr1 | L | L | L | L |
| 12 | 12 | Fr1 | V | V | V | V |
| 13 | 13 | Fr1 | Q | Q | Q | Q |
| 14 | 14 | Fr1 | P | P | P | P |
| 15 | 15 | Fr1 | G | G | G | G |
| 16 | 16 | Fr1 | G | G | G | G |

TABLE 9-continued

Humanized 18C5 VH Regions

| Linear residue # | Kabat residue # | FR or CDR | Murine 18C5 VH (SEQ ID NO: 81) | Acceptor 5VZY-VH_huFrwk (CreneFab) Acc. # 5VZY (SEQ ID NO: 83) | hu18C5-VH_v1 (SEQ ID NO: 85) | hu18C5-VH_v2 (SEQ ID NO: 86) |
|---|---|---|---|---|---|---|
| 17 | 17 | Fr1 | S | S | S | S |
| 18 | 18 | Fr1 | L | L | L | L |
| 19 | 19 | Fr1 | N | R | R | R |
| 20 | 20 | Fr1 | L | L | L | L |
| 21 | 21 | Fr1 | S | S | S | S |
| 22 | 22 | Fr1 | C | C | C | C |
| 23 | 23 | Fr1 | V | A | A | A |
| 24 | 24 | Fr1 | A | A | A | A |
| 25 | 25 | Fr1 | S | S | S | S |
| 26 | 26 | CDR-H1 | G | G | G | G |
| 27 | 27 | CDR-H1 | F | F | F | F |
| 28 | 28 | CDR-H1 | D | T | D | D |
| 29 | 29 | CDR-H1 | F | F | F | F |
| 30 | 30 | CDR-H1 | S | S | S | S |
| 31 | 31 | CDR-H1 | R | S | R | R |
| 32 | 32 | CDR-H1 | F | Y | F | F |
| 33 | 33 | CDR-H1 | W | G | W | W |
| 34 | 34 | CDR-H1 | M | M | M | M |
| 35 | 35 | CDR-H1 | S | S | S | S |
| 36 | 35A | CDR-H1 | — | — | — | — |
| 37 | 35B | CDR-H1 | — | — | — | — |
| 38 | 36 | Fr2 | W | W | W | W |
| 39 | 37 | Fr2 | A | V | V | A |
| 40 | 38 | Fr2 | R | R | R | R |
| 41 | 39 | Fr2 | Q | Q | Q | Q |
| 42 | 40 | Fr2 | A | A | A | A |
| 43 | 41 | Fr2 | P | P | P | P |
| 44 | 42 | Fr2 | G | G | G | G |
| 45 | 43 | Fr2 | R | K | K | K |
| 46 | 44 | Fr2 | G | G | G | G |
| 47 | 45 | Fr2 | Q | L | L | Q |
| 48 | 46 | Fr2 | E | E | E | E |
| 49 | 47 | Fr2 | W | L | L | W |
| 50 | 48 | Fr2 | I | V | V | I |
| 51 | 49 | Fr2 | G | A | A | G |
| 52 | 50 | CDR-H2 | E | S | E | E |
| 53 | 51 | CDR-H2 | I | I | I | I |
| 54 | 52 | CDR-H2 | N | N | N | N |
| 55 | 52A | CDR-H2 | P | S | P | P |
| 56 | 52B | CDR-H2 | — | — | — | — |
| 57 | 52C | CDR-H2 | — | — | — | — |
| 58 | 53 | CDR-H2 | G | N | G | G |
| 59 | 54 | CDR-H2 | S | G | S | S |
| 60 | 55 | CDR-H2 | S | G | S | S |
| 61 | 56 | CDR-H2 | T | S | T | T |
| 62 | 57 | CDR-H2 | I | T | I | I |
| 63 | 58 | CDR-H2 | N | Y | N | N |
| 64 | 59 | CDR-H2 | Y | Y | Y | Y |
| 65 | 60 | CDR-H2 | T | P | T | T |
| 66 | 61 | CDR-H2 | P | D | P | P |
| 67 | 62 | CDR-H2 | S | S | S | S |
| 68 | 63 | CDR-H2 | L | V | L | L |
| 69 | 64 | CDR-H2 | K | K | K | K |
| 70 | 65 | CDR-H2 | D | G | D | D |
| 71 | 66 | Fr3 | K | R | R | R |
| 72 | 67 | Fr3 | F | F | F | F |
| 73 | 68 | Fr3 | I | T | T | T |
| 74 | 69 | Fr3 | I | I | I | I |
| 75 | 70 | Fr3 | S | S | S | S |
| 76 | 71 | Fr3 | R | R | R | R |
| 77 | 72 | Fr3 | D | D | D | D |
| 78 | 73 | Fr3 | N | N | N | N |
| 79 | 74 | Fr3 | A | A | A | A |
| 80 | 75 | Fr3 | K | K | K | K |
| 81 | 76 | Fr3 | N | N | N | N |
| 82 | 77 | Fr3 | T | S | S | S |
| 83 | 78 | Fr3 | L | L | L | L |
| 84 | 79 | Fr3 | F | Y | Y | Y |
| 85 | 80 | Fr3 | L | L | L | L |
| 86 | 81 | Fr3 | Q | Q | Q | Q |
| 87 | 82 | Fr3 | M | M | M | M |
| 88 | 82A | Fr3 | S | N | N | N |
| 89 | 82B | Fr3 | K | S | S | S |
| 90 | 82C | Fr3 | V | L | L | L |

TABLE 9-continued

Humanized 18C5 VH Regions

| Linear residue # | Kabat residue # | FR or CDR | Murine 18C5 VH (SEQ ID NO: 81) | Acceptor 5VZY-VH_huFrwk (CreneFab) Acc. # 5VZY (SEQ ID NO: 83) | hu18C5-VH_v1 (SEQ ID NO: 85) | hu18C5-VH_v2 (SEQ ID NO: 86) |
|---|---|---|---|---|---|---|
| 91 | 83 | Fr3 | R | R | R | R |
| 92 | 84 | Fr3 | S | A | A | A |
| 93 | 85 | Fr3 | E | E | E | E |
| 94 | 86 | Fr3 | D | D | D | D |
| 95 | 87 | Fr3 | S | T | T | T |
| 96 | 88 | Fr3 | A | A | A | A |
| 97 | 89 | Fr3 | L | V | V | V |
| 98 | 90 | Fr3 | Y | Y | Y | Y |
| 99 | 91 | Fr3 | Y | Y | Y | Y |
| 100 | 92 | Fr3 | C | C | C | C |
| 101 | 93 | Fr3 | A | A | A | A |
| 102 | 94 | Fr3 | R | S | S | R |
| 103 | 95 | CDR-H3 | L | G | L | L |
| 104 | 96 | CDR-H3 | G | — | G | G |
| 105 | 97 | CDR-H3 | Y | — | Y | Y |
| 106 | 98 | CDR-H3 | G | — | G | G |
| 107 | 99 | CDR-H3 | N | — | N | N |
| 108 | 100 | CDR-H3 | Y | — | Y | Y |
| 109 | 100A | CDR-H3 | G | — | G | G |
| 110 | 100B | CDR-H3 | W | — | W | W |
| 111 | 100C | CDR-H3 | A | — | A | A |
| 112 | 100D | CDR-H3 | L | — | L | L |
| 113 | 100E | CDR-H3 | — | — | — | — |
| 114 | 100F | CDR-H3 | — | — | — | — |
| 115 | 100G | CDR-H3 | — | — | — | — |
| 116 | 100H | CDR-H3 | — | — | — | — |
| 117 | 100I | CDR-H3 | — | — | — | — |
| 118 | 100J | CDR-H3 | — | — | — | — |
| 119 | 100K | CDR-H3 | — | — | — | — |
| 120 | 101 | CDR-H3 | D | D | D | D |
| 121 | 102 | CDR-H3 | Y | Y | Y | Y |
| 122 | 103 | Fr4 | W | W | W | W |
| 123 | 104 | Fr4 | G | G | G | G |
| 124 | 105 | Fr4 | Q | Q | Q | Q |
| 125 | 106 | Fr4 | G | G | G | G |
| 126 | 107 | Fr4 | T | T | T | T |
| 127 | 108 | Fr4 | S | T | T | T |
| 128 | 109 | Fr4 | V | V | V | V |
| 129 | 110 | Fr4 | T | T | T | T |
| 130 | 111 | Fr4 | V | V | V | V |
| 131 | 112 | Fr4 | S | S | S | S |
| 132 | 113 | Fr4 | S | S | S | S |

TABLE 10

$V_H$, $V_L$ Backmutations and Other Mutations for Humanized 18C5

| $V_H$ or $V_L$ Variant | $V_H$ or $V_L$ Exon Acceptor Sequence | Changes from Acceptor Framework Residues (based on Kabat/Chothia Composite CDRs) |
|---|---|---|
| hu18C5-VH_v1 (SEQ ID NO: 85) | Acceptor 5VZY-VH_huFrwk (CreneFab) Acc. # 5VZY (SEQ ID NO: 83) | None |
| hu18C5-VH_v2 (SEQ ID NO: 86) | Acceptor 5VZY-VH_huFrwk (CreneFab) Acc. # 5VZY (SEQ ID NO: 83) | H37, H45, H47, H48, H49, H94 |
| hu18C5-VL_v1 (SEQ ID NO: 91) | Acceptor 5VZY-VL_huFrwk (CreneFab) Acc. # 5VZY (SEQ ID NO: 89) | none |
| hu18C5-VL_v2 (SEQ ID NO: 92) | Acceptor 5VZY-VL_huFrwk (CreneFab) Acc. # 5VZY (SEQ ID NO: 89) | L2, L45 |

TABLE 11

Kabat Numbering of Framework Residues (based on Kabat/Chothia Composite CDRs) for Backmutations and Other Mutations in Heavy Chains of Humanized 18C5 Antibodies

| Kabat Residue # | Acceptor 5VZY-VH_huFrwk (CreneFab) Acc. # 5VZY (SEQ ID NO: 83) | Murine 18C5 VH (SEQ ID NO: 81) | hu18C5-VH_v1 (SEQ ID NO: 85) | hu18C5-VH_v2 (SEQ ID NO: 86) |
|---|---|---|---|---|
| H37 | V | A | V | A |
| H45 | L | Q | L | Q |
| H47 | L | W | L | W |
| H48 | V | I | V | I |
| H49 | A | G | A | G |
| H94 | S | R | S | R |

TABLE 12

Kabat Numbering of Framework Residues (based on Kabat/Chothia Composite CDRs) for Backmutations and Other Mutations in Light Chains of Humanized 18C5 Antibodies

| Kabat Residue # | Acceptor 5VZY-VL_huFrwk (CreneFab) Acc. # 5VZY (SEQ ID NO: 89) | Murine 18C5 VL (SEQ ID NO: 87) | hu18C5-VL_v1 (SEQ ID NO: 91) | hu18C5-VL_v2 (SEQ ID NO: 92) |
|---|---|---|---|---|
| L2 | I | V | I | V |
| L45 | Q | K | Q | R |

TABLE 13

Percentage Humanness of Heavy and Light Chains of Humanized 18C5 Antibodies

| $V_H$ or $V_L$ Variant | % Humanness |
|---|---|
| hu18C5-VH_v1 (SEQ ID NO: 85) | 96.2% |
| hu18C5-VH_v2 (SEQ ID NO: 86) | 93.8% |
| hu18C5-VL_v1 (SEQ ID NO: 91) | 88.6% |
| hu18C5-VL_v2 (SEQ ID NO: 92) | 92.4% |

Positions at which Chothia class canonical, vernier, or interface/packing residues differ between mouse and human acceptor sequences are candidates for substitution. Examples of Chothia class canonical residues include Kabat residue H48 in Tables 8 and 9. Examples of interface/packing (VH+VL) residues include Kabat residues H35, H37, H39, H45, H47, H91, H93, H95, H103, L34, L36, L38, L44, L46, L87, L89, L91, L96, and L98 in Tables 8 and 9.

The rationales for selection of the positions indicated in Table 8 in the light chain variable region as candidates for substitution are as follows.

I2V is a backmutation of a Chothia canonical residue.

Q45R is a mutation to IGKV2-30*02 germline residue. Q is rare in human at this position. R is frequent at this position.

hu18C5-VL_v1: CDR-L1, L2, and L3 loops of 18C5-VL grafted onto the framework of CreneFab (5VZY-VL).

hu18C5-VL_v2: reverts all framework substitutions at positions that are key for defining the Chothia canonical classes, are part of the Vernier zone, or locate to the VH/VL domain interface; hu18C5-VL_v2 incorporates backmutations I2V and human acceptor to germline mutation Q45R, to enable assessment of these positions' contributions to antigen-binding affinity and immunogenicity.

Light chain variable regions:

```
hu18C5-VL_1
                                            (SEQ ID NO: 91)
DIVMTQSPLSLPVTPGEPASISCRSSQSIVDSNGNTYLEWYLQKPGQSPQ

LLIYKVSNRFSGVPDRFSGSGSGTDFTLKISRVEAEDVGVYYCFQGSHVP

LTFGQGTKVEIK hu18C5-VL_2
                                            (SEQ ID NO: 92)
DVVMTQSPLSLPVTPGEPASISCRSSQSIVDSNGNTYLEWYLQKPGQSPR

LLIYKVSNRFSGVPDRFSGSGSGTDFTLKISRVEAEDVGVYYCFQGSHVP

LTFGQGTKVEIK
```

The rationales for selection of the positions indicated in Table 9 in the heavy chain variable region as candidates for substitution are as follows.

V37A: is a backmutation in the vernier zone. Val shows repulsive interaction with Trp47.

L45Q: is a backmutation of a core interface residue per Chothia. Leu at this position has repulsive Van der Waals interactions.

L47W: is a backmutation of an interface residue. In murine 18C5 Trp is at 47 position and Trp makes hydrogen bond with Ser 35 thereby stabilizing intrachain beta-sheets. Leu does not establish any interface with any residue and may destabilize conformation.

V48I: is a backmutation of a CDR interacting Vernier zone residue to preserve this interaction.

A49G: is a backmutation of a Vernier zone residue.

S94R: is a backmutation of a Vernier zone residue, to preserve CDR interaction.

hu18C5-VH_v1: CDR-H1, H2, and H3 loops of 18C5-VH grafted onto the framework of CreneFab VH (5VZY-VH).

Hu18C5-VH_v2: reverts all framework substitutions at positions that are key for defining the Chothia canonical classes, are part of the Vernier zone, or localize to the VH/VL domain interface. 18C5-VH_v2 incorporates backmutations V37A, L45Q, L47W, V48I, A49G and S94R, to enable assessment of these positions' contributions to antigen-binding affinity and immunogenicity.

Heavy chain variable regions:

```
hu18C5-VH_1
                                            (SEQ ID NO: 85)
EVQLVESGGGLVQPGGSLRLSCAASGFDFSRFWMSWVRQAPGKGLELVAE

INPGSSTINYTPSLKDRFTISRDNAKNSLYLQMNSLRAEDTAVYYCASLG

YGNYGWALDYWGQGTTVTVSS hu18C5-VH_2
                                            (SEQ ID NO: 86)
EVQLVESGGGLVQPGGSLRLSCAASGFDFSRFWMSWARQAPGKGQEWIGE

INPGSSTINYTPSLKDRFTISRDNAKNSLYLQMNSLRAEDTAVYYCARLG

YGNYGWALDYWGQGTTVTVSS

Sequence Listing:
18C5 VH amino acid sequence with signal peptide
                                            SEQ ID NO: 1
MDFGLIFFIVALLKGVQCEVKLLESGGGLVQPGGSLNLSCVASGFDFSRF

WMSWARQAPGRGQEWIGEINPGSSTINYTPSLKDKFIISRDNAKNTLFLQ

MSKVRSEDSALYYCARLGYGNYGWALDYWGQGTSVTVSS nucleotide sequence encoding mouse 18C5 VH with
signal peptide
                                            SEQ ID NO: 2
ATGGATTTTGGGCTGATTTTTTTCATTGTTGCCCTTTTAAAAGGGGTCCA

GTGTGAGGTAAAGCTTCTCGAGTCTGGAGGTGGCCTGGTGCAGCCTGGAG

GATCCCTGAATCTCTCCTGTGTAGCCTCAGGATTCGATTTTAGTAGATTC

TGGATGAGTTGGGCTCGGCAGGCTCCAGGGAGAGGACAGGAATGGATTGG

AGAGATTAATCCAGGAAGCAGTACGATAAACTATACGCCATCTCTGAAGG

ATAAATTCATCATCTCCAGAGACAACGCCAAAAATACGCTGTTCCTGCAA

ATGAGCAAAGTGAGATCTGAGGACTCAGCCCTTTATTACTGTGCAAGACT
```

GGGGTATGGTAACTACGGATGGGCTCTGGACTACTGGGGTCAAGGAACCT

CAGTCACCGTCTCCTCA

18C5 VL amino acid sequence with signal peptide
SEQ ID NO: 3
MKLPVRLLVLMFWIPASRSDVLMTQTPLSLPVSLGDQASISCRSSQSIVD

SNGNTYLEWYLQKPGQSPKLLIYKVSNRFSGVPDRFSGSGSGTDFTLKIS

RVEAEDLGIYYCFQGSHVPLTFGAGTKLELK nucleotide sequence encoding mouse 18C5 VL with signal peptide
SEQ ID NO: 4
ATGAAGTTGCCTGTTAGGCTGTTGGTGCTGATGTTCTGGATTCCTGCTTC

CAGAAGTGATGTTTTGATGACCCAAACTCCACTCTCCCTGCCTGTCAGTC

TTGGAGATCAAGCCTCCATCTCTTGCAGATCTAGTCAGAGCATTGTAGAT

AGTAATGGAAACACCTATTTAGAATGGTACCTGCAGAAACCAGGCCAGTC

TCCAAAGCTCCTGATCTACAAAGTTTCCAACCGATTTTCTGGGGTCCCAG

ACAGGTTCAGTGGCAGTGGATCAGGGACAGATTTCACACTCAAGATCAGC

AGAGTGGAGGCTGAGGATCTGGGAATTTATTACTGCTTTCAAGGTTCACA

TGTTCCGCTCACGTTCGGTGCTGGGACCAAGTTGGAGCTGAAA amino acid sequence of an 18C5 CDR-H1
SEQ ID NO: 5
GFDFSRFWMS nucleic acid sequence encoding an 18C5 CDR-H1
SEQ ID NO: 6
GGATTCGATTTTAGTAGATTCTGGATGAGT amino acid sequence of an 18C5 CDR-H2
SEQ ID NO: 7
EINPGSSTINYTPSLKD nucleic acid sequence encoding an 18C5 CDR-H2
SEQ ID NO: 8
GAGATTAATCCAGGAAGCAGTACGATAAACTATACGCCATCTCTGAAGGA

T amino acid sequence of an 18C5 CDR-H3
SEQ ID NO: 9
LGYGNYGWALDY nucleic acid sequence encoding an 18C5 CDR-H3
SEQ ID NO: 10
CTGGGGTATGGTAACTACGGATGGGCTCTGGACTAC amino acid sequence of an 18C5 CDR-L1
SEQ ID NO: 11
RSSQSIVDSNGNTYLE nucleic acid sequence encoding an 18C5 CDR-L1
SEQ ID NO: 12
AGATCTAGTCAGAGCATTGTAGATAGTAATGGAAACACCTATTTAGAA amino acid sequence of an 18C5 CDR-L2
SEQ ID NO: 13
KVSNRFS nucleic acid sequence encoding an 18C5 CDR-L2
SEQ ID NO: 14
AAAGTTTCCAACCGATTTTCT amino acid sequence of an 18C5 CDR-L3
SEQ ID NO: 15
FQGSHVPLT nucleic acid sequence encoding an 18C5 CDR-L3
SEQ ID NO: 16
TTTCAAGGTTCACATGTTCCGCTCACG amino acid sequence of a chimeric 18C5 heavy chain constant region (human IgG1)
SEQ ID NO: 17
ASTKGPSVFPLAPSSKSTSGGTAALGCLVKDYFPEPVTVSWNSGALTSGV

HTFPAVLQSSGLYSLSSVVTVPSSSLGTQTYICNVNHKPSNTKVDKRVEP

KSCDKTHTCPPCPAPELLGGPSVFLFPPKPKDTLMISRTPEVTCVVVDVS

HEDPEVKFNWYVDGVEVHNAKTKPREEQYNSTYRVVSVLTVLHQDWLNGK

EYKCKVSNKALPAPIEKTISKAKGQPREPQVYTLPPSREEMTKNQVSLTC

LVKGFYPSDIAVEWESNGQPENNYKTTPPVLDSDGSFFLYSKLTVDKSRW

QQGNVFSCSVMHEALHNHYTQKSLSLSPGK nucleic acid encoding a chimeric 18C5 heavy chain constant region (human IgG1)
SEQ ID NO: 18
GCCTCCACCAAGGGCCCATCGGTCTTCCCCCTGGCACCCTCCTCCAAGAG

CACCTCTGGGGGCACAGCGGCCCTGGGCTGCCTGGTCAAGGACTACTTCC

CCGAACCGGTGACGGTGTCGTGGAACTCAGGCGCCCTGACCAGCGGCGTG

CACACCTTCCCGGCTGTCCTACAGTCCTCAGGACTCTACTCCCTCAGCAG

CGTGGTGACCGTGCCCTCCAGCAGCTTGGGCACCCAGACCTACATCTGCA

ACGTGAATCACAAGCCCAGCAACACCAAGGTGGACAAGAGAGTTGAGCCC

AAATCTTGTGACAAAACTCACACATGCCCACCGTGCCCAGCACCTGAACT

CCTGGGGGGACCGTCAGTCTTCCTCTTCCCCCCAAAACCCAAGGACACCC

TCATGATCTCCCGGACCCCTGAGGTCACATGCGTGGTGGTGGACGTGAGC

CACGAAGACCCTGAGGTCAAGTTCAACTGGTACGTGGACGGCGTGGAGGT

GCATAATGCCAAGACAAAGCCGCGGGAGGAGCAGTACAACAGCACGTACC

GTGTGGTCAGCGTCCTCACCGTCCTGCACCAGGACTGGCTGAATGGCAAG

GAGTACAAGTGCAAGGTCTCCAACAAAGCCCTCCCAGCCCCCATCGAGAA

AACCATCTCCAAAGCCAAAGGGCAGCCCCGAGAACCACAGGTGTACACGC

TGCCCCCATCCCGGGAGGAGATGACCAAGAACCAGGTCAGCCTGACCTGC

CTGGTCAAAGGCTTCTATCCCAGCGACATCGCCGTGGAGTGGGAGAGCAA

TGGGCAGCCGGAGAACAACTACAAGACCACGCCTCCCGTGCTGGACTCCG

ACGGCTCCTTCTTCCTCTATAGCAAGCTCACCGTGGACAAGAGCAGGTGG

CAGCAGGGGAACGTCTTCTCATGCTCCGTGATGCATGAGGCTCTGCACAA

CCACTACACGCAGAAGAGCCTCTCCCTGTCCCCGGGTAAATGA amino acid sequence of a chimeric 18C5 light chain constant region (human kappa)
SEQ ID NO: 19
RTVAAPSVFIFPPSDEQLKSGTASVVCLLNNFYPREAKVQWKVDNALQSG

NSQESVTEQDSKDSTYSLSSTLTLSKADYEKHKVYACEVTHQGLSSPVTK

SFNRGEC nucleic acid sequence encoding an amino acid sequence of a chimeric 18C5 light chain constant region (human kappa)
SEQ ID NO: 20
CGGGGAACTGTGGCTGCACCATCTGTCTTCATCTTCCCGCCATCTGATGA

GCAGTTGAAATCTGGAACTGCCTCTGTTGTGTGCCTGCTGAATAACTTCT

```
ATCCCAGAGAGGCCAAAGTACAGTGGAAGGTGGATAACGCCCTCCAATCG
GGTAACTCCCAGGAGAGTGTCACAGAGCAGGACAGCAAGGACAGCACCTA
CAGCCTCAGCAGCACCCTGACGCTGAGCAAAGCAGACTACGAGAAACACA
AAGTCTACGCCTGCGAAGTCACCCATCAGGGCCTGAGCTCGCCCGTCACA
AAGAGCTTCAACAGGGGAGAGTGTTAG
``` amino acid sequence of an exemplary IgG1 heavy
chain constant region
SEQ ID NO: 21
```
ASTKGPSVFPLAPSSKSTSGGTAALGCLVKDYFPEPVTVSWNSGALTSGV
HTFPAVLQSSGLYSLSSVVTVPSSSLGTQTYICNVNHKPSNTKVDKRVEP
KSCDKTHTCPPCPAPELLGGPSVFLFPPKPKDTLMISRTPEVTCVVVDVS
HEDPEVKFNWYVDGVEVHNVKTKPREEQYNSTYRVVSVLTVLHQDWLNGK
EYKCKVSNKALPAPIEKTISKAKGQPREPQVYTLPPSREEMTKNQVSLTC
LVKGFYPSDIAVEWESNGQPENNYKTTPPVLDSDGSFFLYSKLTVDKSRW
QQGNVFSCSVMHEALHNHYTQKSLSLSPGK
``` amino acid sequence of an exemplary IgG1 G1m3
heavy chain constant region
SEQ ID NO: 22
```
ASTKGPSVFPLAPSSKSTSGGTAALGCLVKDYFPEPVTVSWNSGALTSGV
HTFPAVLQSSGLYSLSSVVTVPSSSLGTQTYICNVNHKPSNTKVDKRVEP
KSCDKTHTCPPCPAPELLGGPSVFLFPPKPKDTLMISRTPEVTCVVVDVS
HEDPEVKFNWYVDGVEVHNAKTKPREEQYNSTYRVVSVLTVLHQDWLNGK
EYKCKVSNKALPAPIEKTISKAKGQPREPQVYTLPPSREEMTKNQVSLTC
LVKGFYPSDIAVEWESNGQPENNYKTTPPVLDSDGSFFLYSKLTVDKSRW
QQGNVFSCSVMHEALHNHYTQKSLSLSPGK
``` amino acid sequence of an exemplary IgG1 G1m3
heavy chain constant region
SEQ ID NO: 23
```
ASTKGPSVFPLAPSSKSTSGGTAALGCLVKDYFPEPVTVSWNSGALTSGV
HTFPAVLQSSGLYSLSSVVTVPSSSLGTQTYICNVNHKPSNTKVDKRVEP
KSCDKTHTCPPCPAPEAAGGPSVFLFPPKPKDTLMISRTPEVTCVVVDVS
HEDPEVKFNWYVDGVEVHNAKTKPREEQYNSTYRVVSVLTVLHQDWLNGK
EYKCKVSNKALPAPIEKTISKAKGQPREPQVYTLPPSREEMTKNQVSLTC
LVKGFYPSDIAVEWESNGQPENNYKTTPPVLDSDGSFFLYSKLTVDKSRW
QQGNVFSCSVMHEALHNHYTQKSLSLSPGK
``` amino acid sequence of an exemplary light chain
constant region with N-terminal Arginine
SEQ ID NO: 24
```
RTVAAPSVFIFPPSDEQLKSGTASVVCLLNNFYPREAKVQWKVDNALQSG
NSQESVTEQDSKDSTYSLSSTLTLSKADYEKHKVYACEVTHQGLSSPVTK
SFNRGEC
``` amino acid sequence of an exemplary light chain
constant region without N-terminal Arginine
SEQ ID NO: 25
```
TVAAPSVFIFPPSDEQLKSGTASVVCLLNNFYPREAKVQWKVDNALQSGN
SQESVTEQDSKDSTYSLSSTLTLSKADYEKHKVYACEVTHQGLSSPVTKS
FNRGEC
``` amino acid sequence of human transthyretin set
forth in accession number P02766.1 (UniProt)
SEQ ID NO: 26
```
MASHRLLLLCLAGLVFVSEAGPTGTGESKCPLMVKVLDAVRGSPAINVAV
HVFRKAADDTWEPFASGKTSESGELHGLTTEEEFVEGIYKVEIDTKSYWK
ALGISPFHEHAEVVFTANDSGPRRYTIAALLSPYSYSTTAVVTNPKE
``` amino acid sequence of human transthyretin set
forth in accession number AAB35639.1 (GenBank)
SEQ ID NO: 27
```
GPTGTGESKCPLMVKVLDAVRGSPAINVAVHVFRKAADDTWEPFASGKTS
ESGELHGLTTEEEFVEGIYKVEIDTKSYWKALGISPFHEHAEVVFTANDS
GPRRYTIAALLSPYSYSTTAVVTNPKE
``` amino acid sequence of human transthyretin set
forth in accession number AAB35640.1 (GenBank)
SEQ ID NO: 28
```
GPTGTGESKCPLMVKVLDAVRGSPAINVAVHVFRKAADDTWEPFASGKTS
ESGELHGLTTEEEFVEGIYKVEIDTKSYWKALGISPFHEHAEVVFTANDS
GPRRYTIAALLSPYSYSTTAVVTNPKE
``` amino acid sequence of human transthyretin set
forth in accession number and ABI63351.1 (GenBank)
SEQ ID NO: 29
```
MASHRLLLLCLAGLVFVSEAGPTGTGESKCPLMVKVLDAVRGSPAINVAV
HVFRKAADDTWEPFASGKTSESGELHGLTTEEEFVEGIYKVEIDTKSYWK
ALGISPFHEHAEVVFTANDSGPRRYSYSTTAVVTNPKE
``` amino acid sequence of residues 101-109 of human
transthyretin
SEQ ID NO: 30
```
GPRRYTIAA
``` amino acid sequence of residues 87-127 of human
transthyretin
SEQ ID NO: 31
```
FHEHAEVVFTANDSGPRRYTIAALLSPYSYSTTAVVTNPKE
``` nucleic acid sequence encoding an exemplary IgG1
G1m3 heavy chain constant region
SEQ ID NO: 32
```
GCCTCCACCAAGGGTCCATCGGTCTTCCCCCTGGCACCCTCCTCCAAGAG
CACCTCTGGGGGCACAGCGGCCCTGGGCTGCCTGGTCAAGGACTACTTCC
CCGAACCGGTGACGGTGTCGTGGAACTCAGGCGCCCTGACCAGCGGCGTG
CACACCTTCCCGGCTGTCCTACAGTCCTCAGGACTCTACTCCCTCAGCAG
CGTGGTGACCGTGCCCTCCAGCAGCTTGGGCACCCAGACCTACATCTGCA
ACGTGAATCACAAGCCCAGCAACACCAAGGTGGACAAGAGAGTTGAGCCC
AAATCTTGTGACAAAACTCACACATGCCCACCGTGCCCAGCACCTGAACT
CCTGGGGGGACCGTCAGTCTTCCTCTTCCCCCCAAAACCCAAGGACACCC
TCATGATCTCCCGGACCCCTGAGGTCACATGCGTGGTGGTGGACGTGAGC
CACGAAGACCCTGAGGTCAAGTTCAACTGGTACGTGGACGGCGTGGAGGT
GCATAATGCCAAGACAAAGCCGCGGGAGGAGCAGTACAACAGCACGTACC
GTGTGGTCAGCGTCCTCACCGTCCTGCACCAGGACTGGCTGAATGGCAAG
GAGTACAAGTGCAAGGTCTCCAACAAAGCCCTCCCAGCCCCCATCGAGAA
AACCATCTCCAAAGCCAAAGGGCAGCCCCGAGAACCACAGGTGTACACCC
TGCCCCCATCCCGGGAGGAGATGACCAAGAACCAGGTCAGCCTGACCTGC
CTGGTCAAAGGCTTCTATCCCAGCGACATCGCCGTGGAGTGGGAGAGCAA
```

TGGGCAGCCGGAGAACAACTACAAGACCACGCCTCCCGTGCTGGACTCCG

ACGGCTCCTTCTTCCTCTATAGCAAGCTCACCGTGGACAAGAGCAGGTGG

CAGCAGGGGAACGTCTTCTCATGCTCCGTGATGCATGAGGCTCTGCACAA

CCACTACACGCAGAAGAGCCTCTCCCTGTCCCCGGGTAAA nucleic acid sequence encoding an exemplary light
chain constant region with N-terminal Arginine
SEQ ID NO: 33
CGAACTGTGGCTGCACCATCTGTCTTCATCTTCCCGCCATCTGATGAGCA

GTTGAAATCTGGAACTGCCTCTGTTGTGTGCCTGCTGAATAACTTCTATC

CCAGAGAGGCCAAAGTACAGTGGAAGGTGGATAACGCCCTCCAATCGGGT

AACTCCCAGGAGAGTGTCACAGAGCAGGACAGCAAGGACAGCACCTACAG

CCTCAGCAGCACCCTGACGCTGAGCAAAGCAGACTACGAGAAACACAAG

TCTACGCCTGCGAAGTCACCCATCAGGGCCTGAGCTCGCCCGTCACAAAG

AGCTTCAACAGGGGAGAGTGT nucleic acid sequence encoding an exemplary light
chain constant region without N-terminal Arginine
SEQ ID NO: 34
ACTGTGGCTGCACCATCTGTCTTCATCTTCCCGCCATCTGATGAGCAGTT

GAAATCTGGAACTGCCTCTGTTGTGTGCCTGCTGAATAACTTCTATCCA

GAGAGGCCAAAGTACAGTGGAAGGTGGATAACGCCCTCCAATCGGGTAAC

TCCCAGGAGAGTGTCACAGAGCAGGACAGCAAGGACAGCACCTACAGCCT

CAGCAGCACCCTGACGCTGAGCAAAGCAGACTACGAGAAACACAAAGTCT

ACGCCTGCGAAGTCACCCATCAGGGCCTGAGCTCGCCCGTCACAAAGAGC

TTCAACAGGGGAGAGTGT amino acid sequence of a heavy chain constant
region signal peptide
SEQ ID NO: 35
MNFGLSLIFLVLVLKGVQC nucleic acid sequence encoding a heavy chain
constant region signal peptide
SEQ ID NO: 36
ATGAACTTTGGGCTCAGCTTGATTTTCCTTGTCCTTGTTTTAAAAGGTGT

CCAGTGT amino acid sequence of a light chain constant
region signal peptide
SEQ ID NO: 37
MESHTQVFVFVFLWLSGVDG nucleic acid sequence encoding a light chain
constant region signal peptide
SEQ ID NO: 38
ATGGAGTCACATACTCAGGTCTTTGTATTCGTGTTTCTCTGGTTGTCTGG

TGTTGACGGA amino acid sequence of a Kabat CDR-H1 of 14G8
SEQ ID NO: 39
SYTMS amino acid sequence of a Kabat CDR-H2 of 14G8
SEQ ID NO: 40
EINNSGDTTYYPDTVKG amino acid sequence of a Kabat CDR-H3 of 14G8
SEQ ID NO: 41
HYYYGGGYGGWFFDV amino acid sequence of a Kabat CDR-L1 of 14G8
SEQ ID NO: 42
RSNKSLLHSNGNTYLY amino acid sequence of a Kabat CDR-L2 of 14G8
SEQ ID NO: 43
RVSNLAS amino acid sequence of a Kabat CDR-L3 of 14G8
SEQ ID NO: 44
MQHLEYPLT epitope of 5A1
SEQ ID NO: 45
EHAEVVFTA amino acid sequence of a Kabat CDR-H1 of 5A1
SEQ ID NO: 46
NYAMS amino acid sequence of a Kabat CDR-H2 of 5A1
SEQ ID NO: 47
SISSGGSTYYPDSVKG amino acid sequence of a Kabat CDR-H3 of 5A1
SEQ ID NO: 48
YYYGQYFDF amino acid sequence of a Kabat CDR-L1 of 5A1
SEQ ID NO: 49
KASQDVSTTVA amino acid sequence of a Kabat CDR-L2 of 5A1
SEQ ID NO: 50
SASYRCT amino acid sequence of a Kabat CDR-L3 of 5A1
SEQ ID NO: 51
QQHYSTPLT amino acid sequence of a Kabat CDR-H1 of 6C1
SEQ ID NO: 52
NYYMS amino acid sequence of a Kabat CDR-H2 of 6C1
SEQ ID NO: 53
YISIDGNNIYHPDSVKG amino acid sequence of a Kabat CDR-H3 of 6C1
SEQ ID NO: 54
DSDYGYFDV amino acid sequence of a Kabat CDR-L1 of 6C1
SEQ ID NO: 55
RSSQSIVHSNGNTYLE amino acid sequence of a Kabat CDR-L2 of 6C1
SEQ ID NO: 56
KVSKRFS amino acid sequence of a Kabat CDR-L3 of 6C1
SEQ ID NO: 57
FQGSHVPLT amino acid sequence of VH region of AD7F6
SEQ ID NO: 58
EVQLVESGGDLVKPGGSLKLSCAASGFTFSNYGMSWIRQTPDKRLEWVAT

ISSSGTYTYYTESVKGRFTVSRDNAKNTLSLQMSNLKSDDTAMYYCTRQA

YGREYFDVWGTGTTVTVSSAKTTPPSVYPLAPGCGDTTGSSVTLGCLVKG

YFPESVTVTWNSGSLSSSVHTFPALLQSGLYTMSSSVTVPSSTWPSQTVT

CSVAHPASSTTVDKKLEPSGPISTINPCPPCKECHKCPAPNLEGGPSVFI

FPPNIKDVLMISLTPKVTCVVVDVSEDDPDVRISWFVNNVEVHTAQTQTH

REDYNSTIRVVSALPIQHQDWMSGKEFKCKVNNKDLPSPIERTISKIKGL

-continued

VRAPQVYILPPPAEQLSRKDVSLTCLVVGFNPGDISVEWTSNGHTEENYK

DTAPVLDSDGSYFIYSKLDIKTSTVGENRFLLMQRETRGSEKLLPEEDHL

PSPGK amino acid sequence of VL region of AD7F6
SEQ ID NO: 59

DIVMSQSPSSLAVSAGEKVTMSCKSSQSLFDSRTRKNYLAWYQQKPGQSP

KLLIYWASNRESGVPDRFIGSGSGTDFTLTISSVQAEDLAVYFCKQSNYL

RTFGGGTRVEIKRADAAPTVSIFPPSSEQLTSGGASVVCFLNNFYPKDIN

VKWKIDGSERQNGVLNSWTDQDSKDSTYSMSSTLTLTKDEYERHNSYTCE

ATHKTSTSPIVKSFNRNEC amino acid sequence of CDR-H1 of RT24
SEQ ID NO: 60
RYWIT amino acid sequence of CDR-H2 of RT24
SEQ ID NO: 61
DIYPGSGRTNYNEKFKN amino acid sequence of CDR-H3 of RT24
SEQ ID NO: 62
YYGSTYFYV amino acid sequence of CDR-L1 of RT24
SEQ ID NO: 63
RSSKSLLYKDGKTYLN amino acid sequence of CDR-L2 of RT24
SEQ ID NO: 64
LMSTRAS amino acid sequence of CDR-L3 of RT24
SEQ ID NO: 65
QQLVEYPRT amino acid sequence of CDR-H1 of NI-301.35G11
SEQ ID NO: 66
SYAMS amino acid sequence of CDR-H2 of NI-301.35G11
SEQ ID NO: 67
SISGSGDTTKYTDSVKG amino acid sequence of CDR-H3 of NI-301.35G11
SEQ ID NO: 68
DGSGRIDPFAL amino acid sequence of CDR-L1 of NI-301.35G11
SEQ ID NO: 69
RSSRSLVYSDGNIYLN amino acid sequence of CDR-L2 of NI-301.35G11
SEQ ID NO: 70
KVSNRDSG amino acid sequence of CDR-L3 of NI-301.35G11
SEQ ID NO: 71
MQGTHWPRT epitope of MFD101, MDF102, MFD103, MFD105,
SEQ ID NO: 72
ADDTWEPFASGKT epitope of MFD107, MFD108, MFD109, MFD111
SEQ ID NO: 73
TSESGELHGLTTE epitope of MFD114
SEQ ID NO: 74
ALLSPYSYSTTAV amino acid sequence of a Kabat CDR-H1 of antibody 9D5
SEQ ID NO: 75
SYTMS amino acid sequence of a Kabat CDR-H2 of antibody 9D5
SEQ ID NO: 76
EISNSGDTTYYPDTVKG amino acid sequence of a Kabat CDR-H3 of antibody 9D5
SEQ ID NO: 77
HYYYGGGYGGWFFDV amino acid sequence of a Kabat CDR-L1 of antibody 9D5
SEQ ID NO: 78
RSSKSLLHSNGNTYLY amino acid sequence of a Kabat CDR-L2 of antibody 9D5
SEQ ID NO: 79
RVSNLAS amino acid sequence of a Kabat CDR-L3 of antibody 9D5
SEQ ID NO: 80
MQHLEYPLT amino acid sequence of a mature heavy chain variable region of the mouse 18C5 antibody
SEQ ID NO: 81
EVKLLESGGGLVQPGGSLNLSCVASGFDFSRFWMSWARQAPGRGQEWIGE

INPGSSTINYTPSLKDKFIISRDNAKNTLFLQMSKVRSEDSALYYCARLG

YGNYGWALDYWGQGTSVTVSS amino acid sequence of a heavy chain variable region of the murine anti-pyroglutamate-Abeta antibody Fab c#17
SEQ ID NO: 82
EVKLVESGGGLVQPGGSRKLSCAASGFTFSDYGMAWVRQAPGKGPEWVAF

ISNLAYSIYYADTVTGRFTISRENAKNTLYLEMSSLRSEDTAMYYCARYD

YDNILDYVMDYWGQGTSVTVSS amino acid sequence of a heavy chain variable region of humanized Crenezumab Fab (CreneFab) PDB: 5VZY
SEQ ID NO: 83
EVQLVESGGGLVQPGGSLRLSCAASGFTFSSYGMSWVRQAPGKGLELVAS

INSNGGSTYYPDSVKGRFTISRDNAKNSLYLQMNSLRAEDTAVYYCASGD

YWGQGTTVTVSS amino acid sequence of a heavy chain variable region of the human germline sequence IGHV3-48*01
SEQ ID NO: 84
EVQLVESGGGLVQPGGSLRLSCAASGFTFSSYSMNWVRQAPGKGLEWVSY

ISSSSSTIYYADSVKGRFTISRDNAKNSLYLQMNSLRAEDTAVYYCARYF

DYWGQGTLVTVSS amino acid sequence of a heavy chain variable region of the humanized 18C5 antibody hu18C5-VH_1
SEQ ID NO: 85
EVQLVESGGGLVQPGGSLRLSCAASGFDFSRFWMSWVRQAPGKGLELVAE

INPGSSTINYTPSLKDRFTISRDNAKNSLYLQMNSLRAEDTAVYYCASLG

YGNYGWALDYWGQGTTVTVSS amino acid sequence of a heavy chain variable
region of the humanized 18C5 antibody hu18C5-VH_2
SEQ ID NO: 86
EVQLVESGGGLVQPGGSLRLSCAASGFDFSRFWMSWARQAPGKGQEWIGE

INPGSSTINYTPSLKDRFTISRDNAKNSLYLQMNSLRAEDTAVYYCARLG

YGNYGWALDYWGQGTTVTVSS amino acid sequence of a mature light chain
variable region of the mouse 18C5 antibody
SEQ ID NO: 87
DVLMTQTPLSLPVSLGDQASISCRSSQSIVDSNGNTYLEWYLQKPGQSPK

LLIYKVSNRFSGVPDRFSGSGSGTDFTLKISRVEAEDLGIYYCFQGSHVP

LTFGAGTKLELK amino acid sequence of a light chain variable
region of the murine anti-pyroglutamate-Abeta
antibody Fab c#17
SEQ ID NO: 88
DVVMTQTPLSLPVSLGDQASISCRSSQSLVHSDGNTYLHWYLQKPGQSPK

LLIYKVSNRFSGVPDRFSGSGSGTDFTLKISRVEAEDLGVYFCSQSTHVP

PTFGGGTKLEIK amino acid sequence of a light chain variable
region of humanized Crenezumab Fab (CreneFab)
PDB: 5VZY
SEQ ID NO: 89
DIVMTQSPLSLPVTPGEPASISCRSSQSLVYSNGDTYLHWYLQKPGQSPQ

LLIYKVSNRFSGVPDRFSGSGSGTDFTLKISRVEAEDVGVYYCSQSTHVP

WTFGQGTKVEIK amino acid sequence of a light chain variable
region of the human germline sequence IGKV2-30*2
SEQ ID NO: 90
DVVMTQSPLSLPVTLGQPASISCRSSQSLVHSDGNTYLNWFQQRPGQSPR

RLIYKVSNRDSGVPDRFSGSGSGTDFTLKISRVEAEDVGVYYCMQGTHWP

WTFGQGTKVEIK amino acid sequence of a light chain variable
region of the humanized 18C5 antibody hu18C5-VL_1
SEQ ID NO: 91
DIVMTQSPLSLPVTPGEPASISCRSSQSIVDSNGNTYLEWYLQKPGQSPQ

LLIYKVSNRFSGVPDRFSGSGSGTDFTLKISRVEAEDVGVYYCFQGSHVP

LTFGQGTKVEIK amino acid sequence of a light chain variable
region of the humanized 18C5 antibody hu18C5-VL_2
SEQ ID NO: 92
DVVMTQSPLSLPVTPGEPASISCRSSQSIVDSNGNTYLEWYLQKPGQSPR

LLIYKVSNRFSGVPDRFSGSGSGTDFTLKISRVEAEDVGVYYCFQGSHVP

LTFGQGTKVEIK amino acid sequence of Kabat CDR-H1 of the mouse
18C5 antibody
SEQ ID NO: 93
RFWMS amino acid sequence of Chothia CDR-H1 of the
mouse 18C5 antibody
SEQ ID NO: 94
GFDFSRF amino acid sequence of Contact CDR-H1 of the
mouse 18C5 antibody
SEQ ID NO: 95
SRFWMS amino acid sequence of Chothia CDR-H2 of the
mouse 18C5 antibody
SEQ ID NO: 96
NPGSST amino acid sequence of AbM CDR-H2 of the mouse
18C5 antibody
SEQ ID NO: 97
EINPGSSTIN amino acid sequence of Contact CDR-H2 of the
mouse 18C5 antibody
SEQ ID NO: 98
WIGEINPGSSTIN amino acid sequence of Contact CDR-H3 of the
mouse 18C5 antibody
SEQ ID NO: 99
ARLGYGNYGWALD amino acid sequence of Contact CDR-L1 of the
mouse 18C5 antibody
SEQ ID NO: 100
NTYLEWY amino acid sequence of Contact CDR-L2 of the
mouse 18C5 antibody
SEQ ID NO: 101
LLIYKVSNRF amino acid sequence of Contact CDR-L3 of the
mouse 18C5 antibody
SEQ ID NO: 102
FQGSHVPL 9D5 mouse VH amino acid sequence
SEQ ID NO: 103
EVKLVESGGGLVQPGGSLKLSCAASGFTFSSYTMSWVRQTPEKRLELVAE

ISNSGDTTYYPDTVKGRFTFSRDNAKNTLYLQMSSLKSEDTAMYYCARHY

YYGGGYGGWFFDVWGTGTTVTVSS

9D5 mouse VL amino acid sequence
SEQ ID NO: 104
DIVMTQAAPSVPVTPGESVSISCRSSKSLLHSNGNTYLYWFLQRPGQSPQ

LLIYRVSNLASGVPDRFSGSGSGTAFTLRISRVEAEDVGVYYCMQHLEYP

LTFGAGTKLELK

---

What is claimed is:

1. A method of detecting misfolded transthyretin (TTR) in a biological sample, the method comprising:
   (a) contacting a biological sample with a capture antibody that specifically binds to an epitope within residues 89-97 of TTR of SEQ ID NO:26, wherein the capture antibody comprises three Kabat heavy chain CDRs, CDR-H1 of SEQ ID NO:75, CDR-H2 of SEQ ID NO:76, and CDR-H3 of SEQ ID NO:77, and three Kabat light chain CDRs, CDR-L1 of SEQ ID NO:78, CDR-L2 of SEQ ID NO:79, and CDR-L3 of SEQ ID NO:80, and a reporter antibody that specifically binds to a different epitope of TTR, wherein the reporter antibody is selected from the group consisting of:

an antibody comprising three Kabat/Chothia Composite heavy chain CDRs, CDR-H1 of SEQ ID NO:5, CDR-H2 of SEQ ID NO:7, CDR-H3 of SEQ ID NO:9, and three Kabat/Chothia Composite light chain CDRs, CDR-L1 of SEQ ID NO:11, CDR-L2 of SEQ ID NO:13, and CDR-L3 of SEQ ID NO:15;

an antibody comprising a heavy chain variable region of SEQ ID NO:58 and a light chain variable region of SEQ ID NO:59 or a chimeric version or humanized version thereof;

an antibody comprising three heavy chain CDRs, CDR-H1 of SEQ ID NO: 60, CDR-H2 of SEQ ID NO:61, CDR-H3 of SEQ ID NO:62, and three light chain CDRs, CDR-L1 of SEQ ID NO:63, CDR-L2 of SEQ ID NO:64, and CDR-L3 of SEQ ID NO:65;

an antibody comprising three heavy chain CDRs, CDR-H1 of SEQ ID NO: 66, CDR-H2 of SEQ ID NO:67, CDR-H3 of SEQ ID NO:68, and three light chain CDRs, CDR-L1 of SEQ ID NO:69, CDR-L2 of SEQ ID NO:70, and CDR-L3 of SEQ ID NO:71; and a polyclonal anti-TTR antibody;

wherein if misfolded TTR is present in the sample, the capture antibody and reporter antibody bind to the misfolded TTR forming a sandwich complex, wherein the biological sample is from a hereditary transthyretin-mediated amyloidosis (ATTR) patient carrying a E89K or E89Q TTR mutation and wherein the misfolded TTR includes the E89K mutation, or the E89Q mutation; and (b) detecting the reporter antibody that forms a sandwich complex in step (a), if any, to indicate presence or absence of the misfolded TTR.

2. The method of claim 1, wherein the capture antibody comprises a mature heavy chain variable region of SEQ ID NO:103 and a mature light chain variable region of SEQ ID NO: 104.

3. The method of claim 2, wherein the capture antibody comprises a mature heavy chain variable region of SEQ ID NO:103 and a mature light chain variable region of SEQ ID NO:104 and the reporter antibody is a polyclonal anti-TTR antibody.

4. The method of claim 1, wherein the biological sample is a first aliquot of a collected sample and the method further comprises repeating step (a) and (b) on a second aliquot of the collected sample further comprising a test antibody that competes with the capture antibody for binding to TTR, wherein reduced reporter antibody forming the sandwich complex on repeating the steps provides an indication of the test antibody's ability to bind to misfolded TTR; and wherein the test antibody is 14G8 (ATCC Deposit No. PTA-124079) or a chimeric or humanized form thereof.

5. The method of claim 4, wherein the capture antibody comprises a mature heavy chain variable region of SEQ ID NO: 103 and a mature light chain variable region of SEQ ID NO: 104, and the reporter antibody is a polyclonal anti-TTR antibody.

6. The method of claim 1, wherein the reporter antibody has an electrochemiluminescent label and is detected by electrochemiluminescence.

7. The method of claim 1, wherein the capture antibody has a biotin label.

8. The method of claim 1, performed quantitatively to indicate an absolute or relative amount of the misfolded TTR.

9. The method of claim 1, wherein the capture antibody is bound to a solid phase before the contacting step.

10. The method of claim 1, wherein the sample is a sample from a human.

11. The method of claim 1, wherein the sample is plasma of a human.

12. The method of claim 1, wherein the biological sample is from a patient receiving treatment for a transthyretin-mediated amyloidosis.

13. The method of claim 1 wherein the sample is from a transgenic mouse with a transgene expressing human TTR.

14. A method of detecting misfolded transthyretin (TTR) in a biological sample, the method comprising:

(a) contacting a biological sample with a capture antibody that specifically binds to an epitope within residues 101-109 of TTR of SEQ ID NO:26, wherein the capture antibody comprises three Kabat-Chothia Composite heavy chain CDRs, CDR-H1 of SEQ ID NO:5, CDR-H2 of SEQ ID NO:7, CDR-H3 of SEQ ID NO:9, and three Kabat-Chothia Composite light chain CDRs, CDR-L1 of SEQ ID NO:11, CDR-L2 of SEQ ID NO:13, and CDR-L3 of SEQ ID NO:15, and a reporter antibody that specifically binds to a different epitope of TTR, wherein the reporter antibody is selected from the group consisting of:

an antibody comprising a mature heavy chain variable region of SEQ ID NO: 103 and a mature light chain variable region of SEQ ID NO: 104 or a chimeric version or humanized version thereof, 14G8 (ATCC Deposit No. PTA-124079) or a chimeric version or humanized version thereof, 5A1 ATCC Deposit No. PTA-124080) or a chimeric version or humanized version thereof, 6C1 (ATCC Deposit No. PTA-124077) or a chimeric version or humanized version thereof, an antibody comprising a heavy chain variable region of SEQ ID NO:58 and a light chain variable region of SEQ ID NO:59 or a chimeric version or humanized version thereof, an antibody comprising three heavy chain CDR-H1 of SEQ ID NO:60, CDR-H2 of SEQ ID NO:61, CDR-H3 of SEQ ID NO:62, and three light chain CDR-L1 of SEQ ID NO:63, CDR-L2 of SEQ ID NO:64, and CDR-L3 of SEQ ID NO:65, an antibody comprising three heavy chain CDRs, CDR-H1 of SEQ ID NO: 66, CDR-H2 of SEQ ID NO:67, CDR-H3 of SEQ ID NO:68, and three light chain CDRs, CDR-L1 of SEQ ID NO:69, CDR-L2 of SEQ ID NO:70, and CDR-L3 of SEQ ID NO:71; and a polyclonal anti-TTR antibody;

wherein if misfolded TTR is present in the sample, the capture antibody and reporter antibody bind to the misfolded TTR forming a sandwich complex; and (b) detecting the reporter antibody that binds to the misfolded TTR in step (a), if any, to indicate presence or absence of the misfolded TTR.

15. The method of claim 14, wherein the biological sample is from a hereditary transthyretin-mediated amyloidosis (ATTR) patient.

16. The method of claim 15, wherein the biological sample is from a hereditary ATTR patient carrying a mutation selected from the group consisting of V30M, Y114C, and S50I.

17. The method of claim 14, wherein the capture antibody comprises a mature heavy chain variable region of SEQ ID NO:81 and a mature light variable region of SEQ ID NO:87.

18. The method of claim 17 wherein the capture antibody comprises a mature heavy chain variable region of SEQ ID NO:81 and a mature light variable region of SEQ ID NO:87 and the reporter antibody is a polyclonal anti-TTR antibody.

19. The method of claim 14, wherein the reporter antibody has an electrochemiluminescent label and is detected by electrochemiluminescence.

20. The method of claim 14, wherein the capture antibody has a biotin label.

21. The method of claim 14, performed quantitatively to indicate an absolute or relative amount of the misfolded TTR.

22. The method of claim 14, wherein the capture antibody is bound to a solid phase before the contacting step.

23. The method of claim 14, wherein the sample is a sample from a human.

24. The method of claim 14, wherein the sample is plasma of a human.

25. The method of claim 14, wherein the biological sample is from a patient receiving treatment for a transthyretin-mediated amyloidosis.

26. The method of claim 14, wherein the sample is from a transgenic mouse with a transgene expressing human TTR.

\* \* \* \* \*

UNITED STATES PATENT AND TRADEMARK OFFICE
CERTIFICATE OF CORRECTION

PATENT NO. : 12,247,985 B2
APPLICATION NO. : 16/753661
DATED : March 11, 2025
INVENTOR(S) : Joshua Reginald Salmans et al.

Page 1 of 1

It is certified that error appears in the above-identified patent and that said Letters Patent is hereby corrected as shown below:

In the Claims

In Column 154, Line 29, Claim 14, delete "ATCC" and insert -- (ATCC --, therefor.

Signed and Sealed this
Tenth Day of June, 2025

Coke Morgan Stewart
*Acting Director of the United States Patent and Trademark Office*